US008933131B2

(12) United States Patent
Federle et al.

(10) Patent No.: US 8,933,131 B2
(45) Date of Patent: Jan. 13, 2015

(54) INTERMEDIATES AND SURFACTANTS USEFUL IN HOUSEHOLD CLEANING AND PERSONAL CARE COMPOSITIONS, AND METHODS OF MAKING THE SAME

(75) Inventors: Thomas Walter Federle, Cincinnati, OH (US); Jeffrey John Scheibel, Loveland, OH (US); Zaiyou Liu, West Chester, OH (US); Phillip Kyle Vinson, Fairfield, OH (US); Howard David Hutton, III, Oregonia, OH (US); John David Carter, Mason, OH (US); Charles Winston Saunders, Fairfield, OH (US); Jun Xu, Mason, OH (US); Phillip Richard Green, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 420 days.

(21) Appl. No.: 13/004,072

(22) Filed: Jan. 11, 2011

(65) Prior Publication Data
US 2011/0171155 A1 Jul. 14, 2011

Related U.S. Application Data

(60) Provisional application No. 61/294,274, filed on Jan. 12, 2010.

(51) Int. Cl.
*A61K 31/045* (2006.01)
*A61K 31/255* (2006.01)
*C12P 7/64* (2006.01)
*C12N 9/90* (2006.01)
*C12N 9/00* (2006.01)

(52) U.S. Cl.
CPC ............... *C12P 7/6409* (2013.01); *C12N 9/90* (2013.01); *C12N 9/93* (2013.01); *C12Y 504/99002* (2013.01); *C12Y 604/01003* (2013.01)
USPC .......................................... 514/709; 514/784

(58) Field of Classification Search
USPC .................................................. 514/709, 784
See application file for complete search history.

(56) References Cited

U.S. PATENT DOCUMENTS

| | | |
|---|---|---|
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer et al. |
| 2,658,072 A | 11/1953 | Kosmin |
| 2,809,971 A | 10/1957 | Bernstein et al. |
| 2,826,551 A | 3/1958 | Geen |
| 2,954,347 A | 9/1960 | St. John et al. |
| 3,236,733 A | 2/1966 | Karsten et al. |
| 3,308,067 A | 3/1967 | Diehl |
| 3,332,880 A | 7/1967 | Kessler et al. |
| 3,455,839 A | 7/1969 | Rauner |
| 3,480,556 A | 11/1969 | DeWitt et al. |
| 3,519,570 A | 7/1970 | McCarty |
| 3,553,139 A | 1/1971 | McCarty |
| 3,600,319 A | 8/1971 | Gedge, III et al. |
| 3,646,015 A | 2/1972 | Hamilton |
| 3,664,961 A | 5/1972 | Norris |
| 3,753,196 A | 8/1973 | Kurtz et al. |
| 3,761,418 A | 9/1973 | Parran, Jr. |
| 3,885,155 A | 5/1975 | Anbar |
| 3,893,929 A | 7/1975 | Basadur |
| 3,929,678 A | 12/1975 | Laughlin et al. |
| 3,933,672 A | 1/1976 | Bartolotta et al. |
| 3,944,470 A | 3/1976 | Diehl et al. |
| 3,958,581 A | 5/1976 | Abegg et al. |
| 3,959,230 A | 5/1976 | Hays |
| 3,962,418 A | 6/1976 | Birkofer |
| 3,964,500 A | 6/1976 | Drakoff |
| 4,000,093 A | 12/1976 | Nicol et al. |
| 4,033,718 A | 7/1977 | Holcombe et al. |
| 4,062,647 A | 12/1977 | Storm et al. |
| 4,075,118 A | 2/1978 | Gault et al. |
| 4,101,457 A | 7/1978 | Place et al. |
| 4,111,855 A | 9/1978 | Barrat et al. |
| 4,133,779 A | 1/1979 | Hellyer et al. |
| 4,140,641 A | 2/1979 | Ramachandran |
| 4,152,416 A | 5/1979 | Spitzer et al. |
| 4,197,865 A | 4/1980 | Jacquet et al. |
| 4,201,824 A | 5/1980 | Violland et al. |
| 4,217,914 A | 8/1980 | Jacquet et al. |
| 4,240,918 A | 12/1980 | Lagasse et al. |

(Continued)

FOREIGN PATENT DOCUMENTS

| | | |
|---|---|---|
| BR | 9502668 | 3/1996 |
| CA | 2 614 237 | 1/2007 |
| DE | 2 335 044 A1 | 1/1974 |
| DE | 196 23 623 A1 | 1/1997 |
| DE | 100 36 533 A1 | 2/2002 |

(Continued)

OTHER PUBLICATIONS

Buzzell, 1997, Journal of Experimental Zoology, vol. 277, p. 99-105.*

(Continued)

*Primary Examiner* — Rebecca Anderson
*Assistant Examiner* — Karen Cheng
(74) *Attorney, Agent, or Firm* — Melissa G Krasovec

(57) ABSTRACT

Disclosed herein are novel mixtures of scattered-branched chain fatty acids and derivatives of scattered-branched chain fatty acids. Further disclosed are uses of these mixtures in cleaning compositions (e.g., dishcare, laundry, hard surface cleaners) and/or personal care compositions (e.g., skin cleansers, shampoo, hair conditioners).

13 Claims, No Drawings

(56) References Cited

U.S. PATENT DOCUMENTS

| | | |
|---|---|---|
| 4,261,868 A | 4/1981 | Hora et al. |
| 4,265,779 A | 5/1981 | Gandolfo et al. |
| 4,275,055 A | 6/1981 | Nachtigal et al. |
| 4,287,082 A | 9/1981 | Tolfo et al. |
| 4,291,071 A | 9/1981 | Harris et al. |
| 4,305,837 A | 12/1981 | Kaminsky et al. |
| 4,316,824 A | 2/1982 | Pancheri |
| 4,323,683 A | 4/1982 | Bolich, Jr. et al. |
| 4,345,080 A | 8/1982 | Bolich, Jr. |
| 4,364,837 A | 12/1982 | Pader |
| 4,375,416 A | 3/1983 | Crisp et al. |
| 4,379,753 A | 4/1983 | Bolich, Jr. |
| 4,381,919 A | 5/1983 | Jacquet et al. |
| 4,404,115 A | 9/1983 | Tai |
| 4,412,934 A | 11/1983 | Chung et al. |
| 4,422,853 A | 12/1983 | Jacquet et al. |
| 4,427,884 A | 1/1984 | Anbar et al. |
| 4,430,243 A | 2/1984 | Bragg |
| 4,452,717 A | 6/1984 | Tai et al. |
| 4,462,922 A | 7/1984 | Boskamp |
| 4,470,919 A | 9/1984 | Goffinet et al. |
| 4,470,982 A | 9/1984 | Winkler |
| 4,483,781 A | 11/1984 | Hartman |
| 4,489,455 A | 12/1984 | Spendel |
| 4,489,574 A | 12/1984 | Spendel |
| 4,507,219 A | 3/1985 | Hughes |
| 4,507,280 A | 3/1985 | Pohl et al. |
| 4,525,524 A | 6/1985 | Tung et al. |
| 4,526,709 A | 7/1985 | Boskamp et al. |
| 4,529,525 A | 7/1985 | Dormal et al. |
| 4,529,586 A | 7/1985 | De Marco et al. |
| 4,530,780 A | 7/1985 | van de Pas et al. |
| 4,537,706 A | 8/1985 | Severson, Jr. |
| 4,537,707 A | 8/1985 | Severson, Jr. |
| 4,545,941 A | 10/1985 | Rosenburg |
| 4,579,681 A | 4/1986 | Ruppert et al. |
| 4,597,898 A | 7/1986 | Vander Meer |
| 4,618,446 A | 10/1986 | Haslop et al. |
| 4,634,551 A | 1/1987 | Burns et al. |
| 4,639,321 A | 1/1987 | Barrat et al. |
| 4,639,489 A | 1/1987 | Aizawa et al. |
| 4,647,393 A | 3/1987 | Ouhadi et al. |
| 4,648,983 A | 3/1987 | Broze et al. |
| 4,652,392 A | 3/1987 | Baginski et al. |
| 4,655,954 A | 4/1987 | Broze et al. |
| 4,659,497 A | 4/1987 | Akred et al. |
| 4,661,280 A | 4/1987 | Ouhadi et al. |
| 4,663,158 A | 5/1987 | Wolfram et al. |
| 4,670,179 A | 6/1987 | Inamorato et al. |
| 4,681,704 A | 7/1987 | Bernardino et al. |
| 4,686,062 A | 8/1987 | Kermode et al. |
| 4,690,771 A | 9/1987 | Ouhadi et al. |
| 4,702,857 A | 10/1987 | Gosselink |
| 4,711,730 A | 12/1987 | Gosselink et al. |
| 4,721,580 A | 1/1988 | Gosselink |
| 4,728,455 A | 3/1988 | Rerek |
| 4,744,916 A | 5/1988 | Adams et al. |
| 4,746,456 A | 5/1988 | Kud et al. |
| 4,749,740 A | 6/1988 | Aizawa et al. |
| 4,751,008 A | 6/1988 | Crossin |
| 4,753,750 A | 6/1988 | Ouhadi et al. |
| 4,787,989 A | 11/1988 | Fanelli et al. |
| 4,790,856 A | 12/1988 | Wixon |
| 4,793,943 A | 12/1988 | Haslop et al. |
| 4,798,679 A | 1/1989 | Castro et al. |
| 4,842,758 A | 6/1989 | Crutzen |
| 4,844,821 A | 7/1989 | Mermelstein et al. |
| 4,844,824 A | 7/1989 | Mermelstein et al. |
| 4,871,467 A | 10/1989 | Akred et al. |
| 4,873,001 A | 10/1989 | Ramachandran et al. |
| 4,877,896 A | 10/1989 | Maldonado et al. |
| 4,891,147 A | 1/1990 | Gray et al. |
| 4,891,160 A | 1/1990 | Vander Meer |
| 4,900,475 A | 2/1990 | Ramachandran et al. |
| 4,908,150 A | 3/1990 | Hessel et al. |
| 4,911,852 A | 3/1990 | Coffindaffer et al. |
| 4,915,854 A | 4/1990 | Mao et al. |
| 4,923,635 A | 5/1990 | Simion et al. |
| 4,925,588 A | 5/1990 | Berrod et al. |
| 4,943,397 A | 7/1990 | Johnson |
| 4,950,424 A | 8/1990 | van der Hoeven et al. |
| 4,956,447 A | 9/1990 | Gosselink et al. |
| 4,966,723 A | 10/1990 | Hodge et al. |
| 4,968,451 A | 11/1990 | Scheibel et al. |
| 4,973,841 A | 11/1990 | Purser |
| 4,978,471 A | 12/1990 | Starch |
| 4,983,316 A | 1/1991 | Starch |
| 5,004,556 A | 4/1991 | Julemont et al. |
| 5,006,273 A | 4/1991 | Machin et al. |
| 5,017,296 A | 5/1991 | Nedonchelle |
| 5,021,195 A | 6/1991 | Machin et al. |
| 5,035,661 A | 7/1991 | Steinhardt et al. |
| 5,057,240 A | 10/1991 | Madore et al. |
| 5,082,585 A | 1/1992 | Hessel et al. |
| 5,102,574 A | 4/1992 | Russell et al. |
| 5,104,646 A | 4/1992 | Bolich, Jr. et al. |
| 5,106,609 A | 4/1992 | Bolich, Jr. et al. |
| 5,114,606 A | 5/1992 | van Vliet et al. |
| 5,114,611 A | 5/1992 | Van Kralingen et al. |
| 5,147,576 A | 9/1992 | Montague et al. |
| 5,153,161 A | 10/1992 | Kerschner et al. |
| 5,156,773 A | 10/1992 | Kochavi et al. |
| 5,160,655 A | 11/1992 | Donker et al. |
| 5,194,416 A | 3/1993 | Jureller et al. |
| 5,207,941 A | 5/1993 | Kroner et al. |
| 5,227,084 A | 7/1993 | Martens et al. |
| 5,230,823 A | 7/1993 | Wise et al. |
| 5,244,594 A | 9/1993 | Favre et al. |
| 5,246,612 A | 9/1993 | Van Dijk et al. |
| 5,246,621 A | 9/1993 | Favre et al. |
| 5,250,212 A | 10/1993 | de Buzzaccarini et al. |
| 5,256,779 A | 10/1993 | Kerschner et al. |
| 5,264,143 A | 11/1993 | Boutique |
| 5,269,960 A | 12/1993 | Gray et al. |
| 5,269,974 A | 12/1993 | Ofosu-Asante |
| 5,274,147 A | 12/1993 | Kerschner et al. |
| 5,275,753 A | 1/1994 | de Buzzaccarini et al. |
| 5,280,117 A | 1/1994 | Kerschner et al. |
| 5,284,944 A | 2/1994 | Madison et al. |
| 5,288,431 A | 2/1994 | Huber et al. |
| 5,288,746 A | 2/1994 | Pramod |
| RE34,584 E | 4/1994 | Grote et al. |
| 5,314,635 A | 5/1994 | Hage et al. |
| 5,356,554 A | 10/1994 | Delwel et al. |
| 5,364,617 A | 11/1994 | Bush et al. |
| 5,376,310 A | 12/1994 | Cripe et al. |
| 5,409,632 A | 4/1995 | Showell et al. |
| 5,415,807 A | 5/1995 | Gosselink et al. |
| 5,422,030 A | 6/1995 | Panandiker et al. |
| 5,431,842 A | 7/1995 | Panandiker et al. |
| 5,431,848 A | 7/1995 | Getty |
| 5,438,194 A | 8/1995 | Koudijs et al. |
| 5,442,100 A | 8/1995 | Bjorkquist et al. |
| 5,445,756 A | 8/1995 | Didier et al. |
| 5,462,963 A | 10/1995 | Bush et al. |
| 5,468,414 A | 11/1995 | Panandiker et al. |
| 5,487,884 A | 1/1996 | Bissett et al. |
| 5,488,157 A | 1/1996 | Bjorkquist et al. |
| 5,489,392 A | 2/1996 | Capeci et al. |
| 5,496,487 A | 3/1996 | Capeci et al. |
| 5,500,137 A | 3/1996 | Bacon et al. |
| 5,500,138 A | 3/1996 | Bacon et al. |
| 5,500,153 A | 3/1996 | Figueroa et al. |
| 5,500,154 A | 3/1996 | Bacon et al. |
| 5,505,866 A | 4/1996 | Bacon et al. |
| 5,510,042 A | 4/1996 | Hartman et al. |
| 5,516,448 A | 5/1996 | Capeci et al. |
| 5,531,910 A | 7/1996 | Severns et al. |
| 5,540,852 A | 7/1996 | Kefauver et al. |
| 5,540,853 A | 7/1996 | Trinh et al. |
| 5,543,083 A | 8/1996 | Sivik et al. |
| 5,547,476 A | 8/1996 | Siklosi et al. |
| 5,554,587 A | 9/1996 | Capeci |
| 5,559,088 A | 9/1996 | Severns et al. |

(56) References Cited

U.S. PATENT DOCUMENTS

| | | |
|---|---|---|
| 5,562,847 A | 10/1996 | Waite et al. |
| 5,565,145 A | 10/1996 | Watson et al. |
| 5,565,422 A | 10/1996 | Del Greco et al. |
| 5,569,645 A | 10/1996 | Dinniwell et al. |
| 5,573,697 A | 11/1996 | Riddick et al. |
| 5,574,005 A | 11/1996 | Welch et al. |
| 5,576,282 A | 11/1996 | Miracle et al. |
| 5,576,285 A | 11/1996 | France et al. |
| 5,578,234 A | 11/1996 | Corona, III |
| 5,580,485 A | 12/1996 | Feringa et al. |
| 5,580,486 A | 12/1996 | Labeque et al. |
| 5,591,236 A | 1/1997 | Roetker |
| 5,595,967 A | 1/1997 | Miracle et al. |
| 5,597,936 A | 1/1997 | Perkins et al. |
| 5,607,980 A | 3/1997 | McAtee et al. |
| 5,630,847 A | 5/1997 | Roetker |
| 5,630,848 A | 5/1997 | Young et al. |
| 5,632,780 A | 5/1997 | Siklosi |
| 5,641,739 A | 6/1997 | Kott et al. |
| 5,652,228 A | 7/1997 | Bissett |
| 5,661,299 A | 8/1997 | Purser |
| 5,665,692 A | 9/1997 | Kaminsky |
| 5,674,478 A | 10/1997 | Dodd et al. |
| 5,681,852 A | 10/1997 | Bissett |
| 5,703,025 A | 12/1997 | Zyngier et al. |
| 5,705,474 A | 1/1998 | Severns et al. |
| 5,707,959 A | 1/1998 | Pancheri et al. |
| 5,741,693 A | 4/1998 | Outtrup et al. |
| 5,750,122 A | 5/1998 | Evans et al. |
| 5,767,052 A | 6/1998 | Shaw, Jr. et al. |
| 5,780,694 A | 7/1998 | Singleton |
| 5,807,956 A | 9/1998 | Czech |
| 5,849,960 A | 12/1998 | Singleton et al. |
| 5,854,200 A | 12/1998 | Severns et al. |
| 5,872,092 A | 2/1999 | Kong-Chan et al. |
| 5,932,202 A | 8/1999 | Guskey et al. |
| 5,942,653 A | 8/1999 | Du Plessis et al. |
| 5,952,289 A | 9/1999 | Wise et al. |
| H1818 H | 11/1999 | Potgieter et al. |
| 5,981,681 A | 11/1999 | Czech |
| 6,004,915 A | 12/1999 | Elliott et al. |
| 6,008,181 A | 12/1999 | Cripe et al. |
| 6,020,303 A | 2/2000 | Cripe et al. |
| 6,046,152 A | 4/2000 | Vinson et al. |
| 6,060,443 A * | 5/2000 | Cripe et al. ............ 510/426 |
| 6,074,996 A | 6/2000 | Elliott et al. |
| 6,093,856 A | 7/2000 | Cripe et al. |
| 6,133,212 A | 10/2000 | Elliott et al. |
| 6,150,322 A | 11/2000 | Singleton et al. |
| 6,165,961 A | 12/2000 | Schmid et al. |
| 6,166,262 A | 12/2000 | Connor |
| 6,207,782 B1 | 3/2001 | Czech et al. |
| 6,221,430 B1 | 4/2001 | Tompsett |
| 6,222,077 B1 | 4/2001 | Singleton |
| 6,235,773 B1 | 5/2001 | Bissett |
| 6,320,080 B2 | 11/2001 | Connor |
| 6,325,995 B1 | 12/2001 | El-Nokaly et al. |
| 6,335,312 B1 | 1/2002 | Coffindaffer et al. |
| 6,395,701 B1 | 5/2002 | Connor et al. |
| 6,433,207 B1 | 8/2002 | Connor |
| 6,482,969 B1 | 11/2002 | Helmrick et al. |
| 6,503,495 B1 | 1/2003 | Alwattari et al. |
| 6,586,649 B1 | 7/2003 | Botha et al. |
| 6,593,285 B1 | 7/2003 | Scheibel et al. |
| 6,602,845 B2 | 8/2003 | Demeyere et al. |
| 6,607,717 B1 | 8/2003 | Johnson et al. |
| 6,696,049 B2 | 2/2004 | Vatter et al. |
| 6,706,931 B2 | 3/2004 | Edwards |
| 6,777,582 B2 | 8/2004 | Gartside et al. |
| 6,891,056 B2 | 5/2005 | Edwards et al. |
| 6,949,502 B2 | 9/2005 | Trinh et al. |
| 7,041,767 B2 | 5/2006 | Lange et al. |
| 7,071,364 B2 | 7/2006 | Edwards et al. |
| 7,175,799 B2 | 2/2007 | Hori et al. |
| 7,183,446 B2 | 2/2007 | Zeller et al. |
| 7,217,777 B2 | 5/2007 | Lange et al. |
| 7,270,828 B2 | 9/2007 | Masuda et al. |
| 7,303,744 B2 | 12/2007 | Wells et al. |
| 7,462,205 B2 | 12/2008 | Murphy |
| 7,465,439 B2 | 12/2008 | Avery et al. |
| 7,501,389 B2 | 3/2009 | Hage et al. |
| 7,635,794 B2 | 12/2009 | Basset et al. |
| 7,637,968 B2 | 12/2009 | Murphy |
| 7,671,224 B2 | 3/2010 | Winde et al. |
| 7,678,932 B2 | 3/2010 | Thurier et al. |
| 7,781,390 B2 | 8/2010 | Singleton et al. |
| 7,871,973 B1 | 1/2011 | Singleton et al. |
| 7,888,307 B2 | 2/2011 | Singleton et al. |
| 7,994,369 B2 | 8/2011 | Scheibel et al. |
| 8,013,287 B2 | 9/2011 | Joung et al. |
| 8,044,249 B2 | 10/2011 | Scheibel et al. |
| 8,067,623 B2 | 11/2011 | Lee |
| 8,070,833 B2 | 12/2011 | Murphy |
| 8,071,799 B2 | 12/2011 | Olson |
| 8,110,670 B2 | 2/2012 | Hu et al. |
| 8,232,431 B2 | 7/2012 | Price et al. |
| 8,232,432 B2 | 7/2012 | Scheibel et al. |
| 8,299,308 B2 | 10/2012 | Scheibel et al. |
| 8,344,052 B2 | 1/2013 | Braksmayer et al. |
| 8,389,625 B2 | 3/2013 | Wu et al. |
| 8,501,973 B2 | 8/2013 | Schrodi et al. |
| 8,551,194 B2 | 10/2013 | Uptain et al. |
| 8,557,283 B2 | 10/2013 | Hsu et al. |
| 8,569,560 B2 | 10/2013 | Schrodi et al. |
| 8,603,197 B2 | 12/2013 | Lemke et al. |
| 8,603,449 B2 | 12/2013 | Sunkel et al. |
| 2002/0010124 A1 | 1/2002 | Creeth et al. |
| 2002/0120958 A1 | 8/2002 | Duhot et al. |
| 2003/0135080 A1 | 7/2003 | Botha et al. |
| 2004/0175347 A1 | 9/2004 | Bissett |
| 2005/0048549 A1 | 3/2005 | Cao et al. |
| 2006/0275237 A1 | 12/2006 | Bissett et al. |
| 2007/0041929 A1 | 2/2007 | Torgerson et al. |
| 2007/0207109 A1 | 9/2007 | Peffly et al. |
| 2007/0286837 A1 | 12/2007 | Torgerson et al. |
| 2008/0033026 A1 | 2/2008 | Zullo et al. |
| 2008/0044494 A1 | 2/2008 | Robinson et al. |
| 2009/0126602 A1 | 5/2009 | Murphy et al. |
| 2009/0217568 A1 | 9/2009 | Murphy et al. |
| 2009/0220443 A1 | 9/2009 | Braksmayer et al. |
| 2009/0221463 A1 | 9/2009 | Kitko et al. |
| 2009/0232873 A1 | 9/2009 | Glenn, Jr. et al. |
| 2009/0259065 A1 | 10/2009 | Abraham et al. |
| 2009/0264672 A1 | 10/2009 | Abraham et al. |
| 2010/0094034 A1 | 4/2010 | Kaido et al. |
| 2010/0105963 A1 | 4/2010 | Hu |
| 2010/0205851 A1 | 8/2010 | Uptain et al. |
| 2010/0242345 A1 | 9/2010 | Keasling et al. |
| 2010/0298612 A1 | 11/2010 | Behrouzian et al. |
| 2010/0323946 A1 | 12/2010 | Connors et al. |
| 2011/0160472 A1 | 6/2011 | Lemke et al. |
| 2011/0166370 A1 | 7/2011 | Saunders et al. |
| 2011/0171155 A1 | 7/2011 | Saunders et al. |
| 2011/0230687 A1 | 9/2011 | Luetkens et al. |
| 2011/0237850 A1 | 9/2011 | Luetkens et al. |
| 2011/0313180 A1 | 12/2011 | Uptain et al. |
| 2012/0012130 A1 | 1/2012 | Hutton, III et al. |
| 2012/0014901 A1 | 1/2012 | Sunkel et al. |
| 2012/0288930 A1 | 11/2012 | Trimbur et al. |
| 2013/0053300 A1 | 2/2013 | Scheibel et al. |
| 2013/0072413 A1 | 3/2013 | Urbin et al. |
| 2013/0072414 A1 | 3/2013 | Price et al. |
| 2013/0072415 A1 | 3/2013 | Scheibel et al. |
| 2013/0115665 A1 | 5/2013 | Hu et al. |

FOREIGN PATENT DOCUMENTS

| | | |
|---|---|---|
| EP | 0 066 915 A2 | 12/1982 |
| EP | 0 111 965 A2 | 6/1984 |
| EP | 0 111 984 A2 | 6/1984 |
| EP | 0 225 654 A1 | 6/1984 |
| EP | 0 112 592 A2 | 7/1984 |
| EP | 0 133 354 A1 | 2/1985 |
| EP | 0 150 872 A1 | 8/1985 |

(56) References Cited

FOREIGN PATENT DOCUMENTS

| | | |
|---|---|---|
| EP | 0 199 405 A2 | 10/1986 |
| EP | 0 200 586 A1 | 11/1986 |
| EP | 0 315 126 A2 | 5/1989 |
| EP | 0 544 490 A1 | 6/1993 |
| EP | 0 549 272 A1 | 6/1993 |
| EP | 0 564 250 A2 | 10/1993 |
| EP | 0 583 534 A1 | 2/1994 |
| EP | 0 583 535 A1 | 2/1994 |
| EP | 0 598 170 A1 | 5/1994 |
| EP | 0 598 973 A1 | 6/1994 |
| EP | 0 619 368 A1 | 10/1994 |
| EP | 0 633 311 A1 | 1/1995 |
| EP | 439316 B1 | 2/1995 |
| EP | 684300 A2 | 11/1995 |
| EP | 0 694 608 A1 | 1/1996 |
| EP | 0 705 900 A1 | 4/1996 |
| EP | 0 709 449 A1 | 5/1996 |
| EP | 0 738 778 A1 | 10/1996 |
| EP | 0 739 977 A1 | 10/1996 |
| EP | 0 743 279 A1 | 11/1996 |
| EP | 0 743 280 A1 | 11/1996 |
| EP | 0 751 210 A1 | 1/1997 |
| EP | 0 751 213 A1 | 1/1997 |
| EP | 0 752 466 A1 | 1/1997 |
| EP | 0 752 469 A1 | 1/1997 |
| EP | 0 753 556 A1 | 1/1997 |
| EP | 0 753 557 A1 | 1/1997 |
| EP | 0 753 558 A1 | 1/1997 |
| EP | 0 753 559 A1 | 1/1997 |
| EP | 0 753 560 A1 | 1/1997 |
| EP | 763525 B1 | 3/1997 |
| GB | 0 514 612 A | 11/1939 |
| GB | 849433 A | 9/1960 |
| GB | 1257679 | 12/1971 |
| GB | 2 292 155 A | 2/1996 |
| GB | 2 292 562 A | 2/1996 |
| GB | 2 297 761 A | 8/1996 |
| GB | 2 297 762 A | 8/1996 |
| GB | 2 297 975 A | 8/1996 |
| WO | WO-96/17916 A1 | 6/1996 |
| WO | WO 96/22352 A1 | 7/1996 |
| WO | WO 96/23048 A1 | 8/1996 |
| WO | WO 96/34082 A1 | 10/1996 |
| WO | WO 96/37589 A1 | 11/1996 |
| WO | WO 96/37595 A1 | 11/1996 |
| WO | WO 97/00843 | 1/1997 |
| WO | WO-97/00930 A1 | 1/1997 |
| WO | WO-97/00936 A1 | 1/1997 |
| WO | WO-97/00937 A1 | 1/1997 |
| WO | WO 97/38956 | 10/1997 |
| WO | WO 97/39088 | 10/1997 |
| WO | WO 98/23566 A1 | 6/1998 |
| WO | WO-99/02072 A1 | 1/1999 |
| WO | WO 99/18217 A1 | 4/1999 |
| WO | WO-01/02324 A1 | 1/2001 |
| WO | WO2006/113313 * | 10/2006 |
| WO | WO-2007/136762 A2 | 11/2007 |
| WO | WO-2008/140468 A2 | 11/2008 |
| WO | WO-2008/151149 A2 | 12/2008 |
| WO | WO-2009/020667 A1 | 2/2009 |
| WO | WO-2009/155086 A2 | 12/2009 |
| WO | WO-2010/034736 A1 | 4/2010 |

OTHER PUBLICATIONS

Harvey, 1989, Biomedical Chromatography, vol. 3, No. 6, p. 251-254.*

Madelein VD Merwe, et al., Branched alcohols and alcohol mixtures, their derivatives and use obtained from FT-feed stocks; *An IP.com Prior Art Database Technical Disclosure*; IP.com Electronic Publication: Aug. 16, 2004; IP.com No. IPCOM000030465D; Sasol Olefins & Surfactants; pp. 1-23.

Suardi, Mainly branched fatty alcohols from conventional and modified oxo-synthesis with a methyl group along the main chain, their mixtures, derivatives and use.; *An IP.com Prior Art Database Technical Disclosure*; IP.com Electronic Publication: Jan. 22, 2010; IP.com No. IPCOM000192536D;Sasol Olefins & Surfactants, pp. 1-38.

"Novel Renewable Chemicals Transforming Markets with New Building Blocks," Elevance Renewable Sciences, PowerPoint Presentation, (Mar. 16, 2010).

Ackman et al., "Some Monomethyl-Branced Fatty Acids from Ruminant Fats: Open-Tubular GLC Separations and Indications of Substitution on Even-Numbered Carbon," *Lipids*, 7(10):683-691 (1972).

Bligh, et al., A rapid method for total lipid extraction and purification, *Can. J. Biochem. Physiol*. 37:911-917 (1959).

Blomquist, G.J. et al., "Methyl-branched fatty acids and their biosynthesis in the housefly, *Musca domestica* L. (Diptera: Muscidae)", Insect Biochemistry and Molecular Biology, 1994, vol. 24, pp. 803-810.

Burgal, J. et al., "Metabolic engineering of hydroxyl fatty acid production in plants: RcDGAT2 drives dramatic increases in ricinoleate levels in seed oil", Plant Biotechnology Journal, 2008, 6, 819-831.

Buckner, J.S. et al., "Purification and properties of malonyl-coenzyme A decarboxylase, a regulatory enzyme from the uropygial gland of goose", Archives of Biochemistry and Biophysics, 1976, 117, 539-551.

Buchmeiser, "Polymer-Supported Well-Defined Metathesis Catalysts," *Chem. Rev.*, 109:303-321 (2009).

Carballeira, N.M. et al., "Characteridation of novel methyl-branched chain fatty acids from a halophilic *Bacilius* species", Journal of Natural Products, 2001, vol. 64, pp. 256-259.

Cropp, T.A. et al., "Fatty-acid biosynthesis in a branched-chain a-keto acid dehydrogenase mutant of *Streptomyces avermitilis*", Can. J. of Microiology, 46(6); 506-514, 2000.

Diver, "Metal Carbenes in Enyne Metathesis: Synthetic and Mechanistic Studies," *Journal of Molecular Catalysis A: Chemical*, 254:29-42 (2006).

Dwyer, "Metathesis: An Industrial Perspective," ISOM XVII, Pasadena, CA, (2007).

Encyclopedia of Polymer Science and Engineering, vol. 15, 2d ed., pp. 204-308, John Wiley & Sons, Inc. (1989).

Kim, Y.S. et al., "Malonyl-CoA decarboxylase from *Mycobacterium tuberculosis* and *Pseudomonas fluorescene*", Archives of Biochemistry and Biophysics, 1979, 196, 543-551.

Kirk Othmer Encyclopedia of Chemical Technology, Third Edition, John Wiley & Sons, Inc., 7:430-447 (1979).

Kirk, "Ruthenium Based Homogeneous Olefin Metathesis," M.S. Dissertation, University of the Free State, South Africa, (2005).

Kolattukudy, P.E. et al., "Developmental pattern of the expression of malonyl-CoA decarboxylase gene and the production of unique lipids in the goose uropygial glands", Archives of Biochemistry and Biophysics, 1987, 256, 446-454.

Komuniecki, R., et al., "Anaerobic metabolism in *Ascaris suum*: acyl CoA intermediates in isolated mitochondria synthesizing 2-methyl branched-chain fatty acids", Molecular and Biochemical Parasitology, 1987, 24, 147-154.

Lomax, E. Amphoteric Surfactants, Second Edition, Ed., Marcel Dekker, Inc. . New York (1996).

Marvy et al., "Ruthenium Carbene Mediated Meathesis of Oleate-Type Fatty Compounds," *Int. J. Mol. Sci.*, 9:615-625 (2008).

Marvy, "Sunflower-based Feedstocks in Nonfood Applications: Perspectives from Olefin Metathesis," *Int. J. Mol. Sci.*, 9:1393-1406 (2008).

McKenna, "Microbial Metabolism of Normal and Branched Chain Alkanes," Degradation of synthetic organic molecules in the biosphere, Proc. Of Conf. San Francisco, National Academy of Sciences, Washington DCpp. 73-97 (1972).

Morr, M. et al., "2R 4R 6R 8R-2 4 6 8 Tetramethyldecanoic and undecanoic acid o f the preen-gland wax from the domestic goose anser-anser-f-domesticus isolation synthesis of derivatives and of the RAC-2 4 6 8 tetramethyldecanoic acid", Liebigs Annalen Der Chemie, No. 5, 1992, pp. 443-439.

Pirnik, "Microbial Oxidation of Methyl Branched Alkanes," *Crit. Rev. Microbiol.* 5(4):413-422 (1977).

(56) References Cited

OTHER PUBLICATIONS

Savvi, S. et al., "Functional characterization of a vitamin B-12 dependent methylmalonyl pathway in *Mycobacterium tuberculosis*: implications for propionate metabolism during growth on fatty acids", Journal of Bacteriology, 2008, 190, 3886-3895.

Schaeffer et al., "Microbial Growth on Hybrocarbons: Terminal Branching Inhibits Biodegradtion," *Appl. Environ. Microbiol.* 38:742-746 (1979).

Scaife, J.R. et al., "Utilisation of methylmalonate for the synthesis of branched-chain fatty acides by preparations of chicken liver and sheep adipose tissue", Biochemical journal, 1978, 176, 799-804.

Scheibel, et al., "The Evolution of Anionic Surfactant Technology to Meet the Requirements of the Laundry Detergent Industry," *Journal of Surfactants and Detergents*, 7(4):319-328 (2004).

Smith et al., "Characterization of Branced-Chain Fatty Acids from Fallow Deer Perinephric Triacylglycerols by Gas Chromatography-Mass Spectrometry," *Lipids*, 14(4):350-335 (1979).

Ting-Wan, L. et al., "Structure-based inhibitor design of AccD5, an essential acyl-CoA carboxylese carboxyltransferase domain of *Mycobacterium tuberculosis*", Proceedings of the National Academy of Sciences of the United States of America, 2006, 103, 3072-3077.

Vougioukalakis et al., "Ruthenium-Based Heterocyclic Carbene-Co-ordinated Olefin Metathesis Catalysts," *Chem Rev.*, 110(3):1746-1787 (2010).

Yu et al., "Location of Methyl Branchings in Fatty Acids: Fatty Acids in Uropygial Secretion of Shanghai Duck by GC-MS of 4,4-Dimethyloxazoline Derivatives," *Lipids*, 23(8):804-810 (1988).

Zhang et al., "Chemical Modification in Mass Spectrometry IV-2-alkenyl-4,4-dimethyloxazolines as Derivatives for the Double Bond Location of Long-Chain Olefinic Acids," *Biomed Env. Mass Spectrom.*, 15:33-44 (1988).

International Search Report for 11567M dated Apr. 27, 2011.

International Search Report for International Application No. PCT/US2011/020949, dated May 13, 2011.

PCT International Search Report, International Application No. PCT/US2011/020949, dated May 13, 2011, containing 20 pages.

Michael Morr, Jens Fortkamp and Stefan 1-18 Ruhe: "Chirale methylverzweigte Tenside und Phospholipide: Synthese und Eigenschaften", Angewandte Chemie, Wiley—V C H Verlag GmbH & Co. KGAA, Weinheim, DE, vol. 109, No. 22, Jan. 1, 1997, pp. 2567-2569.

Carballeira, N.M. et al., "Characteridation of novel methyl-branched chain fatty acids from a halophilic *Bacillus* species", Journal of Natural Products, 2001, vol. 64, pp. 256-259.

Blomquist G 3 et al: "Methyl-branched 1-8 fatty acids and their biosynthesis in the housefly, *Musca domestica* L. (Diptera: Muscidae)", Insect Biochemistry and Molecular Biology, Elsevier Science Ltd, GB, vol. 24, No. 8, Sep. 1, 1994, pp. 803-810, ISSN: 0965-1748.

\* cited by examiner

INTERMEDIATES AND SURFACTANTS USEFUL IN HOUSEHOLD CLEANING AND PERSONAL CARE COMPOSITIONS, AND METHODS OF MAKING THE SAME

CROSS REFERENCE TO RELATED APPLICATION

This application claims priority to U.S. Provisional Patent Application No. 61/294,274, filed Jan. 12, 2010, which is hereby incorporated by reference in its entirety.

FIELD OF THE INVENTION

This disclosure relates to novel mixtures of scattered-branched chain fatty acids, fatty alcohols, fatty acid derivatives, fatty alcohol derivatives, and mixtures thereof, and uses of these mixtures in cleaning compositions (e.g., dishcare, laundry, hard surface cleaners) and/or personal care compositions (e.g., skin cleansers, shampoos, hair conditioners).

BACKGROUND OF THE INVENTION

Surfactants are the single most important cleaning ingredient in household and personal care cleaning products. Environmental regulations, consumer habits, and consumer practices have forced new developments in the surfactant industry to produce lower-cost, higher-performing, and environmentally friendly products. Examples of developments in the surfactant industry are described by J. Scheibel in the Journal of Surfactants and Detergents, "The Evolution of Anionic Surfactant Technology to Meet the Requirements of the Laundry Detergent Industry," volume 7, number 4, October, 2004 ("Scheibel JSD Article" hereinafter), which is incorporated herein by reference. Today, challenges facing the surfactant industry include colder wash temperatures, less efficient builders, liquid products without calcium control, and a push for reduced surfactant use overall because of the perceived environmental impact of surfactants.

Alkylbenzene sulfonates (ABS) are surfactants derived from tetrapropylene that have very complex branching structures (e.g., 3 or 4 branches per molecule). The structure below illustrates one example of a hard ABS molecule, which has branching near the polar head group and in the middle of the surfactant.

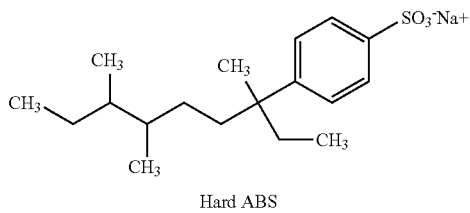

Hard ABS

ABS surfactants were prominent until the early 1960s when they were subjected to environmental regulations for being poorly biodegradable. ABS surfactants were then replaced with the readily biodegradable linear alkylbenzene sulfonate (LAS) surfactants, which are easily obtainable and currently in use today. Use of LAS surfactants and other similar linear surfactants is limited because they have poor solubility in cold- and hard-water conditions. In fact, more than half of the LAS detergent in products may be lost during use due to the formation of multilayered vesicles that resemble large onion-like structures. Formulators can increase the solubility of linear surfactants by, for example, introducing co-surfactants or by using linear alcohol ethoxylated sulfates (AES). However, AES surfactants have lower surface activity as well as lower mass efficiency than LAS surfactants. Further, the use of co-surfactants or AES surfactants limits formulation flexibility and can add substantial cost to the detergent. ABS, LAS, and AES surfactants are described in detail in the Scheibel JSD article.

Surfactants with light, mid-chain branching, such as highly soluble alcohol sulfate (HSAS) surfactants derived from petroleum feedstocks, were then developed for use in consumer products. HSAS surfactants, which are illustrated in the Scheibel JSD article, as well as U.S. Pat. Nos. 6,020,303; 6,060,443; and 6,335,312; and U.S. Patent Application Publication No. 2010/0137649 (each incorporated herein by reference), traditionally contain alkyl branching on carbon atoms that are at both the even and odd-numbered positions of the longest linear chain of the surfactant. HSAS surfactants provide good cleaning ability in cold, hard water, have high solubility, good grease removal properties, and good biodegradability. Because surfactants with mid-chain branching are widely used by consumers, a need exists to further improve their biodegradability.

SUMMARY OF THE INVENTION

In one aspect, the invention relates to a composition that includes mixture of at least two compounds of Formula I:

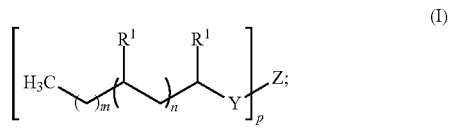

wherein each $R^1$ independently is H or $CH_3$, with the proviso that 1, 2, or 3 $R^1$ is $CH_3$;
m is 1 or 2;
n is 3, 4, 5, 6, 7, 8, or 9;
p is 1, 2, 3, 4, 5, 6, 7, or 8; and,
Y is $CH_2$ or absent, with the proviso that when:

(a) Y is $CH_2$, Z is selected from the group consisting of hydroxyl, an alkoxyl, a sulfate, a disulfate, a sulfonate, a disulfonate, a sulfosuccinate, an amine, a monoalkylamine, a dialkylamine, an amine oxide, a polyhydroxy moiety, a phosphate ester, a polyphosphate ester, a phosphonate, a glycerol ether, a glycerol ether sulfonate, a polygluconate, a monoglycerol ether, a diglyerol ether, a glycerol ether sulfate, a polyglycerol ether, a polyglycerol ether sulfate, a polyglucoside, an ammonioalkanesulfonate, an alkylated quat, an alkyated/hydroxyalkylated quat, an alkylated/polyhydroxyakylated quat, an alkylated/polyhydroxylated oxypropyl quat, a glycol amine quat, a polyoxyalkylene, an alkoxylated sulfate, a pyridinium moiety, a betaine, a sulfobetaine, an aminocarboxylate, an iminodicarboxylate, a phenol ethoxylate, an imidazoline, an O-alkyl ester (i.e., O(C=O)R, wherein R is an alkyl group), and an alkoxylated carboxylate; and, (b) Y is absent, Z is selected from the group consisting of a carboxylic acid, a carboxylate, a glycerol ester sulfonate, a sulfosuccinamate, a glucamide, a taurinate, a sarcosinate, a glycinate, a dialkanolamide, a monoalkanolamide, a monoalkanolamide sulfate, a diglycolamide, a diglycolamide sulfate, a glycerol ester, a glycerol ester sulfate, an amidopropyl betaine, a sugar ester (e.g., a sorbitan ester), a glycerol ester quat, an isethionate, a sulfonated fatty acid, a sulfonated alkyl ester, a C-alkyl ester (i.e., (C=O)OR, wherein R is an alkyl group), an amide, and a polyalkoxylated amidopropyl betaine.

The mixture is present in the composition an amount of at least about 80 wt. %, preferably at least about 90 wt. %, more preferably at least about 95 wt. %, even more preferably at least about 97 wt. %, for example, at least about 99 wt. % or about 100 wt. %, based on the total weight of the composition. Further, the mixture comprises no more than about 5 wt. %, preferably no more than about 3 wt. %, more preferably no more than about 1 wt. % of compounds that have a longest linear carbon chain of 9 carbon atoms or fewer. Further still, the mixture comprises less than about 50 wt. % of compounds of Formula I that have branching on a carbon atom that is within 40% of the nonfunctionalized terminus of the longest carbon chain, based on the total weight of the mixture.

In some embodiments, the mixture of the at least two compounds of Formula I further comprises at least one compound of Formula III:

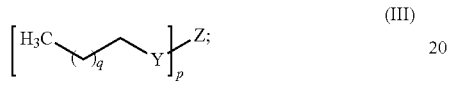

wherein q is 7, 8, 9, 10, 11, 12, 13, 14, 15, 19, 17, 18, 19, or 20; p is 1, 2, 3, 4, 5, 6, 7, or 8; and,
Y is $CH_2$ or absent, with the proviso that when:
(a) Y is $CH_2$, Z is selected from the group consisting of hydroxyl, an alkoxyl, a sulfate, a disulfate, a sulfonate, a disulfonate, a sulfosuccinate, an amine, a monoalkylamine, a dialkylamine, an amine oxide, a polyhydroxy moiety, a phosphate ester, a polyphosphate ester, a phosphonate, a glycerol ether, a glycerol ether sulfonate, a polygluconate, a monoglycerol ether, a diglyerol ether, a glycerol ether sulfate, a polyglycerol ether, a polyglycerol ether sulfate, a polyglucoside, an ammonioalkanesulfonate, an alkylated quat, an alkyated/hydroxyalkylated quat, an alkylated/polyhydroxyakylated quat, an alkylated/polyhydroxylated oxypropyl quat, a glycol amine quat, a polyoxyalkylene, an alkoxylated sulfate, a pyridinium moiety, a betaine, a sulfobetaine, an aminocarboxylate, an iminodicarboxylate, a phenol ethoxylate, an imidazoline, an O-alkyl ester, and an alkoxylated carboxylate; and,
(b) Y is absent, Z is selected from the group consisting of a carboxylic acid, a carboxylate, a glycerol ester sulfonate, a sulfosuccinamate, a glucamide, a taurinate, a sarcosinate, a glycinate, a dialkanolamide, a monoalkanolamide, a monoalkanolamide sulfate, a diglycolamide, a diglycolamide sulfate, a glycerol ester, a glycerol ester sulfate, an amidopropyl betaine, a sugar ester, a glycerol ester quat, an isethionate, a sulfonated fatty acid, a sulfonated alkyl ester, a C-alkyl ester, an amide, and a polyalkoxylated amidopropyl betaine.

The at least one compound of Formula III is present in the mixture in an amount of at least about 1 wt. %, at least about 10 wt. %, at least about 30 wt. %, at least about 50 wt. %, at least about 70 wt. %, at least about 80 wt. %, at least about 90 wt. %, or at least about 95 wt. %, based on the total weight of the mixture. For example, the at least one compound of Formula III can be present in the mixture in an amount of about 1 wt. % to about 95 wt. %, based on the total weight of the mixture.

In some embodiments, the

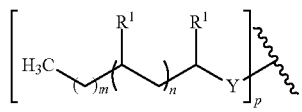

component of the at least two compounds of Formula I has a biobased content of at least about 50%, at least about 60%, at least about 70%, at least about 80%, at least about 90%, at least about 95%, at least about 97%, or about 100%.

In some embodiments, at least one compound of Formula I contains a methyl branch at a position selected from the group consisting of the 2-, 4-, 6-, 8-, 10-, 12-, or 14-position. In some embodiments, a compound of Formula I contains one methyl branch. In these embodiments, the one methyl branch is at a position selected from the group consisting of the 2-, 4-, 6-, 8-, 10-, 12-, or 14-position.

In another aspect, the invention relates to a composition comprising a mixture of at least two compounds of Formula I, as previously described, wherein the mixture is produced by
(a) culturing a cell comprising:
(i) an exogenous or overexpressed polynucleotide comprising a nucleic acid sequence encoding a polypeptide that catalyzes the conversion of propionyl-CoA to methylmalonyl-CoA; and/or,
(ii) an exogenous or overexpressed polynucleotide comprising a nucleic acid sequence encoding a polypeptide that catalyzes the conversion of succinyl-CoA to methylmalonyl-CoA, under conditions allowing expression of the polynucleotide(s) and production a mixture of at least two compounds of Formula II:

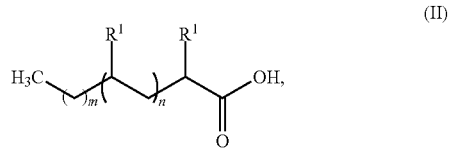

wherein the cell produces more compounds of Formula II than an otherwise similar cell that does not comprise the polynucleotide(s);
(b) extracting from culture the mixture of at least two compounds of Formula II; and,
(c) derivatizing the compounds of Formula (II) to form the mixture of at least two compounds of Formula I.

In yet another aspect, the invention relates to a cleaning composition that includes (a) about 0.001 wt. % to 99.999 wt. % of the composition containing the mixture of at least two compounds of Formula I, as defined above, and (b) about 0.001 wt. % to about 99.999 wt. %, preferably about 1 wt. % to about 80 wt. % of an additional cleaning component. The additional cleaning component can include, for example, a surfactant, an enzyme, a builder, an alkalinity system, an organic polymeric compound, a hueing dye, a bleaching compound, an alkanolamine, a suds suppressor, a soil suspension agent, an anti-redeposition agent, a corrosion inhibitor, or mixtures thereof. The cleaning composition can be, for example, a granular detergent, a bar-form detergent, a liquid laundry detergent, a liquid hand dishwashing composition, a hard surface cleaner, a tablet, a disinfectant, an industrial cleaner, a highly compact liquid, a powder, or a decontaminant. The cleaning composition typically contains a carrier, such as water or other solvents.

In yet another aspect, the invention relates to a personal care composition that includes (a) about 0.001 wt. % to about 99.999 wt. % of the composition containing the mixture of at least two compounds of Formula I, as defined above, and (b) about 0.001 wt. % to about 99.999 wt. %, preferably about 1 wt. % to about 80 wt. % of an additional personal care component. The additional personal care component can include, for example, one or more of a cosmetically acceptable carrier, a hair fixing polymer, a propellant, a surfactant, a cationic surfactant system, a high melting point fatty compound, a cationic polymer, a nonionic polymer, a conditioning agent, an anti-dandruff active, a humectant, a suspending agent, an aqueous carrier, a dispersed particle, a gel matrix, a skin care active, a thickener, a glossing and shine-imparting agent, a dye, a particle, glitter, a colored particle, and mixtures thereof. The personal care composition can be, for example, a shampoo, a hair conditioner, a hair treatment, a facial soap, a body wash, a body soap, a foam bath, a make-up remover, a skin care product, an acne control product, a deodorant, an antiperspirant, a shaving aid, a cosmetic, a depilatory, a fragrance, and a mixture thereof.

DETAILED DESCRIPTION OF THE INVENTION

The invention relates to compositions containing mixtures of at least two scattered-branched chain fatty compounds (i.e., fatty acids, fatty alcohols, fatty acid derivatives, fatty alcohol derivatives, and mixtures thereof that have one, two, or three methyl branches at even-numbered carbon atoms of the longest carbon chain). Similar to compositions that contain fatty compounds with branching at odd-numbered carbon atoms, the compositions of the invention demonstrate excellent performance (e.g., good cleaning ability in cold, hard water; high solubility; and good grease removal properties) when used as surfactants in household and personal care cleaning applications. Advantageously, however, the absence of branching at odd-numbered carbon atoms allows the compositions of the invention, to exhibit improved biodegradability when used in consumer formulations. Further, the mixtures of scattered-branched compounds of the cationic type can form unique ionic crystal liquid concentrates when combined with certain anionic surfactants. These concentrates can be stored and shipped at low cost, and added to a personal care or cleaning composition at will. The even- and odd-numbered positions of an example fatty acid and an example fatty alcohol are illustrated below.

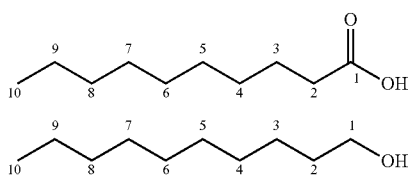

International Patent Application Publication No. WO/1999/02072 (the '722 publication), incorporated herein by reference, describes the use of branched fatty acids, salts of branched fatty acids, and lower esters as useful in formulations, such as for laundry products, personal care products, pharmaceutical compositions, industrial cleaners, and the like. However, the '722 publication does not teach the utility of scattered-branched chain fatty acids, salts of scattered-branched fatty acids or lower esters with methyl branching solely on even-numbered carbons. The '722 publication also does not teach the utility of scattered-branched chain alcohols and their derivatives with methyl branching solely on even-numbered carbons.

U.S. Patent Application No. 2010/0137649 and U.S. Patent Application Ser. No. 61/315,594, each incorporated herein by reference, disclose surfactants derived from isoprene units that have branching at even-numbered carbon atoms, as shown below.

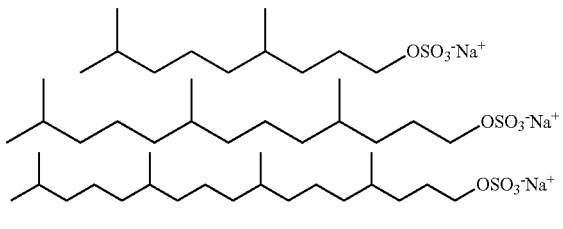

These scattered-branched fatty compounds are limited because the starting materials are isoprene units. The total number of carbon atoms of isoprene-derived surfactants is limited to, for example, 11, 16, or 21 when the surfactant contains, 2, 3, or 4 isoprene units, respectively. Further methyl branching on even-numbered carbon atoms is restricted to a regular distribution of three methylene units between each methyl branch (e.g., methyl branches at the 4, 8, 12, and 16 positions) and does not allow for methyl branching at, for examples, the 2, 6, 10, and 14 positions. This regular distribution of branching also does not allow for compounds that contain 16 or greater carbon atoms in the longest linear chain and less than four methyl branches, or for compounds that have no methyl branching at the 4 position. Further still, isoprene-derived surfactants necessarily contain a methyl branch at the iso-position (i.e., they have near-terminal branching). Surfactants with near-terminal branches disrupt crystallinity less efficiently than surfactants that have mid-chain branching. Even further, the production of isoprene-derived surfactants involves the hydroformylation of farnesene, which can result in the incorporation of a carbon atom that is not derived from a renewable resource.

Similar to compositions that include fatty compounds with branching at odd-numbered carbon atoms, the compositions that contain mixtures of least two scattered-branched fatty compounds have been found to provide excellent performance when used in conditioning applications, such as, for example, hair conditioners. For example, these compositions are stable at low temperatures, dilute quickly and easily, and tolerate hard water conditions, avoiding the precipitation of calcium salts and anionic surfactants, which results in improved performance and desirable hair feel. It was thought that these scattered-branched compounds would destroy the gel networks required for appropriate physical properties in some conditioning formulations. Unexpectedly, it was found that using mixtures of scattered-branched compounds actually allows the phase of the gel networks to be controlled and provides more formulation flexibility for the manufacturer of the consumer goods products containing the scattered-branched compounds. In fact, the composition of the invention can act as a sustainable alternative to silicones in some applications. Advantageously, as previously described, the absence of branching at odd-numbered carbon atoms allows these conditioning compositions to exhibit improved biodegradability.

Biodegradation of fatty compounds involves the oxidation of the fatty compound to its corresponding fatty acid. The fatty acid undergoes beta oxidation, which is a universal pathway in living organisms (e.g., $E.\ coli$) that can metabolize alkanes, fatty alcohols, and fatty acids. This biochemical pathway involves oxidation of the carbon atom that is in the beta position (i.e., an odd-numbered carbon atom) relative to the carboxyl group, and subsequent cleavage of the bond between the beta (i.e., an odd-numbered carbon atom) and alpha (i.e., an even-numbered carbon atom) carbon atoms to shorten the fatty acid by two carbon atoms, as shown below.

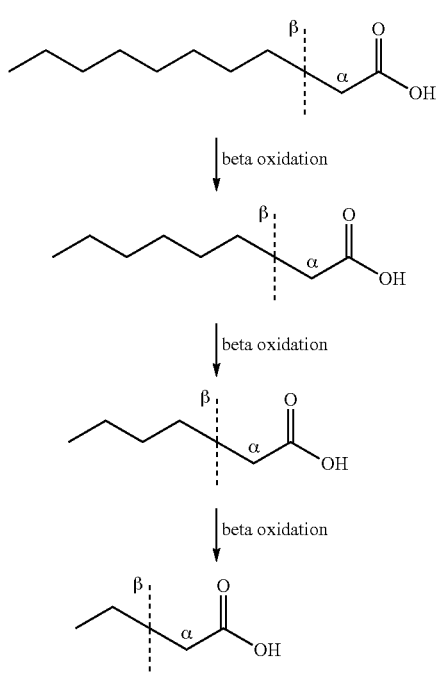

If the fatty acid contains a methyl branch at the alpha position (i.e., an even-numbered carbon atom), beta oxidation occurs to result in the loss of a three carbon atom species, as shown below.

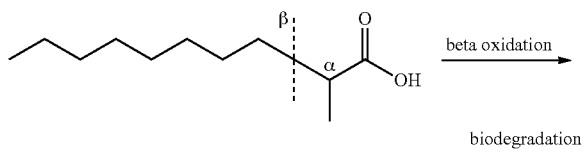

If the fatty acid contains a methyl branch at the beta position (i.e., an odd-numbered carbon atom), beta oxidation cannot not proceed, stopping the biodegradation process, as shown below.

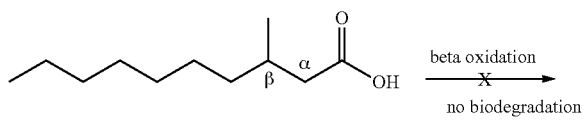

This differential effect of methyl substitution on an alpha versus beta carbon atoms on biodegradation was shown by Schaeffer et al. *Appl. Environ. Microbiol.* 38:742-746 (1979), incorporated herein by reference, who screened 27 octane utilizing strains of bacteria and fungi for growth on 3,6 dimethyl octane, 2,7 dimethyl octane and 2,6 dimethyl octane. Nine strains were found to use the branched hydrocarbons as a sole carbon source with the only substrates used being those with at least methyl on an alpha carbon relative to the terminal carbon (i.e. methyl branch in the 2 or 7 position). In contrast, 3,6 dimethyl octane in which both methyls were located on beta carbons did not support growth of any of the strains. Similar negative effects on biodegradation resulting from methyl substitution on beta carbons have been reported by McKenna, E. J. Microbial metabolism of normal and branched chain alkanes, p. 73-97. In *Degradation of synthetic organic molecules in the biosphere*. National Academy of Sciences, Washington, D.C. (1972); and Pirnik *Crit. Rev. Microbiol.* 5:413-422 (1977), each incorporated herein by reference.

This differential effect between branching on even- and odd-numbered carbon atoms was also shown with surfactants that each had one methyl branch and a total of 17 carbon atoms. When 8-methyl-1-hexadecanol sulfate sodium salt, 10-methyl-1-hexadecanol sodium salt, and 7-methylhexadecanol sulfate sodium salt where each exposed to a bacterial inoculum under identical incubation conditions, they exhibited relative surfactant build-up amounts of 11.67, 1.56, and 100, respectively. The build-up of the surfactants that had a branch on an even-numbered carbon atom was at least an order of magnitude lower than the build-up of the surfactant that had a branch on an odd-numbered carbon atom, demonstrating a greater amoung of biodegradation was occurring. The relative build-up amounts of the surfactants was characterized by GC-MS. The GC-MS method was run on extracts derived from in vitro batch biodegradation assays consisting of a consortium of representative environmental bacterial isolates grown in the presence of 0.1% (wt./vol) surfactant. Sample collection occurred on Twister Bar and analyses was conducted via TDSA-GC/MS/FID. The determination of branched fatty acid was based on extracted ion m/z=87, and the relative data was reported as a sum of the branched homologs of C8-C11 peak areas.

Consequently, fatty compounds undergoing beta oxidation that have methyl branching at even-numbered positions exhibit better biodegradability than branched materials in which methyl branches occur at odd-numbered positions or that have random branching. Furthermore, such targeted location of methyl branches on even-numbered carbon atoms eliminates the occurrence of vicinal methyl substitution, which can lead to even greater recalcitrance than beta substitution. While some microorganisms have been found to have an alpha oxidation pathway, which can shorten an alkyl chain by one carbon thereby unblocking beta oxidation, no reports exist regarding microbes capable of breaking the bond between carbon atoms that are both methyl substituted.

Fatty compounds that contain methyl branches on even- versus odd-numbered carbon atoms provide several biodegradation benefits. These compounds can be biodegraded by a broader range of microbes, they will biodegrade more rapidly due to the need for only a single biodegradation pathway, and biodegradation will be more extensive and complete due to the absence of vicinal substitutions that could result in the formation of persistent metabolites.

The compositions comprising mixtures of at least two scattered-branched fatty compounds of the invention are also advantageous over other surfactants that have mid-chain branching because they contain branches that each include only one carbon atom (i.e., methyl branches), and because they contain a maximum of three of these methyl branches. This particular composition and number of the branches provides a balance between good performance and efficient use of carbon atoms. In general, mid-chain branching on surfactants is beneficial because it interferes with crystal formation in surfactant systems. This interference provides benefits to surfactant compositions, such as keeping oil fluid at low temperatures, allowing the surfactant to function in the presence of calcium ions, and disrupting crystallinity in low temperature wash conditions. These beneficial effects are demonstrated with surfactants that have one, two, or three methyl branches. Additional methyl branching simply adds mass to the fatty compound without providing increased improvement in performance. Similarly, ethyl branching also adds mass to the fatty compound without increasing the beneficial properties of the scattered-branched surfactant.

The at least two scattered-branched fatty compounds of the invention are also advantageous because they necessarily contain at least one methylene carbon between methyl branches and do not allow for adjacent methyl branching. Adjacent methyl branching not only results in decreased biodegradation ability, as previously disclosed, but also is an inefficient use of mass. Fatty compounds that have branching on adjacent carbon atoms (e.g., carbon atoms 4 and 5) function similarly to fatty compounds that have just one methyl branch (e.g., at the 5-position).

The mixtures of the invention are advantageous for use in cleaning compositions (when derivatized to contain, for example, sulfate end groups) and conditioning compositions (when derivatized to contain, for example, hydroxy or cationic end groups on long chain compounds). The light degree of branching on even-numbered carbon atoms of the scattered-chain branched compounds allows facile biodegradation, as previously described.

In household cleaning compositions, the unique structure of the scattered-branched chain compounds, when the correct chain lengths and mixtures are used for said purpose, provides for good cleaning ability in cold, hard water, high solubility, good grease removal, high sudsing ability, and lack of a visible residue on hard surfaces and fabrics. This lack of a visible residue results in low or no odor after use. Further, compositions of the invention have good compaction without low temperature stability issues, dilute quickly and easily, even in cold water, and, in some embodiments, do not precipitate out of solution. The aforementioned properties are highly desired in dishcare, laundry, and shampoo applications.

In personal care compositions, the scattered-branched chain compounds in the mixtures can act as, for example, surfactants, conditioners, or cosurfactant performance boosting agents. The scattered-branched compounds advantageously can be incorporated into a personal care composition as a free surfactant a free conditioning agent, as part of a gel network, or any combination thereof. In personal care applications, the mixtures of the invention provide higher tolerance to precipitation with calcium and magnesium in hard water, have excellent rinsability, particularly with respect to the speed of rinsability, and improved cleaning in cooler wash temperatures.

Anionic surfactants derived from the mixtures of the invention advantageously have good solubility at low temperatures. Nonionic surfactants derived from the mixtures of the invention advantageously have low melting points. Cationic surfactants derived from the mixtures of the invention can complex with anionic surfactants without inducing crystallization. This ability to avoid crystallization is especially advantageous during storage or transport conditions.

The compositions of the invention are further advantageous because they can be tuned to include mixtures of scattered-chain branched compounds that have specific carbon chain lengths to meet the needs of specific cleaning and conditioning applications. For superior cleaning performance, the distribution of chain lengths in mixtures containing scattered-branched surfactants should maximally span 10-23 carbon atoms. For example, mixtures containing scattered-branched compounds with 12, 13, and 14 carbon atoms, or 12 and 13 carbon atoms, or 12 and 15, or 13 and 16, in the longest carbon chain provide desirable sudsing performance. Mixtures containing scattered-branched compounds within a range of 10 to 13 carbon atoms in the longest carbon chain are desirable for dishcare compositions. Mixtures containing scattered-branched compounds within a range of 12 to 15 carbon atoms in the longest carbon chain are desirable for laundry compositions. Mixtures containing scattered-branched compounds within a range of 8 to 12 carbon atoms in the longest carbon chain are desirable for hard surface cleaning compositions. If surfactants with longer carbon chains are used for a hard surface cleaning composition, for example, the surfactants tend to crystallize on surfaces to form a residue, which is a negative performance signal to customers. For example, the mixtures of the invention can contain scattered-chain branched compounds with 12 and 15 total carbon atoms; 12, 13, and 14 total carbon atoms; or 11, 13, and 17 total carbon atoms, e.g., mixtures that could not previously be obtained without excessive cost. Further still, the mixtures of the invention can include specific scattered-chain branched fatty compounds with multiple functions. For example, the mixtures of the invention can include scattered-branched chain compounds with 12 and 18 total carbon atoms, making it useful for both surfactant performance and fabric softening.

In the past, use of scattered-branched fatty compounds in cleaning and conditioning applications was not pursued because these compounds were only found as very low concentration materials in biological systems and were too expensive to produce in commercial quantities via isolation and purification techniques. As such, the mixtures of scattered-branched chain fatty acids found in biological systems are not viable feedstocks and do not allow control of the composition of the scattered-branched chain fatty acids. For example, Ackman et al., Lipids 7(10):683-691 (1966), incorporated herein by reference, discloses the isolation of isomeric methyl esters of C15, C17, and C19 fatty acids having methyl branches on even-numbered carbon atoms from ruminant fats.

Further, the mixtures of scattered-branched fatty compounds that are obtained from biological systems often contain scattered-branched fatty compounds that have less than 10 carbon atoms in their longest linear chain. Fatty compounds that have less than 10 carbon atoms in their longest linear chain are significantly less desirable in cleaning and, especially, conditioning applications. For example, Yu et al., Lipids 23(8):804-810 (1988), incorporated herein by reference, illustrates that the fatty acid component of the preen gland wax of Shanghai ducks includes over 20 wt. % of fatty acids that have nine or less carbon atoms in the longest linear chain, based on the total weight of fatty acids.

Further still, mixtures of scattered-branched fatty compounds that are obtained from biological systems often contain a high proportion of iso-branched compounds and compounds that have more than three methyl branches. As previously described, surfactants with iso-branching disrupt crystallinity less efficiently than compounds with mid-chain branching. Also as previously described, surfactants with greater than three methyl branches have a greater amount of mass without improved benefits. For example, Smith et al., Lipids 14(4):350-355 (1979), incorporated herein by reference, discloses that the perinephric triacylglycerols of semiferal fallow deer contain 15.5 wt. % of branched-chain fatty acids, based on the total weight of fatty acids. Of these branched-chain fatty acids, over 50 wt. % (i.e., 8.96 wt. %) have branching at the iso-position, based on the total weight of branched-chain fatty acids. The deer tallow also includes 2,6,10,14-tetramethylpentadecanoic acid and 3,7,11,15-tetramethylhexadecanoic acid.

Mixtures of Scattered-Branched Fatty Compounds

The invention relates to compositions containing mixtures of at least two scattered-branched fatty compounds. As used herein, the term "fatty compounds" refers to fatty acids, fatty alcohols, fatty acid derivatives, fatty alcohol derivatives, and mixtures thereof. The scattered-branched fatty acids, fatty alcohols, fatty acid derivatives, and fatty alcohol derivatives in the mixtures of the invention can be derivatized to form compounds (e.g., surfactants and conditioners) useful in cleaning and personal care applications.

In one aspect, the invention provides a composition that includes mixture of at least two compounds of Formula I:

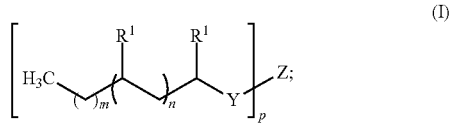

wherein each $R^1$ independently is H or $CH_3$, with the proviso that 1, 2, or 3 $R^1$ is $CH_3$;
m is 1 or 2;
n is 3, 4, 5, 6, 7, 8, or 9;
p is 1, 2, 3, 4, 5, 6, 7, or 8; and, Y is $CH_2$ or absent, with the proviso that when: (a) Y is $CH_2$, Z is selected from the group consisting of hydroxyl, an alkoxyl, a sulfate, a disulfate, a sulfonate, a disulfonate, a sulfosuccinate, an amine, a monoalkylamine, a dialkylamine, an amine oxide, a polyhydroxy moiety, a phosphate ester, a polyphosphate ester, a phosphonate, a glycerol ether, a glycerol ether sulfonate, a polygluconate, a monoglycerol ether, a diglyerol ether, a glycerol ether sulfate, a polyglycerol ether, a polyglycerol ether sulfate, a polyglucoside, an ammonioalkanesulfonate, an alkylated quat, an alkyated/hydroxyalkylated quat, an alkylated/polyhydroxyakylated quat, an alkylated/polyhydroxylated oxypropyl quat, a glycol amine quat, a polyoxyalkylene, an alkoxylated sulfate, a pyridinium moiety, a betaine, a sulfobetaine, an aminocarboxylate, an iminodicarboxylate, a phenol ethoxylate, an imidazoline, an O-alkyl ester (i.e., O(C=O)R, wherein R is an alkyl group), and an alkoxylated carboxylate.

(b) Y is absent, Z is selected from the group consisting of a carboxylic acid, a carboxylate, a glycerol ester sulfonate, a sulfosuccinamate, a glucamide, a taurinate, a sarcosinate, a glycinate, a dialkanolamide, a monoalkanolamide, a monoalkanolamide sulfate, a diglycolamide, a diglycolamide sulfate, a glycerol ester, a glycerol ester sulfate, an amidopropyl betaine, a sugar ester (e.g., a sorbitan ester), a glycerol ester quat, an isethionate, a sulfonated fatty acid, a sulfonated alkyl ester, a C-alkyl ester (i.e., (C=O)OR, wherein R is an alkyl group), an amide, and a polyalkoxylated amidopropyl betaine.

In embodiments where Y is $CH_2$, such as in the fatty alcohol shown below, Y is designated as carbon number 1.

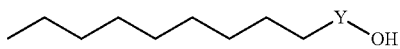

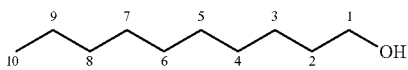

In embodiments where Y is absent, Z comprises a carbonyl moiety and is attached to the compound of Formula I through its carbonyl moiety. In these embodiments, the carbonyl moiety of Z is designated as carbon number 1. For example, when Z is a carboxylic acid, the carbonyl carbon of the carboxylic acid is designated as carbon 1, as shown below.

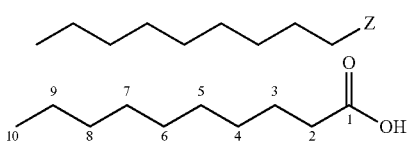

The mixture of the at least two compounds of Formula I is present in the composition an amount of at least about 80 wt. %, preferably at least about 90 wt. %, more preferably at least about 95 wt. %, even more preferably at least about 97 wt. %, for example, at least about 99 wt. %, or about 100 wt. %, based on the total weight of the composition. Further, the mixture contains no more than about 5 wt. %, preferably no more than about 3 wt. %, more preferably no more than about 1 wt. % of compounds that have a longest linear carbon chain of 9 carbon atoms or fewer. Further still, the mixture comprises less than about 50 wt. % of compounds with one or more branches on a carbon atom that is within 40% of the nonfunctionalized terminus of the longest carbon chain, based on the total weight of the mixture. The functionalized end of the fatty compound is that end which contains the acid, alcohol, or derivative moiety. For example, fatty compounds that are 10 carbon atoms in length and have a methyl branch on the 2, 4, and/or 6 positions do not have branching within 40% of the nonfunctionalized terminus of the longest carbon chain. Fatty compounds that are 10 carbon atoms in length and have a methyl branch at the 8 position have branching within 40% of the nonfunctionalized terminus of the longest carbon chain. In this example, a methyl branch at the 8 position is 3 carbon atoms from the end of the nonfunctionalized terminus of the 10 carbon fatty compound (e.g., 3/10× 100%=30%), while a methyl branch at the 6 position is 5 carbon atoms away from the end of the nonfunctionalized terminus of the 10 carbon fatty compound (e.g. 5/10× 100%=50%).

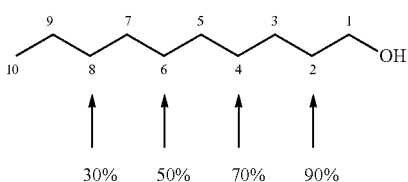

In some embodiments, the mixture of at least two compounds of Formula I comprises a compound that has a methyl branch at a position selected from the group consisting of the 2-, 4-, 6-, 8-, 10-, 12-, or 14-position. In one exemplary embodiment, the mixture of at least two compounds of Formula I comprises the compound,

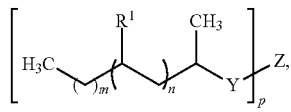

wherein all variables are as defined above.

In another exemplary embodiment, the mixture of at least two compounds of Formula I comprises the compound,

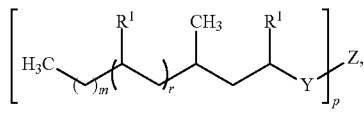

wherein r is 2, 3, 4, 5, 6, 7, or 8, and all other variables are as defined above.

In yet another exemplary embodiment, the mixture of at least two compounds of Formula I comprises the compound,

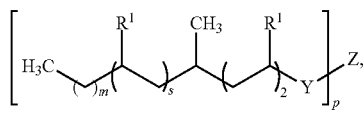

wherein s is 1, 2, 3, 4, 5, 6, or 7, and all other variables are as defined above.

In yet another exemplary embodiment, the mixture of at least two compounds of Formula I comprises the compound,

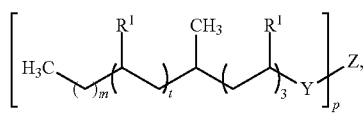

wherein t is 0, 1, 2, 3, 4, 5, or 6, and all other variables are as defined above.

In yet another exemplary embodiment, the mixture of at least two compounds of Formula I comprises the compound,

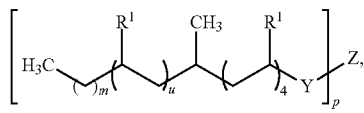

wherein u is 0, 1, 2, 3, 4, or 5, and all other variables are as defined above.

In yet another exemplary embodiment, the mixture of at least two compounds of Formula I comprises the compound,

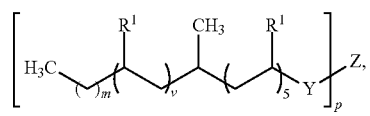

wherein v is 0, 1, 2, 3, or 4, and all other variables are as defined above.

In even yet another exemplary embodiment, the mixture of at least two compounds of Formula I comprises the compound,

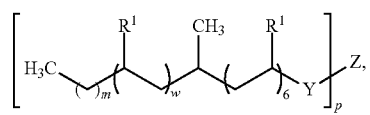

wherein w is 0, 1, 2, or 3, and all other variables are as defined above.

In some embodiments, a compound of Formula I contains only one methyl branch. In some embodiments, the one methyl branch is at a position selected from the group consisting of the 2-, 4-, 6-, 8-, 10-, 12-, or 14-position. Examples of compounds of Formula I containing one methyl branch are shown in Table A.

TABLE A

Compounds of Formula I containing one methyl branch.

| Compound # | Position of Methyl Branch | Example Compounds of Formula I |
|---|---|---|
| 1 | 2 | 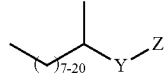 |
| 2 | 4 | 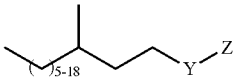 |
| 3 | 6 | 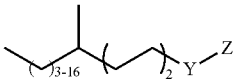 |
| 4 | 8 |  |
| 5 | 10 | 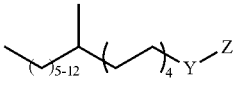 |
| 6 | 12 |  |
| 7 | 14 | 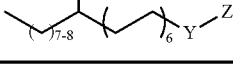 |

In some embodiments, a compound of Formula I contains two methyl branches. Nonlimiting examples of compounds of Formula I containing two methyl branches are shown in Table B.

TABLE B
Compounds of Formula I containing two methyl branches
| Compound # | Position of Methyl Branches | Example Compounds of Formula I |
|---|---|---|
| 1 | 2, 4 | 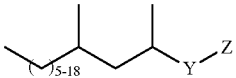 |
| 2 | 2, 6 | 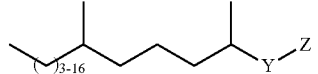 |
| 3 | 2, 8 | 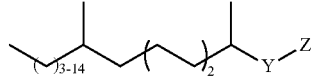 |
| 4 | 2, 10 | 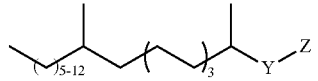 |
| 5 | 2, 12 | 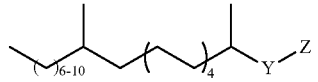 |
| 6 | 2, 14 | 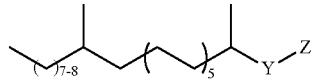 |
| 7 | 4, 6 | 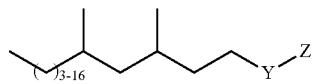 |
| 8 | 4, 8 | 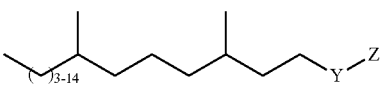 |
| 9 | 4, 10 | 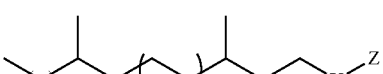 |
| 10 | 4, 12 | 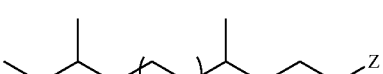 |
| 11 | 4, 14 | 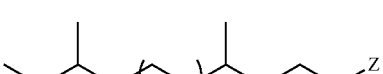 |
| 12 | 6, 8 |  |
| 13 | 6, 10 |  |
| 14 | 6, 12 |  |
| 15 | 6, 14 |  |

TABLE B-continued

Compounds of Formula I containing two methyl branches

| Compound # | Position of Methyl Branches | Example Compounds of Formula I |
|---|---|---|
| 16 | 8, 10 | |
| 17 | 8, 12 | |
| 18 | 8, 14 | |
| 19 | 10, 12 | |
| 20 | 10, 14 | |
| 21 | 12, 14 | |

In some embodiments, a compound of Formula I contains three methyl branches. Nonlimiting examples of compounds of Formula I containing three methyl branches are shown in Table C.

TABLE C

Compounds of Formula I containing three methyl branches

| Compound # | Position of Methyl Branches | Example Compounds of Formula I |
|---|---|---|
| 1 | 2, 4, 6 | |
| 2 | 2, 4, 8 | |
| 3 | 2, 4, 10 | |
| 4 | 2, 4, 12 | |
| 5 | 2, 4, 14 | |
| 6 | 2, 6, 8 | |

TABLE C-continued

Compounds of Formula I containing three methyl branches

| Compound # | Position of Methyl Branches | Example Compounds of Formula I |
|---|---|---|
| 7 | 2, 6, 10 | |
| 8 | 2, 6, 12 | |
| 9 | 2, 6, 14 | |
| 10 | 2, 8, 10 | |
| 11 | 2, 8, 12 | |
| 12 | 2, 8, 14 | |
| 13 | 2, 10, 12 | |
| 14 | 2, 10, 14 | |
| 15 | 2, 12, 14 | |
| 16 | 4, 6, 8 | |
| 17 | 4, 6, 10 | |
| 18 | 4, 6, 12 | |
| 19 | 4, 6, 14 | |
| 20 | 4, 8, 10 | |
| 21 | 4, 8, 12 | |

TABLE C-continued
Compounds of Formula I containing three methyl branches
| Compound # | Position of Methyl Branches | Example Compounds of Formula I |
|---|---|---|
| 22 | 4, 8, 14 | 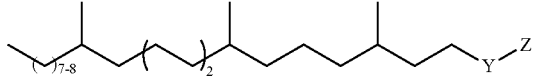 |
| 23 | 4, 10, 12 | 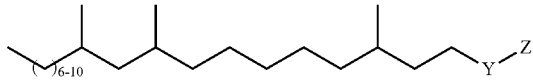 |
| 24 | 4, 10, 14 | 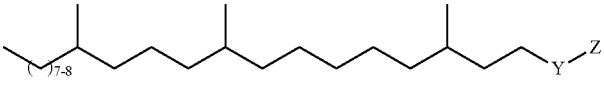 |
| 25 | 4, 12, 14 | 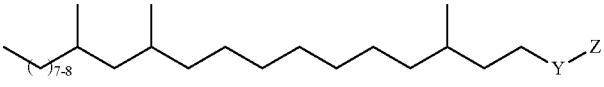 |
| 26 | 6, 8, 10 | 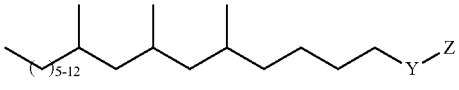 |
| 27 | 6, 8, 12 | 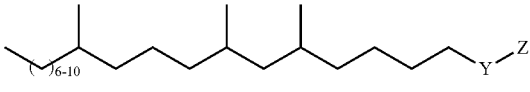 |
| 28 | 6, 8, 14 | 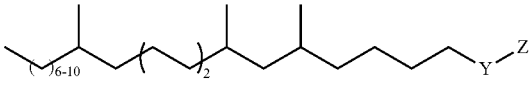 |
| 29 | 6, 10, 12 | 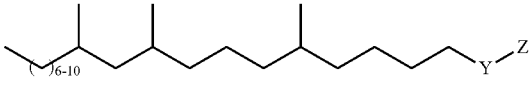 |
| 30 | 6, 10, 14 | 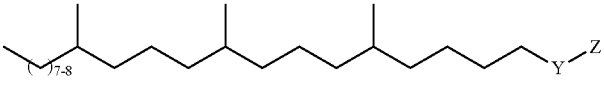 |
| 31 | 6, 12, 14 | 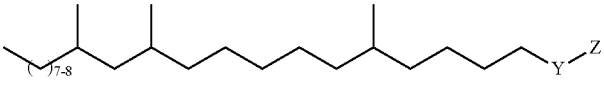 |
| 32 | 8, 10, 12 | 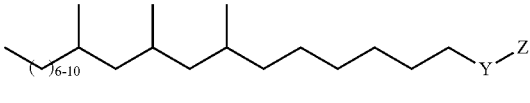 |
| 33 | 8, 10, 14 | 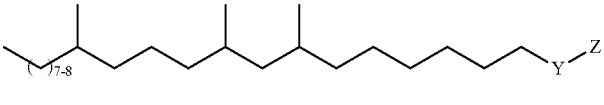 |
| 34 | 8, 12, 14 | 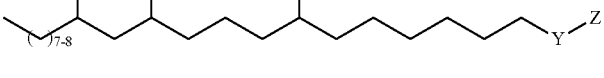 |
| 35 | 10, 12, 14 | 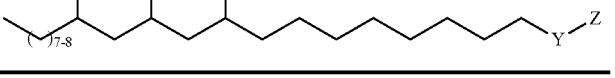 |

In some embodiments, a compound of Formula I can include, for example,

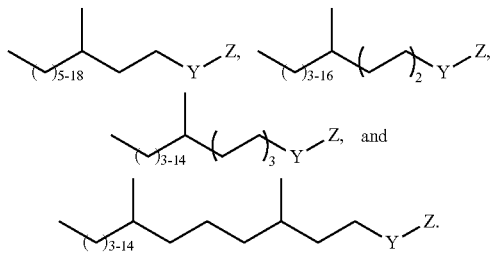

some exemplary embodiments, Z can include, a sulfate, a hydroxyl, or a polyhydroxy moiety.

In some embodiments, the mixture of the at least two compounds of Formula I further comprises at least one linear fatty compound, as described by Formula III:

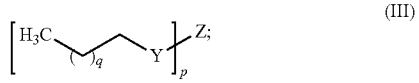

(III)

wherein q is 7, 8, 9, 10, 11, 12, 13, 14, 15, 19, 17, 18, 19, or 20; p is 1, 2, 3, 4, 5, 6, 7, or 8; and,
Y is $CH_2$ or absent, with the proviso that when:

(a) Y is $CH_2$, Z is selected from the group consisting of hydroxyl, an alkoxyl, a sulfate, a disulfate, a sulfonate, a disulfonate, a sulfosuccinate, an amine, a monoalkylamine, a dialkylamine, an amine oxide, a polyhydroxy moiety, a phosphate ester, a polyphosphate ester, a phosphonate, a glycerol ether, a glycerol ether sulfonate, a polygluconate, a monoglycerol ether, a diglycerol ether, a glycerol ether sulfate, a polyglycerol ether, a polyglycerol ether sulfate, a polyglucoside, an ammonioalkanesulfonate, an alkylated quat, an alkyated/hydroxyalkylated quat, an alkylated/polyhydroxyakylated quat, an alkylated/polyhydroxylated oxypropyl quat, a glycol amine quat, a polyoxyalkylene, an alkoxylated sulfate, a pyridinium moiety, a betaine, a sulfobetaine, an aminocarboxylate, an iminodicarboxylate, a phenol ethoxylate, an imidazoline, an O-alkyl ester, and an alkoxylated carboxylate; and, (b) Y is absent, Z is selected from the group consisting of a carboxylic acid, a carboxylate, a glycerol ester sulfonate, a sulfosuccinamate, a glucamide, a taurinate, a sarcosinate, a glycinate, a dialkanolamide, a monoalkanolamide, a monoalkanolamide sulfate, a diglycolamide, a diglycolamide sulfate, a glycerol ester, a glycerol ester sulfate, an amidopropyl betaine, a sugar ester, a glycerol ester quat, an isethionate, a sulfonated fatty acid, a sulfonated alkyl ester, a C-alkyl ester, an amide, and a polyalkoxylated amidopropyl betaine.

The at least one compound of Formula III optionally can be present in the mixture in an amount of at least about 1 wt. %, at least about 10 wt. %, at least about 30 wt. %, at least about 50 wt. %, at least about 70 wt. %, at least about 80 wt. %, at least about 90 wt. %, or at least about 95 wt. %, based on the total weight of the mixture. For example, the at least one compound of Formula III can be present in the mixture in an amount of about 1 wt. % to about 95 wt. %, based on the total weight of the mixture. The linear content can be adjusted according to the process conditions and/or starting materials used to provide desired compounds, or post added to provide a blend. The amount and identity of a linear compound and/or a mid-chain branched compound in the composition depends on the particular application. For example, the amount of linear surfactant in compositions used for sudsing applications can be up to 50 wt. %, based on the total weight of the mixture, while the amount of linear surfactant used for laundry applications can be up to about 10 wt. %, based on the total weight of the composition.

In some embodiments, the at least two compounds of Formula I and/or the at least one compound of Formula III require a counterion. In embodiments when the counterion is an anion, the anion can include bromide, chloride, and methylsulfates. In embodiments when the counterion is a cation, the cation can include, for example, $Li^+$, $Na^+$, $K^+$, $Ca^{2+}$, $Mg^{2+}$, and

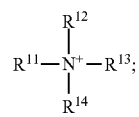

wherein $R^{11}$, $R^{12}$, $R^{13}$, and $R^{14}$ are each independently hydrogen, $(C_1-C_{22})$alkyl, $(C_1-C_6)$alkanol, $(C_1-C_{22})$alkenyl, and mixtures thereof. In some embodiments, the cation is selected from the group consisting of $NH_4^+$, $Na^+$, $K^+$, mono-, di-, or tri-alkyl ammonium, mono-, di, or tri-alkanol ammonium, and mixtures thereof. The monoalkanol ammonium compounds of the present invention can include compounds where $R^{11}$ is $(C_1-C_6)$alkanol and $R^{12}$, $R^{13}$, and $R^{14}$ are hydrogen; dialkanol ammonium compounds of the present invention can include, for example, compounds where $R^{11}$ and $R^{12}$ each independently $(C_{1-6})$alkanol, and $R^{13}$ and $R^{14}$ are hydrogen; trialkanol ammonium compounds of the present invention can include, for example, compounds where each $R^{11}$, $R^{12}$ and $R^{13}$ are independently $(C_{1-6})$alkanol and $R^{14}$ is hydrogen. Preferred alkanol ammonium salts of the present invention are the mono-, di- and tri-quaternary ammonium compounds having the formulas: $H_3N^+(C_2H_4OH)$, $H_2N^+(C_2H_4OH)_2$, and $HN^+(C_2H_4OH)_3$. The cation is preferably $Na^+$, $K^+$, and the C2 alkanol ammonium salts listed above, most preferably sodium.

In any of the above embodiments, Z is preferably selected from the group consisting of a hydroxyl, an alkoxyl, a glycerol ether, a polyglycerol ether, a polyglycoside, a carboxylate, a sulfate, a sulfonate, an amine, a monoalkylamine, a dialkylamine, an amine oxide, a monoalkanolamide, a betaine, a sulfobetaine, an amidopropyl betaine, a polyalkoxylated amidopropyl betaine, an alkylated quat, an alkyated/hydroxyalkylated quat, an alkylated/polyhydroxyakylated quat, a alkoxylated sulfate, a phosphate ester, a polyphosphate ester, an O-alkyl ester, a C-alkyl ester, a glycerol ester, a sugar ester, a glycerol ester quat, an amide, and a sulfonated alkyl ester.

In some embodiments, Z is not a carboxylic acid. In some embodiments, Z is not a carboxylate. In some embodiments, the foregoing selections for Z do not include carboxylic acid. In some embodiments, the foregoing selected for Z do not include carboxylate.

In some embodiments, the

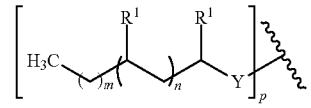

component of the at least two compounds of Formula I has a biobased content of at least about 50%, at least about 60%, at least about 70%, at least about 80%, at least about 90%, at least about 95%, at least about 97%, at least about 99%, or about 100%.

Assessment of the Biobased Content of Materials

As used herein, "biobased content" refers to the amount of bio-carbon in a material as a percent of the weight (mass) of the total organic carbon in the product. For example, polyethylene contains two carbon atoms in its structural unit. If ethylene is derived from a renewable resource, then a homopolymer of polyethylene theoretically has a biobased content of 100% because all of the carbon atoms are derived from a renewable resource. A copolymer of polyethylene could also theoretically have a biobased content of 100% if both the ethylene and the co-monomer are each derived from a renewable resource. In embodiments where the co-monomer is not derived from a renewable resource, the HDPE will typically include only about 1 wt % to about 2 wt. % of the non-renewable co-monomer, resulting in HDPE having a theoretical biobased content that is slightly less than 100%. As another example, polyethylene terephthalate contains ten carbon atoms in its structural unit (i.e., two from the ethylene glycol monomer and eight from the terephthalic acid monomer). If the ethylene glycol portion is derived from a renewable resource, but the terephthalic acid is derived from a petroleum-based resource, the theoretical biobased content of the polyethylene terephthalate is 20%.

A suitable method to assess materials derived from renewable resources is through ASTM D6866, which allows the determination of the biobased content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This $^{14}C$ is immediately oxidized into carbon dioxide, which represents a small, but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide, which causes the release of carbon dioxide back to the atmosphere. Virtually all forms of life on Earth depend on this green plant production of organic molecules to produce the chemical energy that facilitates growth and reproduction. Therefore, the $^{14}C$ that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086, incorporated herein by reference.

The application of ASTM D6866 to derive a "biobased content" is built on the same concepts as radiocarbon dating, but without use of the age equations. The analysis is performed by deriving a ratio of the amount of radiocarbon ($^{14}C$) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of biomass material present in the sample.

The modern reference standard used in radiocarbon dating is a NIST (National Institute of Standards and Technology) standard with a known radiocarbon content equivalent approximately to the year AD 1950. The year AD 1950 was chosen because it represented a time prior to thermo-nuclear weapons testing, which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), preferably at least about 99 pMC, for example, about 100 pMC.

Combining fossil carbon with present day carbon into a material will result in a dilution of the present day pMC content. By presuming that 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biobased content result is derived by assigning 100% equal to 107.5 pMC and 0% equal to 0 pMC. In this regard, a sample measuring 99 pMC will give an equivalent biobased content result of 93%.

Assessment of the materials described herein were done in accordance with ASTM D6866, particularly with Method B. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of bio-component "present" in the material, not the amount of bio-material "used" in the manufacturing process.

Other techniques for assessing the biobased content of materials are described in U.S. Pat. Nos. 3,885,155, 4,427,884, 4,973,841, 5,438,194, and 5,661,299, WO 2009/155086, each incorporated herein by reference.

Methods for Preparing Mixtures of Scattered-Branched Fatty Acids

The mixtures of the at least two compounds of Formula I, as previously defined, can be prepared by derivatizing mixtures of scattered-branched fatty acids produced using biological methods.

As used herein, "endogenous" refers to polynucleotides, polypeptides, or other compounds that are expressed naturally or originate within an organism or cell. That is, endogenous polynucleotides, polypeptides, or other compounds are not exogenous. For instance, an "endogenous" polynucleotide or peptide is present in the cell when the cell was originally isolated from nature.

As used herein, "exogenous" refers to any polynucleotide or polypeptide that is not naturally expressed or produced in the particular cell or organism where expression is desired. Exogenous polynucleotides, polypeptides, or other compounds are not endogenous.

As used herein, "hybridization" includes any process by which a strand of a nucleic acid joins with a complementary nucleic acid strand through base-pairing. Thus, the term refers to the ability of the complement of the target sequence to bind to a test (i.e., target) sequence, or vice-versa.

As used herein, "hybridization conditions" are typically classified by degree of "stringency" of the conditions under which hybridization is measured. The degree of stringency can be based, for example, on the melting temperature ($T_m$) of the nucleic acid binding complex or probe. For example, "maximum stringency" typically occurs at about $T_m$–5° C. (5° below the $T_m$ of the probe); "high stringency" at about 5-10° C. below the $T_m$; "intermediate stringency" at about 10-20° below the $T_m$ of the probe; and "low stringency" at about 20-25° C. below the $T_m$. Alternatively, or in addition, hybridization conditions can be based upon the salt or ionic strength conditions of hybridization and/or one or more stringency washes. For example, 6×SSC=very low stringency; 3×SSC=low to medium stringency; 1×SSC=medium stringency; and 0.5×SSC=high stringency. Functionally, maximum stringency conditions may be used to identify nucleic acid sequences having strict (i.e., about 100%) identity or near-strict identity with the hybridization probe; while high stringency conditions are used to identify nucleic acid sequences having about 80% or more sequence identity with the probe.

As used herein, "identical" or percent "identity" in the context of two or more polynucleotide or polypeptide sequences refers to two or more sequences that are the same or have a specified percentage of nucleotides or amino acid residues that are the same, when compared and aligned for maximum correspondence, as measured using sequence comparison algorithms or by visual inspection.

As used herein, "long-chain fatty acids" refers to fatty acids with aliphatic tails longer than 14 carbons. In some embodiments, long-chain fatty acids are provided that comprise 15, 16, 17, 18, 19, 20, 21, or 22 carbons in the carbon backbone.

As used herein, "medium-chain fatty acids" refers to fatty acids with aliphatic tails between 6 and 14 carbons. In certain embodiments, the medium-chain fatty acids can have from 11 to 13 carbons.

As used herein, "short-chain fatty acids" refers to fatty acids having aliphatic tails with fewer than 6 carbons.

As used herein, "overexpression" refers to expression of a polynucleotide to produce a product (e.g., a polypeptide or RNA) at a higher level than the polynucleotide is normally expressed in the host cell. An overexpressed polynucleotide is generally a polynucleotide native to the host cell, the product of which is generated in a greater amount than that normally found in the host cell. Overexpression is achieved by, for instance and without limitation, operably linking the polynucleotide to a different promoter than the polynucleotide's native promoter or introducing additional copies of the polynucleotide into the host cell.

U.S. Provisional Application No. 61/294,274 ("the '274 application," Procter & Gamble), which is incorporated by reference, describes methods for the biological production of scattered-branched chain fatty acids, and methods for improving the biological production of such scattered-branched chain fatty acids. Specifically, the '274 application describes a method of producing scattered-branched chain fatty acids (e.g., comprising a methyl group on one or more even numbered carbon atoms) using bacteria.

In general, the method includes increasing the supply of methylmalonyl-CoA and/or the conversion of methylmalonyl-CoA to methylmalonyl-ACP within the cell, incorporating the branch from the methylmalonyl-CoA into the fatty acid, and, optionally, using a thioesterase to specify the range of size of the fatty acids. In certain embodiments, the method provides branched-chain fatty acids having a chain length of C12 to C16. In addition, in certain embodiments, the branched-chain fatty acids have from about 0 to about 3 methyl branches, such as from about 1 to about 3 methyl branches, such as, for example, from about 1 to about 2 methyl branches, or 1, 2, or 3 methyl branches positioned on one or more carbons. In certain embodiments, the methyl branches are positioned on even-numbered carbons.

In one embodiment, scattered branched-chain fatty acid production is increased by increasing the production of methylmalonyl-CoA within the cell via, e.g., propionyl-CoA and/or succinyl-CoA intermediates. The method comprises culturing a cell comprising an exogenous or overexpressed polynucleotide comprising a nucleic acid sequence encoding a polypeptide that catalyzes the conversion of propionyl-CoA to methylmalonyl-CoA and/or an exogenous or overexpressed polynucleotide comprising a nucleic acid sequence encoding a polypeptide that catalyzes the conversion of succinyl-CoA to methylmalonyl-CoA. The cell is cultured under conditions allowing expression of the polynucleotide(s) and production of the branched-chain fatty acid. The cell produces more branched-chain fatty acid comprising a methyl branch on one or more even number carbons than an otherwise similar cell that does not comprise the polynucleotide(s) (e.g., a cell of the same cell type or derived from the same organism that does not comprise the polynucleotide(s)). Propionyl-CoA is converted to methylmalonyl-CoA by, e.g., the action of a propionyl-CoA carboxylase. Any propionyl-CoA carboxylase that catalyzes the conversion of propionyl-CoA to methylmalonyl-CoA is suitable for use in the method. An exemplary propionyl-CoA carboxylase is a carboxylase from *Streptomyces coelicolor*, which comprises two heterologous subunits encoded by pccB and by either accA1 or accA2. In certain embodiments, the cell of this method is engineered to produce PccB and AccA1 or PccB and AccA2. In one aspect, the cell comprises one or more polynucleotides encoding polypeptide(s) comprising an amino acid sequence at least about 80% identical (e.g., 85%, 90%, 95%, or 100% identical) to the amino acid sequences set forth in SEQ ID NO: 9 and/or 10. Additional, non-limiting examples of polypeptides that catalyze the conversion of propionyl-CoA to methylmalonyl-CoA are propionyl-CoA carboxylases from *Mycobacterium smegmatis, Homo sapiens, Acinetobacter baumannii, Brucella suis, Saccharopolyspora erythraea, Burkholderia glumae*, and *Aedes aegypti*, as well as the propionyl-CoA carboxylases set forth in Table D.

TABLE D

| Organism | GenBank Accession | Description | SEQ ID NO: |
|---|---|---|---|
| Ehrlichia chaffeensis | YP_507303 | Propionyl-CoA carboxylase alpha subunit (PCCA) | 51 |
| Ehrlichia chaffeensis | YP_507410 | Propionyl-CoA carboxylase beta subunit (PCCB) | 52 |
| Agrobacterium vitis | YP_002547482 | Propionyl-CoA carboxylase alpha subunit (PCCA) | 53 |
| Agrobacterium vitis | YP_002547479 | Propionyl-CoA carboxylase beta subunit (PCCB) | 54 |
| Methylobacterium extorquens | YP_003069256 | Propionyl-CoA carboxylase alpha subunit (PCCA) | 55 |
| Methylobacterium extorquens | YP_003065890 | Propionyl-CoA carboxylase beta subunit (PCCB) | 56 |
| Sinorhizobium meliloti | NP_437988 | Propionyl-CoA carboxylase alpha subunit (PCCA) | 57 |
| Sinorhizobium meliloti | NP_437987 | Propionyl-CoA carboxylase beta subunit (PCCB) | 58 |
| Ruegeria pomeroyi | YP_166352 | Propionyl-CoA carboxylase alpha subunit (PCCA) | 59 |
| Ruegeria pomeroyi | YP_166345 | Propionyl-CoA carboxylase beta subunit (PCCB) | 60 |

Optionally, the cell is modified to increase carbon flow to propionyl-CoA (and then onward to methylmalonyl-CoA) by, for example, increasing expression of (i.e., overexpressing) prpE or other propionyl-CoA synthetase genes. Alternatively or in addition, an exogenous polynucleotide comprising a nucleic acid sequence encoding a propionyl-CoA synthetase is introduced into the host cell to upregulate propionyl-CoA production. Additionally, feeding host cells (e.g., microbes) large amounts of methionine, isoleucine, valine, threonine, propionic acid, and/or odd-chain length fatty acids (such as valeric acid) increases production of the propionyl-CoA precursor of methylmalonyl-CoA.

Methylmalonyl-CoA production via propionyl-CoA also is increased utilizing the metabolic pathway that converts pyruvate to propionyl-CoA, with lactate, lactoyl-CoA, and acrylyl-CoA as intermediates. Carbon flow to propionyl-CoA is upregulated by overproducing the enzymes of the pathway, producing exogenous enzymes catalyzing one or more conversions of the pathway, and/or by providing pyruvate or lactate in larger amounts than normally found in the host cell. For example, the cell comprises an exogenous or overexpressed polynucleotide encoding lactate dehydrogenase, lactate CoA transferase, lactyl-CoA dehydratase, and/or acrylyl-CoA reductase.

In addition, carbon flow to branch pathways not contributing to formation of the desired branched-chain fatty acid can be minimized by attenuation of endogenous enzyme activity responsible for the diversion of carbon. Complete abolishment of endogenous activity is not required; any reduction in activity is suitable in the context of the method. Enzyme activity is attenuated (i.e., reduced or abolished) by, for example, mutating the coding sequence for the enzyme to create a non-functional or reduced-function polypeptide, by removing all or part of the coding sequence for the enzyme from the cellular genome, by interfering with translation of an RNA transcript encoding the enzyme (e.g., using antisense oligonucleotides), or by manipulating the expression control sequences influencing expression of the enzyme. For example, in one aspect, the cell is modified to prevent methylmalonyl-CoA degradation, thereby increasing the amount of methylmalonyl-CoA available for conversion to methylmalonyl-ACP. Methylmalonyl-CoA degradation is reduced by, for example, deleting or inactivating methylmalonyl-CoA decarboxylase from the host. Put another way, the cell is modified to attenuate endogenous methylmalonyl-CoA decarboxylase activity. In E. coli, for example, methylmalonyl-CoA decarboxylase activity is attenuated by, for example, deleting or mutating ygfG. Optionally, endogenous acyl transferase activity is attenuated. Alternatively or in addition, methylmalonyl-CoA production within the cell is increased by preventing alternative metabolism of propionyl-CoA to succinyl-CoA, such as, for example, by deleting or otherwise reducing (attenuating) the activity of an endogenous methylmalonyl-CoA mutase gene. Optionally, methylmalonyl-CoA levels are increased by increasing the degradation of valine directly to methylmalonyl-CoA. Valine degradation comprises the following intermediates: α-ketoisovalerate, isobutyryl-CoA, methacrylyl-CoA, β-hydroxyisobutyryl-CoA, β-hydroxyisobutyrate, and methylmalonate semialdehyde. Optionally, methylmalonate semialdehyde is converted directly to methylmalonyl-CoA or indirectly through a propionyl-CoA intermediate. In an exemplary embodiment, the cell comprises an overexpressed or exogenous polynucleotide comprising a nucleic acid sequence encoding one or more of the following enzymes: L-valine:2-oxoglutarate aminotransferase, 2-oxoisovalerate dehydrogenase, isobutyryl-CoA:FAD oxidoreductase, 3-hydroxy-isobutyryl-CoA hydro-lyase, 3-hydroxyisobutyryl-CoA hydrolase, 3-hydroxyisobutyrate dehydrogenase, and/or methylmalonate-semialdehyde dehydrogenase. Methylmalonate-semialdehyde dehydrogenase catalyzes the production of propanoyl-CoA, which can be converted to methylmalonyl-CoA by propanoyl-CoA carboxylase.

In one aspect, the cell comprises an exogenous or overexpressed polynucleotide comprising a nucleic acid sequence encoding a polypeptide that catalyzes the conversion of succinyl-CoA to methylmalonyl-CoA. An exemplary polypeptide that catalyzes the reaction is methylmalonyl-CoA mutase. In any embodiment, the cell is engineered to overexpress a methylmalonyl-CoA mutase gene, such as, for example, sbm (encoding Sleeping Beauty mutase) in E. coli. Alternatively or in addition, an exogenous polynucleotide comprising a nucleic acid sequence encoding a methylmalonyl-CoA mutase is expressed in the cell. Exemplary methylmalonyl-CoA mutases include, but are not limited to, Sbm from E. coli, MutA and/or MutB from Streptomyces cinnamonensis, and methylmalonyl-CoA mutases from Janibacter sp. HTCC2649, Corynebacterium glutamicum, Euglena gracilis, Homo sapiens, Propionibacterium shermanii, Bacillus megaterium, and Mycobacterium smegmatis. Additional, non-limiting examples of polypeptides that catalyze the conversion of succinyl-CoA to methylmalonyl-CoA are provided in Table E.

TABLE E

| Organism | GenBank Accession | Description | SEQ ID NO. |
|---|---|---|---|
| Bacillus megaterium | YP_003564880 | methylmalonyl-CoA mutase small subunit (mutA) | 61 |
| Bacillus megaterium | YP_003564879 | methylmalonyl-CoA mutase large subunit (mutB) | 62 |
| Mycobacterium tuberculosis | YP_001282809 | methylmalonyl-CoA mutase small subunit (mutA) | 63 |
| Mycobacterium tuberculosis | YP_001282810 | methylmalonyl-CoA mutase large subunit (mutB) | 64 |
| Corynebacterium glutamicum | YP_225814 | methylmalonyl-CoA mutase small subunit (mutA) | 65 |
| Corynebacterium glutamicum | YP_225813 | methylmalonyl-CoA mutase large subunit (mutB) | 66 |
| Rhodococcus erythropolis | YP_002766535 | methylmalonyl-CoA mutase small subunit (mutA) | 67 |
| Rhodococcus erythropolis | YP_002766536 | methylmalonyl-CoA mutase large subunit (mutB) | 68 |
| Porphyromonas gingivalis | NP_905776 | methylmalonyl-CoA mutase small subunit (mutA) | 69 |
| Porphyromonas gingivalis | NP_905777 | methylmalonyl-CoA mutase large subunit (mutB) | 70 |

In one aspect, the cell comprises one or more polynucleotides encoding polypeptide(s) comprising an amino acid sequence at least about 80% identical (e.g., 85%, 90%, 95%, or 100% identical) to the amino acid sequences set forth in SEQ ID NO: 3, 4, and/or 28. The cell can comprise polynucleotides encoding a methylmalonyl-CoA mutase, a propionyl-CoA carboxylase, or both.

Depending on the substrate specificity of the fatty acid synthase produced by the cell, a methylmalonyl-CoA epimerase also may be desired to facilitate use of methylmalonyl-CoA as a precursor in fatty acid synthesis. Thus, in one aspect, the cell further comprises an exogenous or overexpressed polynucleotide comprising a nucleic acid sequence encoding a methylmalonyl-CoA epimerase. Methylmalonyl-CoA epimerases suitable for use in the method include, but are not limited to, Sorangium cellulosum So ce 56 methylmalonyl-CoA epimerase, Streptomyces sviceus ATCC 29083 methylmalonyl-CoA epimerase, Kribbella flavida DSM 17836 methylmalonyl-CoA epimerase, and methylmalonyl-CoA epimerases from Homo sapiens, Bacillus megaterium, and Mycobacterium smegmatis.

Production of branched-chain fatty acid comprising a methyl branch on one or more even number carbons also is enhanced by upregulating conversion of methylmalonyl-CoA to methylmalonyl-ACP. In one or more embodiments, conversion of methylmalonyl-CoA to methylmalonyl-ACP is increased in the cell by engineering the cell to produce an acyl transferase (such as the acyl transferase encoded by fabD in E. coli) to catalyze the formation of methylmalonyl-ACP from methylmalonyl-CoA. Put another way, in one aspect, the cell further comprises an exogenous or overexpressed polynucleotide comprising a nucleic acid sequence encoding an acyl transferase. Any suitable acyl transferase can be used, such as, for example and without limitation, an acyl transferase domain from a polyketide synthase, such as those involved in the synthesis of monensin, epothilone, amphotericin, candicidin, nystatin, pimaricin, ascomycin, rapamycin, avermiectin, spinosad, mycinamicin, niddamycin, oleandomycin, megalomicin, nanchangmycin, picromycin, rifamycin, oligomycin erythromycin, polyenes, and macrolides, and an acyl transferase domain from Mycobacterium mycocerosic acid synthase. Acyl transferase domains from larger fatty acid synthase enzymes, such as Mycobacterium mycocerosic acid synthase, act upon methylmalonyl-CoA in the absence of other enzymatic domains of the larger synthase. Optionally, the acyl transferase lacks polyketide synthesis activity. By "polyketide synthesis activity" is meant enzymatic activity, other than acyl transferase activity, that catalyzes the production of polyketides in a host cell, such as, for example and without limitation, acyltransferase activity, ketoacyl synthase activity, ketoacyl reductase activity, dehydratase activity, enoyl reductase activity, acyl carrier protein activity, and thioesterase activity.

Alternatively, or in addition, in certain embodiments, a 3-ketoacyl-ACP synthase domain, such as, for example, a domain from a polyketide synthase or a mycocerosic acid synthase, is added to the fatty acid synthase of the host cell. In certain embodiments, the host cell (e.g., microbe) is engineered to include both acyl transferase and 3-ketoacyl-ACP synthase domains that can recognize methylmalonyl-CoA. In addition, in certain embodiments, genes for the endogenous acyl transferase and/or 3-ketoacyl-ACP synthase activities can be attenuated (e.g., deleted) to minimize the amount of malonyl-CoA incorporation in fatty acid synthesis.

In certain embodiments, the method includes use of a thioesterase to specify the chain length of the fatty acid, such as, for example, to produce medium-chain fatty acids. In certain embodiments, the host cell further comprises an exogenous or overexpressed polynucleotide comprising a nucleic acid sequence encoding a thioesterase. In one aspect, the host cell (e.g., bacteria) is engineered to produce a thioesterase that assists in the production of medium-chain branched-chain fatty acids. Alternatively, the host cell is engineered to produce (or overproduce) a thioesterase that assists in the production of long-chain branched-chain fatty acids. Exemplary thioesterases include, for example, the mallard uropygial gland thioesterase, the California bay thioesterase, the rat mammary gland thioesterase II, E. coli TesA, the Cuphea wrightii thioesterase, and other thioesterases suitable for production of the desired chain-length fatty acids.

Optionally, the cell is modified to produce (or increase the production of) branched acyl-CoA, which is a substrate for elongase in the production of long chain fatty acid. In this regard, in an exemplary embodiment, the cell comprises an exogenous or overexpressed polynucleotide comprising a nucleic acid encoding a coenzyme-A synthetase, which converts branched-chain fatty acid to branched acyl-CoA. Examples of coenzyme-A synthetases include, but are not limited to, the coenzyme-A synthetase from Leishmania braziliensis (GenBank Accession No. XP_001561614), and the coenzyme-A synthetase from Escherichia coli (GenBank Accession No. YP_541006). Optionally, the cell comprises exogenous or overexpressed polynucleotide(s) comprising a nucleic acid sequence encoding an elongase to increase the length of the carbon backbone. Elongases are enzyme complexes that exhibit 3-ketoacyl-CoA synthase, 3-ketoacyl-CoA reductase, 3-hydroxyacyl-CoA dehydratase, and enoyl- CoA reductase activities, and generally utilize malonyl-CoA as an extension unit for extending the carbon chain. When a methyl-malonyl CoA is used as an extension unit by the enzyme complex, additional methyl branches are introduced at even carbon positions. Exemplary elongases include, but are not limited to, elongases comprising the one or more of the following subunits: *Saccharomyces cerevisiae* 3-ketoacyl-CoA synthase (GenBank Accession No. NP_013476), 3-ketoacyl-CoA reductase (GenBank Accession No. NP_009717), 3-hydroxyacyl-CoA dehydratase (GenBank Accession No. NP_012438) and enoyl-CoA reductase (GenBank Accession No. NP_010269); and *Arabidopsis thaliana* col 3-ketoacyl-CoA synthase (GenBank Accession No. NP_849861), 3-ketoacyl-CoA reductase (GenBank Accession No. NP_564905), 3-hydroxyacyl-CoA dehydratase (GenBank Accession No. NP_193180), and enoyl-CoA reductase (GenBank Accession No. NP_191096).

Any suitable cell or organism, such as, for example, bacterial cells and other prokaryotic cells, and yeast cells, can be used in the context of the method. In one aspect, the method relates to cells, such as *Escherichia* cells (e.g., *E. coli*), which naturally produce Type II fatty acid synthase and/or do not naturally produce scattered branched-chain fatty acid (i.e., branched-chain fatty acid comprising a methyl branch on one or more even numbered carbons). These cells are engineered to produce the branched-chain fatty acids as described herein. Alternatively, the cell naturally produces branched-chain fatty acid and is modified as described herein to produce higher levels of branched-chain fatty acid (or different proportions of different types of branched-chain fatty acid) compared to an unmodified cell. In certain embodiments, fatty acid is manufactured using bacteria known to make the methylmalonyl-CoA precursor, such as *Streptomyces, Mycobacterium* or *Corynebacterium*. These bacteria are, in one aspect, engineered to produce (i) an acyl transferase to increase carbon flux to methylmalonyl-ACP that is incorporated in the fatty acid synthesis pathway and/or (ii) a thioesterase to control the chain length.

Exemplary bacteria that are suitable for use in the method include, but are not limited to, *Spirochaeta aurantia, Spirochaeta littoralis, Pseudomonas maltophilia, Pseudomonas putrefaciens, Xanthomonas campestris, Legionella anisa, Moraxella catarrhalis, Thermus aquaticus, Flavobacterium aquatile, Bacteroides asaccharolyticus, Bacteroides fragilis, Succinimonas amylolytica, Desulfovibrio africanus, Micrococcus agilis, Stomatococcus mucilaginosus, Planococcus citreus, Marinococcus albusb, Staphylococcus aureus, Peptostreptococcus anaerobius, Ruminococcus albus, Sarcina lutea, Sporolactobacillus inulinus, Clostridium thermocellum, Sporosarcina ureae, Desulfotomaculum nigrificans, Listeria monocytogenes, Brochothrix thermosphacta, Renibacterium salmoninarum, Kurthia zopfii, Corynebacterium aquaticum, Arthrobacter radiotolerans, Brevibacterium fermentans, Propionibacterium acidipropionici, Eubacterium lentum, Cytophaga aquatilis, Sphingobacteriuma multivorumb, Capnocytophaga gingivalis, Sporocytophaga myxococcoides, Flexibacter elegans, Myxococcus coralloides, Archangium gephyra, Stigmatella aurantiaca, Oerskovia turbata, Escherichia coli, Bacillus subtilis, Salmonella typhimurium, Corynebacterium glutamicum, Streptomyces coelicolor, Streptomyces lividans, Clostridium thermocellum* and *Saccharomonospora viridis*.

In one aspect, the fatty acid produced by the inventive cell comprises about 80% to about 100% (wt.) (e.g., about 85%, about 90%, or about 95%) linear and branched-chain fatty acid. Of the linear and branched-chain fatty acids produced by the cell, approximately 1% to approximately 95% or more (e.g., 5%, 10%, 15%, 20%, 30%, 50%, 60%, 75%, 85%, or 100%) is branched-chain fatty acid comprising a methyl group on one or more even carbons. In some embodiments, the cell does not produce, or produces only trace amounts of, fatty acid comprising methyl branching on odd numbered carbons. By "trace amount" is meant less than 1% of the total fatty acid content produced by the cell. Alternatively or in addition, in one aspect, the mixture of fatty acids produced by the cell comprises no more than 50% end-terminal-branched fatty acid (i.e., fatty acids that contain branching on a carbon atom that is within 40% of the non-functionalized terminus of the longest carbon chain). Optionally, the cell is modified to preferentially produce branched-chain fatty acid with desired chain lengths, e.g., about six to about 18 carbons or more in the carbon backbone (not including the methyl branch(es)). In some embodiments, the host cell preferentially generates long chain fatty acid, medium-length chain fatty acid, short chain fatty acid, or a desired combination fatty acids (e.g., 60%, 70%, 80%, 85%, 90%, 95% or more of the branched-chain fatty acid produced by the cell comprises the desired number of carbons). In addition, in certain embodiments, the engineered cells tolerate large amounts of branched-chain fatty acid in the growth medium, plasma membrane, or lipid droplets, and/or produce branched-chain fatty acid more economically than an unmodified cell by, e.g., using a less expensive feedstock, requiring less fermentation time, and the like.

The polynucleotide(s) encoding one or more polypeptides that catalyze the reaction(s) for producing branched-chain fatty acid may be derived from any source. Depending on the embodiment, the polynucleotide is isolated from a natural source such as bacteria, algae, fungi, plants, or animals; produced via a semi-synthetic route (e.g., the nucleic acid sequence of a polynucleotide is codon-optimized for expression in a particular host cell, such as *E. coli*); or synthesized de novo. In certain embodiments, it is advantageous to select an enzyme from a particular source based on, e.g., the substrate specificity of the enzyme, the type of branched-chain fatty acid produced by the source, or the level of enzyme activity in a given host cell. In one aspect, the enzyme and corresponding polynucleotide are naturally found in the host cell and overexpression of the polynucleotide is desired. In this regard, in some instances, additional copies of the polynucleotide are introduced in the host cell to increase the amount of enzyme available for fatty acid production. Overexpression of a native polynucleotide also is achieved by upregulating endogenous promoter activity, or operably linking the polynucleotide to a more robust promoter. Exogenous enzymes and their corresponding polynucleotides also are suitable for use in the context of the method, and the features of the biosynthesis pathway or end product can be tailored depending on the particular enzyme used. If desired, the polynucleotide(s) is isolated or derived from the branched-chain fatty acid-producing organisms described herein.

In certain embodiments, the cell produces an analog or variant of a polypeptide described herein. Amino acid sequence variants of the polypeptide include substitution, insertion, or deletion variants, and variants may be substantially homologous or substantially identical to the unmodified polypeptides as set out above. In certain embodiments, the variants retain at least some of the biological activity, e.g., catalytic activity, of the polypeptide. Other variants include variants of the polypeptide that retain at least about 50%, preferably at least about 75%, more preferably at least about 90%, of the biological activity.

Substitution variants typically exchange one amino acid for another at one or more sites within the protein. Substitutions of this kind can be conservative, that is, one amino acid is replaced with one of similar shape and charge. Conservative substitutions include, for example, the changes of: alanine to serine; arginine to lysine; asparagine to glutamine; aspartate to glutamate; cysteine to serine; glutamine to asparagine; glutamate to aspartate; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In some instances, the recombinant cell comprises an analog or variant of the exogenous or overexpressed polynucleotide(s) described herein. Nucleic acid sequence variants include one or more substitutions, insertions, or deletions, and variants may be substantially homologous or substantially identical to the unmodified polynucleotide. Polynucleotide variants or analogs encode mutant enzymes having at least partial activity of the unmodified enzyme. Alternatively, polynucleotide variants or analogs encode the same amino acid sequence as the unmodified polynucleotide. Codon-optimized sequences, for example, generally encode the same amino acid sequence as the parent/native sequence but contain codons that are preferentially expressed in a particular host organism.

A polypeptide or polynucleotide "derived from" an organism contains one or more modifications to the native amino acid sequence or nucleotide sequence and exhibits similar, if not better, activity compared to the native enzyme (e.g., at least 70%, at least 80%, at least 90%, at least 95%, at least 100%, or at least 110% the level of activity of the native enzyme). For example, enzyme activity is improved in some contexts by directed evolution of a parent/native sequence. Additionally or alternatively, an enzyme coding sequence is mutated to achieve feedback resistance. Thus, in one or more embodiments, the polypeptide encoded by the exogenous polynucleotide is feedback resistant and/or is modified to alter the activity of the native enzyme. A polynucleotide "derived from" a reference polynucleotide encompasses, but is not limited to, a polynucleotide comprising a nucleic acid sequence that has been codon-optimized for expression in a desired host cell.

The cell may comprise any combination of polynucleotides described herein to produce branched-chain fatty acid comprising a methyl branch on one or more even number carbons. For example, the method provides a cell comprising (i) an exogenous or overexpressed polynucleotide comprising a nucleic acid sequence encoding an acyl transferase lacking polyketide synthesis activity, and (ii) an exogenous or overexpressed polynucleotide comprising a nucleic acid sequence encoding a propionyl-CoA carboxylase and/or an exogenous or overexpressed polynucleotide comprising a nucleic acid sequence encoding a methylmalonyl-CoA mutase, wherein the polynucleotide(s) are expressed and the cell produces more branched-chain fatty acid comprising a methyl on one or more even number carbons than an otherwise similar cell that does not comprise the polynucleotide(s). Recombinant cells can be produced in any suitable manner to establish an expression vector within the cell. The expression vector can include the exogenous polynucleotide operably linked to expression elements, such as, for example, promoters, enhancers, ribosome binding sites, operators and activating sequences. Such expression elements may be regulatable, for example, inducible (via the addition of an inducer). Alternatively or in addition, the expression vector can include additional copies of a polynucleotide encoding a native gene product operably linked to expression elements. Representative examples of useful promoters include, but are not limited to: the LTR (long terminal 35 repeat from a retrovirus) or SV40 promoter, the *E. coli* lac, tet, or trp promoter, the phage Lambda $P_L$ promoter, and other promoters known to control expression of genes in prokaryotic or eukaryotic cells or their viruses. In one aspect, the expression vector also includes appropriate sequences for amplifying expression. The expression vector can comprise elements to facilitate incorporation of polynucleotides into the cellular genome. Introduction of the expression vector or other polynucleotides into cells can be performed using any suitable method, such as, for example, transformation, electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the expression vector or other polynucleotides can be introduced by infection with a viral vector, by conjugation, by transduction, or by other any other suitable method.

Cells, such as bacterial cells, containing the polynucleotides encoding the proteins described herein can be cultured under conditions appropriate for growth of the cells and expression of the polynucleotides. Cells expressing the protein can be identified by any suitable methods, such as, for example, by PCR screening, screening by Southern blot analysis, or screening for the expression of the protein. In certain embodiments, cells that contain the polynucleotide(s) can be selected by including a selectable marker in the DNA construct, with subsequent culturing of cells containing a selectable marker gene, under conditions appropriate for survival of only those cells that express the selectable marker gene. The introduced DNA construct can be further amplified by culturing genetically modified cells under appropriate conditions (e.g., culturing genetically modified cells containing an amplifiable marker gene in the presence of a concentration of a drug at which only cells containing multiple copies of the amplifiable marker gene can survive). Cells that contain and express polynucleotides encoding the exogenous proteins can be referred to herein as genetically modified cells. Bacterial cells that contain and express polynucleotides encoding the exogenous protein can be referred to as genetically modified bacterial cells.

Exemplary cells include *E. coli* BW25113 comprising pTrcHisA mmat and pZA31-accA1-pccB, which was deposited with American Type Culture Collection (ATCC), 10801 University Blvd., Manassas, Va., on Dec. 14, 2010, under the provisions of the Budapest Treaty for the International Recognition of the Deposit of Microorganisms for the Purpose of Patent Procedure ("Budapest Treaty"), and assigned Deposit Accession No. PTA-11546 on Dec. 14, 2010, and *E. coli* BL21 Star (DE3) comprising pTrcHisA Ec shm So ce epi and pZA31 mmat which was deposited with American Type Culture Collection (ATCC), 10801 University Blvd., Manassas, Va., on Dec. 14, 2010, under the provisions of the Budapest Treaty for the International Recognition of the Deposit of Microorganisms for the Purpose of Patent Procedure ("Budapest Treaty"), and assigned Deposit Accession No. PTA-11545 on Dec. 14, 2010. The method also includes variants or progeny of the cells described herein that retain the phenotypic characteristics of the recombinant microbe. A substantially pure monoculture of the cell described herein (i.e., a culture comprising at least 80% or at least 90% of a desired cell) also is provided.

Any cell culture conditions appropriate for growing a host cell and synthesizing branched-chain fatty acid is suitable for use in the method. Addition of fatty acid synthesis intermediates, precursors, and/or co-factors for the enzymes associated with branched-chain fatty acid synthesis to the culture is contemplated herein. In certain embodiments, the genetically modified cells (such as genetically modified bacterial cells) have an optimal temperature for growth, such as, for example, a lower temperature than normally encountered for growth and/or fermentation. For example, in certain embodiments, incorporation of branched-chain fatty acids into the membrane may increase membrane fluidity, a property normally associated with low growth temperatures. In addition, in certain embodiments, cells may exhibit a decline in growth at higher temperatures as compared to normal growth and/or fermentation temperatures as typically found in cells of the type.

The method optionally comprises extracting branched-chain fatty acid from the culture. Fatty acids can be extracted from the culture medium and measured using any suitable manner. Suitable extraction methods include, for example, methods as described in: Bligh et al., A rapid method for total lipid extraction and purification, *Can. J. Biochem. Physiol.* 37:911-917 (1959). In certain embodiments, production of fatty acids in the culture supernatant or in the membrane fraction of recombinant cells can be measured. In this embodiment, cultures are prepared in the standard manner, although nutrients (e.g., 2-methylbutyrate, isoleucine) that may provide a boost in substrate supply can be added to the culture. Cells are harvested by centrifugation, acidified with hydrochloric or perchloric acid, and extracted with chloroform and methanol, with the fatty acids entering the organic layer. The fatty acids are converted to methyl esters, using methanol at 100° C. The methyl esters are separated by gas chromatography (GC) and compared with known standards of fatty acids (purchased from Larodan or Sigma). Confirmation of chemical identity is carried out by combined GC/mass spec, with further mass spec analysis of fragmented material carried out if necessary.

In one embodiment, the cell utilizes the branched-chain fatty acid as a precursor to make one or more other products. Products biosynthesized (i.e., derived) from branched-chain fatty acid include, but are not limited to, phospholipids, triglycerides, alkanes, olefins, wax esters, fatty alcohols, and fatty aldehydes. Some host cells naturally generate one or more products derived from branched-chain fatty acid; other host cells are genetically engineered to convert branched-chain fatty acid to, e.g., an alkane, olefin, wax ester, fatty alcohol, phospholipid, triglyceride, and/or fatty aldehyde. Organisms and genetic modifications thereof to synthesize products derived from branched-chain fatty acids are further described in, e.g., International Patent Publication Nos. WO 2007/136762, WO 2008/151149, and WO 2010/062480, and U.S. Patent Application Publication US 2010/0298612, all of which are hereby incorporated by reference in their entirety. In one aspect, the inventive method comprises extracting a product derived from branched-chain fatty acid (phospholipid, triglyceride, alkane, olefin, wax ester, fatty alcohol, and/or fatty aldehyde synthesized in the cell from branched-chain fatty acid) from the culture.

Any extraction method is appropriate, including the extraction methods described in International Patent Publication Nos. WO 2007/136762, WO 2008/151149, and WO 2010/062480, and U.S. Patent Application Publication Nos. US 2010/0251601, US 20100242345, US 20100105963, and US 2010/0298612.

The cell preferably produces more branched-chain fatty acid comprising a methyl branch on one or more even number carbons than an otherwise similar cell that does not comprise the polynucleotide(s). Methods of measuring fatty acid released into the fermentation broth or culture media or liberated from cellular fractions are described herein. Branched-chain fatty acid production is not limited to fatty acid accumulated in the culture, however, but also includes fatty acid used as a precursor for downstream reactions yielding products derived from branched-chain fatty acid. Thus, products derived from branched-chain fatty acid (e.g., phospholipids, triglycerides, fatty alcohols, olefins, wax esters, fatty aldehydes, and alkanes) are, in some embodiments, surrogates for measuring branched-chain fatty acid production in a host cell. Methods of measuring fatty acid content in phospholipid in the cell membrane are described herein. Similarly, measurement of degradation products of branched-chain fatty acids also is instructive as to the amount of branched-chain fatty acid is produced in a host cell. Depending on the particular embodiment, the inventive cell produces at least 3%, at least 5%, at least 10%, at least 20%, at least 25%, or at least 50% more branched-chain fatty acid than an otherwise similar cell that does not comprise the polynucleotide(s).

Thus, in another aspect, the invention provides a composition comprising a mixture of at least two compounds of Formula I, as previously described, wherein the mixture is produced by (a) culturing a cell comprising:
(i) an exogenous or overexpressed polynucleotide comprising a nucleic acid sequence encoding a polypeptide that catalyzes the conversion of propionyl-CoA to methylmalonyl-CoA; and/or,
(ii) an exogenous or overexpressed polynucleotide comprising a nucleic acid sequence encoding a polypeptide that catalyzes the conversion of succinyl-CoA to methylmalonyl-CoA, under conditions allowing expression of the polynucleotide(s) and production a mixture of at least two compounds of Formula II:

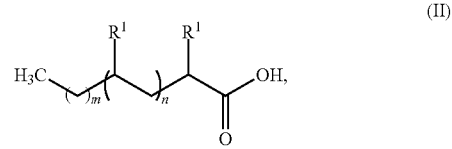

wherein the cell produces more compounds of Formula II than an otherwise similar cell that does not comprise the polynucleotide(s);

(b) extracting from culture the mixture of at least two compounds of Formula II; and, (c) derivatizing the compounds of Formula (II) to form the mixture of at least two compounds of Formula I.

In some embodiments, the polypeptide that catalyzes the conversion of propionyl-CoA to methylmalonyl-CoA is a propionyl-CoA carboxylase and/or the polypeptide that catalyzes the conversion of succinyl-CoA to methylmalonyl-CoA is a methylmalonyl-CoA mutase.

In some embodiments, the propionyl-CoA carboxylase is *Streptomyces coelicolor* PccB and AccA1 or PccB and AccA2, and/or the methylmalonyl-CoA mutase is *Janibacter* sp. HTCC2649 methylmalonyl-CoA mutase, or *S. cinnamonensis* MutA and MutB.

In some embodiments, the methylmalonyl-CoA mutase comprises an amino acid sequence having at least about 80% sequence identity to the amino acid sequence set forth in SEQ ID NOs: 3 or 4 and/or (ii) the propionyl-CoA carboxylase comprises an amino acid sequence having at least about 80% sequence identity to the amino acid sequence set forth in SEQ ID NOs: 9 and 10.

In some embodiments, the cell comprises an exogenous or overexpressed polynucleotide comprising a nucleic acid sequence encoding a methylmalonyl-CoA mutase and further comprises an exogenous or overexpressed polynucleotide comprising a nucleic acid sequence encoding a methylmalonyl-CoA epimerase.

In some embodiments, the cell further comprises an exogenous or overexpressed polynucleotide encoding an acyl transferase lacking polyketide synthesis activity and/or an exogenous or overexpressed polynucleotide comprising a nucleic acid sequence encoding a thioesterase.

In some embodiments, the acyl transferase is FabD, an acyl transferase domain of a polyketide synthase, or an acyl transferase domain of *Mycobacterium* mycocerosic acid synthase.

In some embodiments, the cell has been modified to attenuate endogenous methylmalonyl-CoA mutase activity, endogenous methylmalonyl-CoA decarboxylase activity, and/or endogenous acyl transferase activity.

In some embodiments, the cell produces a Type II fatty acid synthase.

In some embodiments, the cell is *Escherichia coli*.

Methods for Derivatizing Mixtures of Scattered-Branched Fatty Acids

The fatty acids produced by the biological methods previously described can be derivatized to form compositions containing compounds that are useful for cleaning and/or conditioning applications such as for granular, bar-form, and liquid laundry detergents; liquid hand dishwashing compositions; liquid, gel, and bar-form personal cleansing products; shampoos; dentifrices; hard surface cleaners, hair conditioners, and the like.

Unsaturated fatty acids, unsaturated fatty alcohols, and unsaturated fatty esters produced by the biological methods previously described can be reduced using hydrogen and a hydrogenation catalyst to form the corresponding saturated compounds. Reduction can be carried out with a variety of catalysts such as copper chromite, nickel on Kieselguhr, rhodium on silica, and palladium on Kieselguhr. Reaction conditions vary from 20° C. to about 130° C., a hydrogen pressure ranging from 100 psig to about 2000 psig of hydrogen and catalyst loadings can typically be in range of about 1 wt. % to about 5 wt. % on the substrate. Reaction times will vary according to catalyst ratio, temperature chosen and hydrogen pressure. Typical conditions are 150° C. at 1000 psig for 16 hours in batch mode. The process is not limited to batch processes. Continuous reaction can also be applied to the present invention.

Derivatization of the scattered-branched chain fatty acid and fatty alcohol reaction products can occur by any method known in the art. For example, the scattered-branched chain fatty alcohols can be alkyoxylated using standard commercial and laboratory techniques and/or sulfated/sulfonated using any convenient sulfating/sulfonating agent (e.g., chlorosulfonic acid, $SO_3$/air, or oleum) to form detergent compounds and conditioning compounds. U.S. Pat. Nos. 6,395,701 and 6,602,845, each incorporated herein by reference, disclose methods of converting fatty acids to surfactants via ester and amide linkages.

As previously described, the compositions comprising a mixture of at least two compounds of Formula I are useful in cleaning and conditioning applications. In cleaning applications, Z can include, for example, hydroxyl, an alkoxyl, a sulfate, a disulfate, a sulfonate, a disulfonate, a sulfosuccinate, amine, a monoalkylamine, a dialkylamine, an amine oxide, a polyhydroxy moiety, a phosphate ester, a polyphosphate ester, a phosphonate, a glycerol ether, a glycerol ether sulfonate, a polygluconate, a monoglycerol ether, a diglyerol ether, a glycerol ether sulfate, a polyglycerol ether, a polyglycerol ether sulfate, a polyglucoside, an ammonioalkanesulfonate, an alkylated quat, an alkyated/hydroxyalkylated quat, an alkylated/polyhydroxyakylated quat, an alkylated/polyhydroxylated oxypropyl quat, a glycol amine quat, a polyoxyalkylene, an alkoxylated sulfate, a pyridinium moiety, a betaine, a sulfobetaine, an aminocarboxylate, an iminodicarboxylate, a phenol ethoxylate, an imidazoline, an O-alkyl ester, an alkoxylated carboxylate, a carboxylic acid, a carboxylate, a glycerol ester sulfonate, a sulfosuccinamate, a glucamide, a taurinate, a sarcosinate, a glycinate, a dialkanolamide, a monoalkanolamide, a monoalkanolamide sulfate, a diglycolamide, a diglycolamide sulfate, a glycerol ester, a glycerol ester sulfate, an amidopropyl betaine, a sugar ester, a glycerol ester quat, an isethionate, a sulfonated fatty acid, a sulfonated alkyl ester, a C-alkyl ester, an amide, and a polyalkoxylated amidopropyl betaine.

For conditioning application, Z can include, for example, hydroxyl, an alkoxyl, a polyhydroxy moiety, a phosphate ester, a polyphosphate ester, a dialkanolamide, a monoalkanolamide, a diglycolamide, a glycerol ester, a glycerol ether, a sugar ester (e.g., a sorbitan ester), a polyglycerol ether, an amidopropyl betaine, an alkylated quat, an alkyated/hydroxyalkylated quat, an alkylated/polyhydroxyakylated quat, an alkylated/polyhydroxylated oxypropyl quat, a glycol amine quat, a glycerol ester quat, an imidazoline, a sulfonated alkyl ester, an O-alkyl ester, a C-alkyl ester, an amide, an amine, a monoalkylamine, a dialkylamine, a monoglycerol ether, a diglycerol ether, a monoglycerol ester, a polyglycerol ester, a polyglucoside, a polyoxyalkene, an alkoxylated sulfate, an aminocarboxylate, and an alkoxylated carboxylate.

In some preferred embodiments, Z is hydroxyl, an alkoxyl, a glycerol ether, a polyglycerol ether, a polyglycoside, a carboxylate, a sulfate, a sulfonate, an amine, a monoalkylamine, a dialkylamine, an amine oxide, a monoalkanolamide, a betaine, a sulfobetaine, an amidopropyl betaine, a polyalkoxylated amidopropyl betaine, an alkylated quat, an alkyated/hydroxyalkylated quat, an alkylated/polyhydroxyakylated quat, a alkoxylated sulfate, a phosphate ester, a polyphosphate ester, an O-alkyl ester, a C-alkyl ester, a glycerol ester, a sugar ester, a glycerol ester quat, an amide, and a sulfonated alkyl ester, for example, a hydroxyl, carboxylate, a sulfate, a sulfonate, an amine oxide, a monoalkanolamide, amidopropyl betaine, or an alkylated quat. In some embodiments, at least one compound of Formula I requires a counterion, as previously described.

The at least two compounds of Formula I can have a longest linear carbon chain length of about 10 carbon atoms to about 23 carbon atoms, for example, about 16 carbon atoms to about 18 carbon atoms. The exact length of the at least two compounds of Formula I depends on their desired use, as previously described herein.

Characterization of the Scattered-Branched Fatty Compounds

The compositions comprising the mixtures of the at least two scattered-branched fatty compounds can be characterized using two-dimensional (2D) gas chromatography. In this method, the fatty compounds are derivatized and the derivatives are separated by 2D gas chromatography. Mass spectrometry can be used to characterize fragmented samples. The fatty compounds can be derivatized to their 4,4' dimethyloxazoline derivatives prior to analysis via mass spectrometry as described in Zhang, J. Y., Q T. Yu, B. N. Liu and Z. H. Huang,

*Biomed Env. Mass Spectrom.* 15:33 (1988), incorporated herein by reference. By careful examination of minor spectral differences, it possible to determine the location of branch points on the backbones of fatty acid derivatives.

The derivatized samples can be analyzed on a Leco Pegasus 4D Comprehensive 2D gas chromatograph time-of-flight mass spectrometer equipped with a 30M Supelco GammaDex 120 (Supelco 24307) column in the first dimension and a 2M Varian VF5-MS (Varian CP9034) column in the second dimension. Retention times of key chain-length fatty acids (in both first and second dimensions) in test samples can be confirmed by identical preparation and analysis of a standard mixture. Using these columns, 4,4' dimethyloxazoline-derivatized branched-chain fatty acids elute prior to their linear chain-length homologs in the first dimension.

The mass spectral fragmentation pattern of oxazoline derivatives can be used to confirm that the fatty compounds identified using 2D GC contain branches. Oxazoline derivatives fragment along the length of the carbon chain starting from the functional end of the molecule. If a branch point occurs along the backbone, there is a gap in the mass spectrum pattern; which peak is missing (or reduced) depends on the location of the branch.

Blends of the Scattered-Branched Fatty Compounds

The compositions comprising the mixtures of scattered-branched fatty compounds of the invention can be combined with other branched fatty compounds to form compositions useful for consumer products (cleaning and/or personal care compositions). In some embodiments, the compositions of the invention can be combined with fatty compounds derived from isoprene units, such as those compounds described in U.S. Patent Application No. 2010/0137649 and U.S. Patent Application Ser. No. 61/315,594. In some embodiments, the compositions of the invention can be combined with near-terminal branched fatty compounds, such as those compounds described in U.S. patent application Ser. No. 61/364,519. Near-terminal branched fatty compounds have a branch on a carbon that is within 40% of the non-functionalized terminus of the longest carbon chain. In yet other embodiments, the compositions of the invention can be combined with HSAS surfactants derived from renewable resources or petroleum feedstocks. HSAS surfactants are illustrated in the Scheibel JSD article, as well as U.S. Pat. Nos. 6,020,303; 6,060,443; and 6,335,312; and U.S. Patent Application Publication No. 2010/0137649.

Commercial Uses

The compositions of the invention that contain mixtures of scattered-branched chain fatty compounds provide similar performance when used in cleaning compositions and personal care compositions, when compared to fatty compounds that have branching at odd-numbered positions, as previously described. Advantageously, however, the mixtures of the invention provide improved biodegradability.

Thus, in another aspect, the invention relates to cleaning and conditioning compositions containing about 0.001 wt. % to about 99.999 wt. %, preferably about 0.1 wt. % to about 80 wt. %, more preferably about 1 wt. % to about 25 wt % by weight, of the composition comprising the mixture of at least two compounds of Formula I, as previously defined herein, and about 0.001 wt. % to about 99.999 wt. % of one or more additional cleaning components or one or more personal care components.

In cleaning applications, Z can include, for example, hydroxyl, an alkoxyl, a sulfate, a disulfate, a sulfonate, a disulfonate, a sulfosuccinate, an amine, a monoalkylamine, a dialkylamine, an amine oxide, a polyhydroxy moiety, a phosphate ester, a polyphosphate ester, a phosphonate, a glycerol ether, a glycerol ether sulfonate, a polygluconate, a monoglycerol ether, a diglyerol ether, a glycerol ether sulfate, a polyglycerol ether, a polyglycerol ether sulfate, a polyglucoside, an ammonioalkanesulfonate, an alkylated quat, an alkyated/hydroxyalkylated quat, an alkylated/polyhydroxyakylated quat, an alkylated/polyhydroxylated oxypropyl quat, a glycol amine quat, a polyoxyalkylene, an alkoxylated sulfate, a pyridinium moiety, a betaine, a sulfobetaine, an aminocarboxylate, an iminodicarboxylate, a phenol ethoxylate, an imidazoline, an O-alkyl ester, an alkoxylated carboxylate, a carboxylic acid, a carboxylate, a glycerol ester sulfonate, a sulfosuccinamate, a glucamide, a taurinate, a sarcosinate, a glycinate, a dialkanolamide, a monoalkanolamide, a monoalkanolamide sulfate, a diglycolamide, a diglycolamide sulfate, a glycerol ester, a glycerol ester sulfate, an amidopropyl betaine, a sugar ester, a glycerol ester quat, an isethionate, a sulfonated fatty acid, a sulfonated alkyl ester, a C-alkyl ester, an amide, and a polyalkoxylated amidopropyl betaine.

In some embodiments, the cleaning compositions of the invention includes compositions comprising the mixture of at least two compounds of Formula I, as previously defined, having 10 to 19 total carbon atoms, preferably 11 to 18 total carbon atoms, for example, 12 to 14 total carbon atoms, wherein Z is as defined above. In some cleaning composition embodiments, Z can include a carboxylate, a sulfate, a sulfonate, an amine oxide, a monoalkanolamide, an alkoxylated sulfate, a phosphate ester, a polyphosphate ester, and a glycerol ester. For example, Z can be carboxylate, a sulfate, a sulfonate, or an amine oxide. Exemplary scattered-branched chain compounds in the mixtures of this embodiment of the invention can include 2-methyldodecylsulfate, 4-methyldodecylsulfate, 6-methyldodecylsulfate, 8-methyldodecylsulfate, 4,8-dimethyldodecylsulfate, 2-methyldodecylsulfate-1-ethoxylated, 4-methyldodecylsulfate-1-ethoxylated, 6-methyldodecylsulfate-1-ethoxylated, 8-methyldodecylsulfate-1-ethoxylated, 4,8-dimethyldodecylsulfate-1-ethoxylated, 2-methylhexadecylsulfate, 4-methylhexadecylsulfate, 6-methyldodecylsulfate, 8-methylhexadecylsulfate, 4,8-dimethylhexadecylsulfate, 2-methylhexadecylsulfate-1-ethoxylated, 4-methylhexadecylsulfate-1-ethoxylated, 6-methylhexadecylsulfate-1-ethoxylated, 8-methylhexadecylsulfate-1-ethoxylated, and 4,8-dimethylhexadecylsulfate-1-ethoxylated.

In conditioning application, Z can include, for example, hydroxyl, an alkoxyl, a polyhydroxy moiety, a phosphate ester, a polyphosphate ester, a dialkanolamide, a monoalkanolamide, a diglycolamide, a glycerol ester, a glycerol ether, a sugar ester (e.g., a sorbitan ester), a polyglycerol ether, an amidopropyl betaine, an alkylated quat, an alkyated/hydroxyalkylated quat, an alkylated/polyhydroxyakylated quat, an alkylated/polyhydroxylated oxypropyl quat, a glycol amine quat, a glycerol ester quat, an imidazoline, a sulfonated alkyl ester, an O-alkyl ester, a C-alkyl ester, an amide, an amine, a monoalkylamine, a dialkylamine, a monoglycerol ether, a diglycerol ether, a monoglycerol ester, a polyglycerol ester, a polyglucoside, a polyoxyalkene, an alkoxylated sulfate, an aminocarboxylate, and an alkoxylated carboxylate.

In some embodiments, the conditioning compositions of the invention includes compositions comprising the mixture of at least two compounds of Formula I, as previously defined, having 15 to 26 total carbon atoms, wherein Z is as defined above. In some conditioning embodiments, is selected from the group consisting of a hydroxyl, an alkoxyl, a glycerol ether, a polyglycerol ether, a betaine, a sulfobetaine, an amidopropyl betaine, a polyalkoxylated amidopropyl betaine, an alkylated quat, an alkyated/hydroxyalkylated quat, an alkylated/polyhydroxyakylated quat, a phosphate ester, a polyphosphate ester, an O-alkyl ester, a C-alkyl ester, a glycerol ester, a sugar ester, and a glycerol ester quat, an amide, and a sulfonated alkyl ester. For example, Z can be hydroxyl, an alkoxyl, a monoalkanolamide, an amidopropyl betaine, and an alkylated quat. Exemplary scattered-branched chain compounds in the mixtures of this embodiment of the invention can include 4-methylhexadecylpalmitate, 6-methyloctadecylstearate, 4,8-dimethylhexadecyleicosanoate, 4-methylhexadecylstearate, 6-methyloctadecanol, 4-methylhexadecanol, and 4,8-dimethylhexadecanol.

In embodiments when the composition of the invention is incorporated into a personal care composition, the compounds of Formula I can be incorporated into the personal care composition as free detersive surfactants, as discrete conditioning agents, as part of a conditioning ordered gel network, or a combination thereof. The incorporation of gel networks in shampoo compositions is disclosed in U.S. Pat. No. 7,303,744, incorporated herein by reference.

When the compounds of Formula I are derivatized as, for example, sulfates or betaines, they can act as detersive surfactants. In this role, they freely associate with surfaces (e.g., air, water, soil) to provide lather and cleaning benefits. When utilized as detersive surfactants, the compounds of Formula I are added to personal care compositions (e.g., shampoos) as free compounds.

When the compounds of Formula I are derivatized as, for example, cationic surfactants, for conditioning applications, they are incorporated into personal care compositions as part of a liquid crystal structure of an ordered gel network, which acts to increase lubrication and lower friction to, for example, the surface of hair. When formulated as part of the gel network, the compounds of Formula I do not exhibit detersive behavior. In these embodiments, the compound of Formula I is first included in a pre-aggregrate gel network, which is subsequently dispersed into the personal care composition. The compound of Formula I remains part of the gel network after dispersion and is not in equilibrium with the rest of the mixture.

The ordered gel network is derived from a combination of linear fatty alcohols and cationic surfactants (mono-alkyl and/or di-alkyl), and one or more conditioning oils such as silicones. The gel network is processed at elevated temperatures and subsequently cooled to facilitate the formation of lamellar/vesicular structures, translating into a lubricating benefit on the hair, especially in the wet state. The conditioning oils, such as silicone and non-silicone compounds are added to the gel network as dispersions or emulsions after gel network formation. Because these conditioning oils do not interact significantly with the ordered gel phase, they are the primary contributor to dry conditioning and associated benefits. Wax esters can be employed as a partial or full silicone replacement, and can be formulated in both shampoo and rinse off conditioner products. These wax esters are added to the gel network as emulsions/micro-emulsions and, as such, they are not an integral component of the gel network system. In some embodiments, however, the amphiphilic nature of certain wax esters makes possible their incorporation into a gel network phase via appropriate processing techniques and subsequent formulation in either a shampoo or rinse-off conditioner product.

I. Consumer Product Cleaning Compositions

Consumer product cleaning compositions are described in the "Surfactant Science Series", Marcel Dekker, New York, Volumes 1-67 and higher, which is incorporated herein by reference. In particular, liquid compositions are described in detail in Volume 67, "Liquid Detergents," Ed. Kuo-Yann Lai, 1997, ISBN 0-8247-9391-9, incorporated herein by reference. More classical formulations, especially granular type formulations, are described in "Detergent Manufacture including Zeolite Builders and Other New Materials", Ed. M. Sittig, Noyes Data Corporation, 1979, incorporated herein by reference. See also Kirk Othmer's Encyclopedia of Chemical Technology. Nonlimiting examples of consumer product cleaning compositions include light duty liquid deterents (LDL), heavy duty liquid detergents (HDL), heavy duty granular detergents (HDG), softergents (STW), hard surface cleaners (HSC), bar soaps, fabric softeners (FS), and special purpose cleaners (SPC). Any of the aforementioned examples of consumer product cleaning compositions can optionally include perfume, as described in U.S. Pat. No. 5,500,154 and WO 96/02490, each incorporated herein by reference.

Light duty liquid detergents include compositions having surfactancy improving magnesium ions (see, e.g., WO 97/00930A; GB 2,292,562A; U.S. Pat. Nos. 5,376,310; 5,269,974; 5,230,823; 4,923,635; 4,681,704; 4,316,824; 4,133,779, each incorporated herein by reference), organic diamines, various foam stabilizers, foam boosters such as amine oxides (see, e.g., U.S. Pat. No. 4,133,779, incorporated herein by reference), skin feel modifiers of surfactant, emollient, and enzymatic types including proteases, antimicrobial agents, and mixtures thereof (see, e.g., Surfactant Science Series, Vol. 67, pages 240-248, incorporated herein by reference).

Heavy duty liquid detergents include both "structured" (i.e., multi-phase) liquid types (see, e.g., U.S. Pat. Nos. 4,452,717; 4,526,709; 4,530,780; 4,618,446; 4,793,943; 4,659,497; 4,871,467; 4,891,147; 5,006,273; 5,021,195; 5,147,576; 5,160,655, each incorporated herein by reference) and "non-structured" (i.e., isotropic) liquid types, and can be aqueous or nonaqueous (see, e.g., EP 738,778A; WO 97/00937A; WO 97/00936A; EP 752,466A; DE 19623623A; WO 96/10073A; WO 96/10072A; EP 225,654; WO 94/23009; U.S. Pat. Nos. 4,647,393; 4,648,983; 4,655,954; 4,661,280; 4,690,771; 4,744,916; 4,753,750; 4,950,424; 5,004,556; and 5,102,574, each incorporated herein by reference). The HDLs can optionally comprise bleach (see, e.g., U.S. Pat. Nos. 4,470,919; 5,250,212; 5,264,143; 5,275,753; 5,288,746; 5,431,848; and 5,445,756; EP 564,250; WO 94/11483; EP 598,170; EP 598,973; and EP 619,368, each incorporated herein by reference). Additionally or alternatively, the HDLs can optionally comprise enzymes (see, e.g., U.S. Pat. Nos. 3,944,470; 4,111,855; 4,261,868; 4,287,082; 4,305,837; 4,404,115; 4,462,922; 4,529,5225; 4,537,706; 4,537,707; 4,670,179; 4,842,758; 4,900,475; 4,908,150; 5,082,585; 5,156,773; 5,269,960; 5,422,030; 5,431,842; and 5,442,100; WO 92/19709; EP 583,534; EP 583,535; EP 583,536; WO 94/04542; and EP 633,311, each incorporated herein by reference). Also see Surfactant Science Series, Vol. 67, pages 309-324, incorporated herein by reference.

Heavy duty granular detergents include both the "compact" (i.e., agglomerated or otherwise non-spray-dried) type, and the "fluffy" (i.e., spray-dried) type. The compact and fluffy types of HDGs either can be phosphated or nonphosphated. The HDGs can include the anionic-surfactant based type or the "high-nonionic surfactant" type (i.e., the nonionic surfactant is held in or on an absorbent, such as zeolites or other porous inorganic salts). Manufacture of HDGs is disclosed in, e.g., EP 753,571A; WO 96/38531A; U.S. Pat. Nos. 5,576,285; 5,573,697; 5,569,645; 5,565,422; 5,496,487; 5,489,392; and 5,554,587; U.S. Patent Application No. 96/34082A; EP 739,977A; EP 737,739A; WO 96/27655A; WO 96/25482A; WO 96/23048A; WO 96/22352A; EP 709, 449A; WO 96/09370A; and EP 694,608A, each incorporated herein by reference.

Softergents include various granular or liquid softening-through-the wash types of product and can include organic (e.g., quaternary) or inorganic (e.g., clay) softeners (see, e.g., U.S. Pat. Nos. 4,140,641; 4,639,321; 4,751,008; 4,844,821; 4,844,824; 4,873,001; 4,911,852; and 5,017,296; EP 753, 569A; EP 315,126; and EP 422,787, each incorporated herein by reference).

Hard surface cleaners include all-purpose cleaners, such as, for example, cream cleansers, liquid cleaners, and spray cleaners (e.g., glass cleaners, tile cleaners, bleach spray cleaners); and bathroom cleaners (e.g., mildew-removing, bleach-containing, antimicrobial, acidic type, neutral type, basic types). See, for example, EP 743,280A; EP 743,279A, and WO 96/34938 A, each incorporated herein by reference.

Bar soaps include laundry bars. The bar soaps encompass both the synthetic detergent (i.e., syndet) type, the soap-based type, and types with softener (see, e.g., WO 96/35772A; U.S. Pat. No. 5,500,137; and WO 96/01889A, each incorporated herein by reference). These compositions can include those made by common soap-making techniques, such as plodding, and/or more unconventional techniques, such as casting, absorption of surfactant into a porous support, or the like. Other bar soaps, such as those described in BR 9502668; WO 96/04361A; WO 96/04360A; and U.S. Pat. No. 5,540,852, each incorporated herein by reference are also included, as well as other handwash detergents, such as those described in GB 2,292,155 A and WO 96/01306 A, each incorporated herein by reference.

Fabric softeners include both the conventional liquid and liquid concentrate types (see, e.g., EP 754,749A; WO 96/21715A; EP 705,900A; U.S. Pat. Nos. 5,531,910 and 5,500,138, each incorporated herein by reference), as well as dryer-added or substrate-supported types (see, e.g., U.S. Pat. Nos. 5,562,847 and 5,559,088; and EP 704,522A, each incorporated herein by reference). Other fabric softeners include solids, as described in, for example, U.S. Pat. No. 5,505,866, which is incorporated herein by reference.

Special purpose cleaners include home dry cleaning systems (see, e.g., WO 96/30583A; WO 96/30472A; WO 96/30471A; U.S. Pat. No. 5,547,476; WO 96/37652 A); bleach pretreatment products for laundry (see, e.g., EP 751, 210 A); fabric care pretreatment products (see, e.g., EP 752, 469 A); liquid fine fabric detergent types, especially the high-foaming variety; rinse-aids for dishwashing; liquid bleaches including both chlorine type and oxygen bleach type; disinfecting agents; car or carpet cleaners or shampoos (see, e.g., EP 751,213A; WO 96/15308A); metal cleaners; cleaning auxiliaries (e.g., bleach additives, stain-sticks, pre-treatments including special foam type cleaners, as described in EP 753,560A; EP 753,559A; EP 753,558A; EP 753,557A; EP 753,556A, each incorporated herein by reference); and anti-sunfade treatments (see, e.g., WO 96/03486A; WO 96/03481A; WO 96/03369A, each incorporated herein by reference).

Consumer product cleaning compositions, can be formulated into a wide range of forms including, for example, powders, liquids, granules, gels, pastes, tablets, pouches, bars, types delivered in dual-compartment containers, spray or foam detergents and other homogeneous or multiphasic consumer cleaning product forms.

The consumer product compositions of the invention can be applied by hand in unitary or freely alterable dosage, or by automatic dispensing means. The consumer product compositions of the invention are useful in appliances, (e.g., washing machines, dishwashers), in institutional cleaning contexts (e.g., personal cleansing in public facilities), for bottle washing, for surgical instrument cleaning, and/or for cleaning electronic components. The consumer product compositions of the invention can have a wide pH range (e.g., about 2 to about 12, or higher), and a wide range of alkalinity reserve. For example, the consumer product compositions of the invention can be used in very high alkalinity reserves, such as drain unblocking, in which tens of grams of NaOH equivalent can be present per 100 grams of formulation. These mixtures can also be used in medium alkalinity reserves having 1 to 10 grams of NaOH equivalent, and mild or low-alkalinity ranges (e.g, liquid hand cleaners; acidic, hard-surface cleaners). Both high-foaming and low-foaming detergent types are encompassed.

Cleaning Components

A cleaning component is a material required to transform a composition containing only the minimum essential ingredients into a composition useful for laundry or cleaning purposes. The cleaning components are easily recognizable to those of skill in the art as being characteristic of laundry or cleaning products. The precise nature of these cleaning components, and levels of incorporation thereof, depends on the physical form of the composition and the nature of the cleaning operation for which it is to be used.

If the cleaning component is used with bleach, it should have good stability. In some embodiments, the cleaning compositions of the invention should be boron-free and/or phosphate-free, as required by legislation. The cleaning component(s) can be present in the cleaning composition in an amount of about 0.001 wt. % to about 99.999 wt. %, typically about 70 wt. % to about 95 wt. %, based on the total weight of the cleaning composition. When used for a particular application, the concentration of the cleaning composition of the invention can vary widely ranging, for example, from a few parts per million solution to direct application of the neat cleaning composition.

Common cleaning components include, for example, a builder, a surfactant, an enzyme, an enzyme stabilizing system, a polymer, bleach, a bleach activator, a catalytic material, a polymeric soil release agent, a clay soil removal/anti-redeposition agent, a polymeric dispersing agent, a suds suppressor, a brightener, a dyes or a fabric hueing agent, a dye transfer inhibiting agent, a chelating agent, a thickener, a fabric softener, a perfume, an active ingredient, a carrier, a hydrotrope, a processing aid, a dye or a pigment, a solvent for liquid formulations, a solid filler for bar compositions, color speckles, silvercare, an anti-tarnish and/or anti-corrosion agent, a germicide, an alkalinity source, an anti-oxidant, a pro-perfumes, a solubilizing agent, and mixtures thereof.

In some embodiments, the cleaning compositions of the invention (e.g., laundry detergents, laundry detergent additives, hard surface cleaners, synthetic and soap-based laundry bars, fabric softeners and fabric treatment liquids, solids and treatment articles of all kinds) include several cleaning components. In some embodiments, the cleaning compositions of the invention include only one or two cleaning components, such as a bleach additive and a surfactant. A comprehensive list of suitable cleaning components and methods is described in U.S. Pat. Nos. 6,593,285 and 6,020,303, each incorporated herein by reference.

Builders

Detergent builders selected from aluminosilicates and silicates are can be included in the compositions herein, for example to assist in controlling mineral, especially calcium and/or magnesium hardness in wash water, or to assist in the removal of particulate soils from surfaces. Also suitable for use herein are synthesized crystalline ion exchange materials or hydrates thereof, an anhydride form: $x(M_2O).ySiO_2.zM'O$ wherein M is Na and/or K, M' is Ca and/or Mg; y/x is 0.5 to 2.0 and z/x is 0.005 to 1.0 as taught in U.S. Pat. No. 5,427,711, incorporated herein by reference. Detergent builders in place of or in addition to the silicates and aluminosilicates described hereinbefore can optionally be included in the compositions herein, for example to assist in controlling mineral, especially calcium and/or magnesium hardness in wash water or to assist in the removal of particulate soils from surfaces.

Builder level can vary widely depending upon end use and physical form of the composition. Built detergents typically comprise at least about 1 wt. % builder, based on the total weight of the detergent. Liquid formulations typically comprise about 5 wt. % to about 50 wt. %, more typically 5 wt. % to 35 wt. % of builder to the total weight of the detergent. Granular formulations typically comprise from about 10% to about 80%, more typically 15% to 50% builder by weight of the detergent composition. Lower or higher levels of builders are not excluded. For example, certain detergent additive or high-surfactant formulations can be unbuilt.

Suitable builders herein can be selected from the group consisting of phosphates and polyphosphates, especially the sodium salts; carbonates, bicarbonates, sesquicarbonates and carbonate minerals other than sodium carbonate or sesquicarbonate; organic mono-, di-, tri-, and tetracarboxylates especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing detergent compositions.

Detersive Surfactants

In some embodiments, the cleaning compositions of the invention can further comprise additional surfactants, herein also referred to as co-surfactants. The cleaning composition of the present invention typically comprise about 0.1% to about 55%, preferably from about 0.5% to about 15%, by weight of co-surfactants. (e.g., anionic co-surfactants, nonionic co-surfactants, cationic co-surfactants). It is to be understood that the compositions of the invention may be used singly in cleaning compositions or in combination with other detersive surfactants. Typically, fully-formulated cleaning compositions will contain a mixture of surfactant types in order to obtain broad-scale cleaning performance over a variety of soils and stains, and under a variety of usage conditions. One advantage of the compositions of the invention is their ability to be readily formulated in combination with other known surfactant types. Nonlimiting examples of additional surfactants which may be used herein typically at levels from about 1% to about 55%, by weight, include the unsaturated sulfates, the $C_{10}$-$C_{18}$ alkyl alkoxy, $C_{10}$-$C_{18}$ alkyl alkoxy carboxylates, the $C_{10}$-$C_{18}$ glycerol ether sulfates, the $C_{10}$-$C_{18}$ alkyl polyglycosides and their corresponding sulfated polyglycosides, and $C_{12}$-$C_{18}$ alpha-sulfonated fatty acid esters. Nonionic surfactants such as the ethoxylated $C_{10}$-$C_{18}$ alcohols and alkyl phenols can also be used. If desired, other conventional surfactants such as the $C_{12}$-$C_{18}$ betaines and sulfobetaines ("sultaines"), $C_{10}$-$C_{18}$ amine oxides, and the like, can also be included in the overall compositions. The $C_{10}$-$C_{18}$ N-alkyl polyhydroxy fatty acid amides can also be used. See WO 9,206,154, incorporated herein by reference. Other sugar-derived surfactants include the N-alkoxy polyhydroxy fatty acid amides. The N-propyl through N-hexyl $C_{12}$-$C_{18}$ glucamides can be used for low sudsing. $C_{10}$-$C_{20}$ conventional soaps may also be used. If high sudsing is desired, the branched-chain $C_{10}$-$C_{16}$ soaps may be used.

A wide range of these co-surfactants can be used in the detergent compositions of the present invention. A typical listing of anionic, nonionic, ampholytic and zwitterionic classes, and species of these co-surfactants, is given in U.S. Pat. No. 3,664,961, incorporated herein by reference. Amphoteric surfactants are also described in detail in "Amphoteric Surfactants, Second Edition", E. G. Lomax, Editor (published 1996, by Marcel Dekker, Inc.), incorporated herein by reference.

Amine-Neutralized Anionic Surfactants

Anionic surfactants of the present invention and adjunct anionic cosurfactants may be neutralized by amines or, preferably, alkanolamines, and alkanolamines are preferred. Suitable non-limiting examples including monoethanolamine, triethanolamine, and other alkanolamines known in the art.

Enzymes

Enzymes can be included in the present cleaning compositions for a variety of purposes, including removal of protein-based, carbohydrate-based, or triglyceride-based stains from substrates, for the prevention of refugee dye transfer in fabric laundering, and for fabric restoration. Suitable enzymes include proteases, amylases, lipases, cellulases, peroxidases, and mixtures thereof of any suitable origin, such as vegetable, animal, bacterial, fungal and yeast origin. Preferred selections are influenced by factors such as pH-activity and/or stability optima, thermostability, and stability to active detergents, builders and the like. In this respect bacterial or fungal enzymes are preferred, such as bacterial amylases and proteases, and fungal cellulases.

Enzymes are normally incorporated into cleaning compositions at levels sufficient to provide a "cleaning-effective amount." The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the consumer product cleaning composition. Stated otherwise, the compositions herein will typically comprise from 0.001% to 5%, preferably 0.01%-1% by weight of a commercial enzyme preparation.

A range of enzyme materials and means for their incorporation into synthetic detergent compositions is disclosed in WO 9307263 A; WO 9307260 A; WO 8908694 A; U.S. Pat. Nos. 3,553,139; 4,101,457; and 4,507,219, each incorporated herein by reference. Enzyme materials useful for liquid detergent formulations, and their incorporation into such formulations, are disclosed in U.S. Pat. No. 4,261,868, incorporated herein by reference.

Enzyme Stabilizing System

Enzymes for use in detergents can be stabilized by various techniques. Enzyme stabilization techniques are disclosed and exemplified in U.S. Pat. Nos. 3,600,319 and 3,519,570; EP 199,405, EP 200,586; and WO 9401532 A, each incorporated herein by reference. Thus, the enzyme-containing compositions herein may optionally also comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the cleaning composition.

Bleaching Compounds, Bleaching Agents, Bleach Activators, and Bleach Catalysts

In some embodiments, the cleaning compositions can further contain bleaching agents or bleaching compositions containing a bleaching agent and one or more bleach activators. Bleaching agents will typically be present at levels of about 1 wt. % to about 30 wt. %, more typically from about 5 wt. % to about 20 wt. %, based on the total weight of the composition, especially for fabric laundering. If present, the amount of bleach activators will typically be about 0.1 wt. % to about 60 wt. %, more typically about 0.5 wt. % to about 40 wt. % of the bleaching composition comprising the bleaching agent-plus-bleach activator.

Examples of bleaching agents include oxygen bleach, perborate bleach, percarboxylic acid bleach and salts thereof, peroxygen bleach, persulfate bleach, percarbonate bleach, and mixtures thereof. Examples of bleaching agents are disclosed in U.S. Pat. No. 4,483,781, U.S. patent application Ser. No. 740,446, European Patent Application 0,133,354, U.S. Pat. No. 4,412,934, and U.S. Pat. No. 4,634,551, each incorporated herein by reference.

Examples of bleach activators (e.g., acyl lactam activators) are disclosed in U.S. Pat. Nos. 4,915,854; 4,412,934; 4,634,551; 4,634,551; and 4,966,723, each incorporated herein by reference.

In some embodiments, a laundry detergent composition comprises a transition metal catalyst. Preferably, the transition metal catalyst may be encapsulated. The transition metal bleach catalyst typically comprises a transition metal ion, preferably selected from transition metal selected from the group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV), more preferably Mn(II), Mn(III), Mn(IV), Fe(II), Fe(III), Cr(II), Cr(III), Cr(IV), Cr(V), and Cr(VI). The transition metal bleach catalyst typically comprises a ligand, preferably a macropolycyclic ligand, more preferably a cross-bridged macropolycyclic ligand. The transition metal ion is preferably coordinated with the ligand. Preferably, the ligand comprises at least four donor atoms, at least two of which are bridgehead donor atoms. Suitable transition metal bleach catalysts are described in U.S. Pat. No. 5,580,485, U.S. Pat. No. 4,430,243; U.S. Pat. No. 4,728,455; U.S. Pat. No. 5,246,621; U.S. Pat. No. 5,244,594; U.S. Pat. No. 5,284,944; U.S. Pat. No. 5,194,416; U.S. Pat. No. 5,246,612; U.S. Pat. No. 5,256,779; U.S. Pat. No. 5,280,117; U.S. Pat. No. 5,274,147; U.S. Pat. No. 5,153,161; U.S. Pat. No. 5,227,084; U.S. Pat. No. 5,114,606; U.S. Pat. No. 5,114,611, EP 549,271 A1; EP 544,490 A1; EP 549,272 A1; and EP 544,440 A2, each incorporated herein by reference. A suitable transition metal bleach catalyst is a manganese-based catalyst, for example disclosed in U.S. Pat. No. 5,576,282, incorporated herein by reference. Suitable cobalt bleach catalysts are described, for example, in U.S. Pat. No. 5,597,936 and U.S. Pat. No. 5,595,967, each incorporated herein by reference. Such cobalt catalysts are readily prepared by known procedures, such as taught for example in U.S. Pat. No. 5,597,936, and U.S. Pat. No. 5,595,967, each incorporated herein by reference. A suitable transition metal bleach catalyst is a transition metal complex of ligand such as bispidones described in WO 05/042532 A1, incorporated herein by reference.

Bleaching agents other than oxygen bleaching agents are also known in the art and can be utilized herein (e.g., photoactivated bleaching agents such as the sulfonated zinc and/or aluminum phthalocyanines (U.S. Pat. No. 4,033,718, incorporated herein by reference), or pre-formed organic peracids, such as peroxycarboxylic acid or salt thereof, or a peroxysulphonic acid or salt thereof. A suitable organic peracid is phthaloylimidoperoxycaproic acid. If used, consumer product cleaning compositions will typically contain from about 0.025% to about 1.25%, by weight, of such bleaches, especially sulfonate zinc phthalocyanine.

Polymeric Soil Release Agent

Known polymeric soil release agents, hereinafter "SRA" or "SRA's", can optionally be employed in the present cleaning compositions. If utilized, SRA's will generally comprise about 0.01% to about 10.0%, typically about 0.1% to about 5%, preferably about 0.2% to about 3.0% by weight, of the composition.

Preferred SRA's typically have hydrophilic segments to hydrophilize the surface of hydrophobic fibers, such as polyester and nylon, and hydrophobic segments to deposit upon hydrophobic fibers and remain adhered thereto through completion of washing and rinsing cycles, thereby serving as an anchor for the hydrophilic segments. This can enable stains occurring subsequent to treatment with SRA to be more easily cleaned in later washing procedures.

SRA's can include, for example, a variety of charged, e.g., anionic or even cationic (see U.S. Pat. No. 4,956,447, incorporated herein by reference), as well as noncharged monomer units, and structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products. Examples of SRAs are described in U.S. Pat. Nos. 4,968,451; 4,711,730; 4,721,580; 4,702,857; 4,877,896; 3,959,230; 3,893,929; 4,000,093; 5,415,807; 4,201,824; 4,240,918; 4,525,524; 4,201,824; 4,579,681; and 4,787,989; European Patent Application 0 219 048; 279,134 A; 457,205 A; and DE 2,335,044, all of which are incorporated herein by reference.

Clay Soil Removal/Anti-Redeposition Agents

The compositions of the present invention can also optionally contain water-soluble ethoxylated amines having clay soil removal and antiredeposition properties. Granular detergent compositions which contain these compounds typically contain about 0.01% to about 10.0%, by weight, of the water-soluble ethoxylates amines; liquid detergent compositions typically contain about 0.01% to about 5% by weight of these compounds.

Exemplary clay soil removal and antiredeposition agents are described in U.S. Pat. Nos. 4,597,898; 548,744; 4,891,160; European Patent Application Nos. 111,965; 111,984; 112,592; and WO 95/32272, which are all incorporated herein by reference.

Polymeric Dispersing Agents

Polymeric dispersing agents can advantageously be utilized at levels of about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition. Examples of polymeric dispersing agents are found in U.S. Pat. No. 3,308,067, European Patent Application No. 66915, EP 193,360, and EP 193,360, each incorporated herein by reference.

Alkoxylated Polyamines

Soil suspension, grease cleaning, and particulate cleaning polymers may include the alkoxylated polyamines. Such materials include but are not limited to ethoxylated polyethyleneimine, ethoxylated hexamethylene diamine, and sulfated versions thereof. A useful example is 600 g/mol polyethyleneimine core ethoxylated to 20 EO groups per NH and is available from BASF.

Brightener

Any optical brighteners or other brightening or whitening agents known in the art can be incorporated at levels typically of about 0.01% to about 1.2%, by weight, into the cleaning compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982), incorporated herein by reference. Specific examples of optical brighteners which are useful in the present compositions are those identified in U.S. Pat. No. 4,790,856 and U.S. Pat. No. 3,646,015, each incorporated herein by reference.

Fabric Hueing Agents

The compositions of the present invention my include fabric hueing agents. Non-limiting examples include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. In another aspect, suitable polymeric dyes include polymeric dyes selected from the group consisting of fabric-substantive colorants sold under the name of LIQUITINT®(Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of LIQUITINT t® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Dye Transfer Inhibiting Agents

The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise about 0.01% to about 10% by weight of the composition, preferably from about 0.01% to about 5%, and more preferably from about 0.05% to about 2%.

Chelating Agents

The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein. If utilized, these chelating agents will generally comprise about 0.1% to about 15% by weight of the detergent compositions herein. More preferably, if utilized, the chelating agents will comprise from 0.1% to about 3.0% by weight of such compositions.

Suds Suppressors

Compounds for reducing or suppressing the formation of suds can be incorporated into the compositions of the present invention. Suds suppression can be of particular importance in the so-called "high concentration cleaning process" as described in U.S. Pat. Nos. 4,489,455 and 4,489,574, which are incorporated herein by reference, and in front-loading European-style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols. Suds supressors are described in U.S. Pat. Nos. 2,954,347; 4,265,779; 4,265,779; 3,455,839; 3,933,672; 4,652,392; 4,978,471; 4,983,316; 5,288,431; 4,639,489; 4,749,740; and 4,798,679; 4,075,118; European Patent Application No. 89307851.9; EP 150,872; and DOS 2,124,526 which are all incorporated herein by reference.

For any detergent compositions to be used in automatic laundry washing machines, suds should not form to the extent that they overflow the washing machine. Suds suppressors, when utilized, are preferably present in a "suds suppressing amount. By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0% to about 10% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%-3% by weight of the finished compositions.

Structurant/Thickeners

Structured liquids can either be internally structured, whereby the structure is formed by primary ingredients (e.g. surfactant material) and/or externally structured by providing a three dimensional matrix structure using secondary ingredients (e.g. polymers, clay and/or silicate material). The composition may comprise a structurant in an amount of about 0.01 wt. % to 5 wt. %, preferably about 0.1 wt. % to 2.0 wt. %, based on the total weight of the composition. The structurant is typically selected from the group consisting of diglycerides and triglycerides, ethylene glycol distearate, microcrystalline cellulose, cellulose-based materials, microfiber cellulose, biopolymers, xanthan gum, gellan gum, and mixtures thereof. A suitable structurant includes hydrogenated castor oil, and non-ethoxylated derivatives thereof. A suitable structurant is disclosed in U.S. Pat. No. 6,855,680, incorporated herein by reference. Such structurants have a thread-like structuring system having a range of aspect ratios. Other suitable structurants and the processes for making them are described in WO2010/034736, incorporated herein by reference.

Alkoxylated Polycarboxylates

Alkoxylated polycarboxylates, such as those prepared from polyacrylates, are useful herein to provide additional grease removal performance. Such materials are described in WO 91/08281 and PCT 90/01815, incorporated herein by reference. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise about 0.05% to about 10%, by weight, of the compositions herein.

Amphiphilic Graft Co-Polymer

The compositions of the invention, and their mixtures with other cosurfactants and other adjunct ingredients, can be used with an amphilic graft co-polymer, preferably the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan HP22, supplied from BASF.

Fabric Softeners

Various through-the-wash fabric softeners, especially the impalpable smectite clays of U.S. Pat. No. 4,062,647, incorporated herein by reference, as well as other softener clays known in the art, can optionally be used typically at levels of about 0.5% to about 10%, by weight in the present compositions to provide fabric softener benefits concurrently with fabric cleaning. Clay softeners can be used in combination with amine and cationic softeners as disclosed, for example, in U.S. Pat. No. 4,375,416, and U.S. Pat. No. 4,291,071, which are incorporated herein by reference.

Perfumes

Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise about 0.01% to about 2%, by weight, of the detergent compositions herein, and individual lay softeners can be used in combination with amine and cationic softeners perfumery ingredients can comprise about 0.0001% to about 90%, by weight, of a finished perfume composition.

Other Ingredients

A wide variety of other ingredients useful in the cleaning compositions can be included in the compositions herein, including other active ingredients, carriers, hydrotropes, processing aids, dyes or pigments, solvents for liquid formulations, solid fillers for bar compositions, etc. If high sudsing is desired, suds boosters such as the $C_{10}$-$C_{16}$ alkanolamides can be incorporated into the compositions, typically at 1%-10% levels. The $C_{10}$-$C_{13}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$ $CaCl_2$, $CaSO_4$ and the like, can be added at levels of, typically, 0.1%-2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% by weight of such carriers.

The cleaning compositions herein will preferably be formulated such that, during use in aqueous cleaning operations, the wash water will have a pH of between about 6.5 and about 11, preferably between about 7.5 and 10.5. Liquid dishwashing product formulations preferably have a pH between about 6.8 and about 9.0. Laundry products are typically at pH 9-11. Techniques for controlling pH at recommended usage levels include the use of buffers, alkalis, acids, etc., and are well known to those skilled in the art.

Form of the Compositions

The compositions in accordance with the invention can take a variety of physical forms including granular, tablet, bar and liquid forms. Also included are a sachet, a two-in-one pouch containing both solid and liquid compartments. The compositions can be the so-called concentrated granular detergent compositions adapted to be added to a washing machine by means of a dispensing device placed in the machine drum with the soiled fabric load.

The mean particle size of the components of granular compositions in accordance with the invention should preferably be such that no more that 5% of particles are greater than 1.7 mm in diameter and not more than 5% of particles are less than 0.15 mm in diameter.

The term mean particle size as defined herein is calculated by sieving a sample of the composition into a number of fractions (typically 5 fractions) on a series of Tyler sieves. The weight fractions thereby obtained are plotted against the aperture size of the sieves. The mean particle size is taken to be the aperture size through which 50% by weight of the sample would pass.

The bulk density of granular detergent compositions in accordance with the present invention typically have a bulk density of at least 600 g/liter, more preferably from 650 g/liter to 1200 g/liter. Bulk density is measured by means of a simple funnel and cup device consisting of a conical funnel moulded rigidly on a base and provided with a flap valve at its lower extremity to allow the contents of the funnel to be emptied into an axially aligned cylindrical cup disposed below the funnel. The funnel is 130 mm high and has internal diameters of 130 mm and 40 mm at its respective upper and lower extremities. It is mounted so that the lower extremity is 140 mm above the upper surface of the base. The cup has an overall height of 90 mm, an internal height of 87 mm and an internal diameter of 84 mm. Its nominal volume is 500 mm.

To carry out a measurement, the funnel is filled with powder by hand pouring, the flap valve is opened and powder allowed to overfill the cup. The filled cup is removed from the frame and excess powder removed from the cup by passing a straight edged implement eg; a knife, across its upper edge. The filled cup is then weighed and the value obtained for the weight of powder doubled to provide a bulk density in g/L. Replicate measurements are made as required.

Surfactant Agglomerate Particles

One of the preferred methods of delivering surfactant in consumer products is to make surfactant agglomerate particles, which may take the form of flakes, prills, marumes, noodles, ribbons, but preferably take the form of granules. A preferred way to process the particles is by agglomerating powders (e.g. aluminosilicate, carbonate) with high active surfactant pastes and to control the particle size of the resultant agglomerates within specified limits. Such a process involves mixing an effective amount of powder with a high active surfactant paste in one or more agglomerators such as a pan agglomerator, a Z-blade mixer, or more preferably an in-line mixer, such as those manufactured by Schugi (Holland) BV, 29 Chroomstraat 8211 AS, Lelystad, Netherlands, and Gebruder Lödige Maschinenbau GmbH, D-4790 Paderbom 1, Elsenerstrasse 7-9, Postfach 2050, Germany. Most preferably a high shear mixer is used, such as a Lödige CB (Trade Name).

A high active surfactant paste comprising about 50 wt. % to about 95 wt. %, preferably about 70 wt. % to about 85 wt. % of surfactant is typically used. The paste may be pumped into the agglomerator at a temperature high enough to maintain a pumpable viscosity, but low enough to avoid degradation of the anionic surfactants used. A typical operating temperature of the paste includes about 50° C. to about 80° C.

Compacted Liquid or Powder Detergents

The compositions of the invention, and their mixtures with other cosurfactants and other adjunct ingredients, are suited to compact detergent formulations. For liquid detergents, the composition preferably comprises less than about 20 wt. %, or less than about 10 wt. %, or less than about 5 wt. %, or less than about 4 wt. % or less than about 3 wt. % free water, or less than about 2 wt. % free water, or less than about 1 wt. % free water, and may even be anhydrous, typically comprising no deliberately added free water. Free water is typically measured using Karl Fischer titration. The laundry detergent composition (e.g., 2 g) is extracted into 50 mL of dry methanol at room temperature for about 20 minutes and about 1 mL of the solution is analyzed by Karl Fischer titration. For powder detergents, the amount of filler (e.g., sodium sulfate, sodium chloride, clay, or other inert solid ingredients) preferably comprises less than about 20 wt. %, or less than about 10 wt. %, or less than about 5 wt. %, or less than about 4 wt. % or less than about 3 wt. % free water, or less than about 2 wt. % free water, or less than about 1 wt. % filler.

Laundry Washing Method

In some embodiments, the invention provides a method of laundering soiled fabrics comprising contacting the soiled fabrics with an effective amount of a detergent composition described herein.

Machine laundry methods herein typically comprise treating soiled laundry with an aqueous wash solution in a washing machine having dissolved or dispensed therein an effective amount of a machine laundry detergent composition in accord with the invention. By an effective amount of the detergent composition it is meant from 20 g to 300 g of product dissolved or dispersed in a wash solution of volume from 5 to 65 liters, as are typical product dosages and wash solution volumes commonly employed in conventional machine laundry methods.

As noted, the compositions of the invention are used herein in cleaning compositions, preferably in combination with other detersive surfactants, at levels which are effective for achieving at least a directional improvement in cleaning performance. In the context of a fabric laundry composition, such "usage levels" can vary depending not only on the type and severity of the soils and stains, but also on the wash water temperature, the volume of wash water and the type of washing machine (e.g., top-loading, front-loading, top-loading, vertical-axis Japanese-type automatic washing machine)

As can be seen from the foregoing, the compositions of the invention used in a machine-wash laundering context can vary, depending on the habits and practices of the user, the type of washing machine, and the like. In this context, however, one heretofore unappreciated advantage of the compositions of the invention is their ability to provide at least directional improvements in performance over a spectrum of soils and stains, even when used at relatively low levels with respect to the other surfactants (generally anionics or anionic/nonionic mixtures) in the finished compositions.

In addition, another advantage of the compositions of the invention and the detergent compositions containing them is their desirable performance in cold water. The invention herein includes methods for laundering of fabrics at reduced wash temperatures. This method of laundering fabric comprises the step of contacting a laundry detergent composition to water to form a wash liquor, and laundering fabric in said wash liquor, wherein the wash liquor has a temperature of above 0° C. to 20° C., preferably to 19° C., or to 18° C., or to 17° C., or to 16° C., or to 15° C., or to 14° C., or to 13° C., or to 12° C., or to 11° C., or to 10° C., or to 9° C., or to 8° C., or to 7° C., or to 6° C., or even to 5° C. The fabric may be contacted to the water prior to, or after, or simultaneous with, contacting the laundry detergent composition with water.

A further method of use of the materials of the present invention involves pretreatment of stains prior to laundering.

Hand Machine Dishwashing Methods

Any suitable methods for machine washing or cleaning soiled tableware, particularly soiled silverware are envisaged.

A preferred liquid hand dishwashing method involves either the dissolution of the detergent composition into a recepticle containing water, or by the direct application of the liquid hand dishwashing detergent composition onto soiled dishware.

A preferred machine dishwashing method comprises treating soiled articles selected from crockery, glassware, hollowware, silverware and cutlery and mixtures thereof, with an aqueous liquid having dissolved or dispensed therein an effective amount of a machine dishwashing composition in accord with the invention. By an effective amount of the machine dishwashing composition it is meant from 8 g to 60 g of product dissolved or dispersed in a wash solution of volume from 3 to 10 liters, as are typical product dosages and wash solution volumes commonly employed in conventional machine dishwashing methods.

Cleansing Hard Surfaces

Any suitable methods for cleaning hard surfaces, such as wood, ceramic, glass, marble, porcelain, grout or concrete using the compositions described herein are envisaged. In some embodiments, an effective amount of a detergent composition of the invention is directly applied to the hard surface.

Packaging for the Compositions

Commercially marketed executions of the bleaching compositions can be packaged in any suitable container including those constructed from paper, cardboard, plastic materials and any suitable laminates. A preferred packaging execution is described in European Application No. 94921505.7, incorporated herein by reference.

II. Personal Care Compositions

Personal care compositions, which can be aqueous or anhydrous, are described in European Patent No. 1299080, U.S. Patent Application Publication No. 2009/0232873, and U.S. Pat. No. 5,932,202. Nonlimiting examples of personal care products include those intended for use with hair or skin such as a shampoo, a hair conditioner, a hair treatment, a facial soap, a body wash, a body soap (liquid or bar), a foam bath, a make-up remover, a skin care product, an acne control product, a deodorant, an antiperspirant, a shaving aid, a cosmetic, a depilatory, a fragrance, special purpose cleaners and mixtures thereof. See, e.g., WO 96/37595A; WO 96/37592A; WO 96/37591A; WO 96/37589A; WO 96/37588A; GB 2,297,975A; GB 2,297,762A; GB 2,297,761A; WO 96/17916A; WO 96/12468A, each incorporated herein by reference. Personal care cleaning compositions can be formulated into, for example, a wipe, a cloth, a bar, a liquid, a powder, a crème, a lotion, a spray, an aerosol, a foam, a mousse, a serum, a capsule, a gel, an emulsion, a doe foot, a roll-on applicator, a stick, a sponge, an ointment, a paste, an emulsion spray, a tonic, a cosmetic, and mixtures thereof. Products, such as devices, appliances, applicators, implements, combs, brushes, and substrates are also encompassed by the invention. These products can be used alone on the skin or hair, or in combination with the personal care cleaning compositions described herein.

The personal care product of the invention can be applied by hand in unitary or freely alterable dosage, or by automatic dispensing means. The personal care composition of the invention also can be dispensed from an article, such as, for example, a bottle, a jar, a tube, a sachet, a pouch, a container, a tottle, a vial, an ampule, or a compact, or can be integrally contained within a delivery form, such as a wipe.

In some preferred embodiments, the personal care compositions of the present invention may be used in direct application to the skin or in a conventional manner for cleansing, treating or conditioning skin and hair. The compositions herein are useful for cleansing or conditioning the hair and scalp, and other areas of the body and for any other area of skin in need of treatment. The present invention may be used for treating, cleansing, or conditioning of the skin or hair of animals as well. An effective amount of the composition, typically from about 1 g to about 50 g, preferably from about 1 g to about 20 g of the composition, for cleansing and/or conditioning hair, skin or other area of the body, is topically applied to the hair, skin or other area that has preferably been wetted, generally with water, and then rinsed off. Application to the hair typically includes working the composition through the hair.

Personal Care Components

A personal care component is a material required to transform a composition containing only the minimum essential ingredients into a composition useful for personal care purposes. The personal care components are easily recognizable to those of skill in the art as being characteristic of personal care products. The precise nature of these personal care components, and levels of incorporation thereof, depends on the physical form of the composition and the nature of the personal care operation for which it is to be used The personal component(s) can be present in the personal care composition in an amount of about 0.001 wt. % to about 99.999 wt. %, typically about 70 wt. % to about 95 wt. %, based on the total weight of the personal care composition. When used for a particular application, the concentration of the personal care composition of the invention can vary widely ranging, for example, from a few parts per million solution to direct application of the personal care composition.

Common personal care components include, for example, an oil, an emollient, a moisturizer, a carrier, an extract, a vitamin, a mineral, an anti-aging compound, a surfactant, a solvent, a polymer, a preservative, an antimicrobial, a wax, a particle, a colorant, a dye, a fragrance, and mixtures thereof. In some embodiments, the personal care compositions of the invention (e.g.,) include several personal care components. In some embodiments, the personal care compositions include only one or two personal components, such as a detersive surfactant and a hair conditioning active. Lists of personal care components and methods are described in U.S. Patent Application No. 2007/002022 and U.S. Pat. No. 5,932,202, incorporated herein by reference.

The personal care composition can also include thickeners; glossing and shine-imparting agents; dyes or color-imparting agents; particles; glitter or colored particles; and mixtures thereof. Additionally or alternatively, the personal care composition can include at least one silicone comprising an amine group, a surfactant, at least one cosmetically acceptable carrier, cationic polymers, and high melting point fatty compounds.

In one embodiment, the personal care composition is a hair styling composition and further comprises at least one hair fixing polymer and at least one cosmetically acceptable carrier. The hair styling composition may be in a form selected from the group consisting of mousses, hairsprays, pump sprays, gels, foams, and waxes. The hair styling composition may further comprise a propellant wherein said propellant is selected from the group consisting of propane, butane, and nitrogen gas. Other propellants are also suitable, for example 1,1-difluoroethane, compressed air, isobutene, dimethylether. The hair styling composition comprises a hair fixing polymer selected from the group consisting of anionic polymers, cationic polymers, nonionic polymers, zwitterionic polymers, amphoteric polymers, and mixtures thereof. In a preferred embodiment, the hair styling composition comprises a hair fixing polymer which comprises acrylate groups.

In another embodiment, preferred hair fixing polymers are in a quantity of from about 0.01% to about 20% by total weight of the composition, more preferably from about 1% to about 10%. Hair fixing polymers may be selected from polymers with anionic or anionizable groups, polymers with cationic or cationizable groups, zwitterionic and/or amphoteric polymers, and nonionic polymers.

The personal care compositions of the present inventions may include the following components.

Detersive Surfactant

The composition of the present invention may include a detersive surfactant. The detersive surfactant component is included to provide improved cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the personal care composition herein include those which are known for use in hair care or other personal care cleansing compositions. The concentration of the anionic surfactant component in the composition should be sufficient to provide the desired cleaning and lather performance, and generally range from about 5 wt. % to about 50 wt. %, preferably from about 8 wt. % to about 30 wt. %, more preferably from about 10 wt. % to about 25 wt. %, even more preferably from about 12 wt. % to about 22 wt. %, based on the total weight of the personal care composition.

Preferred anionic surfactants suitable for use in the personal care composition are the alkyl and alkyl ether sulfates. These materials have the respective formulae $ROSO_3M$ and $RO(C_2H_4O)_xSO_3M$, wherein R is alkyl or alkenyl of about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with about 0 to about 10, preferably about 2 to about 5, more preferably about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1—SO_3-M]$ where $R^1$ is a straight or branched chain, saturated, aliphatic hydrocarbon radical having about 8 to about 24, preferably about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include alkene sulfonates having about 10 to about 24 carbon atoms. In addition to the true alkene sulfonates and a proportion of hydroxy-alkanesulfonates, the alkene sulfonates can contain minor amounts of other materials, such as alkene disulfonates depending upon the reaction conditions, proportion of reactants, the nature of the starting alkenes and impurities in the alkene stock and side reactions during the sulfonation process. A nonlimiting example of such an alpha-alkene sulfonate mixture is described in U.S. Pat. No. 3,332,880, incorporated herein by reference.

Another class of anionic detersive surfactants suitable for use in the compositions are the beta-alkyloxy alkane sulfonates. These surfactants conform to the formula:

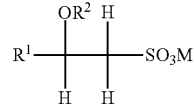

where $R^1$ is a straight chain alkyl group having about 6 to about 20 carbon atoms, $R^2$ is a lower alkyl group having about 1 to about 3 carbon atoms, preferably 1 carbon atom, and M is a water-soluble cation as described hereinbefore.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentration of such amphoteric detersive surfactants preferably are about 0.5 wt. % to about 20 wt. %, preferably about 1 wt. % to about 10 wt. %. Nonlimiting examples of suitable zwitterionic or amphoteric surfactants are described in U.S. Pat. Nos. 5,104,646 and 5,106,609, each incorporated herein by reference.

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The personal care compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Nonlimiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; and 2,528,378, each incorporated herein by reference.

Cationic Surfactant System

The composition of the present invention may comprise a cationic surfactant system. The cationic surfactant system can be one cationic surfactant or a mixture of two or more cationic surfactants. If present, the cationic surfactant system is included in the composition at a level by weight of from about 0.1% to about 10%, preferably from about 0.5% to about 8%, more preferably from about 1% to about 5%, still more preferably from about 1.4% to about 4%, in view of balance among ease-to-rinse feel, rheology and wet conditioning benefits.

A variety of cationic surfactants including mono- and dialkyl chain cationic surfactants can be used in the compositions of the present invention. Among them, preferred are mono-alkyl chain cationic surfactants in view of providing desired gel matrix and wet conditioning benefits. Examples of preferred mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt. Mono-alkyl amines, and primary, secondary, and tertiary fatty amines are useful as cationic surfactants. Nonlimiting examples of cationic surfactants are disclosed in U.S. Pat. No. 4,275,055, incorporated herein by reference.

High Melting Point Fatty Compound

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

The high melting point fatty compound is included in the composition at a level of from about 0.1% to about 40%, preferably from about 1% to about 30%, more preferably from about 1.5% to about 16% by weight of the composition, from about 1.5% to about 8% in view of providing improved conditioning benefits such as slippery feel during the application to wet hair, softness and moisturized feel on dry hair.

Cationic Polymers

The compositions of the present invention may contain a cationic polymer. Concentrations of the cationic polymer in the composition typically range from about 0.05% to about 3%, in another embodiment from about 0.075% to about 2.0%, and in yet another embodiment from about 0.1% to about 1.0%. Suitable cationic polymers will have cationic charge densities of at least about 0.5 meq/gm, in another embodiment at least about 0.9 meq/gm, in another embodiment at least about 1.2 meq/gm, in yet another embodiment at least about 1.5 meq/gm, but in one embodiment also less than about 7 meq/gm, and in another embodiment less than about 5 meq/gm, at the pH of intended use of the composition, which pH will generally range from about pH 3 to about pH 9, in one embodiment between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, in one embodiment between about 50,000 and about 5 million, and in another embodiment between about 100,000 and about 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition.

Suitable cationic polymers are described in U.S. Pat. Nos. 3,962,418; 3,958,581; and U.S. Publication No. 2007/0207109A1, which are all incorporated herein by reference.

Nonionic Polymers

The composition of the present invention may include a nonionic polymer. Polyalkylene glycols having a molecular weight of more than about 1000 are useful herein. Useful are those having the following general formula:

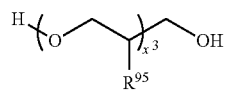

wherein $R^{95}$ is selected from the group consisting of H, methyl, and mixtures thereof.

Conditioning Agents

Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agent typically ranges from about 0.01% to about 10%. Non-limiting examples of suitable silicone conditioning agents, and optional suspending agents for the silicone, are described in U.S. Reissue Pat. No. 34,584, U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; US Patent Application Nos. 2007/0286837A1; 2005/0048549A1; 2007/0041929A1; British Pat. No. 849,433; German Patent No. DE 10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters. Also suitable for use in the compositions herein are the conditioning agents described by the Procter & Gamble Company in U.S. Pat. Nos. 5,674,478, and 5,750,122, incorporated herein by reference. Also suitable for use herein are those conditioning agents described in U.S. Pat. Nos. 4,529,586, 4,507,280, 4,663,158, 4,197,865, 4,217,914, 4,381,919, and 4,422,853, which are all incorporated herein by reference.

Anti-Dandruff Actives

The compositions of the present invention may also contain an anti-dandruff agent. Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982, which are all incorporated herein by reference.

Humectant

The compositions of the present invention may contain a humectant. The humectants herein are selected from the group consisting of polyhydric alcohols, water soluble alkoxylated nonionic polymers, and mixtures thereof. The humectants, when used herein, are preferably used at levels of from about 0.1% to about 20%, more preferably from about 0.5% to about 5%.

Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, preferably from about 0.3% to about 5.0%.

Suspending agents useful herein include anionic polymers and nonionic polymers (e.g., vinyl polymers, acyl derivatives, long chain amine oxides, and mixtures thereof, alkanol amides of fatty acids, long chain esters of long chain alkanol amides, glyceryl esters, primary amines having a fatty alkyl moiety having at least about 16 carbon atoms, secondary amines having two fatty alkyl moieties each having at least about 12 carbon atoms). Examples of suspending agents are described in U.S. Pat. No. 4,741,855, incorporated herein by reference.

Aqueous Carrier

The formulations of the present invention can be in the form of pourable liquids (under ambient conditions). Such compositions will therefore typically comprise an aqueous carrier, which is present at a level of from about 20% to about 95%, more preferably from about 60% to about 85%. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Dispersed Particles

The compositions may optionally comprise particles. The particles may be dispersed water-insoluble particles. The particles may be inorganic, synthetic, or semi-synthetic. In one embodiment, the particles have an average mean particle size of less than about 300 μm.

Gel Matrix

The above cationic surfactants, together with high melting point fatty compounds and an aqueous carrier, may form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

Skin Care Actives

The composition may comprise at least one skin care active, useful for regulating and/or improving the condition and/or appearance of mammalian skin. The skin care active may be soluble in oil or water, and may be present primarily in the oil phase and/or in the aqueous phase. Suitable actives include, but are not limited to, vitamins (e.g., from about 0.001% to about 10%), peptides (e.g., from about $1\times10^{-7}$% to about 20%), sugar amines (e.g., from about 0.01% to about 15%), sunscreens (e.g., from about 1% to about 20%), oil control agents (e.g., from about 0.0001% to about 15%), tanning actives (e.g., 0.1% to about 20%), anti-acne actives (see, e.g., U.S. Pat. No. 5,607,980, incorporated herein by reference; and "Antiacne Agents" in the Personal Care Product Council's International Cosmetic Ingredient Dictionary and Handbook, 13th Ed.) desquamation actives (e.g., from about 0.01% to about 10%), see, e.g., U.S. Pat. Nos. 5,681,852; 5,652,228, incorporated herein by reference), anti-cellulite actives (from about 0.1% to about 10%), chelating agents (see e.g., U.S. Pat. No. 5,487,884, International Publication Nos. WO91/16035 and WO91/16034, incorporated herein by reference), skin lightening agents (e.g., from about 0.1% to about 10%), flavonoids (see, e.g., U.S. Pat. No. 6,235,773, incorporated herein by reference), protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, Nacyl amino acid compounds, antimicrobials, and antifungals (see e.g., U.S. application publication No. US 2006/0275237A1 and US 2004/0175347A1, incorporated herein by reference).

Color Cosmetics

The compositions of the present invention may also be used in cosmetic compositions, i.e., in products suitable for use in, on, or around the eyes, eyebrows, face, neck, chest, lips, hands, feet, or nails. Exemplary cosmetic products include eye liners, eye shadows, eyebrow pencils, mascaras, eye makeup removers, false eyelashes, under-eye concealers, eye creams, concealers, correctors, primers, blushes, bronzers, highlighters, shimmers, foundations, powders, sunscreens, brushes, face creams, lip primers, lip pencils, lipsticks, lip glosses, lip balms, lip stains, lip creams, and lotions. The compositions of the present invention may be combined with materials commonly found in these compositions, such as alkyl dimethicone copolyols, polyols, hydrophilic skin treatment agents, carriers, thickening agent (such as solid waxes, gelling agents, inorganic thickeners, oil soluble polymers, fatty compounds, and mixtures thereof), pigments, film forming agents, preservatives, vitamins, etc. Examples of cosmetic products are found in U.S. Pat. Nos. 6,325,995; 6,696,049; 6,503,495; 7,270,828, which are all incorporated herein by reference.

Other Optional Components

The compositions of the present invention may contain also vitamins and amino acids such as: water soluble vitamins and their derivatives, water soluble amino acids and their salts and/or derivatives, water insoluble amino acids viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives, chelants, proteins, skin active agents, sunscreens, UV absorbers, vitamins, niacinamide, caffeine and minoxidil.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C.I. Names. The compositions of the present invention may also contain antimicrobial agents which are useful as cosmetic biocides.

The compositions of the present invention may also contain chelating agents.

This list of aforementioned personal care additives is not meant to be exclusive, and other components can be used.

Formulations

The hair conditioners and shampoo formulations can be prepared by any conventional method well known in the art. The present invention can also be used in a compact hair care formulation. A compact formulation is a formula which delivers the same benefit to the consumer at a lower usage level. Compact formulations and methods of making compact formulations are described in US Application Publication No 2009/0221463A1, incorporated herein by reference.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES

The following examples illustrate the present invention. It will be appreciated that other modifications of the present invention within the skill of those in the cleansing and conditioning formulation art can be undertaken without departing from the spirit and scope of this invention. All of the formulations exemplified hereinafter are prepared via conventional formulation and mixing methods unless specific methods are given.

All parts, percentages, and ratios herein are by weight unless otherwise specified. Some components may come from suppliers as dilute solutions. The levels given reflect the weight percent of the active material, unless otherwise specified. The excluded diluents and other materials are included as "Minors".

I. Synthetic Procedures

Example A

Preparation of Sodium 4-Methyldodecyl Sulfate

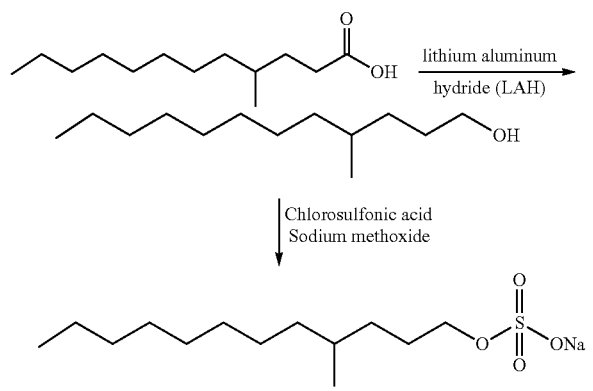

A 500 ml three neck flask is fitted with a magnetic stirrer, thermometer, and a 60 mL addition funnel. Lithium aluminum hydride (2.66 g, 0.07 mol) is placed into the flask under nitrogen and 80 mL of freshly distilled tetrahydrofuran (THF) is added. This mixture is stirred and chilled to 0° C. in an ice bath. A solution of 2.81 g (0.013 mol) of 4-methyldodecanoic acid in 30 mL of THF is placed into the addition funnel and added at a slow drip rate while maintaining the temperature<5° C. The mixture is then refluxed for 60 minutes. The mixture is cooled in a dry ice/acetone bath. At 0° C., 6 mL of water plus 4 mL of THF are slowly added dropwise taking care to keep the temperature<5° C. When addition is complete 4.3 mL of 10% sodium hydroxide solution is added via the addition funnel, the contents of the flask are stirred an additional 15 minutes, and then filtered through a bed of sodium sulfate that is then rinsed with more THF. The filtrate is allowed to stand over magsesium sulfate for 60 minutes, filtered and concentrated in vacuo on a rotary evaporator. The intermediate 4-methyldodecan-1-ol is examined by Karl Fisher water analysis and is found to contain 5200 ppm water. Distilling (Kugelrohr apparatus) from 0.5 gm of calcium oxide, standing over 0.5 g of activated 3A molecular sieves or 0.5 g of potassium carbonate for six days fails to reduce the water content, and the sample is used in the next reaction after filtering.

The above 4-methyldodecan-1-ol (1.3562 g, 0.00677 mol) is placed into a 50 mL three neck flask and magnetically stirred in 6 mL of ether and 6 mL of methylene chloride at room temperature. The material is not completely soluble. With an ice bath standing by, 0.832 g (0.00714 mol) of chlorosulfonic acid is added dropwise via a pipette and under nitrogen. Exothermic activity is controlled by addition rate and by placing the flask in the ice bath as needed. After all the chlorosulfonic acid is added, the mixture is still partly solid and partly a light yellow liquid. Raising the temperature to 30° C. decreases the solids present with resultant darkening of the solution. One neck of the flask is left open to allow the nitrogen to sweep HCl out of the flask. As the solvent is lost due to evaporation in the nitrogen stream, more methylene chloride is added. After about 30 minutes and three refills with methylene chloride, no more HCl can be detected on moist pH paper placed near the open neck of the flask. A vacuum adapter is fitted to the flask and used to carefully apply vacuum to the vessel to remove any residual solvent or HCl. This step is done three times, replacing the solvent each time with 6 mL of fresh methylene chloride. The dark brown oily material is dissolved in 10 mL of methanol and pipetted into a flask containing 1.64 g of 25% sodium methoxide in methanol plus four mL of methanol in an ice bath. The pH is found to be about 9-10. The mixture is stirred for 1 hour and the pH is still found to be about 9-10. The solvent is removed in vacuo on a rotary evaporator and the residue dissolved in 25 mL of water. The residue is freeze dried for 48 hours to provide 1.7 g of solid found to be 77.5% active.

The bulk of the above sample is stirred in 50 mL of methanol for 1 hour and filtered (to remove insoluble impurities). The filtrate is evaporated. The residue is triturated twice with 200 mL of pentane by thoroughly mixing the materials followed by centrifugation and decanting. The residue is dissolved in warm distilled water, freeze dried, placed into a dessicator over $P_2O_5$, and subjected to a high vacuum for 24 hours. The sample is weighed 1.34 g and is still found to be only 79% active.

The sample is further triturated twice with 200 mL of pentane each time by thoroughly mixing the materials followed by centrifugation. The sample is then triturated overnight at room temperature with 150 mL of diethyl ether, centrifuged, followed by rinsing with second 150 mL of diethyl ether and centrifugation. The isolated solid is dried in the centrifuge bottle under a slow nitrogen stream for 4 hours and then transferred to a sample bottle and placed in a desiccator over $P_2O_5$ and subjected to a high vacuum for 24 hours. The resulting sodium 4-methyldodecyl sulfate weighed 1.13 g and is found to be 83% active.

Example B

Preparation of Sodium 6-Methyltetradecyl Sulfate

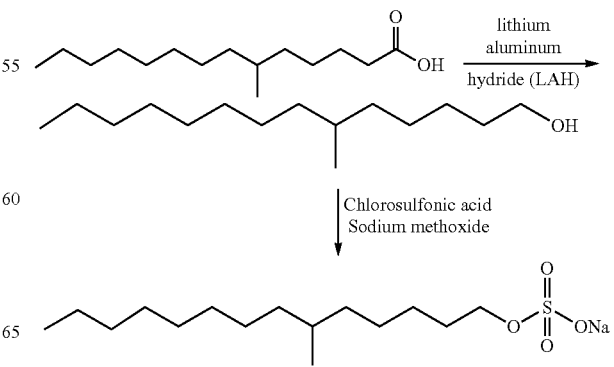

Starting with 2.86 g (0.012 mol) of 6-methyltetradecanoic acid essentially the same procedure applied above is used to prepare 1.17 g of sodium 6-methyltetradecyl sulfate which is found to be 80% active.

Example C

Preparation of Sodium 4,8-Dimethylhexadecyl Sulfate

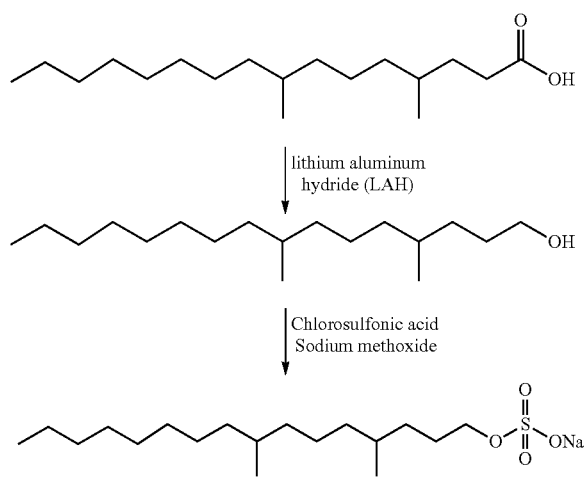

Starting with 2.86 g (0.012 mol) of 4,8-dimethylhexadecanoic acid essentially the same procedure applied above is used to prepare 1.17 g of sodium 4,8-dimethylhexadecyl sulfate which is found to be 80% active.

Example D

4-Methyldocanol/6-Methyltetradecanol (1:1) Alcohol Ethoxylates

About 0.5 mol of 4-methyldocanol obtained in Example 1 and about 0.5 mol of 6-methyltetradecanol obtained in Example 2 above plus sufficient catalyst to facilitate the reaction of the alcohol with ethylene oxide within a suitable period of time and in a controllable manner are charged to a 600 mL stainless steel stirred pressure vessel with a cooling coil. A suitable catalyst is 1.1 grams of a solution consisting of 50% potassium hydroxide in water. Other kinds and quantities of catalyst can be used based upon the demands of the process.

The reactor is heated while applying a vacuum for removing materials that can result in side products, such as water, that may be introduced with the catalyst, at a temperature that does not allow the loss of the alcohol mixture of Example 1, generally between 40° C. and 90° C., but preferably between about 60° C. and about at 80° C., when using a water aspirator as a vacuum source. The removal of water is facilitated by using low speed agitation, generally about 50 rpm, while sparging the mixture with a low level (trickle) stream of inert gas either through a bottom drain valve or through a stainless steel gas dispersion frit or any inert dip-tube or sintered metal fritted material or by sweeping the area above the mixture with inert gas. Samples can be drawn from the reactor and analyzed for water content using an appropriate analytical method such as Karl-Fischer titration.

After completion of the water removal step, ethylene oxide can be added all at once if the reactor system is properly designed to prevent an uncontrolled rate of reaction. However, the best reaction control is obtained by first heating the reactor under a static vacuum (or optionally with added pressure from an inert gas such as nitrogen) to a temperature that is suitable for the reaction of the alcohol-catalyst mixture with ethylene oxide to occur with minimum side products and color generation, generally between 85° and 150° C., but preferably between about 110° C. and 130° C. Once the reactor has reached the desired temperature, 308 grams (7.0 mol) of ethylene oxide is added at a rate that will be controllable by the cooling system, generally over a period of 30 to 60 minutes. After the addition of ethylene oxide is completed, stirring and heating is continued until the ethylene oxide has been consumed by the reaction. The product can then be degassed and removed from the reaction vessel and stored as is or for long term storage the catalyst is neutralized with one equivalent of a acid selected from citric, HCl or sulfuric acid. The neutralized product can be filtered to remove any solid residue. The surfactant is now ready to use.

II. Cleaning Compositions

Example A

Granular Laundry Detergents

| Formula | A wt % | B wt % | C wt % | D wt % | E wt % |
|---|---|---|---|---|---|
| Scattered-Branched Chain Alcohol Sulfate, Sodium Salts (1:1), from Examples IB and IC | 13-25 | 13-25 | 13-25 | 13-25 | 9-25 |
| $C_{12-18}$ Ethoxylate | — | — | 0-3 | — | 0-1 |
| $C_{14-15}$ alkyl ethoxylate (EO = 7) | 0-3 | 0-3 | — | 0-5 | 0-3 |
| Dimethyl hydroxyethyl lauryl ammonium chloride | — | — | 0-2 | 0-2 | 0-2 |
| Sodium tripolyphosphate | 20-40 | — | 18-33 | 12-22 | 0-15 |
| Zeolite | 0-10 | 20-40 | 0-3 | — | — |
| Silicate builder | 0-10 | 0-10 | 0-10 | 0-10 | 0-10 |
| Carbonate | 0-30 | 0-30 | 0-30 | 5-25 | 0-20 |
| Diethylene triamine penta acetate | 0-1 | 0-1 | 0-1 | 0-1 | 0-1 |
| Polyacrylate | 0-3 | 0-3 | 0-3 | 0-3 | 0-3 |
| Carboxy Methyl Cellulose | 0.2-0.8 | 0.2-0.8 | 0.2-0.8 | 0.2-0.8 | 0.2-0.8 |
| Percarbonate | 0-10 | 0-10 | 0-10 | 0-10 | 0-10 |
| Nonanoyloxybenzenesulfonate, sodium salt | — | — | 0-2 | 0-2 | 0-2 |
| Tetraacetylethylenediamine | — | — | 0-0.6 | 0-0.6 | 0-0.6 |

-continued

| Formula | A wt % | B wt % | C wt % | D wt % | E wt % |
|---|---|---|---|---|---|
| Zinc Phthalocyanine Tetrasulfonate | — | — | 0-0.005 | 0-0.005 | 0-0.005 |
| Brightener | 0.05-0.2 | 0.05-0.2 | 0.05-0.2 | 0.05-0.2 | 0.05-0.2 |
| MgSO$_4$ | — | — | 0-0.5 | 0-0.5 | 0-0.5 |
| Enzymes | 0-0.5 | 0-0.5 | 0-0.5 | 0-0.5 | 0-0.5 |
| Minors (perfume, dyes, suds stabilizers) | balance | balance | balance | balance | balance |

Example B

Granular Laundry Detergent

Aqueous Slurry Composition

| Component | % w/w Aqueous slurry |
|---|---|
| A compound having the following general structure: bis((C$_2$H$_5$O)(C$_2$H$_4$O)n)(CH$_3$)—N$^+$—C$_x$H$_{2x}$—N$^+$—(CH$_3$)—bis((C$_2$H$_5$O)(C$_2$H$_4$O)n), wherein n = from 20 to 30, and x = from 3 to 8, or sulfated or sulphonated variants thereof | 1.23 |
| Ethylenediamine disuccinic acid | 0.35 |
| Brightener | 0.12 |
| Magnesium sulfate | 0.72 |
| Acrylate/maleate copolymer | 6.45 |
| Linear alkyl benzene sulphonate, sodium salt | 11.92 |
| Hydroxyethane di(methylene phosphonic acid) | 0.32 |
| Sodium carbonate | 4.32 |
| Sodium sulfate | 47.49 |
| Soap | 0.78 |
| Water | 24.29 |
| Miscellaneous | 0.42 |
| Total Parts | 100.00 |

Spray-Dried Powder Composition

An aqueous slurry having the composition as described in the "Aqueous Slurry Composition" section (above) is prepared having a moisture content of 25.89 wt. %. The aqueous slurry is heated to 72° C. and pumped under high pressure (from 5.5×10$^6$Nm$^{-2}$ to 6.0×10$^6$Nm$^{-2}$), into a counter current spray-drying tower with an air inlet temperature of from 270° C. to 300° C. The aqueous slurry is atomised and the atomised slurry is dried to produce a solid mixture, which is then cooled and sieved to remove oversize material (>1.8 mm) to form a spray-dried powder, which is free-flowing. Fine material (<0.15 mm) is elutriated with the exhaust the exhaust air in the spray-drying tower and collected in a post tower containment system. The spray-dried powder has a moisture content of 1.0 wt %, a bulk density of 427 g/L, and a particle size distribution such that 95.2 wt % of the spray-dried powder has a particle size of from 150 to 710 micrometers. The composition of the spray-dried powder is given below.

| Component | % w/w Spray-dried powder |
|---|---|
| A compound having the following general structure: bis((C$_2$H$_5$O)(C$_2$H$_4$O)n)(CH$_3$)—N$^+$—C$_x$H$_{2x}$—N$^+$—(CH$_3$)—bis((C$_2$H$_5$O)(C$_2$H$_4$O)n), wherein n = from 20 to 30, and x = from 3 to 8, or sulfated or sulphonated variants thereof | 1.62 |
| Ethylenediamine disuccinic acid | 0.46 |
| Brightener | 0.16 |
| Magnesium sulfate | 0.95 |
| Acrylate/maleate copolymer | 8.45 |
| C11.8 Linear alkyl benzene sulphonate, sodium salt blended 2:1 with the Scattered-Branched Chain Alcohol Sulfate sodium salts (1:1) from Example IA&IB. | 12.65 |
| Hydroxyethane di(methylene phosphonic acid) | 0.42 |
| Sodium carbonate | 5.65 |
| Sodium sulfate | 61.98 |
| Soap | 1.02 |
| Water | 1.00 |
| Miscellaneous | 0.55 |
| Total Parts | 100.00 |

Preparation of an Anionic Surfactant Particle 1

The anionic detersive surfactant particle 1 is made on a 520 g batch basis using a Tilt-A-Pin then Tilt-A-Plow mixer (both made by Processall). About 108 g sodium sulfate is added to the Tilt-A-Pin mixer along with 244 g sodium carbonate. About 168 g of 70 wt. % active C$_{25}$E$_3$S paste (sodium ethoxy sulfate based on C$_{12/15}$ alcohol and ethylene oxide) is added to the Tilt-A-Pin mixer. The components are then mixed at 1200 rpm for 10 seconds. The resulting powder is then transferred into a Tilt-A-Plow mixer and mixed at 200 rpm for 2 minutes to form particles. The particles are then dried in a fluid bed dryer at a rate of 2500 L/min at 120° C. until the equilibrium relative humidity of the particles is less than 15 wt. %. The dried particles are then sieved and the fraction through 1180 μm and on 250 μm is retained. The composition of the anionic detersive surfactant particle 1 is as follows:

25.0% w/w C$_{25}$E$_3$ sulfate, sodium salt
18.0% w/w sodium sulfate
57.0% w/w sodium carbonate Preparation of a Cationic Detersive Surfactant Particle 1

The cationic surfactant particle 1 is made on a 14.6 kg batch basis on a Morton FM-50 Loedige mixer. About 4.5 kg of micronised sodium sulfate and 4.5 kg micronised sodium carbonate are premixed in the Morton FM-50 Loedige mixer. About 4.6 kg of 40 wt. % active mono-C12-14 alkyl mono-hydroxyethyl di-methyl quaternary ammonium chloride (cationic surfactant) aqueous solution is added to the Morton FM-50 Loedige mixer whilst both the main drive and the chopper are operating. After approximately two minutes of mixing, a 1.0 kg 1:1 weight ratio mix of micronised sodium sulfate and micronised sodium carbonate is added to the mixer. The resulting agglomerate is collected and dried using a fluid bed dryer on a basis of 2500 L/min air at 100-140° C. for 30 minutes. The resulting powder is sieved and the fraction through 1400 μm is collected as the cationic surfactant particle 1. The composition of the cationic surfactant particle 1 is as follows:

| |
|---|
| 15% w/w mono-C12-14 alkyl mono-hydroxyethyl di-methyl quaternary ammonium chloride |
| 40.76% w/w sodium carbonate |
| 40.76% w/w sodium sulfate |
| 3.48% w/w moisture and miscellaneous |

Preparation of a Granular Laundry Detergent Composition

About 10.84 kg of the spray-dried powder from the "Spray-Dried Powder" section (above), 4.76 kg of the anionic detersive surfactant particle 1, 1.57 kg of the cationic detersive surfactant particle 1 and 7.83 kg (total amount) of other individually dosed thy-added material are dosed into a 1 m diameter concrete batch mixer operating at 24 rpm. After all of the materials are dosed into the mixer, the mixture is mixed for 5 minutes to form a granular laundry detergent composition. The formulation of the granular laundry detergent composition is described below:

| Component | A. % w/w granular laundry detergent composition | B. % w/w granular laundry detergent composition |
|---|---|---|
| Spray-dried powder from the "Spray-Dried Powder" section (above) | 43.34 | 15 |
| 91.6 wt. % active linear alkyl benzene sulphonate, sodium salt flake supplied by Stepan under the tradename NACCONOL 90G ® | 0.22 | 2 |
| Citric acid | 5.00 | 0 |
| Sodium percarbonate (having from 12% to 15% washing active oxygen (active AvOx)) | 14.70 | 0 |
| Photobleach particle | 0.01 | 0 |
| Lipase (11.00 mg active/g) | 0.70 | 0.90 |
| Amylase (21.55 mg active/g) | 0.33 | 0.50 |
| Protease (56.00 mg active/g) | 0.43 | 0.60 |
| Tetraacetyl ethylene diamine agglomerate (92 wt % active) | 4.35 | 4.0 |
| Suds suppressor agglomerate (11.5 wt % active) | 0.87 | 1.0 |
| Acrylate/maleate copolymer particle (95.7 wt % active) | 0.29 | 0 |
| Green/Blue carbonate speckle | 0.50 | 0 |
| Anionic detersive surfactant particle 1 | 19.04 | 10 |
| Cationic detersive surfactant particle 1 | 6.27 | 3 |
| Sodium sulfate | balance | balance |
| Solid perfume particle | 0.63 | 0.7 |
| Total Parts | 100.00 | 100.00 |

Example C

Liquid Laundry Detergents

| Ingredient | A wt. % | B wt. % | C wt. % | D wt. % | E wt. % |
|---|---|---|---|---|---|
| C12-15 EO$_{1.8}$ sulfate sodium salt | 14.4 | 0 | 9.2 | 5.4 | 0 |
| Scattered-Branched Alcohol Sulfate, sodium salts (1:1) from Example IA&B. | 4.4 | 12.2 | 5.7 | 1.3 | 20 |
| Alkyl ethoxylate | 2.2 | 8.8 | 8.1 | 3.4 | 0 |
| Amine oxide | 0.7 | 1.5 | 0 | 0 | 0 |
| Citric acid | 2.0 | 3.4 | 1.9 | 1.0 | 1.6 |
| HLAS (linear alkylbenzene sulfonate, acid form) | 3.0 | 0 | 0 | 0 | 5.0 |
| Protease | 1.0 | 0.7 | 1.0 | 0 | 2.5 |
| Amylase | 0.2 | 0.2 | 0 | 0 | 0.3 |
| Lipase | 0 | 0 | 0.2 | 0 | 0 |
| Borax | 1.5 | 2.4 | 2.9 | 0 | 0 |
| Calcium and sodium formate | 0.2 | 0 | 0 | 0 | 0 |
| Formic acid | 0 | 0 | 0 | 0 | 1.1 |
| Ethoxylated polyamine polymer or polymers | 1.7 | 2.0 | 0 | 0.8 | 0 |
| Sodium polyacrylate copolymer | 0 | 0 | 0.6 | 0 | 0 |
| DTPA[1] | 0.1 | 0 | 0 | 0 | 0.9 |
| DTPMP[2] | 0 | 0.3 | 0 | 0 | 0 |
| EDTA[3] | 0 | 0 | 0 | 0.1 | 0 |
| Fluorescent whitening agent | 0.15 | 0.2 | 0.12 | 0.12 | 0.2 |
| Ethanol | 2.5 | 1.4 | 1.5 | 0 | 0 |
| Propanediol | 6.6 | 4.9 | 4.0 | 0 | 15.7 |
| Sorbitol | 0 | 0 | 4.0 | 0 | 0 |
| Ethanolamine | 1.5 | 0.8 | 0.1 | 0 | 11.0 |
| Sodium hydroxide | 3.0 | 4.9 | 1.9 | 1.0 | 0 |
| Sodium cumene sulfonate | 0 | 2.0 | 0 | 0 | 0 |
| Silicone suds suppressor | 0 | 0.01 | 0 | 0 | 0 |
| Perfume | 0.3 | 0.7 | 0.3 | 0.4 | 0.6 |

-continued

| | | | | | |
|---|---|---|---|---|---|
| Opacifier[4] | 0 | 0.30 | 0.20 | 0 | 0.50 |
| Water | balance | balance | balance | balance | balance |
| | 100.0% | 100.0% | 100.0% | 100.0% | 100.0% |

[1]diethylenetriaminepentaacetic acid, sodium salt
[2]diethylenetriaminepentakismethylenephosphonic acid, sodium salt
[3]ethylenediaminetetraacetic acid, sodium salt
[4]Acusol OP 301

| Ingredient | F wt. % | G wt. % | H wt. % | I wt. % | J wt. % | K wt. % |
|---|---|---|---|---|---|---|
| Alkylbenzene sulfonic acid | 7 | 7 | 4.5 | 1.2 | 1.5 | 12.5 |
| C12-14 EO$_3$ sulfate, sodium salt | 2.3 | 2.3 | 4.5 | 4.5 | 7 | 18 |
| Scattered-Branched Chain Alcohol Ethoxylates from Example I.D. | 5 | 5 | 2.5 | 2.6 | 4.5 | 4 |
| C12 alkyl dimethyl amine oxide | — | 2 | — | — | — | — |
| C12-14 alkyl hydroxyethyl dimethyl ammonium chloride | — | — | — | 0.5 | — | — |
| C12-18 Detergent acid | 2.6 | 3 | 4 | 2.6 | 2.8 | 11 |
| Citric acid | 2.6 | 2 | 1.5 | 2 | 2.5 | 3.5 |
| Protease enzyme | 0.5 | 0.5 | 0.6 | 0.3 | 0.5 | 2 |
| Amylase enzyme | 0.1 | 0.1 | 0.15 | — | 0.05 | 0.5 |
| Mannanase enzyme | 0.05 | — | 0.05 | — | — | 0.1 |
| Diethylenetriaminepenta(methylene-phosphonic) acid | 0.2 | 0.3 | — | — | 0.2 | — |
| Hydroxyethane diphosphonic acid | — | — | 0.45 | — | — | 1.5 |
| FWA | 0.1 | 0.1 | 0.1 | — | — | 0.2 |
| Solvents (1,2 propanediol, ethanol), stabilizers | 3 | 4 | 1.5 | 1.5 | 2 | 4.3 |
| Hydrogenated castor oil derivative structurant | 0.4 | 0.3 | 0.3 | 0.1 | 0.3 | — |
| Boric acid | 1.5 | 2 | 2 | 1.5 | 1.5 | 0.5 |
| Na formate | — | — | — | 1 | — | — |
| Reversible protease inhibitor | — | — | 0.002 | — | — | — |
| Perfume | 0.5 | 0.7 | 0.5 | 0.5 | 0.8 | 1.5 |
| Buffers (sodium hydroxide, Monoethanolamine) | | | To pH 8.2 | | | |
| Water and minors (antifoam, aesthetics, etc.) | | | To 100 | | | |

| Ingredient | L wt. % | M wt. % | N wt. % | O wt. % | P wt. % | Q wt. % |
|---|---|---|---|---|---|---|
| C11.6 Linear Alkylbenzene Sulfonic Acid, sodium salt | 5.5 | 2.7 | 2.2 | 12.2 | 5.2 | 5.2 |
| C12-14 EO$_3$ sulfate, sodium salt | 16.5 | 20 | 9.5 | 7.7 | 1.8 | 1.8 |
| Scattered-Branched Chain Alcohol sulfates from Example I.A, B and C | 8.9 | 6.5 | 2.9 | — | — | — |
| Scattered-Branched Chain Alcohol Ethoxylates from Example I.D | — | — | — | — | 0.15 | 0.15 |
| C12-14 alkyl 7-ethoxylate | — | — | — | — | 0.15 | 0.15 |
| C14-15 alkyl 8-ethoxylate | — | — | — | — | 3.5 | 3.5 |
| C12-15 alkyl 9-ethoxylate | 1.7 | 0.8 | 0.3 | 18.1 | — | — |
| C12-18 Detergent acid | 2.2 | 2.0 | — | 1.3 | 2.6 | 2.6 |
| Citric acid | 3.5 | 3.8 | 2.2 | 2.4 | 2.5 | 2.5 |
| Protease enzyme | 1.7 | 1.4 | 0.4 | — | 0.5 | 0.5 |
| Amylase enzyme | 0.4 | 0.3 | — | — | 0.1 | 0.1 |
| Mannanase enzyme | — | — | — | — | 0.04 | 0.04 |
| PEG-PVAc Polymer[1] | — | — | — | — | — | 0.3 |
| Ethoxyed Hexamethylene Diamine Dimethyl Quat Disulfate | — | — | — | — | — | 0.7 |
| Diethylenetriaminepenta(methylene-phosphonic) acid | — | — | — | — | 0.2 | 0.2 |
| Solvents (1,2 propanediol, ethanol, stabilizers | 7 | 7.2 | 3.6 | 3.7 | 1.9 | 1.9 |
| Hydrogenated castor oil derivative structurant | 0.3 | 0.2 | 0.2 | 0.2 | 0.35 | 0.35 |
| Polyacrylate | — | — | — | 0.1 | — | — |
| Polyacrylate copolymer[2] | — | — | — | 0.5 | — | — |
| Sodium carbonate | — | — | — | 0.3 | — | — |
| Sodium silicate | — | — | — | — | — | — |
| Borax | 3 | 3 | 2 | 1.3 | — | — |
| Boric acid | 1.5 | 2 | 2 | 1.5 | 1.5 | 1.5 |
| Perfume | 0.5 | 0.5 | 0.5 | 0.8 | 0.5 | 0.5 |

-continued

| | | |
|---|---|---|
| Buffers (sodium hydroxide, monoethanolamine) | 3.3 | 3.3 |
| Water, dyes and miscellaneous | Balance | |

[1] PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Alco 725 (styrene/acrylate)

Example D

Liquid Laundry Detergent

| Ingredient | Wt % |
|---|---|
| Propylene glycol | 4.75 |
| Sodium citrate | 2.8 |
| NaOH (50%) | 0.43 |
| Monoethanolamine | 0.23 |
| LAS, acid form | 6.0 |
| Coconut fatty acid | 0.77 |
| 6-Methyltetradecyl EO2 sulfate | 10.5 |
| Nonionic surfactant | 6.6 |
| 1-decanol | 6.0 |
| protease | 0.45 |
| Lipase | 0.25 |
| perfume | 0.2 |
| Water | Balance to 100 |

Example E

Liquid Dish Handwashing Detergents

| Composition | A wt. % | B wt. % |
|---|---|---|
| $C_{12-13}$ Natural AE0.6S (S is sulfate, sodium salt) blended 50:50 by weight with Scattered-Branched Alcohol Sulfate, sodium salts (1:1) from Example IA&B. | 27.0 | 24.0 |
| 4-Methyl dodecyl-N,N-dimethyl amine oxide | — | 6.0 |
| Scattered-Branched Chain Alcohol Ethoxylates from Example I.D. | 2.0 | 5.0 |
| $C_{12-14}$ Linear Amine Oxide | 6.0 | — |
| SAFOL ® 23 Amine Oxide | 1.0 | 1.0 |
| $C_{11}E_9$ Nonionic[1] | 2.0 | 2.0 |
| Ethanol | 4.5 | 4.5 |
| Sodium cumene sulfonate | 1.6 | 1.6 |
| Polypropylene glycol 2000 | 0.8 | 0.8 |
| NaCl | 0.8 | 0.8 |
| 1,3 BAC Diamine[2] | 0.5 | 0.5 |
| Suds boosting polymer[3] | 0.2 | 0.2 |
| Water | Balance | Balance |

[1] Nonionic may be $C_{11}$ Alkyl ethoxylated surfactant containing 9 ethoxy groups.
[2] 1,3, BAC is 1,3 bis(methylamine)-cyclohexane.
[3] (N,N-dimethylamino)ethyl methacrylate homopolymer

Example F

Automatic Dishwasher Detergent

| | A wt. % | B wt. % | C wt. % | D wt. % | E wt. % |
|---|---|---|---|---|---|
| Polymer dispersant[2] | 0.5 | 5 | 6 | 5 | 5 |
| Carbonate | 35 | 40 | 40 | 35-40 | 35-40 |
| Sodium tripolyphosphate | 0 | 6 | 10 | 0-10 | 0-10 |
| Silicate solids | 6 | 6 | 6 | 6 | 6 |
| Bleach and bleach activators | 4 | 4 | 4 | 4 | 4 |
| Polymer[1] | 0.05-10 | 1 | 2.5 | 5 | 10 |
| Enzymes | 0.3-0.6 | 0.3-0.6 | 0.3-0.6 | 0.3-0.6 | 0.3-0.6 |
| Disodium citrate dihydrate | 0 | 0 | 0 | 2-20 | 0 |
| Scattered-Branched Chain Alcohol Ethoxylates from Example I.D. | 0.8-5 | 0.8-5 | 0.8-5 | 0.8-5 | 0.8-5 |
| Water, e, perfume, dyes and other adjuncts | Balance to 100% | Balance to 100% | Balance to 100% | Balance to 100% | Balance to 100% |

[1] An amphiphilic alkoxylated polyalkylenimine polymer.
[2] Such as ACUSOL ® 445N available from Rohm & Haas or ALCOSPERSE ® from Alco.

Example G

Hard Surface Cleaner

A hard surface cleaner comprises 5% total nonionic surfactant (4-methyldecanol sulfate sodium salt), 0.2% citric acid, perfume 0.3%, and water to 100%.

III. Personal Care Compositions

Example A

Rinse-Off Conditioner Compositions

| | | Control (%) | A (%) | B (%) | C (%) |
|---|---|---|---|---|---|
| Stage A | Water | To 100% | To 100% | To 100% | To 100% |
| | Behentrimonium Methosulfate/IPA | 2.2 | 2.2 | 2.2 | 2.2 |
| | Ethylenediamine-tetraacetic acid (EDTA) | 0.12 | 0.12 | 0.12 | 0.12 |
| | 6-Methyloctadecanol | — | 0.75 | — | 0.75 |
| | 4-Methylhexadecanol | — | 0.75 | 0.75 | — |
| | 4,8-Dimethylhexadecanol | — | — | 0.75 | 0.75 |
| | Cetyl Alcohol | 1.5 | — | — | — |
| | Stearyl Alcohol | 3.7 | 3.7 | 3.7 | 3.7 |

-continued

|  |  | Control (%) | A (%) | B (%) | C (%) |
|---|---|---|---|---|---|
|  | Benzyl Alcohol | 0.4 | 0.4 | 0.4 | 0.4 |
|  | Preservative (e.g., KATHON ™ CG) | 0.03 | 0.03 | 0.03 | 0.03 |
| Stage B | Amodimethicone | 0.5 | 0.5 | 0.5 | 0.5 |
|  | Pathenol | 0.1 | 0.1 | 0.1 | 0.1 |
|  | Perfume | 0.4 | 0.4 | 0.4 | 0.4 |
| TOTAL |  | 100.0 | 100.0 | 100.0 | 100.0 |

Example B

Rinse-Off Conditioner Compositions

|  |  | Control (%) | A (%) | B (%) | C (%) |
|---|---|---|---|---|---|
| Stage A | Water | To 100% | To 100% | To 100% | To 100% |
|  | EDTA | 0.13 | 0.13 | 0.13 | 0.13 |
|  | Stearyl Alcohol | 2.3 | 2.3 | 2.3 | 2.3 |
|  | 6-Methyloctadecanol | — | 0.45 | — | 0.45 |
|  | 4-Methylhexadecanol | — | 0.45 | 0.45 | — |
|  | 4,8-Dimethylhexadecanol | — | — | 0.45 | 0.45 |
|  | Cetyl Alcohol | 0.9 | — | — | — |
|  | VARISOFT ®432PPG, quaternary ammonium dialkyl solution | 0.5 | 0.5 | 0.5 | 0.5 |
|  | BehentrimoniumMethosulfate/IPA | 1.4 | 1.4 | 1.4 | 1.4 |
|  | Benzyl Alcohol | 0.4 | 0.4 | 0.4 | 0.4 |
|  | Preservative (e.g. KATHON ™ CG) | 0.03 | 0.03 | 0.03 | 0.03 |
| Stage B | Amodimethicone | 0.8 | 0.8 | 0.8 | 0.8 |
|  | Panthenol | 0.1 | 0.1 | 0.1 | 0.1 |
|  | Perfume | 0.3 | 0.3 | 0.3 | 0.3 |
| TOTAL |  | 100.0 | 100.0 | 100.0 | 100.0 |

The mixtures of scattered-branched chain alcohols (6-methyloctadecanol, 4-methylhexadecanol and 4,8-dimethylhexadecanol) in Examples A and B can be substituted with any mixture of scattered-branched chain alcohols with 15 to 23 carbon atoms, as described in Formula I above. Nonlimiting examples of scattered-branched chain alcohols that can be substituted for 6-methyloctadecanol, 4-methylhexadecanol and 4,8-dimethylhexadecanol in the above conditioning compositions are Compounds 1-7 in Table A, Compounds 1-21 in Table B, and Compounds 1-35 in Table C, where Z is OH.

The cationic compounds in the above table can be substituted with any appropriate cationic compound such as, for example, cetyltrimonium chloride (CTAC), stearyltrimonium chloride (STAC), stearoylamidopropyldimethyl amine (SAPDMA), and distearyldimethylammonium chloride.

Example C

Shampoo Compositions

| Component | Formulation | | | |
|---|---|---|---|---|
|  | A (%) | B (%) | C (%) | D (%) |
| $C_{12-14}$ Natural AE1S (S is sulfate, sodium salt) blended 50:50 by weight with Scattered-Branched Alcohol Sulfate, sodium salts (1:1) from Formula 1 above | 12 | 10 | — | 20 |
| $C_{12-14}$ Natural AS (S is sulfate, sodium salt) blended 50:50 by weight with Scattered-Branched Alcohol Sulfate, sodium salts (1:1) from Formula 1 above | — | 2 | 12 | — |
| Cocobetaine (CocoB) | 1-2 | 1-2 | 1-2 | 1-4 |
| Cationic polymer (e.g., AM:TRI, cationic guar gum) | 0-0.5 | 0-0.5 | 0-0.5 | 0-0.5 |
| Silicone | 0-2 | 0-2 | 0-2 | 0-2 |
| Ethylene glycol distearate (EGDS) | 1.5 | 1.5 | 1.5 | 1.5 |
| Gel Network (as described in Conditioning Examples) | 0-3 | 0-3 | 0-3 | 0-3 |
| Finishing Agents (e.g., perfume, pH adjusters, water) | To 100 | To 100 | To 100 | To 100 |

The mixtures of scattered-branched chain sulfates (e.g. the sodium or ammonium salts of 2-methyldodecylsulfate, 4-methyldodecylsulfate, 6-methyldodecylsulfate, 2-methyldodecylsulfate-4-methyldecanol sulfate sodium salt-1-ethoxylated, and 4-methyldodecylsulfate-1-ethoxylated) can be substituted with any mixture of scattered-branched chain anionic surfactants with 11 to 17 carbon atoms, as described herein.

Nonlimiting examples of scattered-branched chain anionic surfactants that can be substituted for the sodium or ammonium salts of 2-methyldodecylsulfate, 4-methyldodecylsulfate, 4-methyldodecylsulfate-1-ethoxylated, and 6-methyldodecylsulfate-1-ethoxylated in the above conditioning compositions are Compounds 1-5 in Table A, Compounds 1-4, 7-9, 12, 13, and 16 in Table B, and Compounds 1-3, 6, 7, 16, 17, 20, and 26 in Table C, where Z is preferably selected from the group consisting of a hydroxyl, an alkoxyl, a glycerol ether, a polyglycerol ether, a polyglycoside, a carboxylate, a sulfate, a sulfonate, an amine, a monoalkylamine, a dialkylamine, an amine oxide, a monoalkanolamide, a betaine, a sulfobetaine, an amidopropyl betaine, a polyalkoxylated amidopropyl betaine, an alkylated quat, an alkyated/hydroxyalkylated quat, an alkylated/polyhydroxyakylated quat, a alkoxylated sulfate, a phosphate ester, a polyphosphate ester, an O-alkyl ester, a C-alkyl ester, a glycerol ester, a sugar ester, a glycerol ester quat, and a sulfonated alkyl ester.

Anti-Dandruff actives (i.e., salts of zinc, such as zinc pyrithione, and selenium, such as selenium sulfide, can be added to any of compositions A-D in Example C to result in an anti-dandruff shampoo.

One or more additional co-surfactants can be added to any of the above shampoo compositions such as, for example, CAPB (cocoamidopropyl betaine), Cocobetaine (CocoB), sodium lauroylamphoacetate (NaLAA), laurylhydroxysultaine (LHS), and cocomonoethanol amide (CMEA).

Example D

Silicone Free Conditioning Shampoo Compositions

| | Formulation | | |
|---|---|---|---|
| Component | A (%) | B (%) | C (%) |
| Water | To 100 | To 100 | To 100 |
| 4-Methylhexadecylstearate* | 0.5-3 | — | 0.25-1.5 |
| Wax ester* (from Formula I above) | — | 0.5-3 | 0.25-1.5 |
| Catonic Guar[1] | 0.25 | 0.25 | 0.25 |
| Sodium Laureth Sulfate[2] | 8.5 | 8.5 | 8.5 |
| Sodium Lauryl Sulfate[3] | 6.5 | 6.5 | 6.5 |
| CMEA[4] | 0.8 | 0.8 | 0.8 |
| Cocoamidopropyl Betaine[5] | 2.0 | 2.0 | 2.0 |
| Fragrance | 0.70 | 0.70 | 0.70 |
| Preservatives, pH, viscosity adjustment | Up to 3% | Up to 3% | Up to 3% |

[1]Jaguar Excel, from Rhodia
[2]Sodium Laureth Sulfate, from P&G
[3]Sodium Lauryl Sulfate, from P&G
[4]Ninol Comf, from Stepan
[5]Amphosol HCA-B, from Stepan
*The wax ester can include compounds of the invention having one or more scattered methyl branches on the fatty acid portion of the wax ester, one or more scattered methyl branches on the fatty alcohol portion of the wax ester, or compounds having one or more scattered methyl branches on both hydrophobic carbon chains of the wax ester.

The mixtures of scattered-branched chain wax esters can include any scattered-branched chain wax ester with 12 to 24 carbon atoms in the fatty acid portion and 12 to 24 carbon atoms in the ester portion. For example, the wax ester can include 4-methylhexadecylpalmitate, 6-methyloctadecylstearate and 4,8-dimethylhexadecyleicosanoate. The wax esters can be prepared by transesterification or via reaction of the fatty acid chloride component with the fatty alcohol, all known methods in the art. They can also be prepared by metathesis of an existing unsaturated wax ester, resulting in a scattered-branched unsaturated wax ester of the invention. Hydrogenation by conventional means will yield a scattered-branched saturated wax ester of the invention.

One or more additional co-surfactants can be added to any of the above shampoo compositions such as, for example, cocobetaine (CocoB), sodium lauroylamphoacetate (NaLAA), laurylhydroxysultaine (LHS), and cocomonoethanol amide (CMEA).

The composition in Example D can be used in conditioning shampoos, conditioners, and compact shampoos.

Wax Ester Emulsion Preparation

Wax ester emulsions can be prepared by typical emulsion preparation procedures and typically have a 1 micron emulsion droplet size. On the small scale for laboratory samples a solid sample is weighed into Flack Tek Speedmixer cup at a level to represent 50% of the final mixture. NEODOL® 1-5 is added at a level to represent 5% of the final mixture. This combination is heated until the wax ester material has liquefied. The mixture is allowed to mix for 0.5 min on the speedmixer at 2000 rpm Ammonium lauryl sulfate solution (28% active) is added at a level to represent about 10% of the final preparation any additional water required is added at this point, and the mixture re-heated to insure the wax ester material is again liquefied. The preparation in then mixed on the speed mixer for 5 minutes at 3450 rpm. The particle size of the resulting emulsion is checked by simple light microscopy to insure it is in the right domain, e.g. about 1 micron.

On a larger scale the ammonium lauryl sulfate can be added to the de-ionized water amount required and the mixture heated to about 80 C. The wax ester material is combined with the NEODOL® 1-5 and the mixture heated until liquefied. This mixture is added in a controlled manor to aqueous ammonium lauryl sulfate solution with high speed mixing, e.g a Divtech Eurostar with Turbine. The particle size is verified by light microscopy.

What is claimed:

1. A composition comprising a mixture of at least two compounds of Formula I:

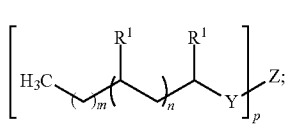

(I)

wherein each R¹ independently is H or CH₃, with the proviso that 1, 2, or 3 R¹ is CH₃;
m is 1 or 2;
n is 3, 4, 5, 6, 7, 8, or 9;
p is 1, 2, 3, 4, 5, 6, 7, or 8; and,
Y is CH₂ or absent, with the proviso that when:
(a) Y is CH₂, Z is selected from the group consisting of hydroxyl, a sulfate, or a sulfonate; and,
(b) Y is absent, Z is a carboxylic acid;

wherein at least one compound of Formula I is selected from the group consisting of:

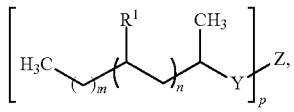

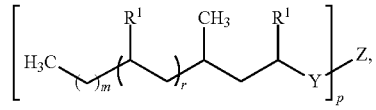

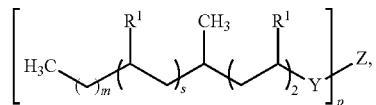

-continued

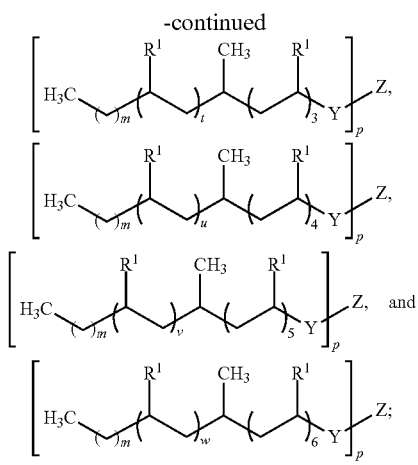

wherein:
r is 2, 3, 4, 5, 6, 7, or 8;
s is 1, 2, 3, 4, 5, 6, or 7;
t is 0, 1, 2, 3, 4, 5, or 6;
u is 0, 1, 2, 3, 4, or 5;
v is 0, 1, 2, 3, or 4; and,
w is 0, 1, 2, or 3;
wherein the mixture is present in an amount of at least about 80 wt. %, based on the total weight of the composition;
wherein the mixture comprises no more than about 5 wt. % of compounds that have a longest linear carbon chain of 9 carbon atoms or fewer, and less than about 50 wt. % of compounds of Formula I that contain branching on a carbon atom that is within 40% of the nonfunctionalized terminus of the longest carbon chain, based on the total weight of the mixture, and;
wherein the mixture further comprises at least one compound of Formula III:

(III)
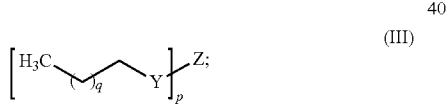

wherein q is 7, 8, 9, 10, 11, 12, 13, 14, 15, 16, 17, 18, 19, or 20;
p is 1 or 2;
Y is $CH_2$ or absent, with the proviso that when:
(a) Y is $CH_2$, Z is selected from the group consisting of hydroxyl, a sulfate, or a sulfonate; and,
(b) Y is absent, Z is a carboxylic acid;
wherein the compound of Formula III is present in an amount of about 1 wt. % to about 99 wt. %, based on the total weight of the mixture.

2. A composition comprising a mixture of at least two compounds of Formula I:

(I)
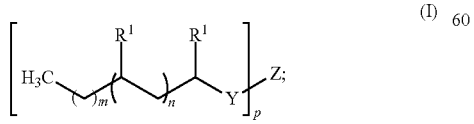

wherein each $R^1$ independently is H or $CH_3$, with the proviso that 1, 2, or 3 $R^1$ is $CH_3$;

m is 1 or 2;
n is 3, 4, 5, 6, 7, 8, or 9;
p is 1, 2, 3, 4, 5, 6, 7, or 8; and,
Y is $CH_2$ or absent, with the proviso that when:
(a) Y is $CH_2$, Z is selected from the group consisting of hydroxyl, a sulfate, or a sulfonate; and,
(b) Y is absent, Z is a carboxylic acid;
wherein at least one compound of Formula I is selected from the group consisting of

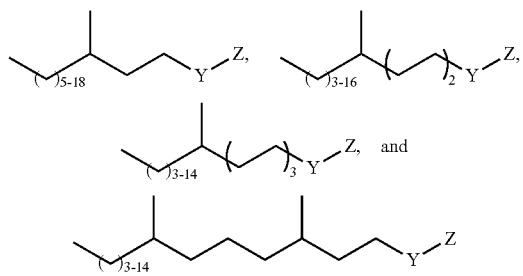

wherein the mixture is present in an amount of at least about 80 wt. %, based on the total weight of the composition;
wherein the mixture comprises no more than about 5 wt. % of compounds that have a longest linear carbon chain of 9 carbon atoms or fewer, and less than about 50 wt. % of compounds of Formula I that contain branching on a carbon atom that is within 40% of the nonfunctionalized terminus of the longest carbon chain, based on the total weight of the mixture, and;
wherein the mixture further comprises at least one compound of Formula III:

(III)
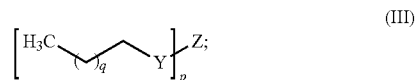

wherein q is 7, 8, 9, 10, 11, 12, 13, 14, 15, 16, 17, 18, 19, or 20;
p is 1 or 2;
Y is $CH_2$ or absent, with the proviso that when:
(a) Y is $CH_2$, Z is selected from the group consisting of hydroxyl, a sulfate, or a sulfonate; and,
(b) Y is absent, Z is a carboxylic acid;
wherein the compound of Formula III is present in an amount of about 1 wt. % to about 99 wt. %, based on the total weight of the mixture.

3. A cleaning composition comprising:
(i) about 0.001 wt. % to about 99.999 wt. % of the composition according to claim 1; and,
(ii) about 0.001 wt. % to about 99.999 wt. % of one or more additional cleaning components.

4. The composition of claim 3, wherein the cleaning composition comprises about 0.1 wt. % to about 80 wt. % the composition according to claim 5.

5. The composition of claim 3, wherein the

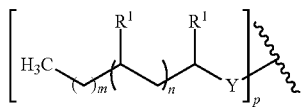

portion of the compound of Formula I has a total of 11 to 17 carbon atoms.

6. The composition of claim 3, wherein the additional cleaning component is selected from the group consisting of a surfactant, an enzyme, a builder, an alkalinity system, an organic polymeric compound, a hueing dye, a bleaching compound, an alkanolamine, a suds suppressor, a soil suspension agent, an anti-redeposition agent, and a corrosion inhibitor.

7. The composition of claim 3, wherein the cleaning composition is selected from the group consisting of a granular detergent, a bar-form detergent, a liquid laundry detergent, a liquid hand dishwashing composition, a hard surface cleaner, a tablet, a disinfectant, an industrial cleaner, a highly compact liquid, a powder, and a decontaminant.

8. The composition of claim 3, wherein the cleaning composition is enclosed within a sachet or a multi-compartment pouch comprising both solid and liquid compartments.

9. A cleaning composition comprising:
(i) about 0.001 wt. % to about 99.999 wt. % of the composition according to claim 2; and,
(ii) about 0.001 wt. % to about 99.999 wt. % of one or more additional cleaning components.

10. The composition of claim 9, wherein the cleaning composition comprises about 0.1 wt. % to about 80 wt. % the composition according to claim 2.

11. The composition of claim 9 wherein the additional cleaning component is selected from the group consisting of a surfactant, an enzyme, a builder, an alkalinity system, an organic polymeric compound, a hueing dye, a bleaching compound, an alkanolamine, a suds suppressor, a soil suspension agent, an anti-redeposition agent, and a corrosion inhibitor.

12. The composition of claim 9, wherein the cleaning composition is selected from the group consisting of a granular detergent, a bar-form detergent, a liquid laundry detergent, a liquid hand dishwashing composition, a hard surface cleaner, a tablet, a disinfectant, an industrial cleaner, a highly compact liquid, a powder, and a decontaminant.

13. The composition of claim 9, wherein the cleaning composition is enclosed within a sachet or a multi-compartment pouch comprising both solid and liquid compartments.

\* \* \* \* \*

```
                        SEQUENCE LISTING

<160> NUMBER OF SEQ ID NOS: 70

<210> SEQ ID NO 1
<211> LENGTH: 1917
<212> TYPE: DNA
<213> ORGANISM: Escherichia coli

<400> SEQUENCE: 1
atggcaagca cggaccaggg taccaacccg gcagacaccg acgacctgac gccaaccact       60
ctgagtctgg cgggcgattt tccgaaagca accgaagaac agtgggagcg cgaagtggag      120
aaagttctga accgtggccg tccgccggag aaacagctga cgtttgcgga atgtctgaaa      180
cgcctgacgg tccacacagt agacggcatt gacattgtgc caatgtatcg cccgaaagat      240
gcgccgaaga aactgggtta cccaggcgtt gccccatta cacgtgggac cacggttcgt      300
aatggcgata tggacgcatg ggatgtccgt gcactgcatg aagatccgga tgagaaattt      360
acgcgcaaag cgattctgga agggctgaa cgcgggtta catctctgct gctgcgtgtg       420 gaccccggacg ctattgctcc agaacacctg gatgaagtgc tgtctgacgt gctgctggag    480
atgaccaaag tagaagtctt tagtcgttac gatcaaggcg ccgctgccga ggcgctggta      540
tctgtgtacg agcgcagcga taaaccggct aaggacctgg ctctgaatct gggtctggac      600
ccgatcgcct tcgcggcact gcaggggacg gaacctgatc tgactgtcct gggtgattgg     660
```

-continued

```
gtgcgtcgcc tggcaaaatt tagcccagat tctcgtgcag tgaccatcga tgcgaacatt      720
tatcataatg cgggtgcggg cgatgtagca gagctggctt gggccctggc taccggtgcg      780
gaatatgttc gtgcactggt agaacaaggt tttacggcga ccgaggcgtt cgatacgatt      840
aactttcgtg tgaccgcaac ccatgatcag tttctgacaa tcgcgcgtct gcgcgcactg      900
cgtgaggcgt gggcgcgcat tggggaggta tttggggttg atgaggataa acgtggcgcc      960
cgtcaaaatg cgatcacgag ttggcgcgat gtgacacgcg aggacccgta tgtgaatatc     1020
ctgcgcggga gcatcgctac attttctgca agcgtgggtg gggccgaaag tattacaact     1080
ctgcctttta cccaggcact gggtctgcca aagacgatt ttccgctgcg tatcgctcgt      1140
aataccggta tcgttctggc cgaagaagtg aacatcggtc gtgttaatga tccggccggc     1200
ggtagctatt acgtggaaag tctgactcgt agtctggccg atgcagcgtg aaagagttc      1260
caagaagtgg agaaactggg cggcatgagc aaggcggtga tgacggaaca tgtaacgaaa     1320
gtgctggatg cctgcaatgc agaacgcgcg aaacgcctgg ccaatcgcaa acagccgatt     1380
accgcagtaa gcgaatttcc tatgattggg gcgcgctcta tcgaaacgaa acctttctcct   1440
gccgcaccgg cccgtaaagg tctggcatgg catcgcgaca gtgaagtatt cgaacaactg     1500
atggatcgca gcaccagtgt gagtgaacgt ccaaaggttt tcctggcgtg cctgggcaca     1560
cgtcgtgact cggtggtcg tgagggtttt agcagcccag tgtggcatat cgcaggcatt      1620
gacacccac aggttgaggg tggcacaacc gcagaaatcg tagaagcatt caagaaatct      1680
ggggcacaag ttgcggatct gtgctctagc gccaaagtgt acgctcagca gggtctggag     1740
gtggccaaag ctctgaaagc agctggcgcc aaagccctgt atctgagcgg tgcctttaag     1800
gagttcggcg atgatgcggc tgaggcggag aaactgatcg atggtcgcct gtttatgggt     1860
atggatgtgg ttgacactct gtctagtacg ctggacattc tgggtgtagc aaagtaa       1917
```

<210> SEQ ID NO 2
<211> LENGTH: 2193
<212> TYPE: DNA
<213> ORGANISM: Escherichia coli

<400> SEQUENCE: 2

```
atgagtacac tgcctcgttt tgactctgtt gacctgggga acgcgcctgt tccggcggat       60
gcggcccgtc gcttcgagga actggcggca aaagcgggca cgggtgaggc gtgggagacc      120
gcggagcaga ttccggttgg tacactgttc aatgaagacg tttacaaaga tatggactgg      180
ctggacacgt acgccgggat ccgccattc gttcacggcc cgtacgcgac gatgtacgct       240
ttccgtccgt ggacaattcg tcaatacgcc gggtttagca cggcgaaaga aagtaatgct      300
ttctaccgcc gtaacctggc ggcgggggcaa aagggtctgt ctgtggcatt cgacctgccg      360
acccaccgcg gttacgatag cgataatccg cgcgtggcag gggacgtggg tatggccggg      420
gtggccatcg acagtattta cgacatgcgt gaactgtttg caggcattcc gctggaccag     480
atgagcgtga gtatgacgat gaatggtgcc gtcctgccga ttctggcact gtatgtggtt     540
acagccgaag aacaaggtgt gaagccggaa cagctggctg caccatcca gaacgatatt      600
ctgaaggagt tcatggtgcg taacacctat atctatccgc cgcaaccgtc tatgcgcatc     660
atcagtgaga tctttgcgta tactagtgca aatatgccga gtggaactc tatcagtatt      720
agtggctatc acatgcagga ggcgggcgcc actgccgata tcgaaatggc ctatacgctg     780
gccgatggcg ttgattatat tcgtgcaggc gaaagcgtcg gtctgaacgt ggaccagttc     840
gccccgcgtc tgagcttctt tggggtatt ggcatgaatt tctttatgga agtcgcaaaa     900
```

```
ctgcgtgccg cccgcatgct gtgggccaaa ctggtgcacc aattcggccc gaagaacccg      960
aagagcatga gcctgcgcac gcacagtcaa accagcggct ggagcctgac cgcgcaggac     1020
gtatataaca acgtagttcg cacctgtatt gaggcgatgg cagccaccca gggtcacacc     1080
cagagcctgc atacaaactc tctggacgag gccatcgcac tgccgacaga cttcagcgcc     1140
cgcatcgcgc gtaatactca actgtttctg caacaggaaa gcggtactac ccgtgtgatc     1200
gatccgtggt ctggcagtgc atatgtcgag gaactgacct gggatctggc ccgtaaagcg     1260
tggggtcata tccaggaagt cgagaaagtg gtggtatgg ctaaagcaat tgagaaaggc     1320
atcccgaaaa tgcgcattga agaagcggca gcgcgcaccc aagcacgcat cgacagcggt     1380
cgccagccgc tgattggcgt gaacaaatat cgcctggaac atgaaccgcc actggatgtt     1440
ctgaaagtag ataactctac cgtcctggcg gagcagaaag cgaaactggt taagctgcgt     1500
gcggaacgcg atcctgagaa agttaaagcg gcgctggata aaatcacttg gccgcgggc     1560 aacccggatg ataaagaccc agaccgtaat ctgctgaagc tgtgtattga cgcgggtcgt     1620
gctatggcga ctgtcggcga aatgagcgat gcgctggaga agtatttgg tcgttatacc     1680 gcgcaaattc gtactatttc tggtgtctat agcaaggaag ttaagaatac tccagaagta     1740
gaagaagcgc gtgaactggt agaagaattt gagcaggctg aaggtcgccg tccacgcatt     1800
ctgctggcca aaatgggcca ggatggccat gatcgcggtc agaaagttat tgctactgct     1860
tatgctgatc tgggcttcga tgttgatgtc ggccctctgt tccagactcc agaggaaact     1920
gcccgccagg ctgttgaagc tgacgtccat gtcgttggcg ttagctctct ggctggcggc     1980
catctgaccc tggtccctgc tctgcgcaag gaactggata agctgggccg ccctgatatt     2040
ctgattactg tcggcggcgt cattcctgaa caggatttcg atgaactgcg caaggatggc     2100
gctgtcgaaa tttataccc tggcaccgtc attcctgaat ctgctatttc tctggtcaag     2160
aagctgcgcg ctagcctgga tgcctaactc gag                                  2193
```

<210> SEQ ID NO 3
<211> LENGTH: 671
<212> TYPE: PRT
<213> ORGANISM: Janibacter sp. HTCC2649

<400> SEQUENCE: 3

```
Met Ala Arg Thr Tyr Ala Gly His Ser Ser Ala Ala Ser Asn Ala
1               5                   10                  15

Leu Tyr Arg Arg Asn Leu Ala Lys Gly Gln Thr Gly Leu Ser Val Ala
                20                  25                  30

Phe Asp Leu Pro Thr Gln Thr Gly Tyr Asp Pro Asp His Val Leu Ala
            35                  40                  45

Arg Gly Glu Val Gly Lys Val Gly Val Pro Ile Ser His Ile Gly Asp
        50                  55                  60

Met Arg Ala Leu Phe Asp Gln Ile Pro Leu Gly Gln Met Asn Thr Ser
65                  70                  75                  80

Met Thr Ile Asn Ala Thr Ala Met Trp Leu Leu Ala Met Tyr Gln Val
                85                  90                  95

Ala Ala Glu Asp Gln Ala Thr Ala Asp Glu Asp Pro Ala Ser Val
            100                 105                 110

Val Lys Ala Leu Gly Gly Thr Thr Gln Asn Asp Ile Ile Lys Glu Tyr
        115                 120                 125

Leu Ser Arg Gly Thr Tyr Val Phe Ala Pro Ala Pro Ser Leu Arg Leu
    130                 135                 140
```

```
Ile Thr Asp Met Val Ser Tyr Thr Val Ser Asp Ile Pro Lys Trp Asn
145                 150                 155                 160

Pro Ile Asn Ile Cys Ser Tyr His Leu Gln Glu Ala Gly Ala Thr Pro
                165                 170                 175

Val Gln Glu Ile Ala Tyr Ala Met Ser Thr Ala Ile Ala Val Leu Asp
            180                 185                 190

Ala Val Arg Asp Ala Gly Gln Val Pro Gln Glu Arg Phe Gly Glu Val
        195                 200                 205

Val Ala Arg Ile Ser Phe Phe Val Asn Ala Gly Val Arg Phe Val Glu
    210                 215                 220

Glu Met Cys Lys Met Arg Ala Phe Val Glu Leu Trp Asp Glu Leu Thr
225                 230                 235                 240

Arg Glu Arg Tyr Gly Val Thr Asp Ala Lys Gln Arg Arg Phe Arg Tyr
                245                 250                 255

Gly Val Gln Val Asn Ser Leu Gly Leu Thr Glu Ala Gln Pro Glu Asn
                260                 265                 270

Asn Val Gln Arg Ile Val Leu Glu Met Leu Ala Val Thr Leu Ser Lys
                275                 280                 285

Gly Ala Arg Ala Arg Ala Val Gln Leu Pro Ala Trp Asn Glu Ala Leu
290                 295                 300

Gly Leu Pro Arg Pro Trp Asp Gln Gln Trp Ser Leu Arg Met Gln Gln
305                 310                 315                 320

Val Leu Ala Tyr Glu Ser Asp Leu Leu Glu Tyr Glu Asp Leu Phe Glu
                325                 330                 335

Gly Ser Ala Val Val Glu Ala Lys Val Ala Glu Leu Val Ala Gly Ala
                340                 345                 350

Lys Ala Glu Ile Ala Arg Val Ala Glu Leu Gly Gly Ala Val Ala Ala
                355                 360                 365

Val Glu Ser Gly Tyr Met Lys Ser Ala Leu Val Ala Ser His Ala Leu
    370                 375                 380

Arg Arg Gln Arg Ile Glu Ala Gly Glu Asp Ile Val Val Gly Val Asn
385                 390                 395                 400

Lys Phe Glu Thr Thr Glu Pro Asn Pro Leu Thr Ala Asp Leu Asp Thr
                405                 410                 415

Ala Ile Gln Ser Val Asp Ala Gly Val Glu Ala Ala Ala Lys Ala
                420                 425                 430

Val Arg Glu Trp Arg Glu Thr Arg Asp Ala Asp Pro Val Lys Arg Glu
            435                 440                 445

Arg Ala Val Ala Ala Leu Ala Arg Leu Lys Ala Ala Gln Thr Asp
        450                 455                 460

Glu Asn Leu Met Glu Ala Ser Ile Glu Cys Ala Arg Ala Glu Val Thr
465                 470                 475                 480

Thr Gly Glu Trp Ala Gln Ala Leu Arg Glu Val Phe Gly Glu Phe Arg
                485                 490                 495

Ala Pro Thr Gly Val Thr Gly Thr Val Gly Leu Thr Gly Ala Ala
                500                 505                 510

Gly Ala Glu Leu Ser Ala Val Arg Glu Arg Val Ala Gly Leu Arg Asp
                515                 520                 525

Glu Leu Gly Glu Thr Leu Arg Val Leu Val Gly Lys Pro Gly Leu Asp
            530                 535                 540

Gly His Ser Asn Gly Ala Glu Gln Ile Ala Val Arg Ala Arg Asp Ala
545                 550                 555                 560
```

```
Gly Phe Glu Val Ile Tyr Gln Gly Ile Arg Leu Thr Pro Glu Gln Ile
            565                 570                 575

Val Ala Ala Val Ser Glu Asp Val His Leu Val Gly Ile Ser Ile
        580                 585                 590

Leu Ser Gly Ser His Met Glu Leu Ile Pro Glu Val Leu Asp Arg Leu
        595                 600                 605

Arg Glu Ala Gly Ala Gly Asp Ile Pro Val Ile Val Gly Gly Ile Ile
610                 615                 620

Pro Glu Ser Asp Ala Ala Lys Leu Lys Ala Ile Gly Val Ala Glu Val
625                 630                 635                 640

Phe Thr Pro Lys Asp Phe Gly Leu Asn Asp Ile Met Gly Arg Phe Val
                645                 650                 655

Asp Val Ile Arg Asp Ser Arg Leu Thr Thr Ala Ala Pro Thr Val
                660                 665                 670

<210> SEQ ID NO 4
<211> LENGTH: 571
<212> TYPE: PRT
<213> ORGANISM: Escherichia coli

<400> SEQUENCE: 4

Met Thr Val Ala Pro Lys Arg Pro Ala Ala Met Thr Leu Ala Ala His
1               5                   10                  15

Phe Pro Glu Arg Thr Gln Glu Gln Trp Arg Asp Leu Val Ala Gly Val
                20                  25                  30

Val Asn Lys Gly Arg Pro Glu Asp Gln His Leu Ser Gly Asp Asp Ala
            35                  40                  45

Val Ala Thr Met Arg Ser His Leu Glu Gly Gly Leu Asp Ile Glu Pro
    50                  55                  60

Leu Tyr Met Lys Ser Ser Asp Pro Val Pro Leu Gly Val Pro Gly Ala
65                  70                  75                  80

Met Pro Phe Thr Arg Gly Arg Ala Leu Arg Asp Ala Asp Val Pro Trp
                85                  90                  95

Asp Val Arg Gln Val His Asp Pro Asp Ala Ala Thr Arg Gln
                100                 105                 110

Leu Val Leu Ala Asp Leu Glu Asn Gly Val Thr Ser Val Trp Leu His
            115                 120                 125

Val Gly Ala Asp Gly Leu Ala Pro Asn Asp Val Ala Glu Ala Leu Ala
    130                 135                 140

Glu Val Arg Leu Glu Leu Ala Pro Val Val Ser Ser Trp Asp Asp
145                 150                 155                 160

Gln Thr Ala Ala Asp Ala Leu Tyr Ala Val Leu Ser Gly Ser Arg
                165                 170                 175

Ala Ser Ser Gly Asn Leu Gly His Asp Pro Leu Gly Ala Ala Ala Arg
            180                 185                 190

Thr Gly Ser Ala Pro Asp Leu Ala Pro Leu Ala Asp Ala Val Arg Arg
    195                 200                 205

Leu Ala Asp His Gly Glu Ile Arg Ala Ile Thr Val Asp Thr Arg Val
210                 215                 220

His Gly Asp Ala Gly Val Thr Val Thr Asp Glu Val Ala Phe Ala Leu
225                 230                 235                 240

Ala Thr Gly Val Ala Tyr Leu Arg His Leu Glu Ser Glu Gly Val Asp
                245                 250                 255

Val Ala Glu Ala Phe Arg Asn Ile Glu Phe Arg Val Ser Ala Thr Ala
            260                 265                 270
```

```
Asp Gln Phe Leu Thr Ala Ala Ala Leu Arg Ala Leu Arg Arg Ala Trp
            275                 280                 285

Ala Arg Ile Gly Glu Ser Val Gly Val Pro Glu Thr Ser Arg Gly Ala
290                 295                 300

Phe Thr His Ala Val Thr Ser Gly Arg Ile Phe Thr Arg Asp Asp Ala
305                 310                 315                 320

Trp Thr Asn Ile Leu Arg Ser Thr Leu Ala Thr Phe Gly Ala Ser Leu
                325                 330                 335

Gly Gly Ala Asp Ala Ile Thr Val Leu Pro Phe Asp Thr Val Ser Gly
                340                 345                 350

Leu Pro Thr Pro Phe Ser Arg Arg Ile Ala Arg Asn Thr Gln Ile Leu
                355                 360                 365

Leu Ala Glu Glu Ser Asn Val Ala Arg Val Thr Asp Pro Ala Gly Gly
                370                 375                 380

Ser Trp Tyr Val Glu Thr Leu Thr Asp Asp Val Ala Lys Ala Ala Trp
385                 390                 395                 400

Glu Thr Phe Gln Glu Ile Glu Ser Ala Gly Gly Met Val Ala Ala Leu
                405                 410                 415

Ala Asn Gly Leu Val Ala Gln Arg Ile Leu Ala Ala Val Ala Glu Arg
                420                 425                 430

Asp Ala Ala Leu Ala Thr Arg Ser Thr Pro Ile Thr Gly Val Ser Thr
                435                 440                 445

Phe Pro Leu Ala Gly Glu Lys Pro Leu Glu Arg Val Val Arg Ala Glu
                450                 455                 460

Leu Pro Val Gln Pro Asn Ala Leu Ala Pro His Arg Asp Ser Ala Ile
465                 470                 475                 480

Phe Glu Ala Leu Arg Asp Arg Ser Ala Ala Tyr Ala Thr Glu His Gly
                485                 490                 495

His Ala Pro Arg Val Ser Val Pro Thr Leu Asp Val Pro Arg Ala Ala
                500                 505                 510

Asp Arg Arg Ile Asp Ala Val Asn Leu Leu Thr Val Ala Gly Ile Asp
                515                 520                 525

Ala Val Asp Gly Asp Thr Glu Ser Ala Ala Ala Leu Thr Gly Thr Asp
                530                 535                 540

Lys Gly Tyr Glu Gly Val Ala Lys Asp Met Asp Val Val Ala Phe Leu
545                 550                 555                 560

Ser Asp Leu Leu Asp Thr Thr Gly Ala Pro Ala
                565                 570

<210> SEQ ID NO 5
<211> LENGTH: 146
<212> TYPE: PRT
<213> ORGANISM: Escherichia coli

<400> SEQUENCE: 5

Met Leu Thr Arg Ile Asp His Ile Gly Ile Ala Cys Phe Asp Leu Asp
1               5                   10                  15

Lys Thr Val Glu Phe Tyr Arg Ala Thr Tyr Gly Phe Glu Val Phe His
                20                  25                  30

Ser Glu Val Asn Glu Glu Gln Gly Val Arg Glu Ala Met Leu Lys Ile
                35                  40                  45

Asn Glu Thr Ser Asp Gly Gly Ala Ser Tyr Leu Gln Leu Leu Glu Pro
            50                  55                  60

Thr Arg Pro Asp Ser Thr Val Ala Lys Trp Leu Asp Lys Asn Gly Glu
```

```
                65                  70                  75                  80
Gly Val His His Ile Ala Phe Gly Thr Ala Asp Val Asp Gln Asp Ala
                    85                  90                  95

Ala Asp Ile Lys Asp Lys Gly Val Arg Val Leu Tyr Glu Glu Pro Arg
                100                 105                 110

Arg Gly Ser Met Gly Ser Arg Ile Thr Phe Leu His Pro Lys Asp Cys
            115                 120                 125

His Gly Val Leu Thr Glu Leu Val Thr Ser Ala Pro Val Glu Ser Pro
        130                 135                 140

Glu His
145

<210> SEQ ID NO 6
<211> LENGTH: 146
<212> TYPE: PRT
<213> ORGANISM: Streptomyces sviceus

<400> SEQUENCE: 6

Met Leu Thr Arg Ile Asp His Ile Gly Ile Ala Cys Phe Asp Leu Asp
1               5                   10                  15

Lys Thr Val Glu Phe Tyr Arg Ala Thr Tyr Gly Phe Glu Val Phe His
                20                  25                  30

Ser Glu Val Asn Glu Glu Gln Gly Val Arg Glu Ala Met Leu Lys Ile
            35                  40                  45

Asn Glu Thr Ser Asp Gly Gly Ala Ser Tyr Leu Gln Leu Leu Glu Pro
        50                  55                  60

Thr Arg Pro Asp Ser Thr Val Ala Lys Trp Leu Asp Lys Asn Gly Glu
65                  70                  75                  80

Gly Val His His Ile Ala Phe Gly Thr Ala Asp Val Asp Gln Asp Ala
                    85                  90                  95

Ala Asp Ile Lys Asp Lys Gly Val Arg Val Leu Tyr Glu Glu Pro Arg
                100                 105                 110

Arg Gly Ser Met Gly Ser Arg Ile Thr Phe Leu His Pro Lys Asp Cys
            115                 120                 125

His Gly Val Leu Thr Glu Leu Val Thr Ser Ala Pro Val Glu Ser Pro
        130                 135                 140

Glu His
145

<210> SEQ ID NO 7
<211> LENGTH: 1773
<212> TYPE: DNA
<213> ORGANISM: Streptomyces coelicolor
<300> PUBLICATION INFORMATION:
<308> DATABASE ACCESSION NUMBER: GenBank / AF113603.1
<309> DATABASE ENTRY DATE: 1999-12-08
<313> RELEVANT RESIDUES IN SEQ ID NO: (1)..(1773)

<400> SEQUENCE: 7
gtgcgcaagg tgctcatcgc caatcgtggc gaaatcgctg tccgcgtggc ccgggcctgc      60
cgggacgccg ggatcgcgag cgtggccgtc tacgcggatc cggaccggga cgcgttgcac     120
gtccgtgccg ctgatgaggc gttcgccctg ggtggtgaca cccccgcgac cagctatctg     180
gacatcgcca aggtcctcaa agccgcgcgc gagtcgggcg cggacgccat ccaccccggc     240
tacggattcc tctcggagaa cgccgagttc gcgcaggcgg tcctgacgc cggcctgatc     300 tggatcggcc cgccccgca cgccatccgc gaccgtggcg aaaaggtcgc cgcccgccac     360
```

| | |
|---|---|
| atcgcccagc gggccggcgc ccccctggtc gccggcaccc ccgacccgt ctccggcgcg | 420 |
| gacgaggtcg tcgccttcgc caaggagcac ggcctgccca tcgccatcaa ggccgccttc | 480 |
| ggcggcggcg ggcgcggcct caaggtcgcc cgcaccctcg aagaggtgcc ggagctgtac | 540 |
| gactccgccg tccgcgaggc cgtggccgcc ttcggccgcg gggagtgctt cgtcgagcgc | 600 |
| tacctcgaca agccccgcca cgtggagacc cagtgcctgg ccgacaccca cggcaacgtg | 660 |
| gtcgtcgtct ccaccgcga ctgctccctc cagcgccgcc accaaaagct cgtcgaggag | 720 |
| gcccccgcgc cctttctctc cgaggcccag acggagcagc tgtactcatc ctccaaggcc | 780 |
| atcctgaagg aggccggcta cggcggcgcc ggcaccgtgg agttcctcgt cggcatggac | 840 |
| ggcacgatct tcttcctgga ggtcaacacc cgcctccagg tcgagcaccc ggtcaccgag | 900 |
| gaagtcgccg gcatcgactt ggtccgcgag atgttccgca tcgccgacgg cgaggaactc | 960 |
| ggttacgacg accccgccct gcgcggccac tccttcgagt tccgcatcaa cggcgaggac | 1020 |
| cccggccgcg gcttcctgcc cgcccccggc accgtcaccc tcttcgacgc gcccaccggc | 1080 |
| cccggcgtcc gcctggacgc cggcgtcgag tccggctccg tcatcggccc cgcctgggac | 1140 |
| tccctcctcg ccaaactgat cgtcaccggc cgcaccccgcg ccgaggcact ccagcgcgcg | 1200 |
| gccccgcgcc tggacgagtt caccgtcgag ggcatggcca ccgccatccc cttccaccgc | 1260 |
| acggtcgtcc gcgacccggc cttcgccccc gaactcaccg gctccacgga ccccttcacc | 1320 |
| gtccacaccc ggtggatcga gacggagttc gtcaacgaga tcaagcccctt caccacgccc | 1380 |
| gccgacaccg agacggacga ggagtcgggc cgggagacgg tcgtcgtcga ggtcggcggc | 1440 |
| aagcgcctgg aagtctccct ccctccagc ctgggcatgt cctggcccg caccggcctg | 1500 |
| gccgccgggg cccgccccaa gcgccgcgcg gccaagaagt ccggccccgc cgcctcgggc | 1560 |
| gacaccctcg cctccccgat gcagggcacg atcgtcaaga tcgccgtcga ggaaggccag | 1620 |
| gaagtccagg aaggcgacct catcgtcgta ctcgaggcga tgaagatgga acagcccctc | 1680 |
| aacgcccaca gtccggcac catcaagggc ctcaccgccg aggtcggcgc ctccctcacc | 1740 |
| tccggcgccg ccatctgcga gatcaaggac tga | 1773 |

<210> SEQ ID NO 8
<211> LENGTH: 1593
<212> TYPE: DNA
<213> ORGANISM: Streptomyces coelicolor
<300> PUBLICATION INFORMATION:
<308> DATABASE ACCESSION NUMBER: GenBank / AF113605.1
<309> DATABASE ENTRY DATE: 1999-12-08
<313> RELEVANT RESIDUES IN SEQ ID NO: (1)..(1593)

<400> SEQUENCE: 8

| | |
|---|---|
| atgtccgagc cggaagagca gcagcccgac atccacacga ccgcgggcaa gctcgcggat | 60 |
| ctcaggcgcc gtatcgagga agcgacgcac gccggttccg cacgcgccgt cgagaagcag | 120 |
| cacgccaagg gcaagctgac ggctcgtgaa cgcatcgacc tcctcctcga cgagggttcc | 180 |
| ttcgtcgagc tggacgagtt cgcccggcac cgctccacca acttcggcct cgacgccaac | 240 |
| cgccccctacg gcgacggcgt cgtcaccggc tacggcaccg tcgacggccg cccgtggcc | 300 |
| gtcttctccc aggacttcac cgtcttcggc ggcgcgctgg gcgaggtcta cggccagaag | 360 |
| atcgtcaagg tgatggactt cgcccctcaag accggctgcc cggtcgtcgg catcaacgac | 420 |
| tccggcggcg cccgcatcca ggagggcgtg gcctccctcg cgcctacgg cgagatcttc | 480 |
| cgccgcaaca cccacgcctc cggcgtgatc ccgcagatca gctggtcgt cggccgtgt | 540 |
| gcgggcggcg cggtgtactc ccccgcgatc accgacttca cggtgatggt ggaccagacc | 600 |

```
agccacatgt tcatcaccgg tcccgacgtc atcaagacgg tcaccggcga ggacgtcggc    660
ttcgaggagc tgggcggcgc ccgcacccac aactccacct cgggcgtggc ccaccacatg    720
gccggcgacg agaaggacgc ggtcgagtac gtcaagcagc tcctgtcgta cctgccgtcc    780
aacaacctct ccgagccccc cgccttcccg gaggaggcgg acctcgcggt cacggacgag    840
gacgccgagc tggacacgat cgtcccggac tcggcgaacc agccctacga catgcactcc    900
gtcatcgagc acgtcctgga cgacgccgag ttcttcgaga cgcaacccct cttcgcgccg    960
aacatcctca ccggcttcgg ccgcgtggag ggccgcccgg tcggcatcgt cgccaaccag   1020
cccatgcagt tcgccggctg cctggacatc acggcctccg agaaggcggc ccgcttcgtg   1080
cgcacctgcg acgccttcaa cgtccccgtc ctcaccttcg tggacgtccc cggcttcctg   1140
cccggcgtcg accaggagca cgacggcatc atccgccgcg cgccaagct gatcttcgcc    1200 tacgccgagg ccacggtgcc gctcatcacg gtcatcaccc gcaaggcctt cggcggcgcc   1260
tacgacgtca tgggctccaa gcacctgggc gccgacctca acctggcctg cccaccgcc    1320 cagatcgccg tcatgggcgc ccaaggcgcg gtcaacatcc tgcaccgccg caccatcgcc   1380
gacgccggtg acgacgccga ggccaccccgg gcccgcctga tccaggagta cgaggacgcc   1440
ctcctcaacc cctacacggc ggccgaacgc ggctacgtcg acgccgtgat catgccctcc   1500
gacactcgcc gccacatcgt ccgcggcctg cgccagctgc gcaccaagcg cgagtccctg   1560
cccccgaaga agcacggcaa catccccctg taa                                 1593
```

<210> SEQ ID NO 9
<211> LENGTH: 590
<212> TYPE: PRT
<213> ORGANISM: Streptomyces coelicolor
<300> PUBLICATION INFORMATION:
<308> DATABASE ACCESSION NUMBER: GenBank / AF113603.1
<309> DATABASE ENTRY DATE: 1999-12-08
<313> RELEVANT RESIDUES IN SEQ ID NO: (1)..(590)

<400> SEQUENCE: 9

```
Met Arg Lys Val Leu Ile Ala Asn Arg Gly Glu Ile Ala Val Arg Val
1               5                   10                  15

Ala Arg Ala Cys Arg Asp Ala Gly Ile Ala Ser Val Ala Val Tyr Ala
            20                  25                  30

Asp Pro Asp Arg Asp Ala Leu His Val Arg Ala Ala Asp Glu Ala Phe
        35                  40                  45

Ala Leu Gly Gly Asp Thr Pro Ala Thr Ser Tyr Leu Asp Ile Ala Lys
    50                  55                  60

Val Leu Lys Ala Ala Arg Glu Ser Gly Ala Asp Ala Ile His Pro Gly
65                  70                  75                  80

Tyr Gly Phe Leu Ser Glu Asn Ala Glu Phe Ala Gln Ala Val Leu Asp
                85                  90                  95

Ala Gly Leu Ile Trp Ile Gly Pro Pro His Ala Ile Arg Asp Arg
            100                 105                 110

Gly Glu Lys Val Ala Ala Arg His Ile Ala Gln Arg Ala Gly Ala Pro
        115                 120                 125

Leu Val Ala Gly Thr Pro Asp Pro Val Ser Gly Ala Asp Glu Val Val
    130                 135                 140

Ala Phe Ala Lys Glu His Gly Leu Pro Ile Ala Ile Lys Ala Ala Phe
145                 150                 155                 160

Gly Gly Gly Gly Arg Gly Leu Lys Val Ala Arg Thr Leu Glu Glu Val
                165                 170                 175
```

```
Pro Glu Leu Tyr Asp Ser Ala Val Arg Glu Ala Val Ala Ala Phe Gly
            180                 185                 190

Arg Gly Glu Cys Phe Val Glu Arg Tyr Leu Asp Lys Pro Arg His Val
        195                 200                 205

Glu Thr Gln Cys Leu Ala Asp Thr His Gly Asn Val Val Val Val Ser
    210                 215                 220

Thr Arg Asp Cys Ser Leu Gln Arg Arg His Gln Lys Leu Val Glu Glu
225                 230                 235                 240

Ala Pro Ala Pro Phe Leu Ser Glu Ala Gln Thr Gln Leu Tyr Ser
                245                 250                 255

Ser Ser Lys Ala Ile Leu Lys Glu Ala Gly Tyr Gly Gly Ala Gly Thr
            260                 265                 270

Val Glu Phe Leu Val Gly Met Asp Gly Thr Ile Phe Phe Leu Glu Val
        275                 280                 285

Asn Thr Arg Leu Gln Val Glu His Pro Val Thr Glu Glu Val Ala Gly
    290                 295                 300

Ile Asp Leu Val Arg Glu Met Phe Arg Ile Ala Asp Gly Glu Glu Leu
305                 310                 315                 320

Gly Tyr Asp Asp Pro Ala Leu Arg Gly His Ser Phe Glu Phe Arg Ile
                325                 330                 335

Asn Gly Glu Asp Pro Gly Arg Gly Phe Leu Pro Ala Pro Gly Thr Val
            340                 345                 350

Thr Leu Phe Asp Ala Pro Thr Gly Pro Gly Val Arg Leu Asp Ala Gly
        355                 360                 365

Val Glu Ser Gly Ser Val Ile Gly Pro Ala Trp Asp Ser Leu Leu Ala
    370                 375                 380

Lys Leu Ile Val Thr Gly Arg Thr Arg Ala Glu Ala Leu Gln Arg Ala
385                 390                 395                 400

Ala Arg Ala Leu Asp Glu Phe Thr Val Glu Gly Met Ala Thr Ala Ile
                405                 410                 415

Pro Phe His Arg Thr Val Arg Asp Pro Ala Phe Ala Pro Glu Leu
            420                 425                 430

Thr Gly Ser Thr Asp Pro Phe Thr Val His Thr Arg Trp Ile Glu Thr
        435                 440                 445

Glu Phe Val Asn Glu Ile Lys Pro Phe Thr Thr Pro Ala Asp Thr Glu
    450                 455                 460

Thr Asp Glu Glu Ser Gly Arg Glu Thr Val Val Glu Val Gly Gly
465                 470                 475                 480

Lys Arg Leu Glu Val Ser Leu Pro Ser Ser Leu Gly Met Ser Leu Ala
                485                 490                 495

Arg Thr Gly Leu Ala Ala Gly Ala Arg Pro Lys Arg Arg Ala Ala Lys
            500                 505                 510

Lys Ser Gly Pro Ala Ala Ser Gly Asp Thr Leu Ala Ser Pro Met Gln
        515                 520                 525

Gly Thr Ile Val Lys Ile Ala Val Glu Glu Gly Gln Glu Val Gln Glu
    530                 535                 540

Gly Asp Leu Ile Val Val Leu Glu Ala Met Lys Met Glu Gln Pro Leu
545                 550                 555                 560

Asn Ala His Arg Ser Gly Thr Ile Lys Gly Leu Thr Ala Glu Val Gly
                565                 570                 575

Ala Ser Leu Thr Ser Gly Ala Ala Ile Cys Glu Ile Lys Asp
            580                 585                 590
```

<210> SEQ ID NO 10
<211> LENGTH: 530
<212> TYPE: PRT
<213> ORGANISM: Streptomyces coelicolor
<300> PUBLICATION INFORMATION:
<308> DATABASE ACCESSION NUMBER: GenBank / AF113605.1
<309> DATABASE ENTRY DATE: 1999-12-08
<313> RELEVANT RESIDUES IN SEQ ID NO: (1)..(530)

<400> SEQUENCE: 10

```
Met Ser Glu Pro Glu Glu Gln Gln Pro Asp Ile His Thr Thr Ala Gly
1               5                   10                  15

Lys Leu Ala Asp Leu Arg Arg Arg Ile Glu Glu Ala Thr His Ala Gly
            20                  25                  30

Ser Ala Arg Ala Val Glu Lys Gln His Ala Lys Gly Lys Leu Thr Ala
        35                  40                  45

Arg Glu Arg Ile Asp Leu Leu Leu Asp Glu Gly Ser Phe Val Glu Leu
    50                  55                  60

Asp Glu Phe Ala Arg His Arg Ser Thr Asn Phe Gly Leu Asp Ala Asn
65                  70                  75                  80

Arg Pro Tyr Gly Asp Gly Val Val Thr Gly Tyr Gly Thr Val Asp Gly
                85                  90                  95

Arg Pro Val Ala Val Phe Ser Gln Asp Phe Thr Val Phe Gly Gly Ala
            100                 105                 110

Leu Gly Glu Val Tyr Gly Gln Lys Ile Val Lys Val Met Asp Phe Ala
        115                 120                 125

Leu Lys Thr Gly Cys Pro Val Val Gly Ile Asn Asp Ser Gly Gly Ala
    130                 135                 140

Arg Ile Gln Glu Gly Val Ala Ser Leu Gly Ala Tyr Gly Glu Ile Phe
145                 150                 155                 160

Arg Arg Asn Thr His Ala Ser Gly Val Ile Pro Gln Ile Ser Leu Val
                165                 170                 175

Val Gly Pro Cys Ala Gly Gly Ala Val Tyr Ser Pro Ala Ile Thr Asp
            180                 185                 190

Phe Thr Val Met Val Asp Gln Thr Ser His Met Phe Ile Thr Gly Pro
        195                 200                 205

Asp Val Ile Lys Thr Val Thr Gly Glu Asp Val Gly Phe Glu Glu Leu
    210                 215                 220

Gly Gly Ala Arg Thr His Asn Ser Thr Ser Gly Val Ala His His Met
225                 230                 235                 240

Ala Gly Asp Glu Lys Asp Ala Val Glu Tyr Val Lys Gln Leu Leu Ser
                245                 250                 255

Tyr Leu Pro Ser Asn Asn Leu Ser Glu Pro Pro Ala Phe Pro Glu Glu
            260                 265                 270

Ala Asp Leu Ala Val Thr Asp Glu Asp Ala Glu Leu Asp Thr Ile Val
        275                 280                 285

Pro Asp Ser Ala Asn Gln Pro Tyr Asp Met His Ser Val Ile Glu His
    290                 295                 300

Val Leu Asp Asp Ala Glu Phe Phe Glu Thr Gln Pro Leu Phe Ala Pro
305                 310                 315                 320

Asn Ile Leu Thr Gly Phe Gly Arg Val Glu Gly Arg Pro Val Gly Ile
                325                 330                 335

Val Ala Asn Gln Pro Met Gln Phe Ala Gly Cys Leu Asp Ile Thr Ala
            340                 345                 350

Ser Glu Lys Ala Ala Arg Phe Val Arg Thr Cys Asp Ala Phe Asn Val
```

```
                355                 360                 365
Pro Val Leu Thr Phe Val Asp Val Pro Gly Phe Leu Pro Gly Val Asp
    370                 375                 380
Gln Glu His Asp Gly Ile Ile Arg Arg Gly Ala Lys Leu Ile Phe Ala
385                 390                 395                 400
Tyr Ala Glu Ala Thr Val Pro Leu Ile Thr Val Ile Thr Arg Lys Ala
                405                 410                 415
Phe Gly Gly Ala Tyr Asp Val Met Gly Ser Lys His Leu Gly Ala Asp
                420                 425                 430
Leu Asn Leu Ala Trp Pro Thr Ala Gln Ile Ala Val Met Gly Ala Gln
                435                 440                 445
Gly Ala Val Asn Ile Leu His Arg Arg Thr Ile Ala Asp Ala Gly Asp
    450                 455                 460
Asp Ala Glu Ala Thr Arg Ala Arg Leu Ile Gln Glu Tyr Glu Asp Ala
465                 470                 475                 480
Leu Leu Asn Pro Tyr Thr Ala Ala Glu Arg Gly Tyr Val Asp Ala Val
                485                 490                 495
Ile Met Pro Ser Asp Thr Arg Arg His Ile Val Arg Gly Leu Arg Gln
                500                 505                 510
Leu Arg Thr Lys Arg Glu Ser Leu Pro Pro Lys Lys His Gly Asn Ile
                515                 520                 525
Pro Leu
    530

<210> SEQ ID NO 11
<211> LENGTH: 116
<212> TYPE: DNA
<213> ORGANISM: Streptomyces coelicolor

<400> SEQUENCE: 11
aattgtgagc ggataacaat tgacattgtg agcggataac aagatactga gcacatcagc    60
aggacgcact gaccgaattc aataattttg tttaacttta agaaggagat atacat        116

<210> SEQ ID NO 12
<211> LENGTH: 1773
<212> TYPE: DNA
<213> ORGANISM: Streptomyces coelicolor

<400> SEQUENCE: 12
atgcgcaaag tgctgattgc gaaccgtggt gaaatcgccg ttcgtgtggc acgcgcgtgt    60
cgtgatgcag gtattgcaag tgttgcggtg tatgccgatc ggatcgcga tgcgctgcat    120 gttcgtgcgg ccgatgaagc ctttgcactg gcggtgata ccccggcaac gagctatctg    180
gatattgcaa aagtgctgaa agcagcgcgc gaaagcggtg cggatgccat ccatccgggc    240
tacggttttc tgtctgaaaa tgcagaattt gcacaggcgg ttctggatgc aggtctgatt    300
tggatcggtc cgccgccgca tgcaattcgt gatctgggcg ataaagtggc cgcacgccac    360
atcgcccagc gtgcaggcgc gccgctggtt gcgggcaccc cggacccggt ttctggtgca    420
gatgaagtgg ttgcgtttgc caaagaacat ggcctgccga ttgcgatcaa agcagcattc    480
ggcggtggcg gtcgcggtct gaaagtggcc cgtaccctgg aagaagttcc ggaactgtat    540
gatagcgcag ttcgcgaagc ggtggcagcg tttggccgtg gtgaatgctt cgtggaacgc    600
tacctggata aaccgcgtca tgttgaaacc cagtgtctgg cggatacgca cggcaacgtg    660
gttgtggtta gcacccgcga ttgctctctg caacgtcgcc accagaaact ggtggaagaa    720
```

```
gcaccggcgc cgtttctgag cgaagcccag accgaacagc tgtatagctc tagtaaagcg      780
attctgaaag aagccggtta cgtgggcgcc ggtacggttg aatttctggt gggcatggat      840
ggcaccatta gctttctgga agttaacacc cgtctgcaag ttgaacatcc ggtgaccgaa      900
gaagttgcgg gcattgatct ggtgcgcgaa atgtttcgta cgcagatgg cgaagaactg      960 ggttacgatg atccggcgct gcgcggtcac agctttgaat ttcgtattaa tggcgaagat     1020
ccgggccgtg gttttctgcc ggcgccgggc ccgtgacgc tgttcgatgc accgaccggt     1080
ccgggcgttc gtctggatgc cggtgtggaa agtggtagcg ttattggccc ggcatgggat     1140
agcctgctgg cgaaactgat cgttaccggt cgtacgcgcg ccgaagcgct gcaacgtgca     1200
gcacgtgccc tggatgaatt taccgtggaa ggcatggcga cggccattcc gtttcatcgc     1260
accgtggttc gtgatccggc attcgcgccg gaactgaccg gctctaccga tccgttcacc     1320
gtgcacacgc gctggatcga aaccgaattt gttaacgaaa tcaaaccgtt caccacgccg     1380
gcggataccg aaacggatga agaaagtggt cgcgaaacgg tggttgtgga agtgggcggt     1440
aaacgtctgg aagtttctct gccgagcagc ctgggtatga gtctggcgcg taccggtctg     1500
gcggccggcg cccgtccgaa acgtcgcgca gcgaaaaaat ctggtccggc cgcaagcggt     1560
gataccctgg ccagtccgat gcagggcacg attgtgaaaa tcgcagtgga agaaggtcag     1620
gaagtgcagg aaggcgatct gattgttgtg ctggaagcga tgaaaatgga acagccgctg     1680
aatgcccatc gtagcggcac catcaaaggc ctgacggccg aagtgggtgc atctctgacc     1740
agtggcgcgg ccatttgcga aatcaaagat taa                                   1773

<210> SEQ ID NO 13
<211> LENGTH: 57
<212> TYPE: DNA
<213> ORGANISM: Streptomyces coelicolor

<400> SEQUENCE: 13
agatctgcgg ccgcatctag aaataatttt gtttaacttt aagaaggaga tatattc          57

<210> SEQ ID NO 14
<211> LENGTH: 1593
<212> TYPE: DNA
<213> ORGANISM: Streptomyces coelicolor

<400> SEQUENCE: 14
atgagtgaac cggaagaaca gcagccggat attcatacca cggcaggcaa actggcggat       60
ctgcgtcgcc gtatcgaaga agcaacccat gcaggtagcg cacgtgcagt ggaaaaacag      120
cacgcgaaag gtaaactgac ggcccgcgaa cgtatcgatc tgctgctgga tgaaggcagt      180
tttgttgaac tggatgaatt tgcacgccac cgtagcacca ctttggtct ggatgcgaat      240 cgcccgtatg gcgatggtgt ggttaccggt tacggtacgg tggatggtcg tccggtggca      300 gttttagcc aggattttac cgtgttcggc ggtgcactgg gcgaagttta cggtcagaaa      360
atcgtgaaag ttatggattt cgcgctgaaa acgggctgcc cggtgttgg tattaacgat      420 agcggcggtg cccgcatcca ggaaggtgtt gcctctctgg gcgcgtatgg cgaaatcttt      480
cgccgtaata cccatgcgag tggcgtgatt ccgcagatca gcctggtggt tggtccgtgt      540
gcgggcggtg ccgtttactc tccggccatt accgatttta cggtgatggt tgatcagacc      600
agtcacatgt tcattacggg cccggatgtg atcaaaaccg ttacgggcga agatgtgggt      660
tttgaagaac tgggcggtgc acgtacccac aacagcacgt ctggcgttgc gcatcacatg      720
gccggtgatg aaaaagatgc cgtggaatat gttaaacagc tgctgagtta cctgccgagc      780
```

```
aacaatctgt ctgaaccgcc ggcgttccgg gaagaagcag acctggcggt gaccgatgaa    840
gatgccgaac tggatacgat cgttccggat tctgcaaatc agccgtacga tatgcacagt    900
gtgattgaac acgttctgga tgatgcggaa ttttttcgaaa cccagccgct gtttgccccg   960
aacattctga cgggtttcgg tcgtgtggaa ggtcgtccgg tgggtatcgt tgcaaatcag   1020
ccgatgcagt ttgcgggttg cctggatatt accgcctctg aaaaagcggc ccgctttgtg   1080
cgtacctgtg atgcgttcaa cgtgccggtt ctgacgtttg tggatgttcc gggcttcctg   1140
ccgggtgttg atcaggaaca tgatggcatt atccgccgtg gtgcgaaact gattttttgcg  1200 tatgccgaag caaccgtgcc gctgattacc gttatcacgc gcaaagcatt cggcggtgcg   1260
tacgatgtga tgggcagcaa acatctgggt gccgatctga acctggcatg gccgaccgca   1320
cagatcgcag tgatgggcgc gcagggtgcc gttaatattc tgcaccgccg taccatcgca   1380
gatgcaggtg atgatgcaga agcgacgcgc gcacgtctga ttcaggaata tgaagatgcg   1440
ctgctgaacc cgtataccgc agcggaacgt ggttacgtgg atgcggttat tatgccgagc   1500
gatacccgcc gtcatatcgt gcgtggtctg cgtcagctgc gtacgaaacg tgaatctctg   1560
ccgccgaaaa aacacggtaa tattccgctg taa                                1593

<210> SEQ ID NO 15
<211> LENGTH: 3539
<212> TYPE: DNA
<213> ORGANISM: Artificial Sequence
<220> FEATURE:
<223> OTHER INFORMATION: Synthetic nucleotide

<400> SEQUENCE: 15
aattgtgagc ggataacaat tgacattgtg agcggataac aagatactga gcacatcagc     60
aggacgcact gaccgaattc aataattttg tttaacttta agaaggagat atacatatgc    120
gcaaagtgct gattgcgaac cgtggtgaaa tcgccgttcg tgtggcacgc gcgtgtcgtg    180
atgcaggtat tgcaagtgtt gcggtgtatg ccgatccgga tcgcgatgcg ctgcatgttc    240
gtgcggccga tgaagccttt gcactgggcg gtgataccc ggcaacgagc tatctggata    300
ttgcaaaagt gctgaaagca gcgcgcgaaa gcggtgcgga tgccatccat ccgggctacg    360
gttttctgtc tgaaaatgca gaatttgcac aggcggttct ggatgcaggt ctgatttgga    420
tcggtccgcc gccgcatgca attcgtgatc tgggcgataa agtggccgca cgccacatcg    480
cccagcgtgc aggcgcgccg ctggttgcgg caccccggga cccggtttct ggtgcagatg    540
aagtggttgc gtttgccaaa gaacatggcc tgccgattgc gatcaaagca gcattcggcg    600
gtggcggtcg cggtctgaaa gtggcccgta ccctggaaga agttccggaa ctgtatgata    660
gcgcagttcg cgaagcggtg gcagcgtttg gcgtgtgta atgcttcgtg gaacgctacc    720
tggataaacc gcgtcatgtt gaaacccagt gtctggcgga tacgcacggc aacgtggttg    780
tggttagcac ccgcgattgc tctctgcaac gtcgccacca gaaactggtg gaagaagcac    840
cggcgccgtt tctgagcgaa gcccagaccg aacagctgta tagctctagt aaagcgattc    900
tgaaagaagc cggttacgtg ggcgccggta cggttgaatt ctggtgggc atggatggca    960 ccattagctt tctggaagtt aacacccgtc tgcaagttga acatccggtg accgaagaag   1020
ttgcgggcat tgatctggtg cgcgaaatgt tcgtatcgc agatggcgaa gaactgggtt   1080
acgatgatcc ggcgctgcgc ggtcacagct ttgaatttcg tattaatggc gaagatccgg   1140
gccgtggttt tctgccggcg ccgggcaccg tgacgctgtt cgatgcaccg accggtccgg   1200
```

-continued

```
gcgttcgtct ggatgccggt gtggaaagtg gtagcgttat tggcccggca tgggatagcc      1260
tgctggcgaa actgatcgtt accggtcgta cgcgcgccga agcgctgcaa cgtgcagcac      1320
gtgccctgga tgaatttacc gtggaaggca tggcgacggc cattccgttt catcgcaccg      1380
tggttcgtga tccggcattc gcgccggaac tgaccggctc taccgatccg ttcaccgtgc      1440
acacgcgctg gatcgaaacc gaatttgtta acgaaatcaa accgttcacc acgccggcgg      1500
ataccgaaac ggatgaagaa agtggtcgcg aaacggtggt tgtggaagtg ggcggtaaac      1560
gtctggaagt ttctctgccg agcagcctgg gtatgagtct ggcgcgtacc ggtctggcgg      1620
ccggcgcccg tccgaaacgt cgcgcagcga aaaaatctgg tccggccgca agcggtgata      1680
ccctggccag tccgatgcag ggcacgattg tgaaaatcgc agtggaagaa ggtcaggaag      1740
tgcaggaagg cgatctgatt gttgtgctgg aagcgatgaa aatggaacag ccgctgaatg      1800
cccatcgtag cggcaccatc aaaggcctga cggccgaagt gggtgcatct ctgaccagtg      1860
gcgcggccat ttgcgaaatc aaagattaaa gatctgcggc cgcatctaga ataattttg       1920
tttaacttta agaaggagat atattcatga gtgaaccgga agaacagcag ccggatattc      1980
ataccacggc aggcaaactg gcggatctgc gtcgccgtat cgaagaagca acccatgcag      2040
gtagcgcacg tgcagtggaa aaacagcacg cgaaaggtaa actgacggcc cgcgaacgta      2100
tcgatctgct gctggatgaa ggcagttttg ttgaactgga tgaatttgca cgccaccgta      2160
gcaccaactt tggtctggat gcgaatcgcc cgtatgcga tggtgtggtt accggttacg       2220
gtacggtgga tggtcgtccg gtggcagttt ttagccagga ttttaccgtg ttcggcggtg      2280
cactgggcga agtttacggt cagaaaatcg tgaaagttat ggatttcgcg ctgaaaacgg      2340
gctgccggt ggttggtatt aacgatagcg gcggtgcccg catccaggaa ggtgttgcct       2400
ctctgggcgc gtatgcgaa atctttcgcc gtaatacccca tgcgagtggc gtgattccgc      2460
agatcagcct ggtggttggt ccgtgtgcgg gcggtgccgt ttactctccg gccattaccg      2520
attttacggt gatggttgat cagaccagtc acatgttcat tacgggcccg gatgtgatca      2580
aaaccgttac gggcgaagat gtgggttttg aagaactggg cggtgcacgt acccacaaca      2640
gcacgtctgg cgttgcgcat cacatggccg gtgatgaaaa agatgccgtg gaatatgtta      2700
aacagctgct gagttacctg ccgagcaaca atctgtctga accgccggcg ttcccggaag      2760
aagcagacct ggcggtgacc gatgaagatg ccgaactgga tacgatcgtt ccggattctg      2820
caaatcagcc gtacgatatg cacagtgtga ttgaacacgt tctggatgat gcggaatttt      2880
tcgaaaccca gccgctgttt gccccgaaca ttctgacggg tttcggtcgt gtggaaggtc      2940
gtccggtggg tatcgttgca aatcagccga tgcagtttgc gggttgcctg gatattaccg      3000
cctctgaaaa agcggccgc tttgtgcgta cctgtgatgc gttcaacgtg ccggttctga      3060
cgtttgtgga tgttccgggc ttcctgccgg gtgttgatca ggaacatgat ggcattatcc      3120
gccgtggtgc gaaactgatt tttgcgtatg ccgaagcaac cgtgccgctg attaccgtta      3180
tcacgcgcaa agcattcggc ggtgcgtacg atgtgatggg cagcaaacat ctgggtgccg      3240
atctgaacct ggcatggccg accgcacaga tcgcagtgat gggcgcgcag ggtgccgtta      3300
atattctgca ccgccgtacc atcgcagatg caggtgatga tgcagaagcg acgcgcgcac      3360
gtctgattca ggaatatgaa gatgcgctgc tgaacccgta taccgcagcg aacgtggtt      3420
acgtggatgc ggttattatg ccgagcgata cccgccgtca tatcgtgcgt ggtctgcgtc      3480
agctgcgtac gaaacgtgaa tctctgccgc cgaaaaaaca cggtaatatt ccgctgtaa      3539
```

-continued

<210> SEQ ID NO 16
<211> LENGTH: 45
<212> TYPE: DNA
<213> ORGANISM: Artificial Sequence
<220> FEATURE:
<223> OTHER INFORMATION: Synthetic primer

<400> SEQUENCE: 16
aaactgcaga ggaggacagc tatgtctttt agcgaatttt atcag 45

<210> SEQ ID NO 17
<211> LENGTH: 36
<212> TYPE: DNA
<213> ORGANISM: Artificial Sequence
<220> FEATURE:
<223> OTHER INFORMATION: Synthetic primer

<400> SEQUENCE: 17
aaaggatccc tattcttcga tcgcctggcg aatttg 36

<210> SEQ ID NO 18
<211> LENGTH: 383
<212> TYPE: PRT
<213> ORGANISM: Mycobacterium bovis

<400> SEQUENCE: 18

```
Leu Val Glu Gly Leu Arg Glu Val Ala Asp Gly Asp Ala Leu Tyr Asp
1               5                   10                  15

Ala Ala Val Gly His Gly Asp Arg Gly Pro Val Trp Val Phe Ser Gly
            20                  25                  30

Gln Gly Ser Gln Trp Ala Ala Met Gly Thr Gln Leu Leu Ala Ser Glu
        35                  40                  45

Pro Val Phe Ala Ala Thr Ile Ala Lys Leu Glu Pro Val Ile Ala Ala
    50                  55                  60

Glu Ser Gly Phe Ser Val Thr Glu Ala Ile Thr Ala Gln Gln Thr Val
65                  70                  75                  80

Thr Gly Ile Asp Lys Val Gln Pro Ala Val Phe Ala Val Gln Val Ala
                85                  90                  95

Leu Ala Ala Thr Met Glu Gln Thr Tyr Gly Val Arg Pro Gly Ala Val
            100                 105                 110

Val Gly His Ser Met Gly Glu Ser Ala Ala Ala Val Val Ala Gly Ala
        115                 120                 125

Leu Ser Leu Glu Asp Ala Ala Arg Val Ile Cys Arg Arg Ser Lys Leu
    130                 135                 140

Met Thr Arg Ile Ala Gly Ala Gly Ala Met Gly Ser Val Glu Leu Pro
145                 150                 155                 160

Ala Lys Gln Val Asn Ser Glu Leu Met Ala Arg Gly Ile Asp Asp Val
                165                 170                 175

Val Val Ser Val Val Ala Ser Pro Gln Ser Thr Val Ile Gly Gly Thr
            180                 185                 190

Ser Asp Thr Val Arg Asp Leu Ile Ala Arg Trp Glu Gln Arg Asp Val
        195                 200                 205

Met Ala Arg Glu Val Ala Val Asp Val Ala Ser His Ser Pro Gln Val
    210                 215                 220

Asp Pro Ile Leu Asp Asp Leu Ala Ala Ala Leu Ala Asp Ile Ala Pro
225                 230                 235                 240

Met Thr Pro Lys Val Pro Tyr Tyr Ser Ala Thr Leu Phe Asp Pro Arg
                245                 250                 255
```

```
Glu Gln Pro Val Cys Asp Gly Ala Tyr Trp Val Asp Asn Leu Arg Asn
            260                 265                 270

Thr Val Gln Phe Ala Ala Ala Val Gln Ala Ala Met Glu Asp Gly Tyr
        275                 280                 285

Arg Val Phe Ala Glu Leu Ser Pro His Pro Leu Leu Thr His Ala Val
    290                 295                 300

Glu Gln Thr Gly Arg Ser Leu Asp Met Ser Val Ala Ala Leu Ala Gly
305                 310                 315                 320

Met Arg Arg Glu Gln Pro Leu Pro His Gly Leu Arg Gly Leu Leu Thr
                325                 330                 335

Glu Leu His Arg Ala Gly Ala Ala Leu Asp Tyr Ser Ala Leu Tyr Pro
            340                 345                 350

Ala Gly Arg Leu Val Asp Ala Pro Leu Pro Ala Trp Thr His Ala Arg
        355                 360                 365

Leu Phe Ile Asp Asp Asp Gly Gln Glu Gln Arg Ala Gln Gly Ala
    370                 375                 380

<210> SEQ ID NO 19
<211> LENGTH: 2111
<212> TYPE: PRT
<213> ORGANISM: Mycobacterium bovis
<300> PUBLICATION INFORMATION:
<308> DATABASE ACCESSION NUMBER: GenBank / YP_97046
<309> DATABASE ENTRY DATE: 2010-12-14
<313> RELEVANT RESIDUES IN SEQ ID NO: (1)..(2111)

<400> SEQUENCE: 19

Met Glu Ser Arg Val Thr Pro Val Ala Val Ile Gly Met Gly Cys Arg
1               5                   10                  15

Leu Pro Gly Gly Ile Asn Ser Pro Asp Lys Leu Trp Glu Ser Leu Leu
            20                  25                  30

Arg Gly Asp Asp Leu Val Thr Glu Ile Pro Pro Asp Arg Trp Asp Ala
        35                  40                  45

Asp Asp Tyr Tyr Asp Pro Glu Pro Gly Val Pro Gly Arg Ser Val Ser
    50                  55                  60

Arg Trp Gly Gly Phe Leu Asp Asp Val Ala Gly Phe Asp Ala Glu Phe
65                  70                  75                  80

Phe Gly Ile Ser Glu Arg Glu Ala Thr Ser Ile Asp Pro Gln Gln Arg
                85                  90                  95

Leu Leu Leu Glu Thr Ser Trp Glu Ala Ile Glu His Ala Gly Leu Asp
            100                 105                 110

Pro Ala Ser Leu Ala Gly Ser Ser Thr Ala Val Phe Thr Gly Leu Thr
        115                 120                 125

His Glu Asp Tyr Leu Val Leu Thr Thr Thr Ala Gly Gly Leu Ala Ser
    130                 135                 140

Pro Tyr Val Val Thr Gly Leu Asn Asn Ser Val Ala Ser Gly Arg Ile
145                 150                 155                 160

Ala His Thr Leu Gly Leu His Gly Pro Ala Met Thr Phe Asp Thr Ala
                165                 170                 175

Cys Ser Ser Gly Leu Met Ala Val His Leu Ala Cys Arg Ser Leu His
            180                 185                 190

Asp Gly Glu Ala Asp Leu Ala Leu Ala Gly Gly Cys Ala Val Leu Leu
        195                 200                 205

Glu Pro His Ala Cys Val Ala Ala Ser Ala Gln Gly Met Leu Ser Ser
    210                 215                 220

Thr Gly Arg Cys His Ser Phe Asp Ala Asp Ala Asp Gly Phe Val Arg
```

```
            225                 230                 235                 240
    Ser Glu Gly Cys Ala Met Val Leu Leu Lys Arg Leu Pro Asp Ala Leu
                        245                 250                 255

Arg Asp Gly Asn Arg Ile Phe Ala Val Val Arg Gly Thr Ala Thr Asn
                        260                 265                 270

Gln Asp Gly Arg Thr Glu Thr Leu Thr Met Pro Ser Glu Asp Ala Gln
                        275                 280                 285

Val Ala Val Tyr Arg Ala Ala Leu Ala Ala Ala Gly Val Gln Pro Glu
                        290                 295                 300

Thr Val Gly Val Val Glu Ala His Gly Thr Gly Thr Pro Ile Gly Asp
    305                 310                 315                 320

Pro Ile Glu Tyr Arg Ser Leu Ala Arg Val Tyr Gly Ala Gly Thr Pro
                        325                 330                 335

Cys Ala Leu Gly Ser Ala Lys Ser Asn Met Gly His Ser Thr Ala Ser
                        340                 345                 350

Ala Gly Thr Val Gly Leu Ile Lys Ala Ile Leu Ser Leu Arg His Gly
                        355                 360                 365

Val Val Pro Pro Leu Leu His Phe Asn Arg Leu Pro Asp Glu Leu Ser
                        370                 375                 380

Asp Val Glu Thr Gly Leu Phe Val Pro Gln Ala Val Thr Pro Trp Pro
    385                 390                 395                 400

Asn Gly Asn Asp His Thr Pro Lys Arg Val Ala Val Ser Ser Phe Gly
                        405                 410                 415

Met Ser Gly Thr Asn Val His Ala Ile Val Glu Glu Ala Pro Ala Glu
                        420                 425                 430

Ala Ser Ala Pro Glu Ser Ser Pro Gly Asp Ala Glu Val Gly Pro Arg
                        435                 440                 445

Leu Phe Met Leu Ser Ser Thr Ser Ser Asp Ala Leu Arg Gln Thr Ala
                        450                 455                 460

Arg Gln Leu Ala Thr Trp Val Glu Glu His Gln Asp Cys Val Ala Ala
    465                 470                 475                 480

Ser Asp Leu Ala Tyr Thr Leu Ala Arg Gly Arg Ala His Arg Pro Val
                        485                 490                 495

Arg Thr Ala Val Val Ala Ala Asn Leu Pro Glu Leu Val Glu Gly Leu
                        500                 505                 510

Arg Glu Val Ala Asp Gly Asp Ala Leu Tyr Asp Ala Ala Val Gly His
                        515                 520                 525

Gly Asp Arg Gly Pro Val Trp Val Phe Ser Gly Gln Gly Ser Gln Trp
    530                 535                 540

Ala Ala Met Gly Thr Gln Leu Leu Ala Ser Glu Pro Val Phe Ala Ala
    545                 550                 555                 560

Thr Ile Ala Lys Leu Glu Pro Val Ile Ala Ala Glu Ser Gly Phe Ser
                        565                 570                 575

Val Thr Glu Ala Ile Thr Ala Gln Gln Thr Val Thr Gly Ile Asp Lys
                        580                 585                 590

Val Gln Pro Ala Val Phe Ala Val Gln Val Ala Leu Ala Ala Thr Met
                        595                 600                 605

Glu Gln Thr Tyr Gly Val Arg Pro Gly Ala Val Val Gly His Ser Met
                        610                 615                 620

Gly Glu Ser Ala Ala Val Val Ala Gly Ala Leu Ser Leu Glu Asp
    625                 630                 635                 640

Ala Ala Arg Val Ile Cys Arg Arg Ser Lys Leu Met Thr Arg Ile Ala
                        645                 650                 655
```

```
Gly Ala Gly Ala Met Gly Ser Val Glu Leu Pro Ala Lys Gln Val Asn
            660                 665                 670

Ser Glu Leu Met Ala Arg Gly Ile Asp Asp Val Val Ser Val Val
        675                 680                 685

Ala Ser Pro Gln Ser Thr Val Ile Gly Gly Thr Ser Asp Thr Val Arg
690                 695                 700

Asp Leu Ile Ala Arg Trp Glu Gln Arg Asp Val Met Ala Arg Glu Val
705                 710                 715                 720

Ala Val Asp Val Ala Ser His Ser Pro Gln Val Asp Pro Ile Leu Asp
                725                 730                 735

Asp Leu Ala Ala Ala Leu Ala Asp Ile Ala Pro Met Thr Pro Lys Val
                740                 745                 750

Pro Tyr Tyr Ser Ala Thr Leu Phe Asp Pro Arg Glu Gln Pro Val Cys
        755                 760                 765

Asp Gly Ala Tyr Trp Val Asp Asn Leu Arg Asn Thr Val Gln Phe Ala
770                 775                 780

Ala Ala Val Gln Ala Ala Met Glu Asp Gly Tyr Arg Val Phe Ala Glu
785                 790                 795                 800

Leu Ser Pro His Pro Leu Leu Thr His Ala Val Glu Gln Thr Gly Arg
                805                 810                 815

Ser Leu Asp Met Ser Val Ala Ala Leu Ala Gly Met Arg Arg Glu Gln
                820                 825                 830

Pro Leu Pro His Gly Leu Arg Gly Leu Leu Thr Glu Leu His Arg Ala
                835                 840                 845

Gly Ala Ala Leu Asp Tyr Ser Ala Leu Tyr Pro Ala Gly Arg Leu Val
850                 855                 860

Asp Ala Pro Leu Pro Ala Trp Thr His Ala Arg Leu Phe Ile Asp Asp
865                 870                 875                 880

Asp Gly Gln Glu Gln Arg Ala Gln Gly Ala Cys Thr Ile Thr Val His
                885                 890                 895

Pro Leu Leu Gly Ser His Val Arg Leu Thr Glu Glu Pro Glu Arg His
                900                 905                 910

Val Trp Gln Gly Asp Val Gly Thr Ser Val Leu Ser Trp Leu Ser Asp
        915                 920                 925

His Gln Val His Asn Val Ala Ala Leu Pro Gly Ala Ala Tyr Cys Glu
        930                 935                 940

Met Ala Leu Ala Ala Ala Ala Glu Val Phe Gly Glu Ala Ala Glu Val
945                 950                 955                 960

Arg Asp Ile Thr Phe Glu Gln Met Leu Leu Leu Asp Glu Gln Thr Pro
                965                 970                 975

Ile Asp Ala Val Ala Ser Ile Asp Ala Pro Gly Val Val Asn Phe Thr
                980                 985                 990

Val Glu Thr Asn Arg Asp Gly Glu  Thr Thr Arg His Ala  Thr Ala Ala
        995                 1000                1005

Leu Arg Ala Ala Glu Asp Asp  Cys Pro Pro Gly  Tyr Asp Ile
        1010                1015                1020

Thr Ala Leu Leu Gln Ala His  Pro His Ala Val Asn  Gly Thr Ala
        1025                1030                1035

Met Arg Glu Ser Phe Ala Glu  Arg Gly Val Thr Leu  Gly Ala Ala
        1040                1045                1050

Phe Gly Gly Leu Thr Thr Ala  His Thr Ala Glu Ala  Gly Ala Ala
        1055                1060                1065
```

```
Thr Val Leu Ala Glu Val Ala Leu Pro Ala Ser Ile Arg Phe Gln
1070            1075                1080

Gln Gly Ala Tyr Arg Ile His Pro Ala Leu Leu Asp Ala Cys Phe
1085            1090                1095

Gln Ser Val Gly Ala Gly Val Gln Ala Gly Thr Ala Thr Gly Gly
1100            1105                1110

Leu Leu Leu Pro Leu Gly Val Arg Ser Leu Arg Ala Tyr Gly Pro
1115            1120                1125

Thr Arg Asn Ala Arg Tyr Cys Tyr Thr Arg Leu Thr Lys Ala Phe
1130            1135                1140

Asn Asp Gly Thr Arg Gly Gly Glu Ala Asp Leu Asp Val Leu Asp
1145            1150                1155

Glu His Gly Thr Val Leu Leu Ala Val Arg Gly Leu Arg Met Gly
1160            1165                1170

Thr Gly Thr Ser Glu Arg Asp Glu Arg Asp Arg Leu Val Ser Glu
1175            1180                1185

Arg Leu Leu Thr Leu Gly Trp Gln Gln Arg Ala Leu Pro Glu Val
1190            1195                1200

Gly Asp Gly Glu Ala Gly Ser Trp Leu Leu Ile Asp Thr Ser Asn
1205            1210                1215

Ala Val Asp Thr Pro Asp Met Leu Ala Ser Thr Leu Thr Asp Ala
1220            1225                1230

Leu Lys Ser His Gly Pro Gln Gly Thr Glu Cys Ala Ser Leu Ser
1235            1240                1245

Trp Ser Val Gln Asp Thr Pro Pro Asn Asp Gln Ala Gly Leu Glu
1250            1255                1260

Lys Leu Gly Ser Gln Leu Arg Gly Arg Asp Gly Val Val Ile Val
1265            1270                1275

Tyr Gly Pro Arg Val Gly Asp Pro Asp Glu His Ser Leu Leu Ala
1280            1285                1290

Gly Arg Glu Gln Val Arg His Leu Val Arg Ile Thr Arg Glu Leu
1295            1300                1305

Ala Glu Phe Glu Gly Glu Leu Pro Arg Leu Phe Val Val Thr Arg
1310            1315                1320

Gln Ala Gln Ile Val Lys Pro His Asp Ser Gly Glu Arg Ala Asn
1325            1330                1335

Leu Glu Gln Ala Gly Leu Arg Gly Leu Leu Arg Val Ile Ser Ser
1340            1345                1350

Glu His Pro Met Leu Arg Thr Thr Leu Ile Asp Val Asp Glu His
1355            1360                1365

Thr Asp Val Glu Arg Val Ala Gln Gln Leu Leu Ser Gly Ser Glu
1370            1375                1380

Glu Asp Glu Thr Ala Trp Arg Asn Gly Asp Trp Tyr Val Ala Arg
1385            1390                1395

Leu Thr Pro Ser Pro Leu Gly His Glu Glu Arg Arg Thr Ala Val
1400            1405                1410

Leu Asp Pro Asp His Asp Gly Met Arg Val Gln Val Arg Arg Pro
1415            1420                1425

Gly Asp Leu Gln Thr Leu Glu Phe Val Ala Ser Asp Arg Val Pro
1430            1435                1440

Pro Gly Pro Gly Gln Ile Glu Val Ala Val Ser Met Ser Ser Ile
1445            1450                1455

Asn Phe Ala Asp Val Leu Ile Ala Phe Gly Arg Phe Pro Ile Ile
```

```
            1460                1465                1470

Asp Asp Arg Glu Pro Gln Leu Gly Met Asp Phe Val Gly Val Val
    1475                1480                1485

Thr Ala Val Gly Glu Gly Val Thr Gly His Gln Val Gly Asp Arg
    1490                1495                1500

Val Gly Gly Phe Ser Glu Gly Gly Cys Trp Arg Thr Phe Leu Thr
    1505                1510                1515

Cys Asp Ala Asn Leu Ala Val Thr Leu Pro Pro Gly Leu Thr Asp
    1520                1525                1530

Glu Gln Ala Ile Thr Ala Ala Thr Ala His Ala Thr Ala Trp Tyr
    1535                1540                1545

Gly Leu Asn Asp Leu Ala Gln Ile Lys Ala Gly Asp Lys Val Leu
    1550                1555                1560

Ile His Ser Ala Thr Gly Gly Val Gly Gln Ala Ala Ile Ser Ile
    1565                1570                1575

Ala Arg Ala Lys Gly Ala Glu Ile Phe Ala Thr Ala Gly Asn Pro
    1580                1585                1590

Ala Lys Arg Ala Met Leu Arg Asp Met Gly Val Glu His Val Tyr
    1595                1600                1605

Asp Ser Arg Ser Val Glu Phe Ala Glu Gln Ile Arg Arg Asp Thr
    1610                1615                1620

Asp Gly Tyr Gly Val Asp Ile Val Leu Asn Ser Leu Thr Gly Ala
    1625                1630                1635

Ala Gln Arg Ala Gly Leu Glu Leu Leu Ala Phe Gly Gly Arg Phe
    1640                1645                1650

Val Glu Ile Gly Lys Ala Asp Val Tyr Gly Asn Thr Arg Leu Gly
    1655                1660                1665

Leu Phe Pro Phe Arg Arg Gly Leu Thr Phe Tyr Tyr Leu Asp Leu
    1670                1675                1680

Ala Leu Met Ser Val Thr Gln Pro Asp Arg Val Arg Glu Leu Leu
    1685                1690                1695

Ala Thr Val Phe Lys Leu Thr Ala Asp Gly Val Leu Thr Ala Pro
    1700                1705                1710

Gln Cys Thr His Tyr Pro Leu Ala Glu Ala Ala Asp Ala Ile Arg
    1715                1720                1725

Ala Met Ser Asn Ala Glu His Thr Gly Lys Leu Val Leu Asp Val
    1730                1735                1740

Pro Arg Ser Gly Arg Arg Ser Val Ala Val Thr Pro Glu Gln Ala
    1745                1750                1755

Pro Leu Tyr Arg Arg Asp Gly Ser Tyr Ile Ile Thr Gly Gly Leu
    1760                1765                1770

Gly Gly Leu Gly Leu Phe Phe Ala Ser Lys Leu Ala Ala Ala Gly
    1775                1780                1785

Cys Gly Arg Ile Val Leu Thr Ala Arg Ser Gln Pro Asn Pro Lys
    1790                1795                1800

Ala Arg Gln Thr Ile Glu Gly Leu Arg Ala Ala Gly Ala Asp Ile
    1805                1810                1815

Val Val Glu Cys Gly Asn Ile Ala Glu Pro Asp Thr Ala Asp Arg
    1820                1825                1830

Leu Val Ser Ala Ala Thr Ala Thr Gly Leu Pro Leu Arg Gly Val
    1835                1840                1845

Leu His Ser Ala Ala Val Val Glu Asp Ala Thr Leu Thr Asn Ile
    1850                1855                1860
```

-continued

Thr Asp Glu Leu Ile Asp Arg Asp Trp Ser Pro Lys Val Phe Gly
1865 1870 1875

Ser Trp Asn Leu His Arg Ala Thr Leu Gly Gln Pro Leu Asp Trp
1880 1885 1890

Phe Cys Leu Phe Ser Ser Gly Ala Ala Leu Leu Gly Ser Pro Gly
1895 1900 1905

Gln Gly Ala Tyr Ala Ala Ala Asn Ser Trp Val Asp Val Phe Ala
1910 1915 1920

His Trp Arg Arg Ala Gln Gly Leu Pro Val Ser Ala Ile Ala Trp
1925 1930 1935

Gly Ala Trp Gly Glu Val Gly Arg Ala Thr Phe Leu Ala Glu Gly
1940 1945 1950

Gly Glu Ile Met Ile Thr Pro Glu Glu Gly Ala Tyr Ala Phe Glu
1955 1960 1965

Thr Leu Val Arg His Asp Arg Ala Tyr Ser Gly Tyr Ile Pro Ile
1970 1975 1980

Leu Gly Ala Pro Trp Leu Ala Asp Leu Val Arg Arg Ser Pro Trp
1985 1990 1995

Gly Glu Met Phe Ala Ser Thr Gly Gln Arg Ser Arg Gly Pro Ser
2000 2005 2010

Lys Phe Arg Met Glu Leu Leu Ser Leu Pro Gln Asp Glu Trp Ala
2015 2020 2025

Gly Arg Leu Arg Arg Leu Leu Val Glu Gln Ala Ser Val Ile Leu
2030 2035 2040

Arg Arg Thr Ile Asp Ala Asp Arg Ser Phe Ile Glu Tyr Gly Leu
2045 2050 2055

Asp Ser Leu Gly Met Leu Glu Met Arg Thr His Val Glu Thr Glu
2060 2065 2070

Thr Gly Ile Arg Leu Thr Pro Lys Val Ile Ala Thr Asn Asn Thr
2075 2080 2085

Ala Arg Ala Leu Ala Gln Tyr Leu Ala Asp Thr Leu Ala Glu Glu
2090 2095 2100

Gln Ala Ala Ala Pro Ala Ala Ser
2105 2110

<210> SEQ ID NO 20
<211> LENGTH: 1149
<212> TYPE: DNA
<213> ORGANISM: Mycobacterium bovis

<400> SEQUENCE: 20
ctggtggaag gcctgcgtga agttgccgat ggtgatgcac tgtatgatgc agcagtgggt 60
catggcgatc gtggtccggt ttgggtgttt agcggccagg gttctcagtg ggcagcgatg 120
ggcacccagc tgctggcaag cgaaccggtt tttgccgcaa cgattgcaaa actggaaccg 180
gtgatcgcgg ccgaaagtgg cttcagcgtt accgaagcaa ttacggcgca gcagaccgtg 240
acgggtatcg ataaagtgca gccggccgtt ttcgcagttc aggtggcgct ggcagcgacg 300
atggaacaga cgtacggcgt tcgtccgggt gcagtggttg gtcacagtat gggtgaaagc 360
gccgcagcgg tggttgcagg cgccctgagt ctggaagatg ccgcacgtgt gatttgccgt 420
cgcagcaaac tgatgacccg tatcgcaggt gcaggtgcga tgggcagcgt ggaactgccg 480
gcaaaacagg ttaactctga actgatggcg cgcggtattg atgatgtggt tgtgtctgtt 540
gtggcgtctc cgcagagtac cgtgattggc ggcaccagtg atacggttcg tgatctgatc 600

| | |
|---|---|
| gcgcgttggg aacagcgcga tgtgatggcg cgcgaagttg ccgtggatgt tgcaagccat | 660 |
| tctccgcagg ttgatccgat tctggatgat ctggcggcgg cactggcaga tattgcaccg | 720 |
| atgaccccga aagtgccgta ttacagcgcg acgctgtttg atccgcgtga acagccggtg | 780 |
| tgtgatggcg cctattgggt tgataacctg cgcaataccg tgcagtttgc ggcggcagtt | 840 |
| caggcggcga tggaagatgg ttaccgtgtg ttcgcggaac tgtctccgca tccgctgctg | 900 |
| acccacgcag tggaacagac gggtcgctct ctggatatga gtgttgcagc actgccggt | 960 |
| atgcgtcgcg aacagccgct gccgcatggc ctgcgtggtc tgctgaccga actgcaccgt | 1020 |
| gcaggtgcag cactggatta tagcgcactg tacccggcag gtcgtctggt ggatgcaccg | 1080 |
| ctgccggcat ggacgcacgc acgtctgttc atcgatgatg atggccagga acagcgcgca | 1140 |
| cagggtgcg | 1149 |

<210> SEQ ID NO 21
<211> LENGTH: 1149
<212> TYPE: DNA
<213> ORGANISM: Mycobacterium bovis

<400> SEQUENCE: 21

```
ctcgtcgagg gtttgcgcga ggtggccgac ggtgacgccc tctatgacgc ggcggtggga     60
cacggtgatc gaggaccggt ctgggtcttc tccgggcaag ggtcgcagtg ggcggcgatg    120
ggcacgcaat tgctcgccag cgaaccagtg ttcgcggcca ccatcgccaa gctggagccg    180
gtgatcgccg cagaatcggg attctcggtg accgaggcga taacggcgca gcagaccgtg    240
accggaatcg acaaagtgca gccggcagtg ttcgccgttc aggtcgcgtt ggccgccacc    300
atggagcaaa cctacggagt gcggccgggc gcggtcgtcg gacactcgat gggtgagtcg    360
gccgcggccg tcgtcgcggg ggcactgtcg ctcgaggacg cggcgcgcgt catttgccgc    420
cgctcgaagc tgatgacccg catagccggt gctggtgcca tgggctcggt ggaattgccc    480
gccaagcaag tgaattcgga gctgatggca cgcggaatcg acgatgttgt ggtctcggtg    540
gtggcgtccc cgcaatccac ggtgatcggc ggtacgagcg acaccgttcg tgacctcatc    600
gcccgttggg agcagcggga cgtgatggcg cgcgaggtgg ccgtcgacgt ggcgtcgcac    660
tcgcctcaag tcgatccgat actcgacgat ttggccgcgg cgctggcgga cattgctccg    720
atgacgccca aggtgccgta ctactcggcg accctgttcg acccgcgcga gcagccggtg    780
tgcgatggcg cttactgggt ggacaatctg cgcaacacgg tgcagttcgc cgcggcggtg    840
caggctgcga tggaggacgg ctaccgggtc ttcgcggagc tgtcgcccca cccgctgctt    900
acccacgccg tcgaacagac gggccgaagc ctcgacatgt cggtcgccgc cctggccggc    960
atgcggcgag agcagcctct gccgcatggt ctgcgcggct tgctgacgga gctgcaccgc   1020
gcgggcgccg ctttggacta ttcggcgctg tatcccgctg ggcggctggt ggatgcgccg   1080
ctgccggcgt ggacccacgc ccgcctattc atcgacgatg atgggcaaga acagcgggca   1140
caaggtgcc                                                           1149
```

<210> SEQ ID NO 22
<211> LENGTH: 628
<212> TYPE: PRT
<213> ORGANISM: Salmonella enterica
<300> PUBLICATION INFORMATION:
<308> DATABASE ACCESSION NUMBER: GenBank / AAC44817
<309> DATABASE ENTRY DATE: 1999-08-05
<313> RELEVANT RESIDUES IN SEQ ID NO: (1)..(628)

```
<400> SEQUENCE: 22

Met Ser Phe Ser Glu Phe Tyr Gln Arg Ser Ile Asn Glu Pro Glu Ala
1               5                   10                  15

Phe Trp Ala Glu Gln Ala Arg Arg Ile Asp Trp Arg Gln Pro Phe Thr
            20                  25                  30

Gln Thr Leu Asp His Ser Arg Pro Phe Ala Arg Trp Phe Cys Gly
        35                  40                  45

Gly Thr Thr Asn Leu Cys His Asn Ala Val Asp Arg Trp Arg Asp Lys
    50                  55                  60

Gln Pro Glu Ala Leu Ala Leu Ile Ala Val Ser Ser Glu Thr Asp Glu
65                  70                  75                  80

Glu Arg Thr Phe Thr Phe Ser Gln Leu His Asp Glu Val Asn Ile Val
                85                  90                  95

Ala Ala Met Leu Leu Ser Leu Gly Val Gln Arg Gly Asp Arg Val Leu
            100                 105                 110

Val Tyr Met Pro Met Ile Ala Glu Ala Gln Ile Thr Leu Leu Ala Cys
        115                 120                 125

Ala Arg Ile Gly Ala Ile His Ser Val Val Phe Gly Gly Phe Ala Ser
    130                 135                 140

His Ser Val Ala Ala Arg Ile Asp Asp Ala Arg Pro Ala Leu Ile Val
145                 150                 155                 160

Ser Ala Asp Ala Gly Ala Arg Gly Gly Lys Ile Leu Pro Tyr Lys Lys
                165                 170                 175

Leu Leu Asp Asp Ala Ile Ala Gln Ala Gln His Gln Pro Lys His Val
            180                 185                 190

Leu Leu Val Asp Arg Gly Leu Ala Lys Met Ala Trp Val Asp Gly Arg
        195                 200                 205

Asp Leu Asp Phe Ala Thr Leu Arg Gln Gln His Leu Gly Ala Ser Val
    210                 215                 220

Pro Val Ala Trp Leu Glu Ser Asn Glu Thr Ser Cys Ile Leu Tyr Thr
225                 230                 235                 240

Ser Gly Thr Thr Gly Lys Pro Lys Gly Val Gln Arg Asp Val Gly Gly
                245                 250                 255

Tyr Ala Val Ala Leu Ala Thr Ser Met Asp Thr Ile Phe Gly Gly Lys
            260                 265                 270

Ala Gly Gly Val Phe Phe Cys Ala Ser Asp Ile Gly Trp Val Val Gly
        275                 280                 285

His Ser Tyr Ile Val Tyr Ala Pro Leu Leu Ala Gly Met Ala Thr Ile
    290                 295                 300

Val Tyr Glu Gly Leu Pro Thr Tyr Pro Asp Cys Gly Val Trp Trp Lys
305                 310                 315                 320

Ile Val Glu Lys Tyr Gln Val Asn Arg Met Phe Ser Ala Pro Thr Ala
                325                 330                 335

Ile Arg Val Leu Lys Lys Phe Pro Thr Ala Gln Ile Arg Asn His Asp
            340                 345                 350

Leu Ser Ser Leu Glu Ala Leu Tyr Leu Ala Gly Glu Pro Leu Asp Glu
        355                 360                 365

Pro Thr Ala Ser Trp Val Thr Glu Thr Leu Gly Val Pro Val Ile Asp
    370                 375                 380

Asn Tyr Trp Gln Thr Glu Ser Gly Trp Pro Ile Met Ala Leu Ala Arg
385                 390                 395                 400

Ala Leu Asp Asp Arg Pro Ser Arg Leu Gly Ser Pro Gly Val Pro Met
                405                 410                 415
```

```
Tyr Gly Tyr Asn Val Gln Leu Leu Asn Glu Val Thr Gly Glu Pro Cys
            420                 425                 430

Gly Ile Asn Glu Lys Gly Met Leu Val Ile Glu Gly Pro Leu Pro Pro
            435                 440                 445

Gly Cys Ile Gln Thr Ile Trp Gly Asp Asp Ala Arg Phe Val Lys Thr
450                 455                 460

Tyr Trp Ser Leu Phe Asn Arg Gln Val Tyr Ala Thr Phe Asp Trp Gly
465                 470                 475                 480

Ile Arg Asp Ala Glu Gly Tyr Tyr Phe Ile Leu Gly Arg Thr Asp Asp
                485                 490                 495

Val Ile Asn Ile Ala Gly His Arg Leu Gly Thr Arg Glu Ile Glu Glu
            500                 505                 510

Ser Ile Ser Ser Tyr Pro Asn Val Ala Glu Val Ala Val Val Gly Ile
            515                 520                 525

Lys Asp Ala Leu Lys Gly Gln Val Ala Val Ala Phe Val Ile Pro Lys
530                 535                 540

Gln Ser Asp Thr Leu Ala Asp Arg Glu Ala Ala Arg Asp Glu Glu Asn
545                 550                 555                 560

Ala Ile Met Ala Leu Val Asp Asn Gln Ile Gly His Phe Gly Arg Pro
                565                 570                 575

Ala His Val Trp Phe Val Ser Gln Leu Pro Lys Thr Arg Ser Gly Lys
            580                 585                 590

Met Leu Arg Arg Thr Ile Gln Ala Ile Cys Glu Gly Arg Asp Pro Gly
            595                 600                 605

Asp Leu Thr Thr Ile Asp Asp Pro Ala Ser Leu Gln Gln Ile Arg Gln
610                 615                 620

Ala Ile Glu Glu
625

<210> SEQ ID NO 23
<211> LENGTH: 1884
<212> TYPE: DNA
<213> ORGANISM: Salmonella enterica

<400> SEQUENCE: 23
atgtctttta gcgaatttta tcagcgttcc attaacgaac cggaggcgtt ctgggccgag      60
caggcccggc gtatcgactg cgacagccg tttacgcaga cgctggatca tagccgtcca     120
ccgtttgccc gctggttttg cggcggcacc actaacttat gtcataacgc cgtcgaccgc     180
tggcgggata aacagccgga ggcgctggcg ctgattgccg tctcatcaga gaccgatgaa     240
gagcgcacat ttaccttcag ccagttgcat gatgaagtca acattgtggc cgccatgttg     300
ctgtcgctgg gcgtgcagcg tggcgatcgc gtattggtct atatgccgat gattgccgaa     360
gcgcagataa ccctgctggc ctgcgcgcgc attggcgcga tccattcggt ggtctttggc     420
ggttttgcct cgcacagcgt ggcggcgcgc attgacgatg ccagaccggc gctgattgtg     480
tcggcggatg ccggagcgcg gggcggtaaa atcctgccgt ataaaaagct gctcgatgac     540
gctattgcgc aggcgcagca tcagccgaaa cacgttctgc tggtggacag agggctggcg     600
aaaatggcat gggtggatgg cgcgatctg attttgcca cgttgcgcca gcagcatctc     660
ggcgcgagcg tgccggtggc gtggctggaa tccaacgaaa cctcgtgcat tctttacacc     720
tccggcacta ccggcaaacc gaaaggcgtc agcgcgacg tcggcggtta tgcggtggcg     780
ctggcaacct cgatggacac catttttggc ggcaaggcgg gcggcgtatt cttttgcgca     840
```

-continued

```
tcggatatcg gctgggtcgt cggccactcc tatatcgttt acgcgccgtt gctggcaggc    900
atggcgacta ttgtttacga aggactgccg acgtacccgg actgcggggt ctggtggaaa    960
attgtcgaga ataccaggt taaccggatg ttttccgccc cgaccgcgat tcgcgtgctg    1020
aaaaaattcc cgacggcgca aatccgcaat cacgatctct cctcgctgga ggcgctttat    1080
ctggccggtg agccgctgga cgagccgacg gccagttggg taacggagac gctgggcgta    1140
ccggtcatcg acaattattg gcagacggag tccggctggc cgatcatggc gctgccccgc    1200
gcgctggacg acaggccgtc gcgtctggga agtcccggcg tgccgatgta cggttataac    1260
gtccagctac tcaatgaagt caccggcgaa ccttgcggca taaatgaaaa ggggatgctg    1320
gtgatcgaag ggccgctgcc gccgggctgt attcagacta tttggggcga cgatgcgcgt    1380
tttgtgaaga cttactggtc gctgtttaac cgtcaggttt atgccacttt cgactgggga    1440
atccgcgacg ccgaggggta ttactttatt ctgggccgta ccgatgatgt gattaatatt    1500
gcgggtcatc ggctggggac gcgagaaata gaagaaagta tctccagcta cccgaacgta    1560
gcggaagtgg cggtagtggg gataaaagac gctctgaaag ggcaggtagc ggtggcgttt    1620
gtcattccga agcagagcga tacgctggcg gatcgcgagg cggcgcgcga cgaggaaaac    1680
gcgattatgg cgctggtgga caaccagatc ggtcactttg gtcgtccggc gcatgtctgg    1740
tttgtttcgc agctccccaa aacgcgttcc ggaaagatgc ttcgccgcac gatccaggcg    1800
atctgcgaag gccgcgatcc gggcgatctg acaaccattg acgatcccgc gtcgttgcag    1860
caaattcgcc aggcgatcga agaa                                          1884
```

<210> SEQ ID NO 24
<211> LENGTH: 616
<212> TYPE: PRT
<213> ORGANISM: Streptomyces cinnamonensis

<400> SEQUENCE: 24

```
Met Thr Val Leu Pro Asp Asp Gly Leu Ser Leu Ala Ala Glu Phe Pro
1               5                   10                  15

Asp Ala Thr His Glu Gln Trp His Arg Leu Val Glu Gly Val Val Arg
            20                  25                  30

Lys Ser Gly Lys Asp Val Ser Gly Thr Ala Ala Glu Ala Leu Ser
        35                  40                  45

Thr Thr Leu Glu Asp Gly Leu Thr Thr Arg Pro Leu Tyr Thr Ala Arg
    50                  55                  60

Asp Ala Ala Pro Asp Ala Gly Phe Pro Gly Phe Ala Pro Phe Val Arg
65                  70                  75                  80

Gly Ser Val Pro Glu Gly Asn Thr Pro Gly Gly Trp Asp Val Arg Gln
                85                  90                  95

Arg Tyr Ala Ser Ala Asp Pro Ala Arg Thr Asn Glu Ala Val Leu Thr
            100                 105                 110

Asp Leu Glu Asn Gly Val Thr Ser Leu Trp Leu Thr Leu Gly Ser Ala
        115                 120                 125

Gly Leu Pro Val Thr Gly Leu Glu Arg Ala Leu Asp Gly Val Tyr Leu
    130                 135                 140

Asp Leu Val Pro Val Ala Leu Asp Ala Gly Ser Glu Ala Ala Thr Ala
145                 150                 155                 160

Ala Arg Glu Leu Leu Arg Leu Tyr Glu Ala Ala Gly Val Ala Asp Asp
                165                 170                 175

Ala Val Arg Gly Thr Leu Gly Ala Asp Pro Leu Gly His Glu Ala Arg
            180                 185                 190
```

```
Thr Gly Glu Lys Ser Thr Ser Phe Ala Ala Val Ala Glu Leu Ala Arg
        195                 200                 205

Leu Cys Gly Glu Arg Tyr Pro Gly Leu Arg Ala Leu Thr Val Asp Ala
    210                 215                 220

Leu Pro Tyr His Glu Ala Gly Ser Ala Ala Gln Glu Leu Gly Ala
225                 230                 235                 240

Ser Leu Ala Thr Gly Val Glu Tyr Leu Arg Ala Leu His Asp Lys Gly
                245                 250                 255

Leu Gly Val Glu Lys Ala Phe Ala Gln Leu Glu Phe Arg Phe Ala Ala
                260                 265                 270

Thr Ala Asp Gln Phe Leu Thr Ile Ala Lys Leu Arg Ala Arg Arg
            275                 280                 285

Leu Trp Ala Arg Val Ala Glu Val Ser Gly Val Pro Ala Ala Gly Ala
    290                 295                 300

Gln Arg Gln His Ala Val Thr Ser Pro Val Met Met Thr Arg Arg Asp
305                 310                 315                 320

Pro Trp Val Asn Met Leu Arg Thr Thr Val Ala Cys Leu Gly Ala Gly
                325                 330                 335

Val Gly Gly Ala Asp Ala Val Thr Val Leu Pro Phe Asp His Glu Leu
                340                 345                 350

Gly Leu Pro Asp Ala Phe Ala Arg Arg Ile Ala Arg Asn Thr Ser Thr
            355                 360                 365

Ile Leu Leu Glu Glu Ser His Leu Ala Arg Val Ile Asp Pro Ala Gly
    370                 375                 380

Gly Ser Trp Tyr Val Glu Arg Leu Thr Asp Glu Leu Ala His Ala Ala
385                 390                 395                 400

Trp Asp Phe Phe Lys Glu Ile Glu Arg Ala Asp Gly Gln Val Ala Ala
                405                 410                 415

Leu Arg Ser Gly Leu Val Gly Asp Arg Ile Ala Ala Thr Trp Ala Glu
                420                 425                 430

Arg Arg Lys Lys Leu Ala Arg Arg Glu Pro Ile Thr Gly Val Ser
            435                 440                 445

Glu Phe Pro Leu Leu Thr Glu Arg Pro Val Glu Arg Glu Pro Ala Pro
    450                 455                 460

Ala Ala Pro Pro Gly Gly Leu Pro Arg Val Arg Arg Asp Glu Ala Tyr
465                 470                 475                 480

Glu Glu Leu Arg Gly Arg Ser Asp Ala His Leu Glu Ala Thr Gly Ala
                485                 490                 495

Arg Pro Lys Val Phe Ile Ala Ala Leu Gly Pro Ala Ala His Thr
            500                 505                 510

Ala Arg Ala Thr Phe Ala Ala Asn Leu Phe Met Ala Gly Gly Val Glu
    515                 520                 525

Pro Val His Asp Pro Val Ser Val Asp Ala Glu Thr Ala Ala Glu Ala
530                 535                 540

Phe Ala Ala Ser Gly Ala Thr Val Ala Cys Leu Cys Ser Ser Asp Val
545                 550                 555                 560

Leu Tyr Ala Glu Gln Ala Glu Ala Val Ala Arg Ala Leu Lys Ser Ala
                565                 570                 575

Gly Ala Leu Arg Val Phe Leu Ala Gly Arg Gly Glu Phe Ala Asp Ile
            580                 585                 590

Asp Glu Tyr Val Phe Ala Gly Cys Asp Ala Val Ala Val Leu Thr Ser
            595                 600                 605
```

```
Thr Leu Asp Arg Met Gly Val Ala
    610                 615
```

<210> SEQ ID NO 25
<211> LENGTH: 733
<212> TYPE: PRT
<213> ORGANISM: Streptomyces cinnamonensis

<400> SEQUENCE: 25

```
Met Arg Ile Pro Glu Phe Asp Asp Ile Glu Leu Gly Ala Gly Gly Gly
1               5                   10                  15

Pro Ser Gly Ser Ala Glu Gln Trp Arg Ala Val Lys Glu Ser Val
            20                  25                  30

Gly Lys Ser Glu Ser Asp Leu Leu Trp Glu Thr Pro Glu Gly Ile Ala
        35                  40                  45

Val Lys Pro Leu Tyr Thr Gly Ala Asp Val Glu Gly Leu Asp Phe Leu
    50                  55                  60

Glu Thr Tyr Pro Gly Val Ala Pro Tyr Leu Arg Gly Pro Tyr Pro Thr
65                  70                  75                  80

Met Tyr Val Asn Gln Pro Trp Thr Ile Arg Gln Tyr Ala Gly Phe Ser
                85                  90                  95

Thr Ala Glu Glu Ser Asn Ala Phe Tyr Arg Arg Asn Leu Ala Ala Gly
            100                 105                 110

Gln Lys Gly Leu Ser Val Ala Phe Asp Leu Pro Thr His Arg Gly Tyr
        115                 120                 125

Asp Ser Asp His Pro Arg Val Thr Gly Asp Val Gly Met Ala Gly Val
    130                 135                 140

Ala Ile Asp Ser Ile Tyr Asp Met Arg Gln Leu Phe Asp Gly Ile Pro
145                 150                 155                 160

Leu Asp Lys Met Thr Val Ser Met Thr Met Asn Gly Ala Val Leu Pro
                165                 170                 175

Val Leu Ala Leu Tyr Ile Val Ala Ala Glu Glu Gln Gly Val Pro Pro
            180                 185                 190

Glu Lys Leu Ala Gly Thr Ile Gln Asn Asp Ile Leu Lys Glu Phe Met
        195                 200                 205

Val Arg Asn Thr Tyr Ile Tyr Pro Pro Lys Pro Ser Met Arg Ile Ile
    210                 215                 220

Ser Asp Ile Phe Ala Tyr Thr Ser Gln Lys Met Pro Arg Tyr Asn Ser
225                 230                 235                 240

Ile Ser Ile Ser Gly Tyr His Ile Gln Glu Ala Gly Ala Thr Ala Asp
                245                 250                 255

Leu Glu Leu Ala Tyr Thr Leu Ala Asp Gly Val Glu Tyr Leu Arg Ala
            260                 265                 270

Gly Gln Glu Ala Gly Leu Asp Val Asp Ala Phe Ala Pro Arg Leu Ser
        275                 280                 285

Phe Phe Trp Ala Ile Gly Met Asn Phe Phe Met Glu Val Ala Lys Leu
    290                 295                 300

Arg Ala Ala Arg Leu Leu Trp Ala Lys Leu Val Lys Gln Phe Asp Pro
305                 310                 315                 320

Lys Asn Ala Lys Ser Leu Ser Leu Arg Thr His Ser Gln Thr Ser Gly
                325                 330                 335

Trp Ser Leu Thr Ala Gln Asp Val Phe Asn Asn Val Thr Arg Thr Cys
            340                 345                 350

Val Glu Ala Met Ala Ala Thr Gln Gly His Thr Gln Ser Leu His Thr
        355                 360                 365
```

```
Asn Ala Leu Asp Glu Ala Leu Ala Leu Pro Thr Asp Phe Ser Ala Arg
    370                 375                 380
Ile Ala Arg Asn Thr Gln Leu Leu Ile Gln Gln Glu Ser Gly Thr Thr
385                 390                 395                 400
Arg Thr Ile Asp Pro Trp Gly Gly Ser Ala Tyr Val Glu Lys Leu Thr
                405                 410                 415
Tyr Asp Leu Ala Arg Arg Ala Trp Gln His Ile Glu Glu Val Glu Ala
            420                 425                 430
Ala Gly Gly Met Ala Gln Ala Ile Asp Ala Gly Ile Pro Lys Leu Arg
        435                 440                 445
Val Glu Glu Ala Ala Ala Arg Thr Gln Ala Arg Ile Asp Ser Gly Arg
    450                 455                 460
Gln Pro Val Ile Gly Val Asn Lys Tyr Arg Val Asp Thr Asp Glu Gln
465                 470                 475                 480
Ile Asp Val Leu Lys Val Asp Asn Ser Val Arg Ala Gln Gln Ile
                485                 490                 495
Glu Lys Leu Arg Arg Leu Arg Glu Glu Arg Asp Ala Ala Cys Gln
            500                 505                 510
Asp Ala Leu Arg Ala Leu Thr Ala Ala Ala Glu Arg Gly Pro Gly Gln
        515                 520                 525
Gly Leu Glu Gly Asn Leu Leu Ala Leu Ala Val Asp Ala Ala Arg Ala
    530                 535                 540
Lys Ala Thr Val Gly Glu Ile Ser Asp Ala Leu Glu Ser Val Tyr Gly
545                 550                 555                 560
Arg His Ala Gly Gln Ile Arg Thr Ile Ser Gly Val Tyr Arg Thr Glu
                565                 570                 575
Ala Gly Gln Ser Pro Ser Val Glu Arg Thr Arg Ala Leu Val Asp Ala
            580                 585                 590
Phe Asp Glu Ala Glu Gly Arg Arg Pro Arg Ile Leu Val Ala Lys Met
        595                 600                 605
Gly Gln Asp Gly His Asp Arg Gly Gln Lys Val Ile Ala Ser Ala Phe
    610                 615                 620
Ala Asp Leu Gly Phe Asp Val Asp Val Gly Pro Leu Phe Gln Thr Pro
625                 630                 635                 640
Ala Glu Val Ala Arg Gln Ala Val Glu Ala Asp Val His Ile Val Gly
                645                 650                 655
Val Ser Ser Leu Ala Ala Gly His Leu Thr Leu Val Pro Ala Leu Arg
            660                 665                 670
Glu Glu Leu Ala Ala Glu Gly Arg Asp Asp Ile Met Ile Val Val Gly
        675                 680                 685
Gly Val Ile Pro Pro Gln Asp Val Glu Ala Leu His Glu Ala Gly Ala
    690                 695                 700
Thr Ala Val Phe Pro Pro Gly Thr Val Ile Pro Asp Ala Ala His Asp
705                 710                 715                 720
Leu Val Lys Arg Leu Ala Ala Asp Leu Gly His Glu Leu
                725                 730
```

<210> SEQ ID NO 26
<211> LENGTH: 146
<212> TYPE: PRT
<213> ORGANISM: Streptomyces sviceus

<400> SEQUENCE: 26

Met Leu Thr Arg Ile Asp His Ile Gly Ile Ala Cys Phe Asp Leu Asp

```
             1               5              10              15
Lys Thr Val Glu Phe Tyr Arg Ala Thr Tyr Gly Phe Glu Val Phe His
              20                  25                  30

Ser Glu Val Asn Glu Glu Gln Gly Val Arg Glu Ala Met Leu Lys Ile
              35                  40                  45

Asn Glu Thr Ser Asp Gly Gly Ala Ser Tyr Leu Gln Leu Leu Glu Pro
              50                  55                  60

Thr Arg Pro Asp Ser Thr Val Ala Lys Trp Leu Asp Lys Asn Gly Glu
 65                  70                  75                  80

Gly Val His His Ile Ala Phe Gly Thr Ala Asp Val Asp Gln Asp Ala
                  85                  90                  95

Ala Asp Ile Lys Asp Lys Gly Val Arg Val Leu Tyr Glu Glu Pro Arg
                 100                 105                 110

Arg Gly Ser Met Gly Ser Arg Ile Thr Phe Leu His Pro Lys Asp Cys
                 115                 120                 125

His Gly Val Leu Thr Glu Leu Val Thr Ser Ala Pro Val Glu Ser Pro
                 130                 135                 140

Glu His
145

<210> SEQ ID NO 27
<211> LENGTH: 4553
<212> TYPE: DNA
<213> ORGANISM: Artificial Sequence
<220> FEATURE:
<223> OTHER INFORMATION: Synthetic nucleotide

<400> SEQUENCE: 27
gaattcaaaa ttaagaggta tatattaatg accgtgctgc cggatgacgg tctgagtctg      60
gcagccgaat tccggatgc gacgcatgaa cagtggcacc gtctggttga aggcgtggtt     120
cgcaaatcag gcaaagatgt ctcgggcacc gcagctgaag aagccctgag caccacgctg     180
gaagacggtc tgaccacgcg tccgctgtat acggcacgtg atgcagcacc ggacgctggt     240
tttccgggtt tcgcgccgtt tgtgcgtggc tcagttccgg agggtaacac cccgggcggt     300
tgggatgtgc gtcaacgtta cgcatcggca gacccggcac gtaccaacga agcagtgctg     360
acggatctgg aaaatggtgt taccagcctg tggctgacgc tgggttctgc aggtctgccg     420
gtgaccggtc tggaacgtgc actggatggt gtttatctgg acctggtccc ggtggcactg     480
gatgcaggta gcgaagcagc taccgcagca cgtgaactgc tgcgtctgta cgaagcagct     540
ggtgttgctg atgacgcagt ccgtggcacg ctgggtgcag atccgctggg ccatgaagca     600
cgcaccggtg aaaaaagtac gtcctttgca gcagtggcag aactggcacg tctgtgcggt     660
gaacgttatc cgggtctgcg cgctctgacc gttgatgcgc tgccgtacca tgaagctggc     720
gcgtcagcag ctcaggaact gggcgcttcg ctggcgaccg tgtggaata tctgcgtgcg     780 ctgcacgata aaggcctggg tgttgaaaaa gccttcgcac agctggaatt cgcttcgcg     840 gccaccgcgg accaatttct gacgattgcc aaactgcgtg cagctcgtcg cctgtgggca     900
cgtgttgcag aagtcagtgg cgtgccggca gcaggtgcac agcgtcaaca tgcagtcacc     960
tccccggtga tgatgacgcg tcgcgatccg tgggtgaaca tgctgcgtac cacggttgct    1020
tgtctgggtg caggtgtcgg cggtgctgat gcagttaccg tcctgccgtt cgatcacgaa    1080
ctgggtctgc cggacgcctt tgcacgtcgc attgcgcgta taccagtac gatcctgctg    1140 gaagaatccc atctggcccg tgtcattgat ccggcaggcg gtagctggta tgtggaacgc    1200
```

```
ctgaccgatg aactggccca cgcagcttgg gacttttcca agaaatcga acgtgcagat   1260
ggtcaggtcg cagcactgcg tagcggcctg gtgggtgacc gcattgcagc tacctgggca   1320
gaacgtcgca aaaaactggc gcgtcgccgt gaaccgatca ccggtgtgtc tgaatttccg   1380
ctgctgacgg aacgcccggt tgaacgtgaa ccggcaccgg cagcaccgcc gggcggtctg   1440
ccgcgcgtgc gccgtgatga agcctacgaa gaactgcgtg gtcgttctga cgcacacctg   1500
gaagctaccg gtgcacgtcc gaaagtgttc attgcagctc tgggtccggc agcagcacat   1560
accgctcgtg cgacgttcgc tgcgaacctg tttatggcgg gcggtgttga accggtccac   1620
gatcctgtga gcgttgacgc ggaaaccgcc gcagaagcct ttgctgcgtc tggcgccacg   1680
gttgcatgcc tgtgtagctc tgatgtcctg tatgcggaac aagccgaagc agtcgctcgt   1740
gcgctgaaaa gtgccggtgc actgcgtgtt ttcctggcag gccgcggtga atttgcggat   1800
atcgacgaat acgtgtttgc aggttgcgat gctgtcgcag tgctgacctc cacgctggac   1860
cgtatgggtg ttgcgtaatg cgtattccgg aatttgatga catcgaactg ggtgccggcg   1920
gtggcccgtc aggttcggca gaacagtggc gtgcagcagt gaaagaaagc gttggtaaaa   1980
gcgaatctga tctgctgtgg gaaaccccgg aaggcattgc tgttaaaccg ctgtacacgg   2040
gtgccgatgt cgaaggcctg gacttcctgg aaacctatcc gggtgtcgca ccgtacctgc   2100
gtggtccgta tccgaccatg tacgtgaacc agccgtggac gatccgccaa tacgcgggtt   2160
ttagcaccgc cgaagaatct aacgcattct atcgtcgcaa tctggcagct ggccagaaag   2220
gtctgagtgt ggcgtttgat ctgccgaccc atcgtggcta cgattccgac cacccgcgtg   2280
tcacgggtga cgtgggtatg gccggcgtgg caattgatag catctatgac atgcgtcagc   2340
tgttcgatgg tattccgctg acaaaatga ccgtttctat gacgatgaac ggcgctgtgc   2400
tgccggttct ggcgctgtat atcgtggcgg ccgaagaaca gggtgttccg ccggaaaaac   2460
tggcgggcac catccaaaac gatatcctga agaatttat ggttcgtaac acgtacatct   2520
accegeegaa accgagtatg cgcattatct ccgatatctt cgcctatacc tcacagaaaa   2580
tgccgcgcta caacagtatc tccatctcag gttatcatat ccaagaagca ggcgctaccg   2640
cggatctgga actggcctac acgctggcag acggtgttga atatctgcgt gctggtcagg   2700
aagcgggcct ggatgtcgac gcctttgcac cgcgcctgag ctttttctgg gccattggca   2760
tgaactttt catggaagtg gcaaaactgc gtgcagctcg cctgctgtgg gcgaaactgg   2820
ttaaacagtt tgatccgaaa aatgcgaaat cgctgagcct gcgtacccac tcccagacgt   2880
caggttggtc gctgaccgcc caagatgttt caacaatgt cacccgcacg tgcgtggaag   2940
caatggcagc aacccagggt catacgcaat cactgcacac caacgcgctg gatgaagctc   3000
tggcgctgcc gaccgacttt tcggctcgta ttgcgcgcaa tacgcagctg ctgatccagc   3060
aagaaagcgg caccacgcgt accattgatc cgtggggtgg ctctgcgtat gtggaaaaac   3120
tgacgtacga cctggcacgt cgcgcatggc agcatatcga agaagttgaa gcagcgggtg   3180
gcatggccca agcaattgat gcgggcatcc cgaaactgcg tgtggaagaa gcggcagcac   3240
gtacccaggc acgcattgat tctggtcgtc aaccggtcat cggcgtgaac aaatatcgcg   3300
tggatacgga cgaacagatt gatgttctga agtcgacaa tagctctgtt cgcgcgcagc   3360
aaatcgaaaa actgcgtcgc ctgcgtgaag aacgcgatga cgctgcgtgt caggatgctc   3420
tgcgtgcact gaccgcagca gctgaacgtg gtccgggtca gggtctggaa ggtaatctgc   3480
tggctctggc agtggatgca gcacgtgcca aagcaaccgt tggcgaaatt tcagacgcac   3540
tggaatcggt ctacggtcgt catgcgggcc agattcgcac catcagtggt gtgtatcgca   3600
```

-continued

```
cggaagcggg ccaatctccg agtgtcgaac gtacccgcgc cctggtggat gcatttgacg    3660
aagctgaagg tcgtcgcccg cgtattctgg ttgccaaaat gggtcaggat ggccacgacc    3720
gcggccaaaa agtcatcgct tccgcgtttg ccgatctggg tttcgatgtc gacgtgggtc    3780
cgctgttcca gaccccggcc gaagtggcac gtcaagctgt ggaagcggat gttcatattg    3840
ttggtgtcag ttccctggca gctggtcacc tgacgctggt tccggcactg cgtgaagaac    3900
tggcggccga aggtcgcgat gacattatga tcgtggttgg tggcgtcatt ccgccgcagg    3960
atgtggaagc cctgcatgaa gcaggtgcta ccgcggtttt tccgccgggc acggtcatcc    4020
cggatgcagc tcatgacctg gtgaaacgtc tggcagcaga tctgggtcac gaactgtaaa    4080
agcttaaaat taagaggtat atattaatgc tgacccgcat cgatcacatt ggcatcgcat    4140
gctttgatct ggataaaacc gtagagttct atcgcgccac ctacggcttt gaggtgtttc    4200
atagcgaagt aaacgaagaa cagggcgtgc gtgaagccat gctgaaaatc aacgaaacta    4260
gtgatggtgg ggcgagctat ctgcaactgc tggaaccgac acgcccggac tctacagttg    4320
ctaagtggct ggacaagaat ggcgaaggcg ttcatcacat tgcgttcggt acggctgatg    4380
tggatcaaga cgcggcagat attaaagata agggtgtgcg tgttctgtac gaggagccac    4440
gccgtggtag catgggtagc cgtattacgt tcctgcaccc taaagactgt catggtgtgc    4500
tgactgagct ggtcacctct gccccggtcg aaagtccgga acattaaggt acc            4553
```

<210> SEQ ID NO 28
<211> LENGTH: 717
<212> TYPE: PRT
<213> ORGANISM: Escherichia coli

<400> SEQUENCE: 28

```
Met Ser Arg Met Ser Asn Val Gln Glu Trp Gln Gln Leu Ala Asn Lys
1               5                   10                  15

Glu Leu Ser Arg Arg Glu Lys Thr Val Asp Ser Leu Val His Gln Thr
            20                  25                  30

Ala Glu Gly Ile Ala Ile Lys Pro Leu Tyr Thr Glu Ala Asp Leu Asp
        35                  40                  45

Asn Leu Glu Val Thr Gly Thr Leu Pro Gly Leu Pro Pro Tyr Val Arg
    50                  55                  60

Gly Pro Arg Ala Thr Met Tyr Thr Ala Gln Pro Trp Thr Ile Arg Gln
65                  70                  75                  80

Tyr Ala Gly Phe Ser Thr Ala Lys Glu Ser Asn Ala Phe Tyr Arg Arg
                85                  90                  95

Asn Leu Ala Ala Gly Gln Lys Gly Leu Ser Val Ala Phe Asp Leu Ala
            100                 105                 110

Thr His Arg Gly Tyr Asp Ser Asp Asn Pro Arg Val Ala Gly Asp Val
        115                 120                 125

Gly Lys Ala Gly Val Ala Ile Asp Thr Val Glu Asp Met Lys Val Leu
    130                 135                 140

Phe Asp Gln Ile Pro Leu Asp Lys Met Ser Val Ser Met Thr Met Asn
145                 150                 155                 160

Gly Ala Val Leu Pro Val Leu Ala Phe Tyr Ile Val Ala Ala Glu Glu
                165                 170                 175

Gln Gly Val Thr Pro Asp Lys Leu Thr Gly Thr Ile Gln Asn Asp Ile
            180                 185                 190

Leu Lys Glu Tyr Leu Cys Arg Asn Thr Tyr Ile Tyr Pro Pro Lys Pro
        195                 200                 205
```

```
Ser Met Arg Ile Ile Ala Asp Ile Ile Ala Trp Cys Ser Gly Asn Met
    210                 215                 220

Pro Arg Phe Asn Thr Ile Ser Ile Ser Gly Tyr His Met Gly Glu Ala
225                 230                 235                 240

Gly Ala Asn Cys Val Gln Gln Val Ala Phe Thr Leu Ala Asp Gly Ile
                245                 250                 255

Glu Tyr Ile Lys Ala Ala Ile Ser Ala Gly Leu Lys Ile Asp Asp Phe
                260                 265                 270

Ala Pro Arg Leu Ser Phe Phe Phe Gly Ile Gly Met Asp Leu Phe Met
            275                 280                 285

Asn Val Ala Met Leu Arg Ala Ala Arg Tyr Leu Trp Ser Glu Ala Val
290                 295                 300

Ser Gly Phe Gly Ala Gln Asp Pro Lys Ser Leu Ala Leu Arg Thr His
305                 310                 315                 320

Cys Gln Thr Ser Gly Trp Ser Leu Thr Glu Gln Asp Pro Tyr Asn Asn
                325                 330                 335

Val Ile Arg Thr Thr Ile Glu Ala Leu Ala Ala Thr Leu Gly Gly Thr
                340                 345                 350

Gln Ser Leu His Thr Asn Ala Phe Asp Glu Ala Leu Gly Leu Pro Thr
            355                 360                 365

Asp Phe Ser Ala Arg Ile Ala Arg Asn Thr Gln Ile Ile Gln Glu
370                 375                 380

Glu Ser Glu Leu Cys Arg Thr Val Asp Pro Leu Ala Gly Ser Tyr Tyr
385                 390                 395                 400

Ile Glu Ser Leu Thr Asp Gln Ile Val Lys Gln Ala Arg Ala Ile Ile
                405                 410                 415

Gln Gln Ile Asp Glu Ala Gly Gly Met Ala Lys Ala Ile Glu Ala Gly
            420                 425                 430

Leu Pro Lys Arg Met Ile Glu Glu Ala Ser Ala Arg Glu Gln Ser Leu
            435                 440                 445

Ile Asp Gln Gly Lys Arg Val Ile Val Gly Val Asn Lys Tyr Lys Leu
450                 455                 460

Asp His Glu Asp Glu Thr Asp Val Leu Glu Ile Asp Asn Val Met Val
465                 470                 475                 480

Arg Asn Glu Gln Ile Ala Ser Leu Glu Arg Ile Arg Ala Thr Arg Asp
                485                 490                 495

Asp Ala Ala Val Thr Ala Ala Leu Asn Ala Leu Thr His Ala Ala Gln
                500                 505                 510

His Asn Glu Asn Leu Leu Ala Ala Ala Val Asn Ala Ala Arg Val Arg
            515                 520                 525

Ala Thr Leu Gly Glu Ile Ser Asp Ala Leu Glu Val Ala Phe Asp Arg
530                 535                 540

Tyr Leu Val Pro Ser Gln Cys Val Thr Gly Val Ile Ala Gln Ser Tyr
545                 550                 555                 560

His Gln Ser Glu Lys Ser Ala Ser Glu Phe Asp Ala Ile Val Ala Gln
                565                 570                 575

Thr Glu Gln Phe Leu Ala Asp Asn Gly Arg Arg Pro Arg Ile Leu Ile
                580                 585                 590

Ala Lys Met Gly Gln Asp Gly His Asp Arg Gly Ala Lys Val Ile Ala
            595                 600                 605

Ser Ala Tyr Ser Asp Leu Gly Phe Asp Val Asp Leu Ser Pro Met Phe
610                 615                 620
```

```
Ser Thr Pro Glu Glu Ile Ala Arg Leu Ala Val Glu Asn Asp Val His
625                 630                 635                 640

Val Val Gly Ala Ser Ser Leu Ala Ala Gly His Lys Thr Leu Ile Pro
            645                 650                 655

Glu Leu Val Glu Ala Leu Lys Lys Trp Gly Arg Glu Asp Ile Cys Val
            660                 665                 670

Val Ala Gly Gly Val Ile Pro Pro Gln Asp Tyr Ala Phe Leu Gln Glu
        675                 680                 685

Arg Gly Val Ala Ala Ile Tyr Gly Pro Gly Thr Pro Met Leu Asp Ser
    690                 695                 700

Val Arg Asp Val Leu Asn Leu Ile Ser Gln His His Asp
705                 710                 715
```

<210> SEQ ID NO 29
<211> LENGTH: 2166
<212> TYPE: DNA
<213> ORGANISM: Artificial Sequence
<220> FEATURE:
<223> OTHER INFORMATION: Synthetic nucleotide

<400> SEQUENCE: 29

```
ggatccatgt ctagaatgag caacgtgcag gaatggcagc agctggcgaa taaagaactg      60
agccgtcgcg aaaaaacggt tgattctctg gtgcatcaga ccgccgaagg tatcgcaatt     120
aaaccgctgt ataccgaagc ggatctggat aacctggaag tgaccggtac gctgccgggt     180
ctgccgccgt atgttcgtgg tccgcgtgcg accatgtaca cggcacagcc gtggacgatt     240
cgtcagtatg cgggcttcag caccgccaaa gaatctaacg catttaccg tcgcaatctg     300
gcggcgggtc agaaaggtct gagcgtggcg tttgatctgg ccacccaccg tggttacgat     360
tctgataacc gcgcgttgc gggcgatgtg ggtaaagcag cgttgcgat cgatacggtg     420
gaagatatga agttctgtt cgatcagatt ccgctggata aaatgagtgt tagcatgacc     480
atgaatggcg cggttctgcc ggtgctggcc ttttatatcg tggcagcgga gaacagggt     540
gttacgccgg ataaactgac cggcacgatc cagaacgata ttctgaaaga atacctgtgc     600
cgtaatacct atatttaccc gccgaaaccg tctatgcgca ttatcgcaga tattatcgcg     660
tggtgtagtg gtaacatgcc gcgtttcaat acgatctcta ttagtggcta tcatatgggt     720
gaagccggcg caaactgcgt tcagcaggtg gcctttaccc tggcagatgg tatcgaatac     780
attaaagccg caatcagtgc gggcctgaaa attgatgatt cgccccgcg cctgagcttt     840
ttctttggca ttggtatgga tctgtttatg aatgtggcca tgctgcgtgc ggcccgctat     900
ctgtggagcg aagcagtttc tggctttggc gcgcaggacc cgaaaagcct ggcactgcgt     960
acccattgcc agacgagtgg ttggagcctg accgaacagg accgtacaa caatgtgatc    1020
cgcaccacga ttgaagcgct ggcagcaacc ctgggtggta cgcagagcct gcacaccaac    1080
gcgttcgatg aagccctggg tctgccgacg gatttagcg cccgtatcgc acgcaatacc    1140
cagattatca ttcaggaaga atctgaactg tgtcgtacgg ttgatccgct ggcgggcagt    1200
tattacatcg aaagcctgac cgatcagatt gttaaacagg cgcgtgcgat cattcagcag    1260
attgatgaag caggcggtat ggcaaaagcg atcgaagcgg gcctgccgaa acgtatgatt    1320
gaagaagcct ctgcacgcga acagagtctg atcgatcagg gtaaacgtgt gattgttggc    1380
gtgaacaaat acaaactgga tcatgaagat gaaaccgatg tgctggaaat cgataacgtt    1440
atggtgcgta atgaacagat cgccagcctg aacgtattc gcgcaacccg cgatgatgcc    1500
gcagttacgg cggccctgaa cgcactgacc catgcagcgc agcacaacga aaatctgctg    1560
```

-continued

```
gccgcagcgg tgaatgccgc acgtgttcgc gcgacgctgg gtgaaatttc tgatgcactg      1620
gaagtggcgt tcgatcgcta tctggttccg agtcagtgcg ttaccggcgt gatcgcccag      1680
agttaccatc agagcgaaaa aagcgcatct gaatttgatg cgattgtggc ccagaccgaa      1740
cagtttctgg cagataacgg ccgtcgcccg cgtatcctga ttgccaaaat gggtcaggat      1800
ggccacgatc gcggtgcgaa agtgatcgcg tctgcctata gtgatctggg cttcgatgtt      1860
gatctgtctc cgatgtttag tacgccgaaa gaaattgcac gtctggcggt tgaaaatgat      1920
gtgcatgtgg ttggtgccag ctctctggcg gcgggtcaca aaaccctgat tccggaactg      1980
gtggaagcgc tgaaaaaatg gggtcgcgaa gatatctgtg tggttgcggg cggtgtgatt      2040
ccgccgcagg attatgcgtt tctgcaagaa cgtggtgttg cagcaatcta cggtccgggc      2100
accccgatgc tggatagtgt tcgcgatgtg ctgaatctga ttagccagca tcacgattaa      2160
gagctc                                                                2166
```

<210> SEQ ID NO 30
<211> LENGTH: 1206
<212> TYPE: DNA
<213> ORGANISM: Artificial Sequence
<220> FEATURE:
<223> OTHER INFORMATION: Synthetic nucleotide

<400> SEQUENCE: 30

```
ggatccatga aaataaaaac aggtgcacgc atcctcgcat tatccgcatt aacgacgatg        60
atgttttccg cctcggctct cgccaaaatc gaagaaggta aactggtaat ctggattaac       120
ggcgataaag gctataacgg tctcgctgaa gtcggtaaga aattcgagaa agataccgga       180
attaaagtca ccgttgagca tccggataaa ctggaagaga aattcccaca ggttgcggca       240
actggcgatg gccctgacat tatcttctgg gcacacgacc gctttggtgg ctacgctcaa       300
tctggcctgt tggctgaaat caccccggac aaagcgttcc aggacaagct gtatccgttt       360
acctgggatg ccgtacgtta caacggcaag ctgattgctt acccgatcgc tgttgaagcg       420
ttatcgctga tttataacaa agacctgctg ccgaacccgc caaaaaccctg gaagagatc       480 ccggcgctgg ataaagaact gaaagcgaaa ggtaagagcg cgctgatgtt caacctgcaa       540
gaaccgtact tcacctggcc gctgattgct gctgacgggg ttatgcgttc aagtatgaa       600 aacggcaagt acgacattaa agacgtgggc gtggataacg ctggcgcgaa agcgggtctg       660
accttcctgg ttgacctgat taaaaacaaa cacatgaatg cagacaccga ttactccatc       720
gcagaagctg cctttaataa aggcgaaaca gcgatgacca tcaacggccc gtgggcatgg       780
tccaacatcg acaccagcaa agtgaattat ggtgtaacgg tactgccgac cttcaagggt       840
caaccatcca aaccgttcgt tggcgtgctg agcgcaggta ttaacgccgc cagtccgaac       900
aaagagctgg cgaaagagtt cctcgaaaac tatctgctga ctgatgaagg tctggaagcg       960
gttaataaag acaaaccgct gggtgccgta gcgctgaagt cttacgagga agagttggcg      1020
aaagatccac gtattgccgc caccatggaa aacgcccaga aggtgaaat catgccgaac      1080 atcccgcaga tgtccgcttt ctggtatgcc gtgcgtactg cggtgatcaa cgccgccagc      1140
ggtcgtcaga ctgtcgatga agccctgaaa gacgcgcaga ctcgtatcac caagtctaga      1200
gagctc                                                                1206
```

<210> SEQ ID NO 31
<211> LENGTH: 38
<212> TYPE: DNA

<213> ORGANISM: Artificial Sequence
<220> FEATURE:
<223> OTHER INFORMATION: Synthetic primer

<400> SEQUENCE: 31
gagaggtacc atgggggtt ctcatcatca tcatcatc 38

<210> SEQ ID NO 32
<211> LENGTH: 38
<212> TYPE: DNA
<213> ORGANISM: Artificial Sequence
<220> FEATURE:
<223> OTHER INFORMATION: Synthetic primer

<400> SEQUENCE: 32
cagccaagct tttattacgc accctgtgcg cgctgttc 38

<210> SEQ ID NO 33
<211> LENGTH: 1263
<212> TYPE: DNA
<213> ORGANISM: Artificial Sequence
<220> FEATURE:
<223> OTHER INFORMATION: Synthetic nucleotide

<400> SEQUENCE: 33 atgggggtt ctcatcatca tcatcatcat ggtatggcta gcatgactgg tggacagcaa 60
atgggtcggg atctgtacga cgatgacgat aaggatcgat ggggatccct ggtggaaggc 120
ctgcgtgaag ttgccgatgg tgatgcactg tatgatgcag cagtgggtca tggcgatcgt 180
ggtccggttt gggtgtttag cggccagggt tctcagtggg cagcgatggg cacccagctg 240
ctggcaagcg aaccggtttt tgccgcaacg attgcaaaac tggaaccggt gatcgcggcc 300
gaaagtggct tcagcgttac cgaagcaatt acggcgcagc agaccgtgac gggtatcgat 360
aaagtgcagc cggccgtttt cgcagttcag gtggcgctgg cagcgacgat ggaacagacg 420
tacggcgttc gtccgggtgc agtggttggt cacagtatgg gtgaaagcgc cgcagcggtg 480
gttgcaggcg ccctgagtct ggaagatgcc gcacgtgtga tttgccgtcg cagcaaactg 540
atgacccgta tcgcaggtgc aggtgcgatg ggcagcgtgg aactgccggc aaaacaggtt 600
aactctgaac tgatggcgcg cggtattgat gatgtggttg tgtctgttgt ggcgtctccg 660
cagagtaccg tgattggcgg caccagtgat acggttcgtg atctgatcgc gcgttgggaa 720
cagcgcgatg tgatggcgcg cgaagttgcc gtggatgttg caagccattc tccgcaggtt 780
gatccgattc tggatgatct ggcggcggca ctggcagata ttgcaccgat gaccccgaaa 840
gtgccgtatt acagcgcgac gctgtttgat ccgcgtgaac agccggtgtg tgatggcgcc 900
tattgggttg ataacctgcg caataccgtg cagtttgcgg cggcagttca ggcggcgatg 960
gaagatggtt accgtgtgtt cgcggaactg tctccgcatc cgctgctgac ccacgcagtg 1020
gaacagacgg gtcgctctct ggatatgagt gttgcagcac tggccggtat gcgtcgcgaa 1080
cagccgctgc cgcatggcct gcgtggtctg ctgaccgaac tgcaccgtgc aggtgcagca 1140
ctggattata gcgcactgta cccggcaggt cgtctggtgg atgcaccgct gccggcatgg 1200
acgcacgcac gtctgttcat cgatgatgat ggccaggaac agcgcgcaca gggtgcgtaa 1260
taa 1263

<210> SEQ ID NO 34
<211> LENGTH: 419
<212> TYPE: PRT
<213> ORGANISM: Mycobacterium bovis

```
<400> SEQUENCE: 34

Met Gly Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Leu Val Glu Gly Leu Arg Glu Val Ala Asp Gly Asp
        35                  40                  45

Ala Leu Tyr Asp Ala Ala Val Gly His Gly Asp Arg Gly Pro Val Trp
    50                  55                  60

Val Phe Ser Gly Gln Gly Ser Gln Trp Ala Ala Met Gly Thr Gln Leu
65              70                  75                  80

Leu Ala Ser Glu Pro Val Phe Ala Ala Thr Ile Ala Lys Leu Glu Pro
                85                  90                  95

Val Ile Ala Ala Glu Ser Gly Phe Ser Val Thr Glu Ala Ile Thr Ala
                100                 105                 110

Gln Gln Thr Val Thr Gly Ile Asp Lys Val Gln Pro Ala Val Phe Ala
            115                 120                 125

Val Gln Val Ala Leu Ala Ala Thr Met Glu Gln Thr Tyr Gly Val Arg
130                 135                 140

Pro Gly Ala Val Val Gly His Ser Met Gly Glu Ser Ala Ala Ala Val
145                 150                 155                 160

Val Ala Gly Ala Leu Ser Leu Glu Asp Ala Ala Arg Val Ile Cys Arg
                165                 170                 175

Arg Ser Lys Leu Met Thr Arg Ile Ala Gly Ala Gly Ala Met Gly Ser
            180                 185                 190

Val Glu Leu Pro Ala Lys Gln Val Asn Ser Glu Leu Met Ala Arg Gly
        195                 200                 205

Ile Asp Asp Val Val Val Ser Val Val Ala Ser Pro Gln Ser Thr Val
210                 215                 220

Ile Gly Gly Thr Ser Asp Thr Val Arg Asp Leu Ile Ala Arg Trp Glu
225                 230                 235                 240

Gln Arg Asp Val Met Ala Arg Glu Val Ala Val Asp Val Ala Ser His
            245                 250                 255

Ser Pro Gln Val Asp Pro Ile Leu Asp Asp Leu Ala Ala Ala Leu Ala
        260                 265                 270

Asp Ile Ala Pro Met Thr Pro Lys Val Pro Tyr Tyr Ser Ala Thr Leu
    275                 280                 285

Phe Asp Pro Arg Glu Gln Pro Val Cys Asp Gly Ala Tyr Trp Val Asp
290                 295                 300

Asn Leu Arg Asn Thr Val Gln Phe Ala Ala Val Gln Ala Ala Met
305                 310                 315                 320

Glu Asp Gly Tyr Arg Val Phe Ala Glu Leu Ser Pro His Pro Leu Leu
            325                 330                 335

Thr His Ala Val Glu Gln Thr Gly Arg Ser Leu Asp Met Ser Val Ala
            340                 345                 350

Ala Leu Ala Gly Met Arg Arg Glu Gln Pro Leu Pro His Gly Leu Arg
            355                 360                 365

Gly Leu Leu Thr Glu Leu His Arg Ala Gly Ala Ala Leu Asp Tyr Ser
    370                 375                 380

Ala Leu Tyr Pro Ala Gly Arg Leu Val Asp Ala Pro Leu Pro Ala Trp
385                 390                 395                 400

Thr His Ala Arg Leu Phe Ile Asp Asp Asp Gly Gln Glu Gln Arg Ala
```

-continued

<210> SEQ ID NO 35
<211> LENGTH: 464
<212> TYPE: DNA
<213> ORGANISM: Kribbella flavida DSM

<400> SEQUENCE: 35

| | | |
|---|---|---|
| gagctcagga ggaattaacc atggaacacc tgacggcgac ccagaccctg tttgaagcga | 60 |
| ttgaccacgt tggcgttgca gttgcggatt ttgatgaagc agtgcgtttt tatgcagaaa | 120 |
| ccttcggcat gacggtggct catgaagaag ttaacgaaga cagggtgtt cgtgaagcaa | 180 |
| tgctgtcaat tggcgattcg ggtagctcta tccaactgct ggcgccgctg tccgatagtt | 240 |
| ccccgattgc caaatttctg gaccgcaatg gcccgggtat ccagcaactg gcctatcgtg | 300 |
| tccgcgatct ggacgcagtg agcgcaaccc tgcgtgaacg tggcgcgcaa ctgctgtacg | 360 |
| acgaaccgcg tcgcggcacg gctggttctc gtattaactt cattcatccg aaatcggcgg | 420 |
| gcggcgtcct ggtggaactg gtggaaccgg ctcgctaact gcag | 464 |

<210> SEQ ID NO 36
<211> LENGTH: 145
<212> TYPE: PRT
<213> ORGANISM: Kribbella flavida DSM

<400> SEQUENCE: 36

Met Glu His Leu Thr Ala Thr Gln Thr Leu Phe Glu Ala Ile Asp His
1               5                   10                  15

Val Gly Val Ala Val Ala Asp Phe Asp Glu Ala Val Arg Phe Tyr Ala
            20                  25                  30

Glu Thr Phe Gly Met Thr Val Ala His Glu Glu Val Asn Glu Glu Gln
        35                  40                  45

Gly Val Arg Glu Ala Met Leu Ser Ile Gly Asp Ser Gly Ser Ser Ile
    50                  55                  60

Gln Leu Leu Ala Pro Leu Ser Asp Ser Ser Pro Ile Ala Lys Phe Leu
65                  70                  75                  80

Asp Arg Asn Gly Pro Gly Ile Gln Gln Leu Ala Tyr Arg Val Arg Asp
                85                  90                  95

Leu Asp Ala Val Ser Ala Thr Leu Arg Glu Arg Gly Ala Gln Leu Leu
            100                 105                 110

Tyr Asp Glu Pro Arg Arg Gly Thr Ala Gly Ser Arg Ile Asn Phe Ile
        115                 120                 125

His Pro Lys Ser Ala Gly Gly Val Leu Val Glu Leu Val Glu Pro Ala
    130                 135                 140

Arg
145

<210> SEQ ID NO 37
<211> LENGTH: 545
<212> TYPE: DNA
<213> ORGANISM: Sorangium cellulosum

<400> SEQUENCE: 37

| | | |
|---|---|---|
| gagctcagga ggaattaacc atggctccgc cggcaacgcg tccggctccg gctgcaccga | 60 |
| cgggcctgcc gacccaacgt gaaccgatga agaccagat tccgggcttt ctgttcattg | 120 |
| atcatatcgc gatggccgtg ccggcaggcc aactggacgc acaagttaaa gcctatgaaa | 180 |

```
tgctgggctt tcgtgaagtt catcgcgaag aagtccgtgg tgcggatcag gtgcgcgaag      240
ttatgctgcg tattggtgat agcgacaacc acgtccaact gctggaaccg ctgagcccgg      300
aatctccggt tcaaaaactg atcgagaaaa acggcggtcg cggcggtttc gcacatgtgg      360
cttaccgtgt cagtgatgtg caagcggcct tgacgaact gaaagcgcgt ggcttccgca      420
ttatcgatgc agctccgcgt ccgggcagcc gtggcaccac gattttcttt gttcacccgc      480
gctcacgcga cgatgccccg ttcggtcacc tgattgaagt tgtccagtca catggctaac      540
tgcag                                                                  545
```

<210> SEQ ID NO 38
<211> LENGTH: 172
<212> TYPE: PRT
<213> ORGANISM: Sorangium cellulosum

<400> SEQUENCE: 38

```
Met Ala Pro Pro Ala Thr Arg Pro Ala Pro Ala Pro Thr Gly Leu
1               5                   10                  15

Pro Thr Gln Arg Glu Pro Met Lys Asp Gln Ile Pro Gly Phe Leu Phe
                20                  25                  30

Ile Asp His Ile Ala Met Ala Val Pro Ala Gly Gln Leu Asp Ala Gln
            35                  40                  45

Val Lys Ala Tyr Glu Met Leu Gly Phe Arg Glu Val His Arg Glu Glu
50                  55                  60

Val Arg Gly Ala Asp Gln Val Arg Glu Val Met Leu Arg Ile Gly Asp
65                  70                  75                  80

Ser Asp Asn His Val Gln Leu Leu Glu Pro Leu Ser Pro Glu Ser Pro
                85                  90                  95

Val Gln Lys Leu Ile Glu Lys Asn Gly Gly Arg Gly Gly Phe Ala His
            100                 105                 110

Val Ala Tyr Arg Val Ser Asp Val Gln Ala Ala Phe Asp Glu Leu Lys
        115                 120                 125

Ala Arg Gly Phe Arg Ile Ile Asp Ala Ala Pro Arg Pro Gly Ser Arg
    130                 135                 140

Gly Thr Thr Ile Phe Phe Val His Pro Arg Ser Arg Asp Asp Ala Pro
145                 150                 155                 160

Phe Gly His Leu Ile Glu Val Val Gln Ser His Gly
                165                 170
```

<210> SEQ ID NO 39
<211> LENGTH: 26
<212> TYPE: DNA
<213> ORGANISM: Artificial Sequence
<220> FEATURE:
<223> OTHER INFORMATION: Synthetic primer

<400> SEQUENCE: 39

```
taagagctca ggaggaatta accatg                                           26
```

<210> SEQ ID NO 40
<211> LENGTH: 566
<212> TYPE: DNA
<213> ORGANISM: Escherichia coli

<400> SEQUENCE: 40

```
catgccatgg cggacacgtt attgattctg ggtgatagcc tgagcgccgg gtatcgaatg      60
tctgccagcg cggcctggcc tgccttgttg aatgataagt ggcagagtaa aacgtcggta     120
```

```
gttaatgcca gcatcagcgg cgacacctcg caacaaggac tggcgcgcct tccggctctg      180
ctgaaacagc atcagccgcg ttgggtgctg gttgaactgg gcggcaatga cggtttgcgt      240
ggttttcagc cacagcaaac cgagcaaacg ctgcgccaga ttttgcagga tgtcaaagcc      300
gccaacgctg aaccattgtt aatgcaaata cgtctgcctg caaactatgg tcgccgttat      360
aatgaagcct ttagcgccat ttaccccaaa ctcgccaaag agtttgatgt tccgctgctg      420
ccctttttta tggaagaggt ctacctcaag ccacaatgga tgcaggatga cggtattcat      480
cccaaccgcg acgcccagcc gtttattgcc gactggatgg cgaagcagtt gcagccttta      540
gtaaatcatg actcataagg atccgc                                           566
```

```
<210> SEQ ID NO 41
<211> LENGTH: 32
<212> TYPE: DNA
<213> ORGANISM: Artificial Sequence
<220> FEATURE:
<223> OTHER INFORMATION: Synthetic primer

<400> SEQUENCE: 41
catgccatgg cggacacgtt attgattctg gg                                     32

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Met Ala Asp Thr Leu Leu Ile Leu Gly
1               5

<210> SEQ ID NO 43
<211> LENGTH: 36
<212> TYPE: DNA
<213> ORGANISM: Artificial Sequence
<220> FEATURE:
<223> OTHER INFORMATION: Synthetic primer

<400> SEQUENCE: 43
gcggatcctt atgagtcatg atttactaaa ggctgc                                 36

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Ser Asp His Asn Val Leu Pro Gln Leu
1               5

<210> SEQ ID NO 45
<211> LENGTH: 183
<212> TYPE: PRT
<213> ORGANISM: Escherichia coli

<400> SEQUENCE: 45

Met Ala Asp Thr Leu Leu Ile Leu Gly Asp Ser Leu Ser Ala Gly Tyr
1               5                   10                  15

Arg Met Ser Ala Ser Ala Ala Trp Pro Ala Leu Leu Asn Asp Lys Trp
```

```
                20                  25                  30
Gln Ser Lys Thr Ser Val Val Asn Ala Ser Ile Ser Gly Asp Thr Ser
            35                  40                  45

Gln Gln Gly Leu Ala Arg Leu Pro Ala Leu Leu Lys Gln His Gln Pro
        50                  55                  60

Arg Trp Val Leu Val Glu Leu Gly Gly Asn Asp Gly Leu Arg Gly Phe
 65                  70                  75                  80

Gln Pro Gln Gln Thr Glu Gln Thr Leu Arg Gln Ile Leu Gln Asp Val
                85                  90                  95

Lys Ala Ala Asn Ala Glu Pro Leu Leu Met Gln Ile Arg Leu Pro Ala
            100                 105                 110

Asn Tyr Gly Arg Arg Tyr Asn Glu Ala Phe Ser Ala Ile Tyr Pro Lys
        115                 120                 125

Leu Ala Lys Glu Phe Asp Val Pro Leu Leu Pro Phe Phe Met Glu Glu
    130                 135                 140

Val Tyr Leu Lys Pro Gln Trp Met Gln Asp Asp Gly Ile His Pro Asn
145                 150                 155                 160

Arg Asp Ala Gln Pro Phe Ile Ala Asp Trp Met Ala Lys Gln Leu Gln
                165                 170                 175

Pro Leu Val Asn His Asp Ser
            180

<210> SEQ ID NO 46
<211> LENGTH: 33
<212> TYPE: DNA
<213> ORGANISM: Artificial Sequence
<220> FEATURE:
<223> OTHER INFORMATION: Synthetic primer

<400> SEQUENCE: 46
cattactcga gcgcactccc gttctggata atg                              33

<210> SEQ ID NO 47
<211> LENGTH: 35
<212> TYPE: DNA
<213> ORGANISM: Artificial Sequence
<220> FEATURE:
<223> OTHER INFORMATION: Synthetic primer

<400> SEQUENCE: 47
gggaagctta tgagtcatga tttactaaag gctgc                            35

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Ser Asp His Asn Val Leu Pro Gln Leu
 1               5

<210> SEQ ID NO 49
<211> LENGTH: 15
<212> TYPE: DNA
<213> ORGANISM: Artificial Sequence
<220> FEATURE:
<223> OTHER INFORMATION: Synthetic nucleotide

<400> SEQUENCE: 49
```
ggatccatgt ctaga                                                          15

<210> SEQ ID NO 50
<211> LENGTH: 34
<212> TYPE: PRT
<213> ORGANISM: Artificial Sequence
<220> FEATURE:
<223> OTHER INFORMATION: Synthetic peptide

<400> SEQUENCE: 50

Met Gly Gly Ser His His His His His His Gly Met Ala Ser Met Thr
1               5                   10                  15

Gly Gly Gln Gln Met Gly Arg Thr Asp Asp Asp Lys Asp Arg Trp
            20                  25                  30

Gly Ser

<210> SEQ ID NO 51
<211> LENGTH: 655
<212> TYPE: PRT
<213> ORGANISM: Ehrlichia chaffeensis
<300> PUBLICATION INFORMATION:
<308> DATABASE ACCESSION NUMBER: NCBI / YP_507303
<309> DATABASE ENTRY DATE: 2010-05-14
<313> RELEVANT RESIDUES IN SEQ ID NO: (1)..(655)

<400> SEQUENCE: 51

Met Ile Lys Lys Ile Leu Ile Ala Asn Arg Gly Glu Ile Ala Cys Arg
1 5 10 15

Val Met Arg Thr Ala Arg Lys Met Gly Ile Ser Cys Val Ala Val Tyr
20 25 30

Ser Asn Ala Asp Val Tyr Ser Leu His Val Leu Ser Ala Glu Glu Ala
35 40 45

Val Asn Ile Gly Pro Ala Pro Val Asn Gln Ser Tyr Leu Asn Met Glu
50 55 60

Lys Ile Cys Glu Val Ala Cys Asn Thr Gly Val Asp Ala Val His Pro
65 70 75 80

Gly Tyr Gly Phe Leu Ser Glu Asn Ala Asp Phe Pro Glu Lys Leu Glu
85 90 95

Gln Tyr Asn Ile Lys Phe Ile Gly Pro Ser Ser Thr Ser Ile Arg Met
100 105 110

Met Ala Asp Lys Ile Thr Ser Lys Lys Ile Ala Glu Ser Ala Lys Val
115 120 125

Asn Ile Ile Pro Gly Tyr Met Gly Ile Val Asp Ser Val His Glu Ala
130 135 140

Lys Glu Ile Ala Lys Ser Ile Gly Phe Pro Val Met Ile Lys Ala Thr
145 150 155 160

Ala Gly Gly Gly Gly Lys Gly Met Arg Ile Val Lys Ser Ser Glu Glu
165 170 175

Ile Glu Gln Ala Phe Thr Ser Ala Thr Asn Glu Ala Ala Lys Asn Phe
180 185 190

Arg Asp Gly Arg Ile Phe Ile Glu Lys Tyr Val Glu Leu Pro Arg His
195 200 205

Ile Glu Ile Gln Ile Ile Ala Asp Lys His Gly Asn Ile Val Cys Leu
210 215 220

Gly Glu Arg Glu Cys Ser Ile Gln Arg His Asn Gln Lys Val Ile Glu
225 230 235 240

Glu Thr Pro Ser Pro Phe Leu Asp Glu Glu Thr Arg Gln Lys Met Tyr
245 250 255

```
Gln Gln Cys Val Asn Leu Ala Lys Lys Val Gly Tyr Tyr Ser Ala Gly
            260                 265                 270

Thr Ile Glu Phe Ile Val Asp Gln Asp Lys Gln Phe Tyr Phe Leu Glu
        275                 280                 285

Met Asn Thr Arg Leu Gln Val Glu His Pro Val Thr Glu Leu Val Thr
    290                 295                 300

Gly Ile Asp Ile Val Glu Glu Met Ile Arg Ile Ala Asp Gly Glu Glu
305                 310                 315                 320

Leu Arg Phe Thr Gln Gln Asp Val Lys Phe Thr Gly Ser Ala Ile Glu
                325                 330                 335

Ala Arg Val Tyr Ala Glu Asn Pro Thr Lys Asn Phe Leu Pro Ser Ser
            340                 345                 350

Gly Arg Ile Ala Tyr Tyr Ser Ala Pro Met Pro Asn Asp Asn Leu Arg
        355                 360                 365

Ile Asp Ser Gly Val Phe Glu Gly Ala Glu Val Ser Met Phe Tyr Asp
    370                 375                 380

Pro Met Ile Ala Lys Val Cys Thr Tyr Gly Lys Asn Arg Asp Glu Ala
385                 390                 395                 400

Val Ser Phe Met Gln Arg Tyr Leu Asn Glu Phe Tyr Ile Gly Gly Ile
                405                 410                 415

Ala Asn Asn Ile Asp Phe Leu Leu Ser Val Phe His His Pro Val Phe
            420                 425                 430

Ile Ser Gly Asn Ile Asn Thr Lys Phe Ile Glu Gln Phe Tyr Phe Asp
        435                 440                 445

Gly Phe Gln Gly Asn Pro Leu Thr Lys Ala Cys Ile Lys Leu Phe Ile
    450                 455                 460

Leu Thr Ser Leu Cys Ile Phe Phe Gln Asp Glu Tyr Gly Ile His Gly
465                 470                 475                 480

Val Glu Leu Cys Glu Asn Arg Glu Leu Ala Val Tyr Val Asp Gly Gln
                485                 490                 495

Lys Tyr Leu Ile Ser Ala Lys Tyr Glu Asn Gly Arg Val Leu Ala Ile
            500                 505                 510

Tyr Asp Gln Cys Glu Tyr Leu Val Val Ser Thr Trp Asn Val Asn Phe
        515                 520                 525

Lys Ile Leu Gln Ile Gln Val Asn Asn Asp Glu Val Phe His Val Lys
    530                 535                 540

Val Asp Ser Arg Leu Asn Lys Tyr Gln Leu Lys Tyr Ser Ala Met Ser
545                 550                 555                 560

Ala Leu Cys Ala Val Tyr Lys Pro Cys Val Ser Asp Leu Leu Pro Ile
                565                 570                 575

Met Pro Gln Ile Ser Gly Glu Glu Leu Tyr Ser Ser Asn Val Cys Ser
            580                 585                 590

Pro Ile Ser Gly Met Ile Val Lys Ile Tyr Val Lys Gln Gly Glu Glu
        595                 600                 605

Val Gln Pro Gly Gln Pro Leu Leu Val Ile Glu Ala Met Lys Met Glu
    610                 615                 620

Asn Val Ile Tyr Ser Asp Val Lys Ser Ile Val Lys Ser Val Leu Phe
625                 630                 635                 640

Ser Glu Gly Asn Ser Val Ala Thr Gly Asp Val Ile Ile Glu Phe
                645                 650                 655

<210> SEQ ID NO 52
<211> LENGTH: 510
```

```
<212> TYPE: PRT
<213> ORGANISM: Ehrlichia chaffeensis
<300> PUBLICATION INFORMATION:
<308> DATABASE ACCESSION NUMBER: NCBI / YP_507410
<309> DATABASE ENTRY DATE: 2010-05-14
<313> RELEVANT RESIDUES IN SEQ ID NO: (1)..(510)

<400> SEQUENCE: 52
```

| | | | | | | | | | | | | | | | |
|---|---|---|---|---|---|---|---|---|---|---|---|---|---|---|---|
| Met | Asn | Phe | Ala | Gly | Leu | Gln | Asp | Leu | Asn | Asn | Arg | Gln | Ser | Lys | Ser |
| 1 | | | | 5 | | | | | 10 | | | | | 15 | |
| Tyr | Asn | Gly | Gly | Gly | Leu | Ser | Arg | Ile | Glu | Lys | Gln | His | Leu | Lys | Gly |
| | | | 20 | | | | | 25 | | | | | 30 | | |
| Lys | Leu | Thr | Ala | Arg | Glu | Arg | Leu | Thr | Val | Leu | Leu | Asp | Asp | Asn | Ser |
| | | 35 | | | | | 40 | | | | | 45 | | | |
| Phe | Glu | Glu | Tyr | Gly | Ala | Phe | Val | Glu | His | Arg | Cys | Val | Asn | Phe | Ser |
| | 50 | | | | | 55 | | | | | 60 | | | | |
| Met | Asp | Lys | Ser | Lys | Ile | Pro | Gly | Asp | Gly | Val | Val | Gly | Tyr | Gly |
| 65 | | | | | 70 | | | | | 75 | | | | | 80 |
| Thr | Ile | Asn | Gly | Arg | Lys | Val | Cys | Ile | Tyr | Ser | Gln | Asp | Phe | Thr | Val |
| | | | | 85 | | | | | 90 | | | | | 95 | |
| Phe | Gly | Gly | Ser | Leu | Ser | Glu | Ser | Asn | Ala | Lys | Lys | Ile | Cys | Asn | Ile |
| | | | 100 | | | | | 105 | | | | | 110 | | |
| Met | Asp | Lys | Ala | Ala | Ser | Leu | Gly | Ile | Pro | Ile | Ile | Gly | Ile | Asn | Asp |
| | | 115 | | | | | 120 | | | | | 125 | | | |
| Ser | Gly | Gly | Ala | Arg | Ile | Gln | Glu | Gly | Val | Asp | Ser | Leu | Ser | Gly | Tyr |
| | 130 | | | | | 135 | | | | | 140 | | | | |
| Gly | Glu | Ile | Phe | Gln | Arg | Asn | Val | Asn | Leu | Ser | Gly | Val | Val | Pro | Gln |
| 145 | | | | | 150 | | | | | 155 | | | | | 160 |
| Ile | Ser | Leu | Ile | Met | Gly | Pro | Cys | Ala | Gly | Gly | Ala | Val | Tyr | Ser | Pro |
| | | | | 165 | | | | | 170 | | | | | 175 | |
| Ala | Leu | Thr | Asp | Phe | Ile | Phe | Met | Val | Arg | Asn | Thr | Ser | Tyr | Met | Phe |
| | | | 180 | | | | | 185 | | | | | 190 | | |
| Val | Thr | Gly | Pro | Asp | Val | Ile | Lys | Lys | Val | Thr | Tyr | Glu | Glu | Val | Thr |
| | | 195 | | | | | 200 | | | | | 205 | | | |
| Gln | Glu | Asp | Leu | Gly | Gly | Ala | Lys | Val | His | Ala | Ser | Lys | Thr | Gly | Ile |
| | 210 | | | | | 215 | | | | | 220 | | | | |
| Ala | Asp | Leu | Val | Phe | His | Asn | Glu | Ile | Glu | Ala | Leu | Leu | Gln | Val | Arg |
| 225 | | | | | 230 | | | | | 235 | | | | | 240 |
| Arg | Phe | Met | Asn | Phe | Ile | Pro | Ser | Asn | Asn | Met | Glu | Ser | Ile | Gly | Ser |
| | | | | 245 | | | | | 250 | | | | | 255 | |
| Gln | Ser | Ala | Ser | Asn | Phe | Ile | Asn | Met | Glu | Asp | Leu | Ser | Leu | Asn | Thr |
| | | | 260 | | | | | 265 | | | | | 270 | | |
| Leu | Val | Pro | Lys | Asn | Ser | Thr | Thr | Pro | Tyr | Asn | Met | Tyr | Glu | Leu | Leu |
| | | 275 | | | | | 280 | | | | | 285 | | | |
| Glu | Lys | Val | Cys | Asp | Glu | Arg | Leu | Phe | Tyr | Glu | Ile | Lys | Pro | Asp | Phe |
| | 290 | | | | | 295 | | | | | 300 | | | | |
| Ala | Arg | Asn | Ile | Ile | Ile | Gly | Phe | Gly | Lys | Ile | Gly | Gly | Tyr | Asn | Val |
| 305 | | | | | 310 | | | | | 315 | | | | | 320 |
| Gly | Leu | Val | Ala | Asn | Gln | Pro | Leu | His | Leu | Ala | Gly | Cys | Leu | Asp | Ile |
| | | | | 325 | | | | | 330 | | | | | 335 | |
| Asp | Ala | Ser | Arg | Lys | Gly | Ala | Arg | Phe | Ile | Arg | Phe | Cys | Asp | Ala | Phe |
| | | | 340 | | | | | 345 | | | | | 350 | | |
| Asn | Ile | Pro | Val | Ile | Thr | Phe | Ile | Asp | Val | Pro | Gly | Phe | Met | Pro | Gly |
| | | 355 | | | | | 360 | | | | | 365 | | | |
| Val | Asn | Gln | Glu | His | Ser | Gly | Ile | Ile | Ala | His | Gly | Ala | Lys | Leu | Leu |

```
                   370                 375                 380
Tyr Ala Tyr Ala Glu Ala Thr Val Pro Lys Ile Ser Val Ile Val Arg
385                 390                 395                 400

Lys Ala Tyr Gly Gly Ala Tyr Ile Val Met Asn Ser Lys His Leu Cys
                405                 410                 415

Gly Asp Val Asn Tyr Ala Trp Gln Asp Ala Glu Ile Ala Val Met Gly
                420                 425                 430

Ala Glu Gly Ala Val Glu Ile Ile Phe Arg Asn Glu Lys Asp Lys Asp
                435                 440                 445

Lys Ile Gln His Ile Ile Asp Glu Tyr Arg Thr Thr Ile Val Asn Pro
                450                 455                 460

Tyr Val Ala Ala Ser Arg Gly Tyr Ile Asp Asp Ile Ile Val Pro Ser
465                 470                 475                 480

Arg Thr Arg Glu His Leu Phe Lys Ser Leu Gln Phe Leu Glu Lys Lys
                485                 490                 495

Lys Val His Lys Ile Met Arg Lys His Asp Asn Leu Pro Leu
                500                 505                 510

<210> SEQ ID NO 53
<211> LENGTH: 666
<212> TYPE: PRT
<213> ORGANISM: Agrobacterium vitis
<300> PUBLICATION INFORMATION:
<308> DATABASE ACCESSION NUMBER: NCBI / YP_002547482
<309> DATABASE ENTRY DATE: 2010-04-01
<313> RELEVANT RESIDUES IN SEQ ID NO: (1)..(666)

<400> SEQUENCE: 53

Met Ala Ile Ser Lys Ile Leu Ile Ala Asn Arg Gly Glu Ile Ala Cys
1               5                   10                  15

Arg Val Ile Lys Thr Ala Lys Arg Met Gly Ile Ala Thr Val Ala Val
                20                  25                  30

Tyr Ser Asp Ala Asp Ala Asn Ala Leu His Val Lys Leu Ala Asp Glu
            35                  40                  45

Ala Val His Ile Gly Pro Ser Pro Ser Asn Gln Ser Tyr Ile Val Ile
        50                  55                  60

Asp Lys Ile Leu Glu Ala Ile Arg Gln Thr Gly Ala Asp Ala Val His
65                  70                  75                  80

Pro Gly Tyr Gly Phe Leu Ser Glu Asn Ala Ala Phe Ala Glu Ala Leu
                85                  90                  95

Asp Lys Ala Gly Val Ala Phe Ile Gly Pro Pro Val Gly Ala Ile Lys
            100                 105                 110

Ala Met Gly Asp Lys Ile Thr Ser Lys Lys Leu Ala Ala Glu Ala Gly
        115                 120                 125

Val Ser Thr Val Pro Gly His Met Gly Leu Ile Ala Asp Ala Asp Glu
    130                 135                 140

Ala Val Lys Ile Ala Ala Gln Ile Gly Tyr Pro Val Met Ile Lys Ala
145                 150                 155                 160

Ser Ala Gly Gly Gly Gly Lys Gly Met Arg Ile Ala Trp Asn Asp Ala
                165                 170                 175

Glu Ala Arg Glu Gly Phe Gln Ser Lys Asn Glu Ala Met Asn Ser
            180                 185                 190

Phe Gly Asp Asp Arg Ile Phe Ile Glu Lys Phe Val Asp Gln Pro Arg
        195                 200                 205

His Ile Glu Ile Gln Val Leu Gly Asp Lys His Gly Asn Val Leu Tyr
    210                 215                 220
```

```
Leu Gly Glu Arg Glu Cys Ser Ile Gln Arg Arg Asn Gln Lys Val Ile
225                 230                 235                 240

Glu Glu Ala Pro Ser Pro Phe Leu Asp Ala Asp Thr Arg Lys Ala Met
            245                 250                 255

Gly Glu Gln Ala Val Ala Leu Ala Lys Ala Val Gly Tyr Tyr Ser Ala
        260                 265                 270

Gly Thr Val Glu Phe Ile Val Asp Gly Asn Arg Asn Phe Tyr Phe Leu
    275                 280                 285

Glu Met Asn Thr Arg Leu Gln Val Glu His Pro Val Thr Glu Leu Ile
290                 295                 300

Thr Gly Leu Asp Leu Val Glu Gln Met Ile Arg Val Ala Ser Gly Glu
305                 310                 315                 320

Thr Leu Ala Leu Ala Gln Gly Asp Val Thr Leu Thr Gly Trp Ala Val
            325                 330                 335

Glu Ser Arg Leu Tyr Ala Glu Asp Pro Tyr Arg Asn Phe Leu Pro Ser
        340                 345                 350

Ile Gly Arg Leu Ser Arg Tyr Arg Pro Pro Ser Glu Gly Gln Gln Ala
    355                 360                 365

Asp Gly Thr Val Val Arg Asn Asp Thr Gly Val Phe Glu Gly Gly Glu
370                 375                 380

Ile Ser Met Tyr Tyr Asp Pro Met Val Ala Lys Leu Cys Thr Trp Gly
385                 390                 395                 400

Pro Asp Arg Ile Thr Ala Ile Asp Ala Met Ser Ala Ala Leu Asp Arg
            405                 410                 415

Phe Glu Val Glu Gly Ile Gly His Asn Leu Pro Phe Leu Ser Ala Val
        420                 425                 430

Met Gln His Pro Arg Phe Arg Ser Gly Lys Ile Thr Thr Ala Phe Ile
    435                 440                 445

Ala Glu Glu Phe Pro Glu Gly Phe Ser Gly Val Glu Pro Asp Glu Met
450                 455                 460

Ala Gly Lys Thr Leu Ala Ala Ile Ala Ala Leu Val His Gln Arg Arg
465                 470                 475                 480

Glu Ala Arg Ala Ala Gln Val Ser Gly Thr Met Gly Asn His Ala Arg
            485                 490                 495

Thr Ile Gly Arg Asp Trp Val Gly Leu Ala Glu Gln Asn Tyr Pro
        500                 505                 510

Leu Thr Leu Ser Thr Asp Pro Gly Ser Met Met Phe Ala Asp Gly Asn
    515                 520                 525

Val Leu Ser Val Asp Gly Val Trp Gln Pro Gly Gln Thr Leu Ala Ile
530                 535                 540

Phe Thr Val Asn Gly Gln Ser Ile Gly Leu Lys Ile Asp Leu Lys Gly
545                 550                 555                 560

Pro Ala Ile Arg Leu Arg Trp Arg Gly Met Asp Val Val Ala His Val
            565                 570                 575

Arg Asn Pro Arg Val Ala Glu Leu Ala Arg Leu Met Pro Arg Lys Leu
        580                 585                 590

Pro Pro Asp Thr Ser Lys Met Leu Leu Cys Pro Met Pro Gly Val Val
    595                 600                 605

Thr Gly Ile Ala Val Ala Glu Gly Asp Ala Val Glu Ala Gly Gln Ala
610                 615                 620

Leu Ala Thr Val Glu Ala Met Lys Met Glu Asn Ile Leu Lys Ala Glu
625                 630                 635                 640
```

```
Arg Arg Gly Val Val Lys Arg Leu Val Ala Lys Ala Gly Gln Ser Leu
                    645                 650                 655

Ala Val Asp Glu Leu Ile Met Glu Phe Glu
            660                 665

<210> SEQ ID NO 54
<211> LENGTH: 510
<212> TYPE: PRT
<213> ORGANISM: Agrobacterium vitis
<300> PUBLICATION INFORMATION:
<308> DATABASE ACCESSION NUMBER: NCBI / YP_002547479
<309> DATABASE ENTRY DATE: 2010-04-01
<313> RELEVANT RESIDUES IN SEQ ID NO: (1)..(510)

<400> SEQUENCE: 54

Met Pro Thr Ile Leu Asp Gln Leu Glu Ser Arg Arg Ala Glu Ala Arg
1               5                   10                  15

Leu Gly Gly Gly Glu Lys Arg Ile Asp Ala Gln His Ala Lys Gly Lys
                20                  25                  30

Leu Thr Ala Arg Glu Arg Ile Glu Ile Leu Leu Asp Glu Gly Ser Phe
            35                  40                  45

Glu Glu Tyr Asp Met Tyr Val Thr His Arg Cys Ala Asp Phe Gly Met
50                  55                  60

Asp Gly Gln Lys Val Ala Gly Asp Gly Val Val Thr Gly Trp Gly Thr
65                  70                  75                  80

Ile Asn Gly Arg Gln Val Tyr Val Phe Ser Gln Asp Phe Thr Val Leu
                85                  90                  95

Gly Gly Ser Leu Ser Glu Thr His Ala Gln Lys Ile Cys Lys Ile Met
                100                 105                 110

Asp Met Ala Val Arg Val Gly Ala Pro Val Ile Gly Ile Asn Asp Ser
            115                 120                 125

Gly Gly Ala Arg Ile Gln Glu Gly Val Ala Ser Leu Ala Gly Tyr Ala
        130                 135                 140

Glu Val Phe Arg Arg Asn Ala Glu Val Ser Gly Val Ile Pro Gln Ile
145                 150                 155                 160

Ser Val Ile Met Gly Pro Cys Ala Gly Gly Ala Val Tyr Ser Pro Ala
                165                 170                 175

Met Thr Asp Phe Ile Phe Met Val Arg Asp Thr Ser Tyr Met Phe Val
            180                 185                 190

Thr Gly Pro Asp Val Val Lys Thr Val Thr Asn Glu Ile Val Thr Ala
        195                 200                 205

Glu Glu Leu Gly Gly Ala Gly Thr His Thr Lys Lys Ser Ser Val Ala
    210                 215                 220

Asp Gly Ala Phe Glu Asn Asp Val Glu Ala Leu Glu Gln Val Arg Leu
225                 230                 235                 240

Leu Phe Asp Phe Leu Pro Leu Asn Asn Arg Glu Lys Pro Pro Lys Arg
                245                 250                 255

Pro Phe Tyr Asp Asp Pro Ala Arg Leu Glu Met Arg Leu Asp Thr Leu
            260                 265                 270

Ile Pro Asp Ser Ser Thr Lys Pro Tyr Asp Met Lys Glu Leu Ile His
        275                 280                 285

Ala Leu Ala Asp Glu Gly Asp Phe Phe Glu Leu Gln Glu Ala Phe Ala
    290                 295                 300

Lys Asn Ile Ile Thr Gly Phe Ile Arg Leu Glu Gly Gln Thr Val Gly
305                 310                 315                 320

Val Val Ala Asn Gln Pro Met Val Leu Ala Gly Cys Leu Asp Ile Asp
```

```
                        325                 330                 335
Ser Ser Arg Lys Ala Ala Arg Phe Val Arg Phe Cys Asp Ala Phe Ser
                340                 345                 350

Ile Pro Ile Leu Thr Leu Val Asp Val Pro Gly Phe Leu Pro Gly Val
            355                 360                 365

Ala Gln Glu Tyr Gly Gly Val Ile Lys His Gly Ala Lys Leu Leu Phe
        370                 375                 380

Ala Tyr Ser Glu Ala Thr Val Pro Met Val Thr Leu Ile Thr Arg Lys
385                 390                 395                 400

Ala Tyr Gly Gly Ala Tyr Asp Val Met Ala Ser Lys His Ile Gly Ala
                405                 410                 415

Asp Val Asn Tyr Ala Trp Pro Thr Ala Glu Ile Ala Val Met Gly Ala
            420                 425                 430

Lys Gly Ala Thr Glu Ile Leu Tyr Arg Ser Glu Leu Ala Asp Pro Glu
        435                 440                 445

Lys Ile Ala Ala Arg Thr Arg Glu Tyr Glu Glu Arg Phe Ala Asn Pro
    450                 455                 460

Phe Val Ala Ala Glu Arg Gly Phe Ile Asp Glu Val Ile Met Pro His
465                 470                 475                 480

Ser Ser Arg Lys Arg Ile Ala Arg Ala Phe Ala Ser Leu Arg Gly Lys
                485                 490                 495

Gln Val Ala Thr His Trp Lys Lys His Asp Thr Ile Pro Leu
            500                 505                 510

<210> SEQ ID NO 55
<211> LENGTH: 667
<212> TYPE: PRT
<213> ORGANISM: Methylobacterium extorquens
<300> PUBLICATION INFORMATION:
<308> DATABASE ACCESSION NUMBER: NCBI / YP_003069256
<309> DATABASE ENTRY DATE: 2010-04-16
<313> RELEVANT RESIDUES IN SEQ ID NO: (1)..(667)

<400> SEQUENCE: 55

Met Phe Asp Lys Ile Leu Ile Ala Asn Arg Gly Glu Ile Ala Cys Arg
1               5                   10                  15

Ile Ile Lys Thr Ala Gln Lys Met Gly Ile Lys Thr Val Ala Val Tyr
                20                  25                  30

Ser Asp Ala Asp Arg Asp Ala Val His Val Ala Met Ala Asp Glu Ala
            35                  40                  45

Val Asn Ile Gly Pro Ala Pro Ala Ala Gln Ser Tyr Leu Leu Ile Glu
        50                  55                  60

Lys Ile Ile Asp Ala Cys Lys Gln Thr Gly Ala Gln Ala Val His Pro
65                  70                  75                  80

Gly Tyr Gly Phe Leu Ser Glu Arg Glu Ser Phe Pro Lys Ala Leu Ala
                85                  90                  95

Glu Ala Gly Ile Val Phe Ile Gly Pro Asn Pro Gly Ala Ile Ala Ala
            100                 105                 110

Met Gly Asp Lys Ile Glu Ser Lys Lys Ala Ala Ala Ala Glu Val
        115                 120                 125

Ser Thr Val Pro Gly Phe Leu Gly Val Ile Glu Ser Pro Glu His Ala
    130                 135                 140

Val Thr Ile Ala Asp Glu Ile Gly Tyr Pro Val Met Ile Lys Ala Ser
145                 150                 155                 160

Ala Gly Gly Gly Gly Lys Gly Met Arg Ile Ala Glu Ser Ala Asp Glu
                165                 170                 175
```

-continued

Val Ala Glu Gly Phe Ala Arg Ala Lys Ser Glu Ala Ser Ser Ser Phe
                180                 185                 190

Gly Asp Asp Arg Val Phe Val Glu Lys Phe Ile Thr Asp Pro Arg His
            195                 200                 205

Ile Glu Ile Gln Val Ile Gly Asp Lys His Gly Asn Val Ile Tyr Leu
210                 215                 220

Gly Glu Arg Glu Cys Ser Ile Gln Arg Asn Gln Lys Val Ile Glu
225                 230                 235                 240

Glu Ala Pro Ser Pro Leu Leu Asp Glu Glu Thr Arg Arg Lys Met Gly
                245                 250                 255

Glu Gln Ala Val Ala Leu Ala Lys Ala Val Asn Tyr Asp Ser Ala Gly
            260                 265                 270

Thr Val Glu Phe Val Ala Gly Gln Asp Lys Ser Phe Tyr Phe Leu Glu
        275                 280                 285

Met Asn Thr Arg Leu Gln Val Glu His Pro Val Thr Glu Met Ile Thr
    290                 295                 300

Gly Leu Asp Leu Val Glu Leu Met Ile Arg Val Ala Ala Gly Glu Thr
305                 310                 315                 320

Leu Pro Leu Thr Gln Asp Gln Val Lys Leu Asp Gly Trp Ala Val Glu
                325                 330                 335

Ser Arg Val Tyr Ala Glu Asp Pro Thr Arg Asn Phe Leu Pro Ser Ile
            340                 345                 350

Gly Arg Leu Thr Thr Tyr Gln Pro Pro Glu Glu Gly Pro Leu Gly Gly
        355                 360                 365

Ala Ile Val Arg Asn Asp Thr Gly Val Glu Glu Gly Gly Glu Ile Ala
    370                 375                 380

Ile His Tyr Asp Pro Met Ile Ala Lys Leu Val Thr Trp Ala Pro Thr
385                 390                 395                 400

Arg Leu Glu Ala Ile Asp Ala Gln Ala Thr Ala Leu Asp Ala Phe Ala
                405                 410                 415

Ile Glu Gly Ile Arg His Asn Ile Pro Phe Leu Ala Thr Leu Met Ala
            420                 425                 430

His Pro Arg Trp Arg Asp Gly Arg Leu Ser Thr Gly Phe Ile Lys Glu
        435                 440                 445

Glu Phe Pro Glu Gly Phe Ile Ala Pro Glu Pro Glu Gly Pro Val Ala
    450                 455                 460

His Arg Leu Ala Ala Val Ala Ala Ile Asp His Lys Leu Asn Ile
465                 470                 475                 480

Arg Lys Arg Gly Ile Ser Gly Gln Met Arg Asp Pro Ser Leu Leu Thr
                485                 490                 495

Phe Gln Arg Glu Arg Val Val Val Leu Ser Gly Gln Arg Phe Asn Val
            500                 505                 510

Thr Val Asp Pro Asp Gly Asp Asp Leu Leu Val Thr Phe Asp Asp Gly
        515                 520                 525

Thr Thr Ala Pro Val Arg Ser Ala Trp Arg Pro Gly Ala Pro Val Trp
    530                 535                 540

Ser Gly Thr Val Gly Asp Gln Ser Ile Ala Ile Gln Val Arg Pro Leu
545                 550                 555                 560

Leu Asn Gly Val Phe Leu Gln His Ala Gly Ala Ala Glu Ala Arg
                565                 570                 575

Val Phe Thr Arg Arg Glu Ala Glu Leu Ala Asp Leu Met Pro Val Lys
            580                 585                 590

```
Glu Asn Ala Gly Ser Gly Lys Gln Leu Leu Cys Pro Met Pro Gly Leu
            595                 600                 605

Val Lys Gln Ile Met Val Ser Glu Gly Gln Val Lys Asn Gly Glu
610                 615                 620

Pro Leu Ala Ile Val Glu Ala Met Lys Met Glu Asn Val Leu Arg Ala
625                 630                 635                 640

Glu Arg Asp Gly Thr Ile Ser Lys Ile Ala Ala Lys Glu Gly Asp Ser
                645                 650                 655

Leu Ala Val Asp Ala Val Ile Leu Glu Phe Ala
            660                 665

<210> SEQ ID NO 56
<211> LENGTH: 510
<212> TYPE: PRT
<213> ORGANISM: Methylobacterium extorquens
<300> PUBLICATION INFORMATION:
<308> DATABASE ACCESSION NUMBER: NCBI / YP_003065890
<309> DATABASE ENTRY DATE: 2010-04-16
<313> RELEVANT RESIDUES IN SEQ ID NO: (1)..(510)

<400> SEQUENCE: 56

Met Lys Asp Ile Leu Glu Lys Leu Glu Arg Arg Ala Gln Ala Arg
1               5                   10                  15

Leu Gly Gly Gly Glu Lys Arg Leu Glu Ala Gln His Thr Arg Gly Lys
                20                  25                  30

Leu Thr Ala Arg Glu Arg Ile Glu Leu Leu Asp His Gly Ser Phe
            35                  40                  45

Glu Glu Phe Asp Met Phe Val Gln His Arg Ser Thr Asp Phe Gly Met
50                  55                  60

Glu Lys Gln Lys Ile Pro Gly Asp Val Val Thr Gly Trp Gly Thr
65                  70                  75                  80

Val Asn Gly Arg Thr Val Phe Leu Phe Ser Lys Asp Phe Thr Val Phe
                85                  90                  95

Gly Gly Ser Leu Ser Glu Ala His Ala Ala Lys Ile Val Lys Val Gln
            100                 105                 110

Asp Met Ala Leu Lys Met Arg Ala Pro Ile Ile Gly Ile Phe Asp Ala
            115                 120                 125

Gly Gly Ala Arg Ile Gln Glu Gly Val Ala Ala Leu Gly Gly Tyr Gly
        130                 135                 140

Glu Val Phe Arg Arg Asn Val Ala Ala Ser Gly Val Ile Pro Gln Ile
145                 150                 155                 160

Ser Val Ile Met Gly Pro Cys Ala Gly Gly Asp Val Tyr Ser Pro Ala
                165                 170                 175

Met Thr Asp Phe Ile Phe Met Val Arg Asp Thr Ser Tyr Met Phe Val
            180                 185                 190

Thr Gly Pro Asp Val Val Lys Thr Val Thr Asn Glu Val Val Thr Ala
        195                 200                 205

Glu Glu Leu Gly Gly Ala Lys Val His Thr Ser Lys Ser Ser Ile Ala
210                 215                 220

Asp Gly Ser Phe Glu Asn Asp Val Glu Ala Ile Leu Gln Ile Arg Arg
225                 230                 235                 240

Leu Leu Asp Phe Leu Pro Ala Asn Asn Ile Glu Gly Val Pro Glu Ile
                245                 250                 255

Glu Ser Phe Asp Asp Val Asn Arg Leu Asp Lys Ser Leu Asp Thr Leu
            260                 265                 270

Ile Pro Asp Asn Pro Asn Lys Pro Tyr Asp Met Gly Glu Leu Ile Arg
```

```
                275                 280                 285
Arg Val Val Asp Glu Gly Asp Phe Phe Glu Ile Gln Ala Ala Tyr Ala
290                 295                 300

Arg Asn Ile Ile Thr Gly Phe Gly Arg Val Glu Gly Arg Thr Val Gly
305                 310                 315                 320

Phe Val Ala Asn Gln Pro Leu Val Leu Ala Gly Val Leu Asp Ser Asp
                325                 330                 335

Ala Ser Arg Lys Ala Ala Arg Phe Val Arg Phe Cys Asn Ala Phe Ser
            340                 345                 350

Ile Pro Ile Val Thr Phe Val Asp Val Pro Gly Phe Leu Pro Gly Thr
        355                 360                 365

Ala Gln Glu Tyr Gly Gly Leu Ile Lys His Gly Ala Lys Leu Leu Phe
    370                 375                 380

Ala Tyr Ser Gln Ala Thr Val Pro Leu Val Thr Ile Ile Thr Arg Lys
385                 390                 395                 400

Ala Phe Gly Gly Ala Tyr Asp Val Met Ala Ser Lys His Val Gly Ala
                405                 410                 415

Asp Leu Asn Tyr Ala Trp Pro Thr Ala Gln Ile Ala Val Met Gly Ala
            420                 425                 430

Lys Gly Ala Val Glu Ile Ile Phe Arg Ala Glu Ile Gly Asp Ala Asp
        435                 440                 445

Lys Ile Ala Glu Arg Thr Lys Glu Tyr Glu Asp Arg Phe Leu Ser Pro
    450                 455                 460

Phe Val Ala Ala Glu Arg Gly Tyr Ile Asp Glu Val Ile Met Pro His
465                 470                 475                 480

Ser Thr Arg Lys Arg Ile Ala Arg Ala Leu Gly Met Leu Arg Thr Lys
                485                 490                 495

Glu Met Glu Gln Pro Trp Lys Lys His Asp Asn Ile Pro Leu
            500                 505                 510

<210> SEQ ID NO 57
<211> LENGTH: 670
<212> TYPE: PRT
<213> ORGANISM: Sinorhizobium meliloti
<300> PUBLICATION INFORMATION:
<308> DATABASE ACCESSION NUMBER: NCBI / NP_437988
<309> DATABASE ENTRY DATE: 2010-04-01
<313> RELEVANT RESIDUES IN SEQ ID NO: (1)..(670)

<400> SEQUENCE: 57

Met Gly His Met Phe Lys Lys Ile Leu Ile Ala Asn Arg Gly Glu Ile
1               5                   10                  15

Ala Cys Arg Val Ile Arg Thr Thr Lys Ala Leu Gly Ile Pro Thr Val
            20                  25                  30

Ala Val Tyr Ser Asp Ala Asp Arg Asp Ala Met His Val Arg Met Ala
        35                  40                  45

Asp Glu Ala Val His Ile Gly Pro Ser Pro Ser Ser Gln Ser Tyr Ile
    50                  55                  60

Val Ile Glu Asn Ile Leu Ala Ala Ile Arg Arg Thr Gly Ala Asp Ala
65                  70                  75                  80

Val His Pro Gly Tyr Gly Phe Leu Ser Glu Asn Ala Ala Phe Ala Glu
                85                  90                  95

Ala Leu Glu Lys Asp Gly Val Thr Phe Ile Gly Pro Val Arg Ala
            100                 105                 110

Ile Glu Ala Met Gly Asp Lys Ile Thr Ser Lys Lys Leu Ala Ala Glu
        115                 120                 125
```

-continued

```
Ala Gly Val Phe Thr Val Pro Gly His Met Gly Leu Ile Glu Asp Ala
    130                 135                 140

Asp Glu Ala Ala Arg Ile Ala Ala Glu Ile Gly Phe Pro Val Met Ile
145                 150                 155                 160

Lys Ala Ser Ala Gly Gly Gly Lys Gly Met Arg Ile Ala Trp Asn
                165                 170                 175

Glu Arg Glu Ala Arg Glu Gly Phe Gln Ser Ser Arg Asn Glu Ala Lys
                180                 185                 190

Ser Ser Phe Gly Asp Asp Arg Ile Phe Ile Glu Lys Phe Val Thr Glu
    195                 200                 205

Pro Arg His Ile Glu Ile Gln Val Leu Gly Asp Lys His Gly Asn Ile
    210                 215                 220

Leu Tyr Leu Gly Glu Arg Glu Cys Ser Ile Gln Arg Arg Asn Gln Lys
225                 230                 235                 240

Val Ile Glu Glu Ala Pro Ser Pro Phe Leu Asp Glu Lys Thr Arg Arg
                245                 250                 255

Ala Met Gly Glu Gln Ala Val Ala Leu Ala Lys Ala Val Gly Tyr His
                260                 265                 270

Ser Ala Gly Thr Val Glu Phe Ile Val Asp Ala Gly Arg Asn Phe Tyr
    275                 280                 285

Phe Leu Glu Met Asn Thr Arg Leu Gln Val Glu His Pro Val Thr Glu
    290                 295                 300

Leu Val Thr Gly Leu Asp Leu Val Glu Gln Met Ile Arg Val Ala Ala
305                 310                 315                 320

Gly Ala Lys Leu Ala Phe Ala Gln Lys Asp Val Lys Leu Asp Gly Trp
                325                 330                 335

Ala Ile Glu Ser Arg Leu Tyr Ala Glu Asp Pro Tyr Arg Thr Phe Leu
                340                 345                 350

Pro Ser Ile Gly Arg Leu Thr Arg Tyr Arg Pro Pro Glu Glu Gly Thr
    355                 360                 365

Gln Ala Asp Gly Thr Val Ile Arg Asn Asp Thr Gly Val Phe Glu Gly
    370                 375                 380

Gly Glu Ile Ser Met Tyr Tyr Asp Pro Met Ile Ala Lys Leu Cys Thr
385                 390                 395                 400

Trp Gly Pro Asp Arg Leu Thr Ala Val Arg Ala Met Ala Asp Ala Leu
                405                 410                 415

Asp Ala Phe Glu Val Glu Gly Ile Gly His Asn Leu Pro Phe Leu Ala
                420                 425                 430

Ala Val Met Gln Gln Glu Arg Phe His Glu Gly Arg Leu Thr Thr Ala
    435                 440                 445

Tyr Ile Ala Glu Glu Phe Ala Gly Gly Phe His Gly Val Ala Leu Asp
    450                 455                 460

Asp Ala Ser Ala Arg Lys Leu Ala Ala Val Ala Ala Thr Val Asn Gln
465                 470                 475                 480

Thr Leu Gln Glu Arg Ala Ser Arg Ile Ser Gly Thr Ile Gly Asn His
                485                 490                 495

Arg Arg Val Val Gly His Glu Trp Val Thr Ser Leu Asp Gly His Glu
                500                 505                 510

Ile Gln Val Thr Cys Glu Val Ser Ala Asp Gly Thr Tyr Val Arg Phe
    515                 520                 525

Ala Asp Gly Thr Ser Val Ser Val Ala Thr Asp Trp Ala Pro Gly Arg
    530                 535                 540
```

```
Thr Arg Ala Ala Phe Asn Ile Asp Asn Gln Pro Met Ser Val Lys Val
545                 550                 555                 560

Glu Leu Ala Gly Pro Gly Ile Arg Leu Arg Trp Arg Gly Ile Asp Val
                565                 570                 575

Val Ala Arg Val Arg Ser Pro Arg Ile Ala Glu Leu Ala Arg Leu Met
            580                 585                 590

Pro Lys Lys Leu Pro Pro Asp Thr Ser Lys Met Leu Leu Cys Pro Met
        595                 600                 605

Pro Gly Val Val Thr Ser Ile Thr Val Lys Ala Gly Glu Thr Val Glu
    610                 615                 620

Ala Gly Gln Ala Ile Ala Val Glu Ala Met Lys Met Glu Asn Ile
625                 630                 635                 640

Leu Arg Ala Glu Lys Arg Ala Ile Val Lys Arg Val Ala Ile Glu Ala
                645                 650                 655

Gly Ala Ser Leu Ala Val Asp Glu Leu Ile Met Glu Phe Glu
                660                 665                 670

<210> SEQ ID NO 58
<211> LENGTH: 510
<212> TYPE: PRT
<213> ORGANISM: Sinorhizobium meliloti
<300> PUBLICATION INFORMATION:
<308> DATABASE ACCESSION NUMBER: NCBI / NP_437987
<309> DATABASE ENTRY DATE: 2010-04-01
<313> RELEVANT RESIDUES IN SEQ ID NO: (1)..(510)

<400> SEQUENCE: 58

Met Arg Ala Val Leu Glu Gln Val Glu Ala Arg Arg Ala Glu Ala Arg
1               5                   10                  15

Ala Gly Gly Gly Glu Arg Arg Ile Ala Ala Gln His Gly Lys Gly Lys
            20                  25                  30

Leu Thr Ala Arg Glu Arg Ile Asp Val Leu Leu Asp Glu Gly Ser Phe
        35                  40                  45

Glu Glu Tyr Asp Met Tyr Val Thr His Arg Ser Val Asp Phe Gly Met
50                  55                  60

Ala Gly Gln Lys Ile Pro Gly Asp Gly Val Val Thr Gly Trp Gly Thr
65                  70                  75                  80

Ile Asn Gly Arg Gln Val Tyr Val Phe Ser Gln Asp Phe Thr Val Leu
                85                  90                  95

Gly Gly Ser Leu Ser Glu Thr His Ala Gln Lys Ile Cys Lys Ile Met
            100                 105                 110

Asp Met Ala Ala Arg Asn Gly Ala Pro Val Ile Gly Leu Asn Asp Ser
        115                 120                 125

Gly Gly Ala Arg Ile Gln Glu Gly Val Ala Ser Leu Ala Gly Tyr Ala
    130                 135                 140

Glu Val Phe Arg Arg Asn Ala Glu Val Ser Gly Val Ile Pro Gln Ile
145                 150                 155                 160

Ser Val Ile Met Gly Pro Cys Ala Gly Gly Ala Val Tyr Ser Pro Ala
                165                 170                 175

Met Thr Asp Phe Ile Phe Met Val Arg Asp Ser Ser Tyr Met Phe Val
            180                 185                 190

Thr Gly Pro Asp Val Val Lys Thr Val Thr Asn Glu Ile Val Thr Ala
        195                 200                 205

Glu Glu Leu Gly Gly Ala Arg Thr His Thr Thr Lys Ser Ser Val Ala
    210                 215                 220

Asp Gly Ala Tyr Glu Asn Asp Ile Glu Ala Leu Glu His Val Arg Leu
```

```
                225                 230                 235                 240
Leu Phe Asp Phe Leu Pro Leu Asn Asn Arg Glu Lys Pro Pro Val Arg
                245                 250                 255

Pro Phe His Asp Asp Pro Gly Arg Leu Glu Met Arg Leu Asp Ser Leu
                260                 265                 270

Ile Pro Asp Ser Ala Ala Lys Pro Tyr Asp Met Lys Glu Leu Ile Leu
                275                 280                 285

Ala Ile Ala Asp Glu Ala Asp Phe Phe Glu Leu Gln Ala Ser Phe Ala
                290                 295                 300

Arg Asn Ile Ile Thr Gly Phe Ile Arg Ile Glu Gly Gln Thr Val Gly
305                 310                 315                 320

Val Ile Ala Asn Gln Pro Met Val Leu Ala Gly Cys Leu Asp Ile Asp
                325                 330                 335

Ser Ser Arg Lys Ala Ala Arg Phe Val Arg Phe Cys Asp Ala Phe Ser
                340                 345                 350

Ile Pro Ile Leu Thr Leu Val Asp Val Pro Gly Phe Leu Pro Gly Thr
                355                 360                 365

Ala Gln Glu Tyr Gly Gly Val Ile Lys His Gly Ala Lys Leu Leu Phe
                370                 375                 380

Ala Tyr Ser Gln Ala Thr Val Pro Met Val Thr Leu Ile Thr Arg Lys
385                 390                 395                 400

Ala Tyr Gly Gly Ala Tyr Asp Val Met Ala Ser Lys His Ile Gly Ala
                405                 410                 415

Asp Val Asn Tyr Ala Trp Pro Thr Ala Glu Ile Ala Val Met Gly Ala
                420                 425                 430

Lys Gly Ala Thr Glu Ile Leu Tyr Arg Ser Glu Leu Gly Asp Pro Ala
                435                 440                 445

Lys Ile Ala Ala Arg Thr Lys Glu Tyr Glu Arg Phe Ala Asn Pro
                450                 455                 460

Phe Val Ala Ala Glu Arg Gly Phe Ile Asp Glu Val Ile Met Pro His
465                 470                 475                 480

Ser Ser Arg Arg Arg Ile Ala Arg Ala Phe Ala Ser Leu Arg Asn Lys
                485                 490                 495

Gln Val Glu Thr Arg Trp Arg Lys His Asp Thr Ile Pro Leu
                500                 505                 510

<210> SEQ ID NO 59
<211> LENGTH: 681
<212> TYPE: PRT
<213> ORGANISM: Ruegeria pomeroyi
<300> PUBLICATION INFORMATION:
<308> DATABASE ACCESSION NUMBER: NCBI / YP_166352
<309> DATABASE ENTRY DATE: 2010-06-29
<313> RELEVANT RESIDUES IN SEQ ID NO: (1)..(681)

<400> SEQUENCE: 59

Met Phe Asn Lys Ile Leu Ile Ala Asn Arg Gly Glu Ile Ala Cys Arg
1               5                   10                  15

Val Ile Lys Thr Ala Arg Lys Met Gly Ile Ser Thr Val Ala Ile Tyr
                20                  25                  30

Ser Asp Ala Asp Lys Gln Ala Leu His Val Gln Met Ala Asp Glu Ala
                35                  40                  45

Val His Ile Gly Pro Pro Pro Ala Asn Gln Ser Tyr Ile Val Ile Asp
                50                  55                  60

Lys Val Met Ala Ala Ile Arg Ala Thr Gly Ala Gln Ala Val His Pro
65                  70                  75                  80
```

```
Gly Tyr Gly Phe Leu Ser Glu Asn Ser Lys Phe Ala Glu Ala Leu Glu
                85                  90                  95

Ala Glu Gly Val Ile Phe Val Gly Pro Pro Lys Gly Ala Ile Glu Ala
            100                 105                 110

Met Gly Asp Lys Ile Thr Ser Lys Lys Ile Ala Gln Gly Ala Asn Val
            115                 120                 125

Ser Thr Val Pro Gly Tyr Met Gly Leu Ile Glu Asp Ala Asp Glu Ala
130                 135                 140

Val Lys Ile Ser Asn Gln Ile Gly Tyr Pro Val Met Ile Lys Ala Ser
145                 150                 155                 160

Ala Gly Gly Gly Gly Lys Gly Met Arg Ile Ala Trp Asn Asp Gln Glu
                165                 170                 175

Ala Arg Glu Gly Phe Gln Ser Ser Lys Asn Glu Ala Ala Asn Ser Phe
            180                 185                 190

Gly Asp Asp Arg Ile Phe Ile Glu Lys Phe Val Thr Gln Pro Arg His
            195                 200                 205

Ile Glu Ile Gln Val Leu Cys Asp Ser His Gly Asn Gly Ile Tyr Leu
            210                 215                 220

Gly Glu Arg Glu Cys Ser Ile Gln Arg Arg Asn Gln Lys Val Val Glu
225                 230                 235                 240

Glu Ala Pro Ser Pro Phe Leu Asp Glu Ala Thr Arg Arg Ala Met Gly
                245                 250                 255

Glu Gln Ala Val Ala Leu Ala Lys Ala Val Gly Tyr Ala Ser Ala Gly
            260                 265                 270

Thr Val Glu Phe Ile Val Asp Gly Gln Lys Asn Phe Tyr Phe Leu Glu
            275                 280                 285

Met Asn Thr Arg Leu Gln Val Glu His Pro Val Thr Glu Leu Ile Thr
290                 295                 300

Gly Val Asp Leu Val Glu Gln Met Ile Arg Val Ala Ala Gly Glu Pro
305                 310                 315                 320

Leu Ser Ile Thr Gln Gly Asp Val Lys Leu Thr Gly Trp Ala Ile Glu
                325                 330                 335

Asn Arg Leu Tyr Ala Glu Asp Pro Tyr Arg Gly Phe Leu Pro Ser Ile
            340                 345                 350

Gly Arg Leu Thr Arg Tyr Arg Pro Pro Ala Glu Thr Ala Ala Gly Pro
            355                 360                 365

Leu Leu Val Asn Gly Lys Trp Gln Gly Asp Ala Pro Ser Gly Glu Ala
370                 375                 380

Ala Val Arg Asn Asp Thr Gly Val Tyr Glu Gly Gly Glu Ile Ser Met
385                 390                 395                 400

Tyr Tyr Asp Pro Met Ile Ala Lys Leu Cys Thr Trp Ala Pro Thr Arg
                405                 410                 415

Ala Ala Ala Ile Glu Ala Met Arg Ile Ala Leu Asp Ser Phe Glu Val
            420                 425                 430

Glu Gly Ile Gly His Asn Leu Pro Phe Leu Ser Ala Val Met Asp His
            435                 440                 445

Pro Lys Phe Ile Ser Gly Asp Met Thr Thr Ala Phe Ile Ala Glu Glu
450                 455                 460

Tyr Pro Glu Gly Phe Glu Gly Val Asn Leu Pro Glu Thr Asp Leu Arg
465                 470                 475                 480

Arg Val Ala Ala Ala Ala Ala Met His Arg Val Ala Glu Ile Arg
                485                 490                 495
```

```
Arg Thr Arg Val Ser Gly Arg Met Asp Asn His Glu Arg Val Gly
            500                 505                 510

Thr Glu Trp Val Val Thr Leu Gln Gly Ala Asp Phe Pro Val Thr Ile
        515                 520                 525

Ala Ala Asp His Asp Gly Ser Thr Val Ser Phe Asp Asp Gly Ser Ser
        530                 535                 540

Met Arg Val Thr Ser Asp Trp Thr Pro Gly Asp Gln Leu Ala Asn Leu
545                 550                 555                 560

Met Val Asp Gly Ala Pro Leu Val Leu Lys Val Gly Lys Ile Ser Gly
                565                 570                 575

Gly Phe Arg Ile Arg Thr Arg Gly Ala Asp Leu Lys Val His Val Arg
            580                 585                 590

Thr Pro Arg Gln Ala Glu Leu Ala Arg Leu Met Pro Glu Lys Leu Pro
        595                 600                 605

Pro Asp Thr Ser Lys Met Leu Leu Cys Pro Met Pro Gly Leu Ile Val
        610                 615                 620

Lys Val Asp Val Glu Val Gly Gln Glu Val Gln Glu Gly Gln Ala Leu
625                 630                 635                 640

Cys Thr Ile Glu Ala Met Lys Met Glu Asn Ile Leu Arg Ala Glu Lys
                645                 650                 655

Lys Gly Val Val Ala Lys Ile Asn Ala Ser Ala Gly Asn Ser Leu Ala
                660                 665                 670

Val Asp Asp Val Ile Met Glu Phe Glu
            675                 680

<210> SEQ ID NO 60
<211> LENGTH: 510
<212> TYPE: PRT
<213> ORGANISM: Ruegeria pomeroyi
<300> PUBLICATION INFORMATION:
<308> DATABASE ACCESSION NUMBER: NCBI / YP_166345
<309> DATABASE ENTRY DATE: 2010-06-29
<313> RELEVANT RESIDUES IN SEQ ID NO: (1)..(510)

<400> SEQUENCE: 60

Met Lys Asp Ile Leu Ser Glu Leu Glu Thr Arg Arg Glu Ala Ala Arg
1               5                   10                  15

Leu Gly Gly Gly Gln Lys Arg Ile Asp Ala Gln His Ala Arg Gly Lys
                20                  25                  30

Leu Thr Ala Arg Glu Arg Ile Glu Leu Leu Leu Asp Glu Asp Ser Phe
            35                  40                  45

Glu Glu Phe Asp Met Phe Val Ser His Arg Cys Thr Asp Phe Gly Met
        50                  55                  60

Glu Lys Gln Arg Pro Ala Gly Asp Val Val Thr Gly Trp Gly Thr
65                  70                  75                  80

Ile Asn Gly Arg Met Val Tyr Val Phe Ser Gln Asp Phe Thr Val Phe
                85                  90                  95

Gly Gly Ser Leu Ser Glu Thr His Ala Gln Lys Ile Cys Lys Ile Met
            100                 105                 110

Asp Met Ala Val Gln Asn Gly Ala Pro Val Ile Gly Ile Asn Asp Ser
        115                 120                 125

Gly Gly Ala Arg Ile Gln Glu Gly Val Ala Ser Leu Ala Gly Tyr Ala
    130                 135                 140

Glu Val Phe Gln Arg Asn Ile Met Ala Ser Gly Val Val Pro Gln Ile
145                 150                 155                 160

Ser Val Ile Met Gly Pro Cys Ala Gly Gly Ala Val Tyr Ser Pro Ala
```

```
                      165                 170                 175
Met Thr Asp Phe Ile Phe Met Val Lys Asp Thr Ser Tyr Met Phe Val
                180                 185                 190

Thr Gly Pro Asp Val Val Lys Thr Val Thr Asn Glu Val Val Thr Ala
            195                 200                 205

Glu Glu Leu Gly Gly Ala Ser Thr His Thr Arg Lys Ser Ser Val Ala
        210                 215                 220

Asp Gly Ala Phe Glu Asn Asp Val Glu Ala Leu Ala Glu Val Arg Arg
225                 230                 235                 240

Leu Val Asp Phe Leu Pro Leu Asn Asn Arg Glu Lys Pro Pro Val Arg
                245                 250                 255

Pro Phe Phe Asp Glu Pro Gly Arg Ile Glu Ala Ser Leu Asp Thr Leu
            260                 265                 270

Val Pro Glu Asn Ala Asn Thr Pro Tyr Asp Met Lys Glu Leu Ile Asn
        275                 280                 285

Lys Ile Ala Asp Glu Gly Asp Phe Tyr Glu Ile Gln Glu Asp Phe Ala
290                 295                 300

Lys Asn Ile Ile Thr Gly Phe Ile Arg Leu Glu Gly Gln Thr Val Gly
305                 310                 315                 320

Val Val Ala Asn Gln Pro Met Ile Leu Ala Gly Cys Leu Asp Ile Asp
                325                 330                 335

Ser Ser Arg Lys Ala Ala Arg Phe Val Arg Phe Cys Asp Cys Phe Glu
            340                 345                 350

Ile Pro Ile Leu Thr Leu Val Asp Val Pro Gly Phe Leu Pro Gly Thr
        355                 360                 365

Ser Gln Glu Tyr Gly Gly Val Ile Lys His Gly Ala Lys Leu Leu Phe
370                 375                 380

Ala Tyr Gly Glu Ala Thr Val Pro Lys Val Thr Val Ile Thr Arg Lys
385                 390                 395                 400

Ala Tyr Gly Gly Ala Tyr Asp Val Met Ala Ser Lys His Leu Arg Gly
                405                 410                 415

Asp Phe Asn Tyr Ala Trp Pro Thr Ala Glu Ile Ala Val Met Gly Ala
            420                 425                 430

Lys Gly Ala Thr Glu Ile Ile His Arg Ala Asp Leu Gly Asp Ala Asp
        435                 440                 445

Lys Ile Ala Ala His Thr Lys Asp Tyr Glu Gly Arg Phe Ala Asn Pro
450                 455                 460

Phe Val Ala Ala Glu Arg Gly Phe Ile Asp Glu Val Ile Gln Pro Arg
465                 470                 475                 480

Ser Thr Arg Lys Arg Val Ser Arg Ala Phe Ala Ser Leu Arg Gly Lys
                485                 490                 495

Ser Leu Lys Asn Pro Trp Lys Lys His Asp Asn Ile Pro Leu
            500                 505                 510

<210> SEQ ID NO 61
<211> LENGTH: 678
<212> TYPE: PRT
<213> ORGANISM: Bacillus megaterium
<300> PUBLICATION INFORMATION:
<308> DATABASE ACCESSION NUMBER: NCBI / YP_003564880
<309> DATABASE ENTRY DATE: 2010-12-17
<313> RELEVANT RESIDUES IN SEQ ID NO: (1)..(678)

<400> SEQUENCE: 61

Met Lys Thr Asn Thr Leu Ser Phe His Glu Phe Thr Arg Thr Pro Lys
1               5                   10                  15
```

```
Glu Asp Trp Ala Gln Glu Val Ser Lys Asn Thr Ala Ile Ser Ser Lys
             20                  25                  30

Glu Thr Leu Glu Asn Ile Phe Leu Lys Pro Leu Tyr Phe Glu Ser Asp
         35                  40                  45

Thr Ala His Leu Asp Tyr Leu Gln Gln Ser Pro Ala Gly Ile Asp Tyr
 50                  55                  60

Leu Arg Gly Ala Gly Lys Glu Ser Tyr Ile Leu Gly Glu Trp Glu Ile
 65                  70                  75                  80

Thr Gln Lys Ile Asp Leu Pro Ser Ile Lys Glu Ser Asn Lys Leu Leu
                 85                  90                  95

Leu His Ser Leu Arg Asn Gly Gln Asn Thr Ala Ala Phe Thr Cys Ser
            100                 105                 110

Glu Ala Met Arg Gln Gly Lys Asp Ile Asp Glu Ala Thr Glu Ala Glu
            115                 120                 125

Val Ala Ser Gly Ala Thr Ile Ser Thr Leu Glu Asp Val Ala His Leu
130                 135                 140

Phe Gln His Val Ala Leu Glu Ala Val Pro Leu Phe Leu Asn Thr Gly
145                 150                 155                 160

Cys Thr Ser Val Pro Leu Leu Ser Phe Leu Lys Ala Tyr Cys Val Asp
                165                 170                 175

His Asn Phe Asn Met Arg Gln Leu Lys Gly Thr Val Gly Met Asp Pro
            180                 185                 190

Leu Gly Thr Leu Ala Glu Tyr Gly Arg Val Pro Leu Ser Thr Arg Asp
        195                 200                 205

Leu Tyr Asp His Leu Ala Tyr Ala Thr Arg Leu Ala His Ser Asn Val
210                 215                 220

Pro Glu Leu Lys Thr Ile Ile Val Ser Ser Ile Pro Tyr His Asn Ser
225                 230                 235                 240

Gly Ala Asn Ala Val Gln Glu Leu Ala Tyr Met Leu Ala Thr Gly Val
                245                 250                 255

Gln Tyr Ile Asp Glu Cys Ile Lys Arg Gly Leu Ser Leu His Gln Val
            260                 265                 270

Leu Pro His Met Thr Phe Ser Phe Ser Val Ser Ser His Leu Phe Met
        275                 280                 285

Glu Ile Ser Lys Leu Arg Ala Phe Arg Met Leu Trp Ala Asn Val Val
290                 295                 300

Arg Ala Phe Asp Asp Thr Ala Val Ser Val Pro Phe Ile His Thr Glu
305                 310                 315                 320

Thr Ser His Leu Thr Gln Ser Lys Glu Asp Met Tyr Thr Asn Ala Leu
                325                 330                 335

Arg Ser Thr Val Gln Ala Phe Ala Ser Ile Val Gly Gly Ala Asp Ser
            340                 345                 350

Leu His Ile Glu Pro Tyr Asp Ser Val Thr Ser Ser Ser Gln Phe
        355                 360                 365

Ala His Arg Leu Ala Arg Asn Thr His Leu Ile Leu Gln His Glu Thr
370                 375                 380

His Ile Ser Lys Val Met Asp Pro Ala Gly Gly Ser Trp Tyr Val Glu
385                 390                 395                 400

Ala Tyr Thr His Glu Leu Met Thr Lys Ala Trp Glu Leu Phe Gly Asn
                405                 410                 415

Ile Glu Asp His Gly Gly Met Glu Glu Ala Leu Lys Gln Gly Arg Ile
            420                 425                 430
```

Gln Asp Glu Val Glu Gln Met Lys Val Lys Arg Gln Glu Asp Ile Glu
            435                 440                 445

Cys Arg Ile Glu Arg Leu Ile Gly Val Thr His Tyr Ala Pro Lys Gln
        450                 455                 460

Gln Asp Ala Ser Gln Glu Ile Lys Ser Thr Pro Phe Lys Lys Glu Glu
465                 470                 475                 480

Ile Lys Met Asp Lys Tyr Ser Asp Gln Asn Ala Ser Glu Phe Ser Ser
                485                 490                 495

Asn Leu Ser Leu Glu Asp Tyr Thr Lys Leu Ala Ser Lys Gly Val Thr
            500                 505                 510

Ala Gly Trp Met Leu Lys Gln Met Ala Lys Gln Thr Gln Pro Asp Ser
        515                 520                 525

Val Val Pro Leu Thr Lys Trp Arg Ala Ala Glu Lys Phe Glu Lys Ile
530                 535                 540

Arg Val Tyr Thr Lys Gly Met Ser Ile Gly Ile Met Glu Leu Thr Asp
545                 550                 555                 560

Pro Ser Ser Arg Lys Lys Ala Glu Ile Ala Arg Ser Leu Phe Glu Ser
                565                 570                 575

Ala Gly Phe Ala Cys Glu Thr Ile Lys Asn Ile Asp Ser Tyr Val Glu
            580                 585                 590

Ile Ala Asp Trp Met Asn Glu Gln Lys His Glu Ala Tyr Val Ile Cys
        595                 600                 605

Gly Ser Asp Glu Leu Val Glu Lys Leu Leu Thr Lys Ala Met Thr Tyr
        610                 615                 620

Phe Glu Glu Asp Ser Val Tyr Val Tyr Val Val Gly Glu Glu His Val
625                 630                 635                 640

Ser Arg Lys Thr Gln Trp Gln Gln Lys Gly Val Met Ser Val Ile His
                645                 650                 655

Pro Lys Thr Asn Val Ile Gln Cys Val Lys Lys Leu Leu Cys Ala Leu
            660                 665                 670

Glu Val Glu Val His Val
        675

<210> SEQ ID NO 62
<211> LENGTH: 716
<212> TYPE: PRT
<213> ORGANISM: Bacillus megaterium
<300> PUBLICATION INFORMATION:
<308> DATABASE ACCESSION NUMBER: NCBI - YP_003564879
<309> DATABASE ENTRY DATE: 2010-12-17
<313> RELEVANT RESIDUES IN SEQ ID NO: (1)..(716)

<400> SEQUENCE: 62

Met Tyr Lys Lys Pro Ser Phe Ser Asn Ile Pro Leu Ser Phe Ser Lys
1               5                   10                  15

Gln Gln Arg Glu Asp Asp Val Thr Gln Ser Ser Tyr Thr Ala Phe Gln
            20                  25                  30

Thr Asn Glu Gln Ile Glu Leu Lys Ser Val Tyr Thr Lys Lys Asp Arg
        35                  40                  45

Asp Asn Leu Asp Phe Ile His Phe Ala Pro Gly Val Pro Pro Phe Val
50                  55                  60

Arg Gly Pro Tyr Ala Thr Met Tyr Val Asn Arg Pro Trp Thr Ile Arg
65                  70                  75                  80

Gln Tyr Ala Gly Tyr Ser Thr Ala Glu Glu Ser Asn Ala Phe Tyr Arg
                85                  90                  95

Arg Asn Leu Ala Ala Gly Gln Lys Gly Leu Ser Val Ala Phe Asp Leu

```
            100                 105                 110
Ala Thr His Arg Gly Tyr Asp Ser Asp His Pro Arg Val Val Gly Asp
            115                 120                 125

Val Gly Lys Ala Gly Val Ala Ile Asp Ser Met Met Asp Met Lys Gln
            130                 135                 140

Leu Phe Glu Gly Ile Pro Leu Asp Gln Met Ser Val Ser Met Thr Met
145                 150                 155                 160

Asn Gly Ala Val Leu Pro Ile Leu Ala Phe Tyr Ile Val Thr Ala Glu
                165                 170                 175

Glu Gln Gly Val Lys Lys Glu Lys Leu Ala Gly Thr Ile Gln Asn Asp
            180                 185                 190

Ile Leu Lys Glu Tyr Met Val Arg Asn Thr Tyr Ile Tyr Pro Pro Glu
            195                 200                 205

Met Ser Met Arg Ile Ile Ala Asp Ile Phe Lys Tyr Thr Ala Glu Tyr
            210                 215                 220

Met Pro Lys Phe Asn Ser Ile Ser Ile Ser Gly Tyr His Met Gln Glu
225                 230                 235                 240

Ala Gly Ala Pro Ala Asp Leu Glu Leu Ala Tyr Thr Leu Ala Asp Gly
                245                 250                 255

Leu Glu Tyr Val Arg Thr Gly Leu Lys Ala Gly Ile Thr Ile Asp Ala
            260                 265                 270

Phe Ala Pro Arg Leu Ser Phe Phe Trp Ala Ile Gly Met Asn Tyr Phe
            275                 280                 285

Met Glu Val Ala Lys Met Arg Ala Gly Arg Leu Leu Trp Ala Lys Leu
            290                 295                 300

Met Lys Gln Phe Glu Pro Asp Asn Pro Lys Ser Leu Ala Leu Arg Thr
305                 310                 315                 320

His Ser Gln Thr Ser Gly Trp Ser Leu Thr Glu Gln Asp Pro Phe Asn
                325                 330                 335

Asn Val Ile Arg Thr Cys Val Glu Ala Leu Ala Ala Val Ser Gly His
            340                 345                 350

Thr Gln Ser Leu His Thr Asn Ala Leu Asp Glu Ala Ile Ala Leu Pro
            355                 360                 365

Thr Asp Phe Ser Ala Arg Ile Ala Arg Asn Thr Gln Leu Tyr Leu Gln
            370                 375                 380

Asn Glu Thr Glu Ile Cys Ser Val Ile Asp Pro Trp Gly Gly Ser Tyr
385                 390                 395                 400

Tyr Val Glu Ser Leu Thr Asn Glu Leu Met Ile Lys Ala Trp Lys His
                405                 410                 415

Leu Glu Glu Ile Glu Gln Leu Gly Gly Met Thr Lys Ala Ile Glu Ala
            420                 425                 430

Gly Val Pro Lys Met Lys Ile Glu Ala Ala Ala Arg Arg Gln Ala
            435                 440                 445

Arg Ile Asp Ser Gln Ala Glu Ile Ile Val Gly Val Asn Gln Phe Gln
450                 455                 460

Pro Glu Gln Glu Glu Pro Leu Asp Ile Leu Asp Ile Asp Asn Thr Ala
465                 470                 475                 480

Val Arg Met Lys Gln Leu Glu Lys Leu Lys Ile Arg Ser Glu Arg
                485                 490                 495

Asn Glu Gln Ala Val Ile Glu Ala Leu Asn Arg Leu Thr Asn Cys Ala
            500                 505                 510

Lys Thr Gly Glu Gly Asn Leu Leu Ala Phe Ala Val Glu Ala Ala Arg
            515                 520                 525
```

```
Ala Arg Ala Thr Leu Gly Glu Ile Ser Glu Ala Ile Glu Lys Val Ala
            530                 535                 540

Gly Arg His Gln Ala Thr Ser Lys Ser Val Ser Gly Val Tyr Ser Ala
545                 550                 555                 560

Glu Phe Val His Arg Asp Gln Ile Glu Glu Val Arg Lys Leu Thr Ala
                565                 570                 575

Glu Phe Leu Glu Gly Glu Gly Arg Arg Pro Arg Ile Leu Val Ala Lys
                580                 585                 590

Met Gly Gln Asp Gly His Asp Arg Gly Ser Lys Val Ile Ser Thr Ala
                595                 600                 605

Phe Ala Asp Leu Gly Phe Asp Val Asp Ile Gly Pro Leu Phe Gln Thr
                610                 615                 620

Pro Gln Glu Thr Ala Arg Gln Ala Val Glu Asn Asp Val His Val Ile
625                 630                 635                 640

Gly Ile Ser Ser Leu Ala Ala Gly His Lys Thr Leu Leu Pro Gln Leu
                645                 650                 655

Val Asp Glu Leu Lys Lys Leu Glu Arg Asp Asp Ile Val Ile Val
                660                 665                 670

Gly Gly Val Ile Pro Lys Gln Asp Tyr Ser Phe Leu Leu Glu His Gly
                675                 680                 685

Ala Ser Ala Ile Phe Gly Pro Gly Thr Val Ile Pro Lys Ala Ala Val
                690                 695                 700

Ser Val Leu His Glu Ile Lys Lys Arg Leu Glu Glu
705                 710                 715

<210> SEQ ID NO 63
<211> LENGTH: 615
<212> TYPE: PRT
<213> ORGANISM: Mycobacterium tuberculosis
<300> PUBLICATION INFORMATION:
<308> DATABASE ACCESSION NUMBER: NCBI / YP_001282809
<309> DATABASE ENTRY DATE: 2010-05-13
<313> RELEVANT RESIDUES IN SEQ ID NO: (1)..(615)

<400> SEQUENCE: 63

Met Ser Ile Asp Val Pro Glu Arg Ala Asp Leu Glu Gln Val Arg Gly
1                   5                   10                  15

Arg Trp Arg Asn Ala Val Ala Gly Val Leu Ser Lys Ser Asn Arg Thr
                20                  25                  30

Asp Ser Ala Gln Leu Gly Asp His Pro Glu Arg Leu Leu Asp Thr Gln
            35                  40                  45

Thr Ala Asp Gly Phe Ala Ile Arg Ala Leu Tyr Thr Ala Phe Asp Glu
        50                  55                  60

Leu Pro Glu Pro Pro Leu Pro Gly Gln Trp Pro Phe Val Arg Gly Gly
65                  70                  75                  80

Asp Pro Leu Arg Asp Val His Ser Gly Trp Lys Val Ala Glu Ala Phe
                85                  90                  95

Pro Ala Asn Gly Ala Thr Ala Asp Thr Asn Ala Ala Val Leu Ala Ala
                100                 105                 110

Leu Gly Glu Gly Val Ser Ala Leu Leu Ile Arg Val Gly Glu Ser Gly
            115                 120                 125

Val Ala Pro Asp Arg Leu Thr Ala Leu Leu Ser Gly Val Tyr Leu Asn
        130                 135                 140

Leu Ala Pro Val Ile Leu Asp Ala Gly Ala Asp Tyr Arg Pro Ala Cys
145                 150                 155                 160
```

```
Asp Val Met Leu Ala Leu Val Ala Gln Leu Asp Pro Gly Gln Arg Asp
            165                 170                 175

Thr Leu Ser Ile Asp Leu Gly Ala Asp Pro Leu Thr Ala Ser Leu Arg
            180                 185                 190

Asp Arg Pro Ala Pro Pro Ile Glu Glu Val Val Ala Val Ala Ser Arg
            195                 200                 205

Ala Ala Gly Glu Arg Gly Leu Arg Ala Ile Thr Val Asp Gly Pro Ala
            210                 215                 220

Phe His Asn Leu Gly Ala Thr Ala Ala Thr Glu Leu Ala Ala Thr Val
225                 230                 235                 240

Ala Ala Ala Val Ala Tyr Leu Arg Val Leu Thr Glu Ser Gly Leu Val
                245                 250                 255

Val Ser Asp Ala Leu Arg Gln Ile Ser Phe Arg Leu Ala Ala Asp Asp
            260                 265                 270

Asp Gln Phe Met Thr Leu Ala Lys Met Arg Ala Leu Arg Gln Leu Trp
        275                 280                 285

Ala Arg Val Ala Glu Val Val Gly Asp Pro Gly Gly Gly Ala Ala Val
        290                 295                 300

Val His Ala Glu Thr Ser Leu Pro Met Met Thr Gln Arg Asp Pro Trp
305                 310                 315                 320

Val Asn Met Leu Arg Cys Thr Leu Ala Ala Phe Gly Ala Gly Val Gly
                325                 330                 335

Gly Ala Asp Thr Val Leu Val His Pro Phe Asp Val Ala Ile Pro Gly
            340                 345                 350

Gly Phe Pro Gly Thr Ala Ala Gly Phe Ala Arg Arg Ile Ala Arg Asn
        355                 360                 365

Thr Gln Leu Leu Leu Leu Glu Glu Ser His Val Gly Arg Val Leu Asp
        370                 375                 380

Pro Ala Gly Gly Ser Trp Phe Val Glu Glu Leu Thr Asp Arg Leu Ala
385                 390                 395                 400

Arg Arg Ala Trp Gln Arg Phe Gln Ala Ile Glu Ala Arg Gly Gly Phe
                405                 410                 415

Val Glu Ala His Asp Phe Leu Ala Gly Gln Ile Ala Glu Cys Ala Ala
            420                 425                 430

Arg Arg Ala Asp Asp Ile Ala His Arg Arg Leu Ala Ile Thr Gly Val
        435                 440                 445

Asn Glu Tyr Pro Asn Leu Gly Glu Pro Ala Leu Pro Pro Gly Asp Pro
        450                 455                 460

Thr Ser Pro Val Arg Arg Tyr Ala Ala Gly Phe Glu Ala Leu Arg Asp
465                 470                 475                 480

Arg Ser Asp His His Leu Ala Arg Thr Gly Ala Arg Pro Arg Val Leu
                485                 490                 495

Leu Leu Pro Leu Gly Pro Leu Ala Glu His Asn Ile Arg Thr Thr Phe
            500                 505                 510

Ala Thr Asn Leu Leu Ala Ser Gly Gly Ile Glu Ala Ile Asp Pro Gly
        515                 520                 525

Thr Val Asp Ala Gly Thr Val Gly Asn Ala Val Ala Asp Ala Gly Ser
        530                 535                 540

Pro Ser Val Ala Val Ile Cys Gly Thr Asp Ala Arg Tyr Arg Asp Glu
545                 550                 555                 560

Val Ala Asp Ile Val Gln Ala Ala Arg Ala Gly Val Ser Arg Val
                565                 570                 575

Tyr Leu Ala Gly Pro Glu Lys Ala Leu Gly Asp Ala Ala His Arg Pro
```

-continued

```
                580             585             590
Asp Glu Phe Leu Thr Ala Lys Ile Asn Val Val Gln Ala Leu Ser Asn
                    595                 600                 605

Leu Leu Thr Arg Leu Gly Ala
            610             615

<210> SEQ ID NO 64
<211> LENGTH: 750
<212> TYPE: PRT
<213> ORGANISM: Mycobacterium tuberculosis
<300> PUBLICATION INFORMATION:
<308> DATABASE ACCESSION NUMBER: NCBI / YP_001282810
<309> DATABASE ENTRY DATE: 2010-05-13
<313> RELEVANT RESIDUES IN SEQ ID NO: (1)..(750)

<400> SEQUENCE: 64

Met Thr Thr Lys Thr Pro Val Ile Gly Ser Phe Ala Gly Val Pro Leu
1               5                   10                  15

His Ser Glu Arg Ala Ala Gln Ser Pro Thr Glu Ala Ala Val His Thr
            20                  25                  30

His Val Ala Ala Ala Ala Ala His Gly Tyr Thr Pro Glu Gln Leu
        35                  40                  45

Val Trp His Thr Pro Glu Gly Ile Asp Val Thr Pro Val Tyr Ile Ala
    50                  55                  60

Ala Asp Arg Ala Ala Glu Ala Glu Gly Tyr Pro Leu His Ser Phe
65                  70                  75                  80

Pro Gly Glu Pro Pro Phe Val Arg Gly Pro Tyr Pro Thr Met Tyr Val
                85                  90                  95

Asn Gln Pro Trp Thr Ile Arg Gln Tyr Ala Gly Phe Ser Thr Ala Ala
            100                 105                 110

Asp Ser Asn Ala Phe Tyr Arg Arg Asn Leu Ala Ala Gly Gln Lys Gly
        115                 120                 125

Leu Ser Val Ala Phe Asp Leu Ala Thr His Arg Gly Tyr Asp Ser Asp
130                 135                 140

His Pro Arg Val Gln Gly Asp Val Gly Met Ala Gly Val Ala Ile Asp
145                 150                 155                 160

Ser Ile Leu Asp Met Arg Gln Leu Phe Asp Gly Ile Asp Leu Ser Thr
                165                 170                 175

Val Ser Val Ser Met Thr Met Asn Gly Ala Val Leu Pro Ile Leu Ala
            180                 185                 190

Leu Tyr Val Val Ala Glu Glu Gln Gly Val Ala Pro Glu Gln Leu
        195                 200                 205

Ala Gly Thr Ile Gln Asn Asp Ile Leu Lys Glu Phe Met Val Arg Asn
    210                 215                 220

Thr Tyr Ile Tyr Pro Pro Lys Pro Ser Met Arg Ile Ile Ser Asp Ile
225                 230                 235                 240

Phe Ala Tyr Thr Ser Ala Lys Met Pro Lys Phe Asn Ser Ile Ser Ile
                245                 250                 255

Ser Gly Tyr His Ile Gln Glu Ala Gly Ala Thr Ala Asp Leu Glu Leu
            260                 265                 270

Ala Tyr Thr Leu Ala Asp Gly Val Asp Tyr Ile Arg Ala Gly Leu Asn
        275                 280                 285

Ala Gly Leu Asp Ile Asp Ser Phe Ala Pro Arg Leu Ser Phe Phe Trp
    290                 295                 300

Gly Ile Gly Met Asn Phe Phe Met Glu Val Ala Lys Leu Arg Ala Gly
305                 310                 315                 320
```

```
Arg Leu Leu Trp Ser Glu Leu Val Ala Gln Phe Ala Pro Lys Ser Ala
            325                 330                 335
Lys Ser Leu Ser Leu Arg Thr His Ser Gln Thr Ser Gly Trp Ser Leu
        340                 345                 350
Thr Ala Gln Asp Val Phe Asn Asn Val Ala Arg Thr Cys Ile Glu Ala
    355                 360                 365
Met Ala Ala Thr Gln Gly His Thr Gln Ser Leu His Thr Asn Ala Leu
370                 375                 380
Asp Glu Ala Leu Ala Leu Pro Thr Asp Phe Ser Ala Arg Ile Ala Arg
385                 390                 395                 400
Asn Thr Gln Leu Val Leu Gln Gln Glu Ser Gly Thr Thr Arg Pro Ile
                405                 410                 415
Asp Pro Trp Gly Gly Ser Tyr Tyr Val Glu Trp Leu Thr His Arg Leu
            420                 425                 430
Ala Arg Arg Ala Arg Ala His Ile Ala Glu Val Ala Glu His Gly Gly
        435                 440                 445
Met Ala Gln Ala Ile Ser Asp Gly Ile Pro Lys Leu Arg Ile Glu Glu
    450                 455                 460
Ala Ala Ala Arg Thr Gln Ala Arg Ile Asp Ser Gly Gln Gln Pro Val
465                 470                 475                 480
Val Gly Val Asn Lys Tyr Gln Val Pro Glu Asp His Glu Ile Glu Val
                485                 490                 495
Leu Lys Val Glu Asn Ser Arg Val Arg Ala Glu Gln Leu Ala Lys Leu
            500                 505                 510
Gln Arg Leu Arg Ala Gly Arg Asp Glu Pro Ala Val Arg Ala Ala Leu
        515                 520                 525
Ala Glu Leu Thr Arg Ala Ala Glu Gln Gly Arg Ala Gly Ala Asp
    530                 535                 540
Gly Leu Gly Asn Asn Leu Leu Ala Leu Ala Ile Asp Ala Ala Arg Ala
545                 550                 555                 560
Gln Ala Thr Val Gly Glu Ile Ser Glu Ala Leu Glu Lys Val Tyr Gly
                565                 570                 575
Arg His Arg Ala Glu Ile Arg Thr Ile Ser Gly Val Tyr Arg Asp Glu
            580                 585                 590
Val Gly Lys Ala Pro Asn Ile Ala Ala Ala Thr Glu Leu Val Glu Lys
        595                 600                 605
Phe Ala Glu Ala Asp Gly Arg Arg Pro Arg Ile Leu Ile Ala Lys Met
    610                 615                 620
Gly Gln Asp Gly His Asp Arg Gly Gln Lys Val Ile Ala Thr Ala Phe
625                 630                 635                 640
Ala Asp Ile Gly Phe Asp Val Asp Val Gly Ser Leu Phe Ser Thr Pro
                645                 650                 655
Glu Glu Val Ala Arg Gln Ala Ala Asp Asn Asp Val His Val Ile Gly
            660                 665                 670
Val Ser Ser Leu Ala Ala Gly His Leu Thr Leu Val Pro Ala Leu Arg
        675                 680                 685
Asp Ala Leu Ala Gln Val Gly Arg Pro Asp Ile Met Ile Val Val Gly
    690                 695                 700
Gly Val Ile Pro Pro Gly Asp Phe Asp Glu Leu Tyr Ala Ala Gly Ala
705                 710                 715                 720
Thr Ala Ile Phe Pro Pro Gly Thr Val Ile Ala Asp Ala Ala Ile Asp
                725                 730                 735
```

```
Leu Leu His Arg Leu Ala Glu Arg Leu Gly Tyr Thr Leu Asp
        740                 745                 750
```

<210> SEQ ID NO 65
<211> LENGTH: 616
<212> TYPE: PRT
<213> ORGANISM: Corynebacterium glutamicum
<300> PUBLICATION INFORMATION:
<308> DATABASE ACCESSION NUMBER: NCBI / YP_225814
<309> DATABASE ENTRY DATE: 2010-12-14
<313> RELEVANT RESIDUES IN SEQ ID NO: (1)..(616)

<400> SEQUENCE: 65

```
Met Thr Asp Leu Thr Lys Thr Ala Val Pro Glu Glu Leu Ser Glu Asn
1               5                   10                  15

Leu Glu Thr Trp Tyr Lys Ala Val Ala Gly Val Phe Ala Arg Thr Gln
            20                  25                  30

Lys Lys Asp Ile Gly Asp Ile Ala Val Asp Val Trp Lys Lys Leu Ile
        35                  40                  45

Val Thr Thr Pro Asp Gly Val Asp Ile Asn Pro Leu Tyr Thr Arg Ala
    50                  55                  60

Asp Glu Ser Gln Arg Lys Phe Thr Glu Val Pro Gly Glu Phe Pro Phe
65                  70                  75                  80

Thr Arg Gly Thr Thr Val Asp Gly Glu Arg Val Gly Trp Gly Val Thr
                85                  90                  95

Glu Thr Phe Gly His Asp Ser Pro Lys Asn Ile Asn Ala Ala Val Leu
            100                 105                 110

Asn Ala Leu Asn Ser Gly Thr Thr Thr Leu Gly Phe Glu Phe Ser Glu
        115                 120                 125

Glu Phe Thr Ala Ala Asp Leu Lys Val Ala Leu Glu Gly Val Tyr Leu
    130                 135                 140

Asn Met Ala Pro Leu Leu Ile His Ala Gly Gly Ser Thr Ser Glu Val
145                 150                 155                 160

Ala Ala Ala Leu Tyr Thr Leu Ala Glu Glu Ala Gly Thr Phe Phe Ala
                165                 170                 175

Ala Leu Thr Leu Gly Ser Arg Pro Leu Thr Ala Gln Val Asp Gly Ser
            180                 185                 190

His Ser Asp Thr Ile Glu Glu Ala Val Gln Leu Ala Val Asn Ala Ser
        195                 200                 205

Lys Arg Ala Asn Val Arg Ala Ile Leu Val Asp Gly Ser Ser Phe Ser
    210                 215                 220

Asn Gln Gly Ala Ser Asp Ala Gln Glu Ile Gly Leu Ser Ile Ala Ala
225                 230                 235                 240

Gly Val Asp Tyr Val Arg Arg Leu Val Asp Ala Gly Leu Ser Thr Glu
                245                 250                 255

Ala Ala Leu Lys Gln Val Ala Phe Arg Phe Ala Val Thr Asp Glu Gln
            260                 265                 270

Phe Ala Gln Ile Ser Lys Leu Arg Val Ala Arg Arg Leu Trp Ala Arg
        275                 280                 285

Val Cys Glu Val Leu Gly Phe Pro Glu Leu Ala Val Ala Pro Gln His
    290                 295                 300

Ala Val Thr Ala Arg Ala Met Phe Ser Gln Arg Asp Pro Trp Val Asn
305                 310                 315                 320

Met Leu Arg Ser Thr Val Ala Ala Phe Ala Ala Gly Val Gly Gly Ala
                325                 330                 335

Thr Asp Val Glu Val Arg Thr Phe Asp Asp Ala Ile Pro Asp Gly Val
```

```
                    340                 345                 350
Pro Gly Val Ser Arg Asn Phe Ala His Arg Ile Ala Arg Asn Thr Asn
            355                 360                 365
Leu Leu Leu Leu Glu Glu Ser His Leu Gly His Val Val Asp Pro Ala
        370                 375                 380
Gly Gly Ser Tyr Phe Val Glu Ser Phe Thr Asp Asp Leu Ala Glu Lys
385                 390                 395                 400
Ala Trp Ala Val Phe Ser Gly Ile Glu Ala Glu Gly Tyr Ser Ala
                405                 410                 415
Ala Cys Ala Ser Gly Thr Val Thr Ala Met Leu Asp Gln Thr Trp Glu
            420                 425                 430
Gln Thr Arg Ala Asp Val Ala Ser Arg Lys Lys Leu Thr Gly Ile
        435                 440                 445
Asn Glu Phe Pro Asn Leu Ala Glu Ser Pro Leu Pro Ala Asp Arg Arg
    450                 455                 460
Val Glu Pro Ala Gly Val Arg Arg Trp Ala Ala Asp Phe Glu Ala Leu
465                 470                 475                 480
Arg Asn Arg Ser Asp Ala Phe Leu Glu Lys Asn Gly Ala Arg Pro Gln
                485                 490                 495
Ile Thr Met Ile Pro Leu Gly Pro Leu Ser Lys His Asn Ile Arg Thr
            500                 505                 510
Gly Phe Thr Ser Asn Leu Leu Ala Ser Gly Gly Ile Glu Ala Ile Asn
        515                 520                 525
Pro Gly Gln Leu Val Pro Gly Thr Asp Ala Phe Ala Glu Ala Ala Gln
    530                 535                 540
Ala Ala Gly Ile Val Val Val Cys Gly Thr Asp Gln Glu Tyr Ala Glu
545                 550                 555                 560
Thr Gly Glu Gly Ala Val Glu Lys Leu Arg Glu Ala Gly Val Glu Arg
                565                 570                 575
Ile Leu Leu Ala Gly Ala Pro Lys Ser Phe Glu Gly Ser Ala His Ala
            580                 585                 590
Pro Asp Gly Tyr Leu Asn Met Thr Ile Asp Ala Ala Thr Leu Ala
        595                 600                 605
Asp Leu Leu Asp Ala Leu Gly Ala
    610                 615
```

<210> SEQ ID NO 66
<211> LENGTH: 737
<212> TYPE: PRT
<213> ORGANISM: Corynebacterium glutamicum
<300> PUBLICATION INFORMATION:
<308> DATABASE ACCESSION NUMBER: NCBI / YP_225813
<309> DATABASE ENTRY DATE: 2010-12-14
<313> RELEVANT RESIDUES IN SEQ ID NO: (1)..(737)

<400> SEQUENCE: 66

```
Met Thr Ser Ile Pro Asn Phe Ser Asp Ile Pro Leu Thr Ala Glu Thr
1               5                   10                  15
Arg Ala Ser Glu Ser His Asn Val Asp Ala Gly Lys Val Trp Asn Thr
            20                  25                  30
Pro Glu Gly Ile Asp Val Lys Arg Val Phe Thr Gln Ala Asp Arg Asp
        35                  40                  45
Glu Ala Gln Ala Ala Gly His Pro Val Asp Ser Leu Pro Gly Gln Lys
    50                  55                  60
Pro Phe Met Arg Gly Pro Tyr Pro Thr Met Tyr Thr Asn Gln Pro Trp
65                  70                  75                  80
```

```
Thr Ile Arg Gln Tyr Ala Gly Phe Ser Thr Ala Ala Glu Ser Asn Ala
                85                  90                  95
Phe Tyr Arg Arg Asn Leu Ala Ala Gly Gln Lys Gly Leu Ser Val Ala
            100                 105                 110
Phe Asp Leu Ala Thr His Arg Gly Tyr Asp Ser Asp Asn Glu Arg Val
        115                 120                 125
Val Gly Asp Val Gly Met Ala Gly Val Ala Ile Asp Ser Ile Leu Asp
    130                 135                 140
Met Arg Gln Leu Phe Asp Gly Ile Asp Leu Ser Ser Val Ser Val Ser
145                 150                 155                 160
Met Thr Met Asn Gly Ala Val Leu Pro Ile Leu Ala Phe Tyr Ile Val
                165                 170                 175
Ala Ala Glu Glu Gln Gly Val Gly Pro Glu Gln Leu Ala Gly Thr Ile
            180                 185                 190
Gln Asn Asp Ile Leu Lys Glu Phe Met Val Arg Asn Thr Tyr Ile Tyr
        195                 200                 205
Pro Pro Lys Pro Ser Met Arg Ile Ile Ser Asn Ile Phe Glu Tyr Thr
    210                 215                 220
Ser Leu Lys Met Pro Arg Phe Asn Ser Ile Ser Ile Ser Gly Tyr His
225                 230                 235                 240
Ile Gln Glu Ala Gly Ala Thr Ala Asp Leu Glu Leu Ala Tyr Thr Leu
                245                 250                 255
Ala Asp Gly Ile Glu Tyr Ile Arg Ala Gly Lys Glu Val Gly Leu Asp
            260                 265                 270
Val Asp Lys Phe Ala Pro Arg Leu Ser Phe Phe Trp Gly Ile Ser Met
        275                 280                 285
Tyr Thr Phe Met Glu Ile Ala Lys Leu Arg Ala Gly Arg Leu Leu Trp
    290                 295                 300
Ser Glu Leu Val Ala Lys Phe Asp Pro Lys Asn Ala Lys Ser Gln Ser
305                 310                 315                 320
Leu Arg Thr His Ser Gln Thr Ser Gly Trp Ser Leu Thr Ala Gln Asp
                325                 330                 335
Val Tyr Asn Asn Val Ala Arg Thr Ala Ile Glu Ala Met Ala Ala Thr
            340                 345                 350
Gln Gly His Thr Gln Ser Leu His Thr Asn Ala Leu Asp Glu Ala Leu
        355                 360                 365
Ala Leu Pro Thr Asp Phe Ser Ala Arg Ile Ala Arg Asn Thr Gln Leu
    370                 375                 380
Leu Leu Gln Gln Glu Ser Gly Thr Val Arg Pro Val Asp Pro Trp Ala
385                 390                 395                 400
Gly Ser Tyr Tyr Val Glu Trp Leu Thr Asn Glu Leu Ala Asn Arg Ala
                405                 410                 415
Arg Lys His Ile Asp Glu Val Glu Ala Gly Gly Met Ala Gln Ala
            420                 425                 430
Thr Ala Gln Gly Ile Pro Lys Leu Arg Ile Glu Glu Ser Ala Ala Arg
        435                 440                 445
Thr Gln Ala Arg Ile Asp Ser Gly Arg Gln Ala Leu Ile Gly Val Asn
    450                 455                 460
Arg Tyr Val Ala Glu Glu Asp Glu Glu Ile Glu Val Leu Lys Val Asp
465                 470                 475                 480
Asn Thr Lys Val Arg Ala Glu Gln Leu Ala Lys Leu Ala Gln Leu Lys
                485                 490                 495
```

```
Ala Glu Arg Asn Asp Ala Glu Val Lys Ala Ala Leu Asp Ala Leu Thr
            500                 505                 510

Ala Ala Ala Arg Asn Glu His Lys Glu Pro Gly Asp Leu Asp Gln Asn
        515                 520                 525

Leu Leu Lys Leu Ala Val Asp Ala Ala Arg Ala Lys Ala Thr Ile Gly
    530                 535                 540

Glu Ile Ser Asp Ala Leu Glu Val Val Phe Gly Arg His Glu Ala Glu
545                 550                 555                 560

Ile Arg Thr Leu Ser Gly Val Tyr Lys Asp Val Gly Lys Glu Gly
                565                 570                 575

Thr Val Ser Asn Val Glu Arg Ala Ile Ala Leu Ala Asp Ala Phe Glu
            580                 585                 590

Ala Glu Glu Gly Arg Arg Pro Arg Ile Phe Ile Ala Lys Met Gly Gln
        595                 600                 605

Asp Gly His Asp Arg Gly Gln Lys Val Val Ala Ser Ala Tyr Ala Asp
    610                 615                 620

Leu Gly Met Asp Val Asp Val Gly Pro Leu Phe Gln Thr Pro Ala Glu
625                 630                 635                 640

Ala Ala Arg Ala Ala Val Asp Ala Asp Val His Val Val Gly Met Ser
                645                 650                 655

Ser Leu Ala Ala Gly His Leu Thr Leu Leu Pro Glu Leu Lys Lys Glu
            660                 665                 670

Leu Ala Ala Leu Gly Arg Asp Asp Ile Leu Val Thr Val Gly Gly Val
        675                 680                 685

Ile Pro Pro Gly Asp Phe Gln Asp Leu Tyr Asp Met Gly Ala Ala Ala
    690                 695                 700

Ile Tyr Pro Pro Gly Thr Val Ile Ala Glu Ser Ala Ile Asp Leu Ile
705                 710                 715                 720

Thr Arg Leu Ala Ala His Leu Gly Phe Asp Leu Asp Val Asp Val Asn
                725                 730                 735

Glu

<210> SEQ ID NO 67
<211> LENGTH: 631
<212> TYPE: PRT
<213> ORGANISM: Rhodococcus erythropolis
<300> PUBLICATION INFORMATION:
<308> DATABASE ACCESSION NUMBER: NCBI / YP_002766535
<309> DATABASE ENTRY DATE: 2010-05-12
<313> RELEVANT RESIDUES IN SEQ ID NO: (1)..(631)

<400> SEQUENCE: 67

Met Ser Leu Ala Ser Glu Ala Glu Val Glu Gln Ala Tyr Ala Glu
1               5                   10                  15

Trp Gln Arg Ser Val Ala Gly Val Leu Ala Lys Ser Arg Arg Val Asp
                20                  25                  30

Ala Ala Glu Leu Gly Pro Glu Pro Gln Lys Leu Leu Glu Thr Val Thr
            35                  40                  45

Tyr Asp Gly Val Thr Val Ala Pro Leu Tyr Ser Pro Arg Asp Glu Arg
    50                  55                  60

Pro Glu Gln Ser Leu Pro Gly Thr Phe Pro Tyr Val Arg Gly Val Asp
65                  70                  75                  80

Ala His Arg Asp Val Asn Ala Gly Trp Leu Val Ser Ala Ala Phe Gly
                85                  90                  95

Thr Ala Ser Ala Ala Glu Thr Asn Arg Ala Ile Leu Asp Ala Leu Glu
            100                 105                 110
```

-continued

```
Asn Gly Val Ser Ala Leu Trp Leu Lys Val Gly Ala Asp Gly Val Pro
    115                 120                 125
Val Thr Asp Leu Ala Ala Ala Leu Glu Gly Val Leu Leu Asp Leu Ala
130                 135                 140
Pro Leu Thr Leu Asp Ala Gly Ala Glu Val Asn Asp Ala Ala Arg Ala
145                 150                 155                 160
Leu Phe Ser Leu Leu Asp Ala Arg Gly Glu Ala Gly Asp Gly Val Ser
                165                 170                 175
Asp Arg Ser Ser Ile Arg Val His Leu Gly Ala Ala Pro Leu Thr Ser
                180                 185                 190
Ser Phe Ser Gly Ala Ala Asp Val Glu Phe Ala Gly Ala Val Glu Leu
            195                 200                 205
Ala Ala Leu Ala Ala Ala Arg Ala Glu Thr Val His Ala Ile Thr Val
    210                 215                 220
Asp Gly Thr Ala Phe His Asn Ala Gly Ala Gly Asp Ala Glu Glu Leu
225                 230                 235                 240
Gly Ala Ala Ile Ala Ala Gly Leu Glu Tyr Leu Arg Ala Leu Thr Ala
                245                 250                 255
Glu Ser Gly Leu Thr Ile Gly Ala Ala Leu Ser Gln Leu Ala Phe Arg
            260                 265                 270
Tyr Ser Ala Thr Asp Asp Gln Phe Gln Thr Ile Ala Lys Phe Arg Ala
    275                 280                 285
Ala Arg Leu Val Trp Ala Arg Ile Ala Gln Val Cys Gly Ala Ser Asp
290                 295                 300
Phe Gly Gly Ala Pro Gln His Ala Val Thr Ser Ala Ala Met Met Ala
305                 310                 315                 320
Gln Arg Asp Pro Trp Val Asn Met Leu Arg Thr Thr Leu Ala Ala Phe
                325                 330                 335
Gly Ala Gly Val Gly Gly Ala Asp Ala Val Thr Val Leu Pro Phe Asp
            340                 345                 350
Val Ala Leu Ala Asp Gly Thr Leu Gly Val Ser Lys Ser Phe Ser Ser
    355                 360                 365
Arg Ile Ala Arg Asn Thr Gln Leu Leu Leu Glu Glu Ser His Leu
370                 375                 380
Gly Arg Val Leu Asp Pro Ser Ala Gly Ser Trp Tyr Val Glu Asp Leu
385                 390                 395                 400
Thr Gln Gln Ile Ala Ala Thr Ala Trp Glu Phe Phe Gln Glu Ile Glu
                405                 410                 415
Ala Ala Gly Gly Tyr Leu Ala Ala Leu Glu Ala Gly Ile Val Ser Gly
            420                 425                 430
Arg Ile Ala Ala Thr Lys Ala Lys Arg Asp Ser Asp Ile Ala His Arg
    435                 440                 445
Lys Thr Thr Val Thr Gly Val Asn Glu Phe Pro Asn Leu Gly Glu Thr
450                 455                 460
Pro Leu Ser Ala Glu Ala Val Glu Pro Gly Gln Ser Val Ala Arg Tyr
465                 470                 475                 480
Ala Ala Ala Phe Glu Ala Leu Arg Asp Arg Ser Asp Ala Phe Leu Ala
                485                 490                 495
Ala Gly Gly Ala Arg Pro Thr Ala Leu Leu Ala Pro Leu Gly Ser Val
            500                 505                 510
Ala Glu His Asn Val Arg Thr Thr Phe Ala Ser Asn Leu Leu Ala Ser
    515                 520                 525
```

```
Gly Gly Ile Asp Ala Val Asn Pro Gly Pro Leu Glu Val Gly Ala Glu
530                 535                 540
Ala Ile Ser Ala Ala Val Lys Ala Ser Gly Val Thr Val Ala Val Leu
545                 550                 555                 560
Cys Gly Thr Asp Lys Arg Tyr Gly Glu Ser Ala Ala Ala Val Ala
            565                 570                 575
Glu Leu Arg Ala Ala Gly Ile Thr Lys Val Leu Leu Ala Gly Pro Glu
            580                 585                 590
Lys Ala Val Ala Asp Ala Thr Gly Glu Ser Arg Pro Asp Gly Phe Leu
            595                 600                 605
Thr Ala Arg Ile Asp Ala Val Ser Ala Leu Thr Glu Leu Leu Asp Phe
610                 615                 620
Ile Glu Thr Gly Ser Ser Lys
625                 630

<210> SEQ ID NO 68
<211> LENGTH: 750
<212> TYPE: PRT
<213> ORGANISM: Rhodococcus erythropolis
<300> PUBLICATION INFORMATION:
<308> DATABASE ACCESSION NUMBER: NCBI / YP_002766536
<309> DATABASE ENTRY DATE: 2010-05-12
<313> RELEVANT RESIDUES IN SEQ ID NO: (1)..(750)

<400> SEQUENCE: 68

Met Thr Thr Arg Glu Val Lys His Val Ile Gly Ser Phe Ala Glu Val
1               5                   10                  15
Pro Leu Glu Asp Pro Gln Ser Pro Ala Pro Thr Pro Pro Ser Val Glu
            20                  25                  30
Gln Ala Gln Ala Leu Ile Glu Glu Gly Ala Asn Ala Asn Asn Tyr Ala
        35                  40                  45
Ala Glu Gln Val Val Trp Ser Thr Pro Glu Gly Ile Asp Val Lys Pro
    50                  55                  60
Val Tyr Thr Gly Ala Asp Arg Thr Ala Ala Glu Ser Gly Tyr Pro
65              70                  75                  80
Leu Asp Ser Phe Pro Gly Ala Ala Pro Phe Leu Arg Gly Pro Tyr Pro
                85                  90                  95
Thr Met Tyr Val Asn Gln Pro Trp Thr Ile Arg Gln Tyr Ala Gly Phe
            100                 105                 110
Ser Thr Ala Ala Glu Ser Asn Ala Phe Tyr Arg Arg Asn Leu Ala Ala
        115                 120                 125
Gly Gln Lys Gly Leu Ser Val Ala Phe Asp Leu Ala Thr His Arg Gly
    130                 135                 140
Tyr Asp Ser Asp His Pro Arg Val Ala Gly Asp Val Gly Met Ala Gly
145                 150                 155                 160
Val Ala Ile Asp Ser Ile Leu Asp Met Arg Gln Leu Phe Asp Gly Ile
                165                 170                 175
Asp Leu Ser Gln Val Ser Val Ser Met Thr Met Asn Gly Ala Val Leu
            180                 185                 190
Pro Ile Leu Ala Leu Tyr Val Ala Ala Gly Glu Gln Gly Val Thr
        195                 200                 205
Pro Asp Lys Leu Ala Gly Thr Ile Gln Asn Asp Ile Leu Lys Glu Phe
    210                 215                 220
Met Val Arg Asn Thr Tyr Ile Tyr Pro Pro Lys Pro Ser Met Arg Ile
225                 230                 235                 240

Ile Ser Asp Ile Phe Ala Tyr Ser Ser Ala Glu Met Pro Lys Tyr Asn
```

-continued

```
                245                 250                 255
Ser Ile Ser Ile Ser Gly Tyr His Ile Gln Glu Ala Gly Ala Thr Ala
            260                 265                 270
Asp Leu Glu Leu Ala Tyr Thr Leu Ala Asp Gly Val Glu Tyr Ile Arg
        275                 280                 285
Ala Gly Leu Asp Ala Gly Met Asp Ile Asp Lys Phe Ala Pro Arg Leu
    290                 295                 300
Ser Phe Phe Trp Ala Ile Gly Met Asn Phe Phe Met Glu Val Ala Lys
305                 310                 315                 320
Leu Arg Ala Gly Arg Leu Leu Trp Ala Glu Leu Val Ala Lys Phe Asp
                325                 330                 335
Pro Lys Ser Ala Lys Ser Leu Ser Leu Arg Thr His Ser Gln Thr Ser
            340                 345                 350
Gly Trp Ser Leu Thr Ala Gln Asp Val Phe Asn Asn Val Pro Arg Thr
        355                 360                 365
Cys Val Glu Ala Met Ala Ala Thr Gln Gly His Thr Gln Ser Leu His
    370                 375                 380
Thr Asn Ala Leu Asp Glu Ala Ile Ala Leu Pro Thr Asp Phe Ser Ala
385                 390                 395                 400
Arg Ile Ala Arg Asn Thr Gln Leu Leu Leu Gln Gln Glu Ser Gly Thr
                405                 410                 415
Val Arg Pro Ile Asp Pro Trp Gly Gly Ser Tyr Tyr Val Glu Trp Leu
            420                 425                 430
Thr Asn Glu Leu Ala Asn Arg Ala Arg Lys His Ile Glu Glu Val Glu
        435                 440                 445
Glu Ala Gly Gly Met Ala Gln Ala Ile Asn Glu Gly Ile Pro Lys Leu
    450                 455                 460
Arg Ile Glu Glu Ala Ala Arg Thr Gln Ala Arg Ile Asp Ser Gly
465                 470                 475                 480
Arg Gln Pro Leu Val Gly Val Asn Lys Tyr Val Pro Asp Glu Val Asp
                485                 490                 495
Thr Ile Glu Val Leu Lys Val Glu Asn Ser Lys Val Arg Lys Glu Gln
            500                 505                 510
Leu Glu Lys Leu Val Arg Leu Arg Ala Glu Arg Asp Pro Glu Ala Val
        515                 520                 525
Glu Ala Ala Leu Ala Asn Leu Thr Arg Ala Ala Ser Thr Glu Gly
    530                 535                 540
Gly Met Glu Asn Asn Leu Leu Ala Leu Ala Val Val Ala Ala Arg Ala
545                 550                 555                 560
Met Ala Thr Val Gly Glu Ile Ser Asp Ala Leu Glu Lys Val Tyr Gly
                565                 570                 575
Arg His Gln Ala Glu Ile Arg Thr Ile Ser Gly Val Tyr Arg Asp Glu
            580                 585                 590
Ala Gly Thr Val Ser Asn Ile Ser Lys Ala Met Glu Leu Val Glu Lys
        595                 600                 605
Phe Ala Glu Asp Glu Gly Arg Arg Pro Arg Ile Leu Val Ala Lys Met
    610                 615                 620
Gly Gln Asp Gly His Asp Arg Gly Gln Lys Val Ile Ser Thr Ala Phe
625                 630                 635                 640
Ala Asp Ile Gly Phe Asp Val Asp Val Gly Pro Leu Phe Gln Thr Pro
                645                 650                 655
Glu Glu Val Ala Asn Gln Ala Ala Asp Asn Asp Val His Val Val Gly
            660                 665                 670
```

```
Val Ser Ser Leu Ala Ala Gly His Leu Thr Leu Val Pro Ala Leu Arg
        675                 680                 685

Glu Ala Leu Ala Ala Gly Arg Pro Asp Ile Met Ile Val Val Gly
    690                 695                 700

Gly Val Ile Pro Pro Gly Asp Phe Asp Glu Leu Tyr Glu Ala Gly Ala
705                 710                 715                 720

Ala Ala Ile Phe Pro Pro Gly Thr Val Ile Asp Ala Ala Ser Gly
            725                 730                 735

Leu Leu Glu Lys Leu Ser Ala Gln Leu Gly His Asp His Ser
        740                 745                 750

<210> SEQ ID NO 69
<211> LENGTH: 618
<212> TYPE: PRT
<213> ORGANISM: Porphyromonas gingivalis
<300> PUBLICATION INFORMATION:
<308> DATABASE ACCESSION NUMBER: NCBI / NP_905776
<309> DATABASE ENTRY DATE: 2010-06-29
<313> RELEVANT RESIDUES IN SEQ ID NO: (1)..(618)

<400> SEQUENCE: 69

Met Ala Lys Glu Lys Glu Lys Leu Phe Ser Glu Phe Pro Pro Val Ser
1               5                   10                  15

Arg Glu Ala Trp Ile Asp Lys Ile Thr Ala Asp Leu Lys Gly Val Pro
            20                  25                  30

Phe Glu Lys Lys Leu Val Trp Arg Thr Asn Glu Gly Phe Asn Val Asn
        35                  40                  45

Pro Phe Tyr Arg Arg Glu Asp Ile Glu Asp Leu Lys Thr Thr Thr Ser
    50                  55                  60

Leu Pro Asp Glu Tyr Pro Tyr Val Arg Ser Thr Arg Met His Asn Glu
65                  70                  75                  80

Trp Leu Val Arg Gln Asp Ile Val Val Gly Asp Asn Val Ala Glu Ala
                85                  90                  95

Asn Glu Lys Ala Leu Asp Leu Leu Asn Lys Gly Val Asp Ser Leu Gly
            100                 105                 110

Phe Tyr Leu Lys Lys Val His Ile Asn Val Asp Thr Leu Ala Ala Leu
        115                 120                 125

Leu Lys Asp Ile Glu Leu Thr Ala Val Glu Leu Asn Phe Asn Cys Cys
    130                 135                 140

Ile Thr Arg Ala Ala Asp Leu Leu Ser Ala Phe Ser Ala Tyr Val Lys
145                 150                 155                 160

Lys Val Gly Ala Asp Pro Asn Lys Cys His Gly Ser Val Ser Tyr Asp
                165                 170                 175

Pro Phe Lys Gln Leu Val Arg Gly Val Ser Asn Pro Asp Trp Val
        180                 185                 190

Lys Met Thr Leu Pro Val Met Asp Ala Ala Arg Glu Leu Pro Ala Phe
        195                 200                 205

Arg Val Leu Asn Val Asn Ala Val Asn Leu Ser Asp Ala Gly Ala Phe
    210                 215                 220

Ile Thr Gln Glu Leu Gly Tyr Ala Leu Ala Trp Gly Ala Glu Leu Leu
225                 230                 235                 240

Asp Lys Leu Thr Asp Ala Gly Tyr Lys Pro Glu Glu Ile Ala Ser Arg
                245                 250                 255

Ile Lys Phe Asn Phe Gly Ile Gly Ser Asn Tyr Phe Met Glu Ile Ala
            260                 265                 270
```

```
Lys Phe Arg Ala Ala Arg Trp Leu Trp Ala Gln Ile Val Gly Ser Tyr
            275                 280                 285
Gly Asp Gln Tyr Lys Asn Glu Thr Ala Lys Ile His Gln His Ala Thr
        290                 295                 300
Thr Ser Met Trp Asn Lys Thr Val Phe Asp Ala His Val Asn Leu Leu
305                 310                 315                 320
Arg Thr Gln Thr Glu Thr Met Ser Ala Ile Ala Gly Val Asp Ser
                325                 330                 335
Ile Thr Val Leu Pro Phe Asp Val Thr Tyr Gln Gln Ser Asp Asp Phe
            340                 345                 350
Ser Glu Arg Ile Ala Arg Asn Gln Gln Leu Leu Leu Lys Glu Glu Cys
        355                 360                 365
His Phe Asp Lys Val Ile Asp Pro Ser Ala Gly Ser Tyr Tyr Ile Glu
    370                 375                 380
Thr Leu Thr Asn Ser Ile Gly Glu Glu Ala Trp Lys Leu Phe Leu Ser
385                 390                 395                 400
Val Glu Asp Ala Gly Gly Phe Thr Gln Ala Ala Glu Thr Ala Ser Ile
                405                 410                 415
Gln Lys Ala Val Asn Ala Ser Asn Ile Lys Arg His Gln Ser Val Ala
            420                 425                 430
Thr Arg Arg Glu Ile Phe Leu Gly Thr Asn Gln Phe Pro Asn Phe Thr
        435                 440                 445
Glu Val Ala Gly Asp Lys Ile Thr Leu Ala Gln Gly Glu His Asp Cys
    450                 455                 460
Asn Cys Val Lys Ser Ile Glu Pro Leu Asn Phe Ser Arg Gly Ala Ser
465                 470                 475                 480
Glu Phe Glu Ala Leu Arg Leu Ala Thr Glu Lys Ser Gly Lys Thr Pro
                485                 490                 495
Val Val Phe Met Leu Thr Ile Gly Asn Leu Ala Met Arg Leu Ala Arg
            500                 505                 510
Ser Gln Phe Ser Ser Asn Phe Phe Gly Cys Ala Gly Tyr Lys Leu Ile
        515                 520                 525
Asp Asn Leu Gly Phe Lys Ser Val Glu Glu Gly Val Asp Ala Ala Leu
    530                 535                 540
Ala Ala Lys Ala Asp Ile Val Val Leu Cys Ser Ser Asp Glu Tyr
545                 550                 555                 560
Ala Glu Tyr Ala Pro Ala Ala Phe Asp Tyr Leu Ala Gly Arg Ala Glu
                565                 570                 575
Phe Val Val Ala Gly Ala Pro Ala Cys Met Ala Asp Leu Glu Ala Lys
            580                 585                 590
Gly Ile Arg Asn Tyr Val His Val Lys Ser Asn Val Leu Glu Thr Leu
        595                 600                 605
Arg Ala Phe Asn Asp Lys Phe Gly Ile Arg
    610                 615

<210> SEQ ID NO 70
<211> LENGTH: 715
<212> TYPE: PRT
<213> ORGANISM: Porphyromonas gingivalis
<300> PUBLICATION INFORMATION:
<308> DATABASE ACCESSION NUMBER: NCBI / NP_905777
<309> DATABASE ENTRY DATE: 2010-06-29
<313> RELEVANT RESIDUES IN SEQ ID NO: (1)..(715)

<400> SEQUENCE: 70

Met Lys Pro Asn Tyr Lys Asp Ile Asp Ile Lys Ser Ala Gly Phe Val
```

```
            1               5                   10                  15
Ala Lys Asp Ala Thr Arg Trp Ala Glu Glu Lys Gly Ile Val Ala Asp
                    20                  25                  30

Trp Arg Thr Pro Glu Gln Ile Met Val Lys Pro Leu Tyr Thr Lys Asp
                35                  40                  45

Asp Leu Glu Gly Met Glu His Leu Asp Tyr Val Ser Gly Leu Pro Pro
        50                  55                  60

Phe Leu Arg Gly Pro Tyr Ser Gly Met Tyr Pro Met Arg Pro Trp Thr
65                  70                  75                  80

Ile Arg Gln Tyr Ala Gly Phe Ser Thr Ala Glu Glu Ser Asn Ala Phe
                    85                  90                  95

Tyr Arg Arg Asn Leu Ala Ser Gly Gln Lys Gly Leu Ser Val Ala Phe
                100                 105                 110

Asp Leu Ala Thr His Arg Gly Tyr Asp Ala Asp His Ser Arg Val Val
                115                 120                 125

Gly Asp Val Gly Lys Ala Gly Val Ser Ile Cys Ser Leu Glu Asp Met
        130                 135                 140

Lys Val Leu Phe Asp Gly Ile Pro Leu Ser Lys Met Ser Val Ser Met
145                 150                 155                 160

Thr Met Asn Gly Ala Val Leu Pro Ile Leu Ala Phe Tyr Ile Asn Ala
                    165                 170                 175

Gly Leu Glu Gln Gly Ala Lys Leu Glu Glu Met Ala Gly Thr Ile Gln
                180                 185                 190

Asn Asp Ile Leu Lys Glu Phe Met Val Arg Asn Thr Tyr Ile Tyr Pro
                195                 200                 205

Pro Glu Phe Ser Met Arg Ile Ile Ala Asp Ile Phe Glu Tyr Thr Ser
        210                 215                 220

Gln Asn Met Pro Lys Phe Asn Ser Ile Ser Ile Ser Gly Tyr His Met
225                 230                 235                 240

Gln Glu Ala Gly Ala Thr Ala Asp Ile Glu Met Ala Tyr Thr Leu Ala
                    245                 250                 255

Asp Gly Met Gln Tyr Leu Lys Ala Gly Ile Asp Ala Gly Ile Asp Val
                260                 265                 270

Asp Ala Phe Ala Pro Arg Leu Ser Phe Phe Trp Ala Ile Gly Val Asn
                275                 280                 285

His Phe Met Glu Ile Ala Lys Met Arg Ala Ala Arg Leu Leu Trp Ala
        290                 295                 300

Lys Ile Val Lys Ser Phe Gly Ala Lys Asn Pro Lys Ser Leu Ala Leu
305                 310                 315                 320

Arg Thr His Ser Gln Thr Ser Gly Trp Ser Leu Thr Glu Gln Asp Pro
                    325                 330                 335

Phe Asn Asn Val Gly Arg Thr Cys Ile Glu Ala Met Ala Ala Ala Leu
                340                 345                 350

Gly His Thr Gln Ser Leu His Thr Asn Ala Leu Asp Glu Ala Ile Ala
                355                 360                 365

Leu Pro Thr Asp Phe Ser Ala Arg Ile Ala Arg Asn Thr Gln Ile Tyr
        370                 375                 380

Ile Gln Glu Glu Thr Leu Val Cys Lys Glu Ile Asp Pro Trp Gly Gly
385                 390                 395                 400

Ser Tyr Tyr Val Glu Ser Leu Thr Asn Glu Leu Val His Lys Ala Trp
                    405                 410                 415

Thr Leu Ile Lys Glu Val Gln Glu Met Gly Gly Met Ala Lys Ala Ile
                420                 425                 430
```

```
Glu Thr Gly Leu Pro Lys Leu Arg Ile Glu Glu Ala Ala Ala Arg Thr
            435                 440                 445

Gln Ala Arg Ile Asp Ser His Gln Gln Val Ile Val Gly Val Asn Lys
    450                 455                 460

Tyr Arg Leu Pro Lys Glu Asp Pro Ile Asp Ile Leu Glu Ile Asp Asn
465                 470                 475                 480

Thr Ala Val Arg Lys Gln Gln Ile Glu Arg Leu Asn Asp Leu Arg Ser
                485                 490                 495

His Arg Asp Glu Lys Ala Val Gln Glu Ala Leu Glu Ala Ile Thr Lys
                500                 505                 510

Cys Val Glu Thr Lys Glu Gly Asn Leu Leu Asp Leu Ala Val Lys Ala
            515                 520                 525

Ala Gly Leu Arg Ala Ser Leu Gly Glu Ile Ser Asp Ala Cys Glu Lys
    530                 535                 540

Val Val Gly Arg Tyr Lys Ala Val Ile Arg Thr Ile Ser Gly Val Tyr
545                 550                 555                 560

Ser Ser Glu Ser Gly Glu Asp Lys Asp Phe Ala His Ala Lys Glu Leu
                565                 570                 575

Ala Glu Lys Phe Ala Lys Lys Glu Gly Arg Gln Pro Arg Ile Met Ile
                580                 585                 590

Ala Lys Met Gly Gln Asp Gly His Asp Arg Gly Ala Lys Val Val Ala
                595                 600                 605

Thr Gly Tyr Ala Asp Cys Gly Phe Asp Val Asp Met Gly Pro Leu Phe
            610                 615                 620

Gln Thr Pro Glu Glu Ala Ala Arg Gln Ala Val Glu Asn Asp Val His
625                 630                 635                 640

Val Met Gly Val Ser Ser Leu Ala Ala Gly His Lys Thr Leu Ile Pro
                645                 650                 655

Gln Val Ile Ala Glu Leu Glu Lys Leu Gly Arg Pro Asp Ile Leu Val
            660                 665                 670

Thr Ala Gly Gly Val Ile Pro Ala Gln Asp Tyr Asp Phe Leu Tyr Gln
    675                 680                 685

Ala Gly Val Ala Ala Ile Phe Gly Pro Gly Thr Pro Val Ala Tyr Ser
    690                 695                 700

Ala Ala Lys Val Leu Glu Ile Leu Leu Glu Glu
705                 710                 715
```